US012584142B2

(12) United States Patent
Park et al.

(10) Patent No.: US 12,584,142 B2

(45) Date of Patent: Mar. 24, 2026

(54) TRANSGENIC PLANTS HAVING ALTERED BIOMASS COMPOSITION

(71) Applicant: Ceres, Inc., Thousand Oaks, CA (US)

(72) Inventors: Joon-Hyun Park, Thousand Oaks, CA (US); Roger I. Pennell, Malibu, CA (US); Richard Flavell, Thousand Oaks, CA (US); Chuan-Yin Wu, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 508 days.

(21) Appl. No.: 17/678,712

(22) Filed: Feb. 23, 2022

(65) Prior Publication Data

US 2022/0282274 A1 Sep. 8, 2022

Related U.S. Application Data

(62) Division of application No. 16/992,793, filed on Aug. 13, 2020, now Pat. No. 11,299,747, which is a division of application No. 16/406,702, filed on May 8, 2019, now Pat. No. 10,822,616, which is a division of application No. 14/363,151, filed as application No. PCT/US2012/068756 on Dec. 10, 2012, now Pat. No. 10,323,256.

(60) Provisional application No. 61/568,747, filed on Dec. 9, 2011.

(51) Int. Cl.
*C12N 15/82* (2006.01)
*C07K 14/415* (2006.01)

(52) U.S. Cl.
CPC ........ *C12N 15/8297* (2013.01); *C07K 14/415* (2013.01); *C12N 15/8245* (2013.01); *C12N 15/8246* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 4,987,071 | A | 1/1991 | Cech et al. |
| 5,034,323 | A | 7/1991 | Jorgensen et al. |
| 5,204,253 | A | 4/1993 | Sanford et al. |
| 5,231,020 | A | 7/1993 | Jorgensen et al. |
| 5,254,678 | A | 10/1993 | Haseloff et al. |
| 5,538,880 | A | 7/1996 | Lundquist et al. |
| 5,612,191 | A | 3/1997 | Briggs et al. |
| 5,766,847 | A | 6/1998 | Jackle et al. |
| 5,773,282 | A | 6/1998 | Tsusaki et al. |
| 5,874,274 | A | 2/1999 | Jakobsen et al. |
| 5,878,215 | A | 3/1999 | Kling et al. |
| 5,939,533 | A | 8/1999 | Lilja et al. |
| 6,013,863 | A | 1/2000 | Lundquist et al. |
| 6,090,595 | A | 7/2000 | Foody et al. |
| 6,198,021 | B1 | 3/2001 | Lange et al. |
| 6,326,527 | B1 | 12/2001 | Kirihara et al. |
| 6,329,571 | B1 | 12/2001 | Hiei |
| 6,333,181 | B1 | 12/2001 | Ingram et al. |
| 6,423,885 | B1 | 7/2002 | Waterhouse et al. |
| PP13,008 | P2 | 9/2002 | Walsh |
| 6,452,067 | B1 | 9/2002 | Bedbrook et al. |
| 6,455,675 | B1 | 9/2002 | Lange et al. |
| 6,573,099 | B2 | 6/2003 | Graham |
| 6,677,502 | B1 | 1/2004 | Allen et al. |
| 6,723,897 | B2 | 4/2004 | Brown et al. |
| PP14,743 | P2 | 5/2004 | Speichert et al. |
| 6,753,139 | B1 | 6/2004 | Baulcombe et al. |
| 6,777,588 | B2 | 8/2004 | Waterhouse et al. |
| PP15,193 | P2 | 9/2004 | Smith et al. |
| 6,906,244 | B2 | 6/2005 | Fischer et al. |
| 6,921,848 | B2 | 7/2005 | Chory et al. |
| 6,921,849 | B2 | 7/2005 | Amasino et al. |
| PP16,176 | P3 | 1/2006 | Cosner et al. |
| 7,049,490 | B2 | 5/2006 | Tanaka et al. |
| 7,059,993 | B2 | 6/2006 | Ding et al. |
| 7,112,429 | B2 | 9/2006 | Ding et al. |
| 7,195,917 | B2 | 3/2007 | Brown et al. |
| PP18,161 | P2 | 10/2007 | Probst |
| 7,420,102 | B2 | 9/2008 | Amasino et al. |
| 7,575,917 | B2 | 8/2009 | Gilbertson et al. |
| 7,807,878 | B2 | 10/2010 | Eriksson et al. |
| 7,915,050 | B2 | 3/2011 | Matsuoka et al. |
| 7,985,888 | B2 | 7/2011 | Phillips et al. |

(Continued)

FOREIGN PATENT DOCUMENTS

| | | |
|---|---|---|
| EP | 0534858 | 3/1993 |
| WO | WO 93/16096 | 8/1993 |

(Continued)

OTHER PUBLICATIONS

Yamamoto et al. Plant Cell. 22:3589-3602. (Year: 2010).*
Mauriat and Moritz. The Plant Journal. 58(6):989-1003. (Year: 2009).*
Chandler et al. Mol Plant. 1(2):285-294. GenBank: CAP64326.1 (Year: 2008).*
Sun, T. Current Biology. 21: R338-R345. (Year: 2011).*
Harberd et al. The Plant Cell. 21(5):1328-1339. (Year: 2009).*
Tang, et al. Botanical Journal of the Linnean Society. 183(1):1-15. (Year: 2017).*
U.S. Appl. No. 60/505,689, filed Sep. 23, 2003, Cook, et al.
U.S. Appl. No. 60/518,075, filed Nov. 6, 2003, Pennell, et al.
U.S. Appl. No. 60/544,771, filed Feb. 13, 2004, Cook, et al.

(Continued)

*Primary Examiner* — Shubo Zhou
*Assistant Examiner* — David R Byrnes
(74) *Attorney, Agent, or Firm* — Dentons US LLP; Thomas Hiesberger

(57) ABSTRACT

Methods and materials for modulating biomass composition in plants are disclosed. For example, nucleic acids encoding biomass composition-modulating polypeptides are disclosed as well as methods for using such nucleic acids to transform plant cells. Also disclosed are plants having altered biomass composition and plant products produced from plants having altered biomass composition.

8 Claims, 63 Drawing Sheets

Specification includes a Sequence Listing.

(56) References Cited

U.S. PATENT DOCUMENTS

2003/0175783 A1 9/2003 Waterhouse et al.
2003/0175965 A1 9/2003 Lowe et al.
2003/0180945 A1 9/2003 Wang et al.
2003/0217388 A1 11/2003 Feyereisen et al.
2003/0233670 A1 12/2003 Edgerton et al.
2004/0214330 A1 10/2004 Waterhouse et al.
2005/0032221 A1 2/2005 Chang et al.
2005/0223422 A1 10/2005 Cook et al.
2005/0223434 A1 10/2005 Alexandrov et al.
2005/0229270 A1 10/2005 Fischer et al.
2005/0246785 A1 11/2005 Cook et al.
2006/0010518 A1 1/2006 Feldmann et al.
2006/0015970 A1 1/2006 Pennell et al.
2006/0021083 A1 1/2006 Cook et al.
2006/0041952 A1 2/2006 Cook
2006/0057724 A1 3/2006 Alexandrov et al.
2006/0090216 A1 4/2006 Apuya et al.
2006/0112445 A1 5/2006 Dang
2006/0112454 A1 5/2006 Christensen et al.
2006/0134786 A1 6/2006 Feldmann
2006/0143729 A1 6/2006 Alexandrov et al.
2006/0150285 A1 7/2006 Nadzan et al.
2006/0168696 A1 7/2006 Feldmann et al.
2006/0195943 A1 8/2006 Feldmann et al.
2006/0260004 A1 11/2006 Fang et al.
2006/0265777 A1 11/2006 Apuya et al.
2006/0265788 A1 11/2006 Rommens
2006/0294622 A1 12/2006 Sosa et al.
2007/0006335 A1 1/2007 Cook et al.
2007/0006337 A1 1/2007 Cook et al.
2007/0006345 A1 1/2007 Alexandrov et al.
2007/0006346 A1 1/2007 Alexandrov et al.
2007/0011783 A1 1/2007 Liu et al.
2007/0039067 A1 2/2007 Feldmann et al.
2007/0042387 A1 2/2007 Pennel et al.
2007/0056058 A1 3/2007 Olivier et al.
2007/0061914 A1 3/2007 Feldmann
2007/0083953 A1 4/2007 Christensen et al.
2007/0092935 A1 4/2007 Jones et al.
2007/0094750 A1 4/2007 Jofuku
2007/0101460 A1 5/2007 Feldman et al.
2007/0174936 A1 7/2007 Alexandrov et al.
2007/0192907 A1 8/2007 Alexandrov et al.
2007/0214517 A1 9/2007 Alexandrov et al.
2007/0277269 A1 11/2007 Alexandrov et al.
2008/0072340 A1 3/2008 Troukhan et al.
2008/0131581 A1 6/2008 Schneebergr et al.
2009/0031441 A1 1/2009 Matsuoka et al.
2009/0094717 A1 4/2009 Troukhan et al.
2011/0167514 A1* 7/2011 Brover ............... C12N 15/8261 800/290
2011/0214199 A1 9/2011 Coffin
2019/0323030 A1 10/2019 Park et al.

FOREIGN PATENT DOCUMENTS

WO WO 1994/028141 12/1994
WO WO 97/01952 1/1997
WO WO 98/36083 8/1998
WO WO 98/53083 11/1998
WO WO 99/32619 7/1999
WO WO 02/46449 6/2002
WO WO 2005/098007 10/2005
WO WO 2006/005023 1/2006
WO WO 2006/032916 3/2006
WO WO 2006/034479 3/2006
WO WO 2006/036864 4/2006
WO WO 2007/044988 4/2007
WO WO 2007/046403 4/2007
WO WO 2007/055826 5/2007
WO WO 2007/120989 10/2007
WO WO 2008/049183 5/2008
WO WO 2009/009142 1/2009
WO WO 2009/099899 8/2009
WO WO 2009/102965 8/2009
WO WO 2009/134339 11/2009
WO WO 2009/146015 12/2009
WO WO 2010/033564 3/2010
WO WO 2010/083178 7/2010
WO WO 2010/127969 11/2010
WO WO 2011/011412 1/2011
WO WO 2011/140329 11/2011
WO WO 2012/009551 1/2012

OTHER PUBLICATIONS

U.S. Appl. No. 60/558,869, filed Apr. 1, 2004, Cook, et al.
U.S. Appl. No. 60/583,609, filed Jun. 30, 2004, Alexandrov.
U.S. Appl. No. 60/583,691, filed Jun. 30, 2004, Alexandrov, et al.
U.S. Appl. No. 60/612,891, filed Sep. 23, 2004, Kwok.
U.S. Appl. No. 60/619,181, filed Oct. 14, 2004, Medrano.
U.S. Appl. No. 60/637,140, filed Dec. 16, 2004, Feldmann.
U.S. Appl. No. 60/757,544, filed Jan. 9, 2006, Dang.
U.S. Appl. No. 60/776,307, filed Feb. 24, 2006, Kwok.
Abler, et al., "Isolation and characterization of a genomic sequence encoding the maize Cat3 catalase gene," Plant Molecular Biology, 22:1031-1038 (1993).
Akashi, et al., "Gene Discovery by Ribozyme and siRNA Libraries," Nature Reviews Mol. Cell Biology 6:413-422 (2005).
Alonso-Blanco, et al., "*Arabidopsis* Protocols," Methods in Molecular Biology 82:137-146 (1998).
Appleford et al., Physiologia Plantarum 100:534-542 (1997).
Aravind and Koonin, "The DNA-repair protein AlkB, EGL-9, and leprecan define new families of 2-oxoglutarate- and iron-dependent dioxygenases," Genome Biol. 2(3):RESEARCH0007 (2001).
Baerson, et al., "Developmental regulation of an acyl carrier protein gene promoter in vegetative and reproductive tissues," Plant Mol. Biol. 22(2):255-267 (1993).
Bateman, et al., "Pfam 3.1: 1313 multiple alignments and profile HMMs match the majority of proteins," Nucl. Acids Res. 27:260-262 (1999).
Bolle, et al., "PAT1, a new member of the GRAS family, is involved in phytochrome A signal transduction," Genes Dev. 14(10):1269-1278 (2000).
Braga, et al., "Expression of the Cry1 Ab Protein in Genetically Modified Sugarcane for the Control of *Diatraea saccharalis* (Lepidoptera: Crambidae)," Journal of New Seeds 5:209-221 (2003).
Burr, et al. "Gene mapping with recombinant inbreds in maize," Genetics 118(3):519-526 (1998).
Burr, et al., "Mapping Genes with Recombinant Inbreds," The Maize Handbook, pp. 249-254 (1994).
Bustos, et al., "Regulation of B-Glucuronidase Expression in Transgenic Tobacco Plants by an A/T-Rich, cis-Acting Sequence Found Upstream of a French Bean B-Phaseolin Gene," The Plant Cell 1(9): 839-853 (1989).
Cerdan, et al., "A 146 bp fragment of the tobacco Lhcbl*2 promoter confers very-low-fluence and high-irradiance responses of phytochrome to a minimal CaMV 35S promoter," Plant Mol. Biol. 33:245-255 (1997).
Chen, et al., "Functional analysis of regulatory elements in a plant embryo-specific gene," Procedures of the National Academy of Sciences of the United States of America, 83:8560-8564 (1986).
Chenna, et al., "Multiple sequence alignment with the Clustal series of programs," Nucleic Acids Res. 31(13):3497-3500 (2003).
Christian, et al., "Targeting DNA Double-Strand Breaks with TAL Effector Nucleases," Genetics 186:757-761 (2010).
Conceicao, "A cotyledon regulatory region is responsible for the different spatial expression patterns of *Arabidopsis* 2S albumin genes," The Plant Journal 5(4):493-505 (1994).
Conkling, et al., "Isolation of Transcriptionally Regulated Root-Specific Genes from Tobacco," Plant Physiol. 93:1203-1211 (1990).
Dai, et al., "RF2b, a rice bZIP transcription activator, interacts with RF2a and is involved in symptom development of rice tungro disease," Procedures of the National Academy of Sciences of the United States of America 101(2):687-692 (2004).
De Feyter and Gaudron, "Expressing Ribozymes in Plants," Methods in Molecular Biology 74(43).

(56) References Cited

OTHER PUBLICATIONS

Dieffenbach and Dveksler, "PCR Primer: A Laboratory Manual," Cold Spring Harbor Laboratory Press, 520 pages (1995).
Do, et al., "ProbCons: Probabilistic consistency-based multiple sequence alignment," Genome Res. 15(2):330-340 (2005).
Durbin, et al., "Biological Sequence Analysis: Probabilistic Models of Proteins and Nucleic Acids," Cambridge University Press, Cambridge, UK (1998).
Fejes, et al., "A 268 bp upstream sequence mediates the circadian clock-regulated transcription of the wheat Cab-1 gene in transgenic plants," Plant Mol. Biol. 15:921-932 (1990).
Fromm, et al., "An Octopine Synthase Enhancer Element Directs Tissue-Specific Expression and Binds ASF-1, a Factor from Tobacco Nuclear Extracts," The Plant Cell 1:977-984 (1989).
Fujisawa, et al., "Suppression of the heterotrimeric G protein causes abnormal morphology, including dwarfism, in rice," Procedures of the National Academy of Sciences of the United States of America 96:7575-7580 (1999).
Garcia-Hurtado, et al., "The characterization of transgenic tomato over-expressing gibberellin 20-oxidase reveals induction of parthenocarpic fruit growth, higher yield and alteration of the gibberellin biosynthetic pathway," 30 pages.
Gardiner, et al., "Development of a Core RFLP Map in Maize Using an Immortalized F2 Population," Genetics Society of America 134:917-930 (1993).
GenBank Accession No. L05934 GI: 168436, "Isolation and characterization of a genomic sequence encoding the maize Cat3 catalase gene," dated Oct. 22, 1993, 3 pages.
GenBank Accession No. U93215 GI: 20198323, "*Arabidopsis thaliana* chromosome 2 BAC T6B20 genomic sequence," dated Feb. 27, 2002, 37 pages.
GenBank Accession No. AF129516 GI: 4567094, "Mutations in FIE, a WD polycomb group gene, allow endosperm development without fertilization," dated Apr. 6, 1999, 2 pages.
GenBank Accession No. AF096096 GI: 4185500, "Genes controlling fertilization-independent seed development in *Arabidopsis thaliana*," dated Jan. 25, 1999, 2 pages.
Green, et al., "Binding site requirements for pea nuclear protein factor GT-1 correlate with sequences required for light-dependent transcriptional activation of the rbcS-3A gene," The Embo J. 7:4035-4044 (1988).
Hedden and Phillips, "Gibberellin metabolism: new insights revealed by the genes," Trends Plant Sci. 5(12):523-530 (2000).
Hong, et al., "Promoter sequences from two different *Brassica napus* tapetal oleosin-like genes direct tapetal expression of B-glucuronidase in transgenic *Brassica* plants," Plant Mol. Biol. 34(3):549-555 (1997).
Hwang, et al., "Aleurone- and embryo-specific expression of the β-glucuronidase gene controlled by the barley Chi26 and Ltp1 promoters in transgenic rice," Plant Cell Reports 20:647-654 (2001).
Hyrup, et al., "Peptide Nucleic Acids (PNA): Synthesis, Properties and Potential Applications," Bioorganic & Medicinal Chemistry 4(1):5-23 (1996).
International Preliminary Report on Patentability in Application No. PCT/US2012/068756, issued Aug. 19, 2014, 15 pages.
International Search Report and Written Opinion in Application No. PCT/US2012/068756, mailed Mar. 19, 2013, 24 pages.
Jordano, et al., "A Sunflower Helianthinin Gene Upstream Sequence Ensemble Contains an Enhancer and Sites of Nuclear Protein Interaction," The Plant Cell 1:855-866 (1989).
Kaneko, et al., "Where do gibberellin biosynthesis and gibberellin signaling occur in rice plants?" The Plant Journal 35:104-115 (2003).
Kasuga, et al., "Improving plant drought, salt, and freezing tolerance by gene transfer of a single stress-inducible transcription factor," Nature Biotechnology 17:287-291 (1999).
Keller and Baumgartner, "Vascular-Specific Expression of the Bean GRP 1.8 Gene is Negatively Regulated," The Plant Cell 3(10):1051-1061 (1991).
Lam, et al., "Site-specific mutations alter in vitro factor binding and change promoter expression pattern in transgenic plants," Procedures of the National Academy of Sciences of the United States of America 86:7890-7894 (1989).
Li, et al., "Small dsRNAs induce transcriptional activation in human cells," Procedures of the National Academy of Sciences of the United States of America 103(46):17337-42 (2006).
Lloyd, et al., "Targeted mutagenesis using zinc-finger nucleases In *Arabidopsis*," Procedures of the National Academy of Sciences of the United States of America 102:2232-2237 (2005).
Lu, et al., "A study on the application and residues of plant growth regulators in the fruit sugarcane grown in the sub-suitable region," Journal of Agricultural Science 2(4):254-256 (2010).
Luan, et al., "A Rice cab Gene Promoter Contains Separate cis-Acting Elements That Regulate Expression in Dicot and Monocot Plants," The Plant Cell 4:971-981 (1992).
Lubberstedt, et al., "Promoters from Genes for Plastid Proteins Possess Regions with Different Sensitivities toward Red and Blue Light," Plant Physiol. 104:997-1006 (1994).
Martins, et al., "Effects of gibberellin and ethephon on the anatomy of sugar cane plants," Pesq. Agropec. Bras, Brasilia 35(10):1855-1863 (1999).
Matsuoka, et al., "Tissue-specific light-regulated expression directed by the promoter of a C4 gene, maize pyruvate, orthophosphate dikinase, in a C3 plant, rice," Procedures of the National Academy of Sciences of the United States of America, 90:9586-9590 (1993).
Matzke and Birchler, "RNAi-Mediated Pathways in the Nucleus," Nature Reviews Genetics 6:24-35 (2005).
Mccallum, et al., "Targeted screening for induced mutations," Nature Biotechnology 18:455-457 (2000).
Medberry, et al., "The Commelina Yellow Mottle Virus Promoter Is a Strong Promoter in Vascular and Reproductive Tissues," The Plant Cell 4(2):185-192 (1992).
Meier, et al., "Elicitor-Inducible and Constitutive in Vivo DNA Footprints Indicate Novel cis-Acting Elements in the Promoter of a Parsley Gene Encoding Pathogenesis-Related Protein 1," The Plant Cell 3:309-316 (1991).
Mittal, "Improving the Efficiency of RNA Interference in Mammals," Nature Reviews Genetics 5:355-365 (2004).
Moore and Haber, "Cell cycle and genetic requirements of two pathways of nonhomologous end-joining repair of double-strand breaks in *Saccharomyces cerevisiae*," Mol Cell Biol. 16(5):2164-2173 (1996).
Murase, et al., "Gibberellin-induced DELLA recognition by the gibberellin receptor GID1," Nature 456(7221):459-463 (2008).
Nardini, et al., "Alpha/beta hydrolase fold enzymes: the family keeps growing," Curr. Opin. Struct. Biol. 9(6):732-737 (1999).
"Nature Reviews RNA interference collection," Nature.Com (2005), Retrieved from Internet http://www.nature.com/focus/rnai/index.html on Apr. 12, 2012, 2 pages.
Oikawa, et al., "A role of OsGA200x1, encoding an isoform of gibberellin 20-oxidase, for regulation of plant stature in rice," Plant Mol. Biol. 55(5):687-700 (2004).
Ollis, et al., "The alpha/beta hydrolase fold," Protein Eng. 5(3):197-211 (1992).
Perriman, et al., "Effective ribozyme delivery in plant cells," Procedures of the National Academy of Sciences of the United States of America 92(13):6175-6179 (1995).
Pinot and Beisson, "Cytochrome P450 metabolizing fatty acids in plants: characterization and physiological roles," Febs J. 278(2):195-205 (2011).
Pysh, et al., "The GRAS gene family in *Arabidopsis*: sequence characterization and basic expression analysis of the Scarecrow-Like genes," Plant J. 18(1):111-119 (1999).
Refseth, et al., "Hybridization capture of microsatellites directly from genomic DNA," Electrophoresis 18(9):1519-1523 (1997).
Riggs, et al., "Cotyledon Nuclear Proteins Bind to DNA Fragments Harboring Regulatory Elements of Phytohemagglutinin Genes," The Plant Cell 1(6):609-621 (1989).
Rivera, et al., "Genomic evidence for two functionally distinct gene classes," Procedures of the National Academy of Sciences of the United States of America 95:6239-6244 (1998).

(56) References Cited

OTHER PUBLICATIONS

Sheridan, et al., "The macl Gene: Controlling the Commitment to the Meiotic Pathway in Maize," Genetics 142:1009-1020 (1996).
Shibuya, et al., "RNA-directed DNA methylation induces transcriptional activation in plants," Procedures of the National Academy of Sciences of the United States of America 106(5):1660-1665 (2009).
Slocombe, et al., "Temporal and Tissue-Specific Regulation of a *Brassica napus* Stearoyl-Acyl Carrier Protein Desaturase Gene," Plant Physiol. 104(4):167-176 (1994).
Sonnhammer, et al., "Pfam: A Comprehensive Database of Protein Domain Families Based on Seed Alignments," Proteins 28:405-420 (1997).
Sonnhammer, et al., "Pfam: multiple sequence alignments and HMM-profiles of protein domains," Nucl. Acids Res. 26:320-322 (1998).
Stemple, "Tilling—a high-throughput harvest for functional genomics," Nat Rev Genet 5(2):145-50 (2004).
Summerton and Weller, "Morpholino Antisense Oligomers: Design, Preparation, and Properties," Antisense Nucleic Acid Drug Dev. 7:187-195 (1997).
Tovkach, et al., "A toolbox and procedural notes for characterizing novel zinc finger nucleases for genome editing in plant cells," The Plant Journal 57:747-757 (2009).
Townsend, et al., "High-frequency modification of plant genes using engineered zinc-finger nucleases," Nature 459:442-445 (2009).
Truernit, et al., "The promoter of the *Arabidopsis thaliana* SUC2 sucrose-H+ symporter gene directs expression of B-glucuronidase to the phloem: Evidence for phloem loading and unloading by SUC2," Planta 196:564-570 (1995).
Ueguchi-Tanaka, et al., "Rice dwarf mutant d1, which is defective in the subunit of the heterotrimeric G protein, affects gibberellin signal transduction," Proceedings of the National Academy of Sciences of the United States of America 97(21):11638-11643 (2000).
Urao, "Molecular cloning and characterization of a gene that encodes a MYC-related protein in *Arabidopsis*," Plant Mol. Biol. 32(3):571-576 (1996).
Vidal, et al. "The ectopic overexpression of a citrus gibberellin 20-oxidase enhances the non-13-hydroxylation pathway of gibberellin biosynthesis and induces an extremely elongated phenotype in tobacco," Physiologia Plantarum 112(2):251-260 (2001).
Voegele, et al., "Members of the gibberellin receptor gene family GID1 (Gibberellin Insensitive DWARF1) play distinct roles during Lepidium sativum and *Arabidopsis thaliana* seed germination," J. Exp. Botany 62(14):5131-5147 (2011).
Vogel and Jung, "Genetic Modification of Herbaceous Plants for Feed and Fuel," Critical Reviews in Plant Sciences 20(1):15-49 (2001).
Weigel, et al., "Activation Tagging in *Arabidopsis*," Plant Physiology 122:1003-1013 (2000).
Yamamoto, et al., "The Promoter of a Pine Photosynthetic Gene Allows Expression of a B-Glucuronidase Reporter Gene in Transgenic Rice Plants in a Light-Independent but Tissue-Specific Manner," Plant Cell Physiol. 35:773-778 (1994).
Yan, et al., "New Construct Approaches for Efficient Gene Silencing in Plants," Plant Physiol. 141:1508-1518 (2006).
Zhang, et al., "DNA sequences that activate isocitrate lyase gene expression during late embryogenesis and during postgerminative growth," Plant Physiology 110(4):1069-1079 (1996).
Zheng, et al., "SPK1 is an essential S-Phase-Specific gene of *Saccharomyces cerevisiae* that encodes a nuclear serine/threonine/tyrosine kinase," Mol. Cell Biol. 13:5829-5842 (1993).
de Souza et al., 2010, Brazillian Journal of Microbiology 41:850-861.
Sorghum bicolor protein XP_002463483.1, published Jul. 13, 2009.
Keskin et al., 2004, Protein Science 13: 1043-1055.
Guo et al., 2004, Proceedings of the National Academy of Sciences USA 101: 9205-9210.
Thornton et al., 2000, Nature Structural Biology, structural genomic supplement, Nov. 2000: 991-994.
Perez-Flores et al., 2003, Journal of Experimental Botany 54: 2071-2079.
Sorghum bicolor gibberellin 20-oxidase (GA20ox) mRNA, GenBank: AF249881.1, published May 18, 2000.
USPTO: Non-Final Office Action regarding U.S. Appl. No. 16/406,819 mailed Jan. 21, 2020.
GenBank Accession No. XM_015776057, Aug. 7, 2018.
GenBank Accession No. XM_025939797 Jul. 27, 2018.
Response to Non-Final Office Action regarding U.S. Appl. No. 16/406,819, filed Mar. 2, 2020.
USPTO: Final Office Action regarding U.S. Appl. No. 16/406,819 mailed Mar. 12, 2020.
Response to Final Office Action regarding U.S. Appl. No. 16/406,819, filed Apr. 13, 2020.
USPTO: Advisory Action regarding U.S. Appl. No. 16/406,819, filed Apr. 27, 2020.
Supplemental Response to Final Office Action regarding U.S. Appl. No. 16/406,819, filed Jun. 2, 2020.
Notice of Allowance and Fee(s) Due regarding U.S. Appl. No. 16/406,819, dated Jun. 26, 2020.
Paterson et al., The Sorghum bicolor genome and the diversification of grasses, Nature 547:551-556 (2009).
Sorghum bicolorr polypeptide SORBIDRAFT_01g000580, GenBank accession No. XP_002463483, published Jul. 13, 2009.

* cited by examiner

```
SEQ_ID_NO_471   QEQEVVFDAA VLSGQTEIPS QFIWPAEESP GSVA- VEELE   45
SEQ_ID_NO_473   PPPSLVFDAA RLSGLSDIPQ QFLWPADESP TPDA- AEELA   54
SEQ_ID_NO_475   DPPPLVFDAA RLSGLSDIPQ QFIWPADESP TPDS- AEELA   45
SEQ_ID_NO_476   ---QPVFDAA VLSGRADIPS QFIWPEGESP TPDA- AEELH   38
SEQ_ID_NO_477   ---QPVFDAA LLSGQSDIPS QFIWPADESP SPDA- TEELH   38
SEQ_ID_NO_478   ---QPVFDAA VLSGRTDIPS QFIWPEGESP TPDA- TEEMH   38
SEQ_ID_NO_479   ---QPVFDSA VLSGRADIPS QFIWPEGESP TPDA- AEELH   38
SEQ_ID_NO_480   QQRSLVFDAS VLQHETNIPQ QFIWPDNEKP NSKK- SKDLE   62
SEQ_ID_NO_481   RQRSLVFDAS VLQHEGNIPQ QFIWPDHEKP NTQK- SKELE   58
SEQ_ID_NO_482   QKTPLVFDSL LLQHETNIPQ QFIWPDHEKP NLQK- TKELV   57
SEQ_ID_NO_483   EKKTLIFDAS HMKRESNIPT QFIWPDHEKP CAV-- AQQLA   54
SEQ_ID_NO_484   EQKPLVFDAS VLKHQTQIPK QFIWPDDEKP CVN-- APELQ   60
SEQ_ID_NO_485   DKKPLVFDAS KLKRESNIPT QFIWPDDEKP CAV-- AQELP   54
SEQ_ID_NO_487   EQKKLVFDAS VLKFESQIPK EFIWPDDEKP SAN-- APELQ   60
SEQ_ID_NO_488   NQEPLVFDAS VLRHQSNIPK QFIWPDAEKP GDK-- ATELS   60
SEQ_ID_NO_489   EKKPLIFDAS QMKREYNIPT QFVWPDDEKP RAV-- ARELP   58
SEQ_ID_NO_490   DGKSFVFDAQ VLRHQTNIPQ QFIWPDHEKP NTN-- APELQ   65
SEQ_ID_NO_491   VPKPLIFDAS VPQHDPNIPT QFIWPDHEKP AADAD APQLA   49
SEQ_ID_NO_492   HQKQLVFDAS VLRHQTNIPQ QFIWPDEEKP RAN-- APELQ   60
SEQ_ID_NO_493   PQQTLVFDAS ILQHQSNIPS QFVWPDHEKP CLD-- SPQLA   70
SEQ_ID_NO_495   IQTPLIFNPS MLNLQANIPN QFIWPDDEKP SIN-- VLELD   60
```

Figure 1B

```
SEQ_ID_NO_471  VALIDVGAGA -----ERSSV VRQVGEACER HGFFLVVNHG  80
SEQ_ID_NO_473  VPLIDLSG-- -----DAAEV VRQVRRACDL HGFFQVVNHG  87
SEQ_ID_NO_475  VPLIDLSG-- -----DAAEV VRQVRRACDL HGFFQVVGHG  78
SEQ_ID_NO_476  VPLIDIGGML SGDPRATAEV TRLVGEACER HGFFQVVNHG  78
SEQ_ID_NO_477  VPLIDIGGLL SGDRAAAAEV TRLVGDACER HGFFQVVNHG  78
SEQ_ID_NO_478  VPLIDIGGML SGDPRAAAEV TRLVGEACER HGFFQVVNHG  78
SEQ_ID_NO_479  VPLIDIGGML SGDPRAAAEV MRLVGEACER HGFFQVVNHG  78
SEQ_ID_NO_480  VPLIDLGGFL SGRSSSTKEA SKLVGNACQK HGFFLVVNHG  102
SEQ_ID_NO_481  VPLIDLGGFL SGHSCSTKKA SNLVGEACQK HGFFLVVNHG  98
SEQ_ID_NO_482  VPLVDLGGFL SGRPSSAKEA SLVVGDACKK HGFFLVTNHG  97
SEQ_ID_NO_483  VPLIDLRGFL SGDSDAAQQA SKLVGEACRS HGFFLVVNHG  94
SEQ_ID_NO_484  VPLIDLGGFL SDDPVAAKEA SRLVGEACRK HGFFLVVNHG  100
SEQ_ID_NO_485  VSLIDLRGFL SGDPVAAQQA SQLVGDACRS HGFFLVVNHG  94
SEQ_ID_NO_487  VPLIDLGGFL SGDPVATMEA SREISEACQQ HGFFLVVNHG  100
SEQ_ID_NO_488  VPLIDLGGFL SGDPAAAMEA TRLVREACQK HGFFLVVNHG  100
SEQ_ID_NO_489  VPLIDLGGFL SGDPVAAQQA SRLVGEACRN HGFFLVVNHG  98
SEQ_ID_NO_490  VPLVDLGDFL SGNPVAAVEA SRLVGEACKK HGFFLVVNHG  105
SEQ_ID_NO_491  VPLIDLAGFL SGDPAAALQA SRLVGEACKK HGFFLVANHG  89
SEQ_ID_NO_492  VPLIDLRGFL SGDPTAANEA SSLVGKACQK HGFFLVVNHG  100
SEQ_ID_NO_493  IPPIDLGSFL SGDHLAVSKA VELVNEACKK HGFFLVVNHG  110
SEQ_ID_NO_495  VPLIDLQNLL S-DPSSTLDA SRLISEACKK HGFFLVVNHG  99
```

Figure 1C

| Sequence | | | | | |
|---|---|---|---|---|---|
| SEQ_ID_NO_471 | IEAALLEEAH | RCMDAFFTLP | LGEKQRAQRR | AGESCGYASS | 120 |
| SEQ_ID_NO_473 | IDDALLQEAH | RCMDAFFTLP | MSDKQRAQRR | QGDSCGYASS | 127 |
| SEQ_ID_NO_475 | IDAALTAEAH | RCMDAFFTLP | LPDKQRAQRR | QGDSCGYASS | 118 |
| SEQ_ID_NO_476 | IDAELLADAH | RCVDAFFTMP | LPEKQRALRR | PGESCGYASS | 118 |
| SEQ_ID_NO_477 | IDAELLADAH | RCVDAFFTMS | LQGKQRALRR | PGESCGYASS | 118 |
| SEQ_ID_NO_478 | IDAQLLADAH | RCVDAFFTMP | LPEKQRALRR | PGESCGYASS | 118 |
| SEQ_ID_NO_479 | IDAELLADAH | RCVDAFFTMP | LPEKQRALRR | PGESCGYASS | 118 |
| SEQ_ID_NO_480 | VDANLISDAQ | TYMDLFFELP | LSEKQRAQRK | AGESCGYASS | 142 |
| SEQ_ID_NO_481 | VDENLISDAH | QYMDLFFELP | LSEKQRAQRK | AGESCGYASS | 138 |
| SEQ_ID_NO_482 | VDASLIADAH | RYMDLFFELP | LSDKQRAQRK | LGESCGYASS | 137 |
| SEQ_ID_NO_483 | VEANLISNAH | RYMDTFFDLP | LSEKQKAQRK | IGEHCGYASS | 134 |
| SEQ_ID_NO_484 | VDSSLIADAH | RYMDHFFELP | LNEKQRARRK | LGEHCGYASS | 140 |
| SEQ_ID_NO_485 | VDANLISNAH | RYMDTFFDMP | LSEKQKAQRK | IGEHCGYASS | 134 |
| SEQ_ID_NO_487 | VDAKLLADAH | KYMDNFFLLP | LRQKQRAQRK | LGEHCGYASS | 140 |
| SEQ_ID_NO_488 | VDDKLIYKAH | QYMDSFFGLP | LAKKQRAQRK | LGEHCGYASS | 140 |
| SEQ_ID_NO_489 | VNANLISNAH | RYMDMFFDLP | LSEKQKAQRK | LEEHCGYASS | 138 |
| SEQ_ID_NO_490 | VDKTLIAHAH | NYVDTFFKLP | LSEKQKAQRK | IGESCGYASS | 145 |
| SEQ_ID_NO_491 | VDATLISHAH | RYMDHFFQLP | LSDKQKAERK | AGEHCGYASS | 129 |
| SEQ_ID_NO_492 | VDDKLIAHAH | QYIDYFFELP | MSAKQRAQRK | VGEHCGYASS | 140 |
| SEQ_ID_NO_493 | VDSRLIAKAH | EYMEMFFSMP | MMVKQRAQRR | LGDHCGYASS | 150 |
| SEQ_ID_NO_495 | LSEELISDAH | EYTSRFFDMP | LSEKQRVLRK | SGESVGYASS | 139 |

Figure 1D

```
SEQ_ID_NO_471   FTGRFASKLP  WKETLSFRYS  SAGDEE---G  EEGVGEYLVR  157
SEQ_ID_NO_473   FTGRFASKLP  WKETLSFRYS  D--DQG---D  GDVVVDYFVD  162
SEQ_ID_NO_475   FTGRFASKLP  WKETLSFRYT  D--DDDGDKS  KDVVASYFVD  156
SEQ_ID_NO_476   FTGRFASKLP  WKETLSFRSC  P--S-----D  PALVVDYIVA  151
SEQ_ID_NO_477   FTGRFASKLP  WKETLSFRSC  P--S-----E  PDLVVEYIVA  151
SEQ_ID_NO_478   FTGRFASKLP  WKETLSFRSC  P--S-----D  PALVVDYIVA  151
SEQ_ID_NO_479   FTGRFASKLP  WKETLSFRSC  P--S-----D  PALVVDYIVA  151
SEQ_ID_NO_480   FTGRFSSKLP  WKETLSFRFS  A--EKN---S  ADIVKDYFEN  177
SEQ_ID_NO_481   FTGRFSSKLP  WKETLSFQYS  A--DEN---S  SDIVKDYFKD  173
SEQ_ID_NO_482   FTGRFTSKLP  WKETLSFQFS  G--EKS---S  ANGVKDYFEN  172
SEQ_ID_NO_483   FTGRFSSKLP  WKETLSFRYS  A--EEN---S  SHIVEEYFQR  169
SEQ_ID_NO_484   FTGRFSSKLP  WKETLSFRYS  A--EKS--LS  NNIVEDYLLN  176
SEQ_ID_NO_485   FTGRFSSKLP  WKETLSFRYS  A--EED---S  SHIVEEYFQR  169
SEQ_ID_NO_487   FTGRFSTKLP  WKETLSFRYS  A--ENN---S  SKMVEDYLVN  175
SEQ_ID_NO_488   FIGRFSSKLP  WKETLSFSYS  A--EKK---S  SNAVQEYFLN  175
SEQ_ID_NO_489   FTGRFSSKLP  WKETLSFRYS  A--EED---S  SHLVEEYFQN  173
SEQ_ID_NO_490   FTGRFSSKLP  WKETLSFRYK  A--EES---S  SKHIEEYFHN  180
SEQ_ID_NO_491   FTGRFSSKLP  WKEILSFSFS  A--DKT---S  HDIVVDYFQT  164
SEQ_ID_NO_492   FTGRFSFKLP  WKETLSFRSS  A--QPD---S  SNIVQDYLCN  175
SEQ_ID_NO_493   FTGRFSSKLP  WKETLSFRYC  D--DNN---F  SNLVQEYFSN  185
SEQ_ID_NO_495   FTGRFSTKLP  WKETLSFRFC  D--DMS---R  SKSVQDYFCD  174
```

Figure 1E

```
SEQ_ID_NO_471    KLGAEHGRRL GEVYSRYCHE MSRLSLELME VLGESLGIVG    197
SEQ_ID_NO_473    KLGDAY-RHH GEVYGRYCSE MSRLSLELME VLGESLGV--    199
SEQ_ID_NO_475    KLGEGY-RHH GEVYGRYCSE MSRLSLELME VLGESLGV--    193
SEQ_ID_NO_476    TLGEDH-RRL GEVYARYCSE MSRLSLEIME VLGESLGV--    188
SEQ_ID_NO_477    TLGEDH-RRL GEAYARYCSE MSRLSLEIME VLGESLGV--    188
SEQ_ID_NO_478    TLGEDH-RRL GEVYARYCSE MSRLSLEIME VLGESLGV--    188
SEQ_ID_NO_479    TLGEDH-RRL GEVYARYCSE MSRLSLEIME VLGESLGV--    188
SEQ_ID_NO_480    TMGEEF-VRL GKVYQEYCNA MSRLSLGIME LLGLSLGV--    214
SEQ_ID_NO_481    KMGEEF-IRL GNVYQDYCNA MNRLSLGIME LLGMSLGV--    210
SEQ_ID_NO_482    TLGKEF-TRL GKVYQEYCNA MSRLSLGIME LLGMSLGV--    209
SEQ_ID_NO_483    TLGESF-NHL GNVYQEYCNS MNTLSLGIME LLGMSLGV--    206
SEQ_ID_NO_484    TMGDEF-KQF GRVYQDYCES MSRLSLGIME LLAISLGV--    213
SEQ_ID_NO_485    TLGESF-SHL GNIYQEYCNS MSTLSLGIME LLGMSLGI--    206
SEQ_ID_NO_487    KMGNEL-RQL GRVYQDYCEA MSKLSLGIME LLAISLGV--    212
SEQ_ID_NO_488    KMGEDF-SEF GQVYQDYCEA MSTLSLVIME LLGMSLGI--    212
SEQ_ID_NO_489    TMGESF-SHL GNVYQEYCNS MSTLSLGIME LLGMSLGV--    210
SEQ_ID_NO_490    RMGEDF-AEF GTVYQDYCEA MSTLSLGIME LLGMSLGV--    217
SEQ_ID_NO_491    TLGQDF-AHI GKIYQEYCNA MSNLSLGIME LLGMSLGV--    201
SEQ_ID_NO_492    TMGEDF-KPF GKVYQDYCDA MSTLSLGIME LLGMSLGV--    212
SEQ_ID_NO_493    VMGEEF-RQF GKVYQEYCEA MSTLSLRIME LLGLTLGV--    222
SEQ_ID_NO_495    ALGHGF-QPF GKVYQEYCEA MSSLSLKLME LLGLSLGV--    211
```

Figure 1F

```
SEQ_ID_NO_471    DRRHYFRRFF QRNDSIMRLN YYPACQRPLD TLGTGPHCDP   237
SEQ_ID_NO_473    -GRRHFRRFF QGNDSIMRLN YYPPCQRPYD TLGTGPHCDP   238
SEQ_ID_NO_475    -GRRHFRRFF QGNDSIMRLN YYPPCQRPYD TLGTGPHCDP   232
SEQ_ID_NO_476    -GRAHYRRFF EGNDSIMRLN YYPPCQRPME TLGTGPHCDP   227
SEQ_ID_NO_477    -GRAHYRRFF EGNESIMRLN YYPPCQRPNE TLGTGPHCDP   227
SEQ_ID_NO_478    -GRAHYRRFF EGNESIMRLN YYPPCQRPLE TLGTGPHCDP   227
SEQ_ID_NO_479    -GRAHYRRFF EGNDSIMRLN YYPPCQRPYE TLGTGPHCDP   227
SEQ_ID_NO_480    -NRSHFKEFF EENNSIMRLN YYPRCQKPEL TLGTGPHCDP   253
SEQ_ID_NO_481    -SRAHFKEFF QENNSIMRLN YYPPCQKPDL TLGTGPHCDP   249
SEQ_ID_NO_482    -HRAHFKEFF EENDSIMRLN YYPRCQKPDQ TLGTGPHCDP   248
SEQ_ID_NO_483    -EKSHFKEFF EENDSIMRLN YYPPCQKPEL TLGTGPHCDP   245
SEQ_ID_NO_484    -GRAHFKEFF EENDSIMRLN YYPPCQKPEL TLGTGPHCDP   252
SEQ_ID_NO_485    -ERSHFKEFF EENESIMRLN YYPPCQKPEL TLGTGPHCDP   245
SEQ_ID_NO_487    -GRAHFREFF DKNDSIMRLN YYPPCQKPDL TLGTGPHCDP   251
SEQ_ID_NO_488    -GGAHFREFF EENDSIMRLN YYPPCLKPDL TLGTGPHCDP   251
SEQ_ID_NO_489    -GREHFKEFF EENESIMRLN YYPPCQKPDL TLGTGPHCDP   249
SEQ_ID_NO_490    -SREHFREFF NENDSIMRLN YYPPCQKPDL TLGTGPHCDP   256
SEQ_ID_NO_491    -SEKHFREFY QENESIMRLN YYPPCRKPEL TLGTGPHCDP   240
SEQ_ID_NO_492    -SQGHYREFF EENESIMRLN YYPPCQKPDL TLGTGPHCDP   251
SEQ_ID_NO_493    -GRAYFREFF EGNDSIMRLN YYPPCQKPDL TLGTGPHCDP   261
SEQ_ID_NO_495    -KRDYFREFF EENDSIMRLN YYPPCIKPDL TLGTGPHCDP   250
```

Figure 1G

```
SEQ_ID_NO_471  TSLTILHQDH VGGLEVWA-- ---- EGRWRA IRPRPGALVV 271
SEQ_ID_NO_473  TSLTILHQDD VGGLQVFDAA TGPG TGRWRS IRPHPGAFVV 278
SEQ_ID_NO_475  TSLTILHQDD VGGLQVFDAA ---- TLAWRS IRPRPGAFVV 268
SEQ_ID_NO_476  TSLTILHQDN VGGLQVHT-- ---- EGRWRS IRPRADAFVV 261
SEQ_ID_NO_477  TSLTILHQDD VGGLQVHA-- ---- DGRWLS IRPRADAFVV 261
SEQ_ID_NO_478  TSLTILHQDD VGGLQVHT-- ---- DGRWRS IRPRADAFVV 261
SEQ_ID_NO_479  TSLTILHQDD VGGLQVHT-- ---- DGRWRS IRPRADAFVV 261
SEQ_ID_NO_480  TSLTILHQDN VGGLEVFV-- ---- DNEWRS ITPNSNAFVV 287
SEQ_ID_NO_481  TSLTILHQDN VGGLEVFV-- ---- DNEWRS IAPNSQAFVV 283
SEQ_ID_NO_482  TSLTILHQDS VGGLEVFI-- ---- DNEWRS IAPNSNAFVV 282
SEQ_ID_NO_483  TSLTILHQDC VGGLQVFV-- ---- DDEWRS ITPTFNAFVV 279
SEQ_ID_NO_484  TSLTILHQDQ VGGLQVFV-- ---- DNEWRS ISPNFEAFVV 286
SEQ_ID_NO_485  TSLTILHQDC VGGLQVFV-- ---- DNEWRS ISPNFNAFVV 279
SEQ_ID_NO_487  TSLTILHQDR VGGLQVFV-- ---- DNEWHS ISPNFEAFVV 285
SEQ_ID_NO_488  TSLTILHQDQ VGGLQVFV-- ---- DDKWWS ISPNFDAFVV 285
SEQ_ID_NO_489  TSLTILHQDS VGGLQVFV-- ---- DNEWRS ISPNFNAFVV 283
SEQ_ID_NO_490  TSLTILHQDQ VGGLQVFV-- ---- DNEWRS INPNFDAFVV 290
SEQ_ID_NO_491  TSLTILHQDT VGGLQVFV-- ---- DNQWRS IPPNFNAFVV 274
SEQ_ID_NO_492  TSLTILHQDQ VGGLQVFV-- ---- DEEWRS ITPNFNAFVV 285
SEQ_ID_NO_493  TSLTILHQDE VGGLQVFV-- ---- DEKWHS VHPDPQAFVV 295
SEQ_ID_NO_495  TSLTILHQDH VNGLQVFV-- ---- ENQWRS LRPNPKAFVV 284
```

Figure 1H

```
SEQ_ID_NO_471   NVGDTFMALS  NARYRSCLHR  AVVNSTAPRR  SLAFFLCPEM  311
SEQ_ID_NO_473   NI GDTFMALS NGRYRSCLHR  AVVNSRVPRR  SLAFFLCPEM  318
SEQ_ID_NO_475   NI GDTFMALS NGRYRSCLHR  AVVNSRVARR  SLAFFLCPEM  308
SEQ_ID_NO_476   NI GDTFMALS NGRYKSCLHR  AVVNSKVPRK  SLAFFLCPEM  301
SEQ_ID_NO_477   NI GDTFMALS NGRYKSCLHR  AVVNSRVPRK  SLAFFLCPEM  301
SEQ_ID_NO_478   NI GDTFMALS NGRYKSCLHR  AVVNSRVPRK  SLAFFLCPEM  301
SEQ_ID_NO_479   NI GDTFMALS NGRYKSCLHR  AVVNSRVPRK  SLAFFLCPEM  301
SEQ_ID_NO_480   NI GDTFMALS NGRYKSCLHR  AVVNNKTPRK  SLAFFLCPKK  327
SEQ_ID_NO_481   NI GDTFMALS NGRYKSCLHR  AVVNSKTPRK  SLAFFLCPKK  323
SEQ_ID_NO_482   NI GDTFMALS NGRYKSCLHR  AVVNNRLHRK  SLAFFLCPKK  322
SEQ_ID_NO_483   NI GDTFMALS NGRYKSCLHR  AVVNNKTPRK  SLAFFLCPNK  319
SEQ_ID_NO_484   NI GDTFMALS NGRYKSCLHR  AVVNSQTTRK  SLAFFLCPKN  326
SEQ_ID_NO_485   NI GDTFMALS NGRYKSCLHR  AVVNNKTPRK  SLAFFLCPNK  319
SEQ_ID_NO_487   NI GDTFMALS NGRYKSCLHQ  AVVNSHKPRK  SLAFFLCPEG  325
SEQ_ID_NO_488   NI GDTFMALS NGRYKSCLHR  AVVNSQTPRK  SLAFFLCPEK  325
SEQ_ID_NO_489   NI GDTFMALS NGRYKSCLHR  AVVNNKTPRK  SLAFFLCPKK  323
SEQ_ID_NO_490   NI GDTFMALS NGI YRSCLHR AVVNSQTPRK  SLAFFLCPKN  330
SEQ_ID_NO_491   NI GETLMALS NGKYKSCLHR  AVVNSKSPRK  SLAFFLCPKK  314
SEQ_ID_NO_492   NI GDTFMALS NGRYKSCLHR  AVVNSKTPRK  SLAFFLCPKN  325
SEQ_ID_NO_493   NI GDTFMALS NGI FKSCLHR AVVNNRTVRK  SLAFFLCPNM  335
SEQ_ID_NO_495   NI GDTFMALS NDRYKSCLHR  AVVNSESERK  SLAFFLCPKK  324
```

Figure 1I

```
SEQ_ID_NO_471   DTVVRPPEEL VDD- HHPRVY PDFTWRALLD FTQRHYRADM   350
SEQ_ID_NO_473   DKVVRPPAEL VDD- ANPRAY PDFTWRTLLD FTMRHYRSDM   357
SEQ_ID_NO_475   DKVVRPPKEL VDD- ANPRAY PDFTWRTLLD FTMRHYRSDM   347
SEQ_ID_NO_476   DKVVAPPGTL VDA- ANPRAY PDFTWRSLLD FTQKHYRADM   340
SEQ_ID_NO_477   DKVVAPPETL VDE- ANPRAY PDFTWRALLD FTQKHYRADM   340
SEQ_ID_NO_478   DKVVAPPGTL VDA- ANPRAY PDFTWRSLLD FTQKHYRADM   340
SEQ_ID_NO_479   DKVVAPPGTL VDA- ANPRAY PDFTWRSLLD FTQKHYRADM   340
SEQ_ID_NO_480   DKVVSPPKEL VDE- NNPRVY PDFTWATFLE FTQKHYRADM   366
SEQ_ID_NO_481   DKVVSPPEKL VDQ- KNPRIY PDFTWSTFLE FTQKHYRADM   362
SEQ_ID_NO_482   DKVVSPPDEL VDE- NNPRIY PDFTWSTFLE FTQKHYRADM   361
SEQ_ID_NO_483   DKVVSPPNEL VDS- NNPRIY PDFTWPTLLE FTQKHYRADM   358
SEQ_ID_NO_484   DKVVSPPSEL VDTY SSPRIY PDFTWPMLLE FTQKHYRADM   366
SEQ_ID_NO_485   DKVVSPPSKL VDS- NNPRMY PDFTWPTLHE FTQKHYRADM   358
SEQ_ID_NO_487   DKVVTPPAEL VSQ- NSPRVY PDFTWPMLLE FTQKHYRADM   364
SEQ_ID_NO_488   DKVVRPPTEL VDT- NSPRIY PDFTWSNLLE FTQKHYRADM   364
SEQ_ID_NO_489   DKVVSPPTEL VDT- NNPRIY PDFTWPTLLE FTQKHYRADM   362
SEQ_ID_NO_490   DKMVTPPHEL VDT- CNPRIY PDFTWPMLLE FTQKHYRADM   369
SEQ_ID_NO_491   DKVVRPPNEL VDS- SNPRVY PDFTWPTLLE FTQKHYRADM   353
SEQ_ID_NO_492   DKVVSPPSEL VDS- LCPRVY PDFTWPMLLE FTQKHYRADV   364
SEQ_ID_NO_493   EKVVKPPKNL VDS- NNPRLY PDFTWPALLE FTQKYYRADM   374
SEQ_ID_NO_495   DRVVTPPREL LDS- ITSRRY PDFTWSMFLE FTQKHYRADM   363
```

Figure 1J

SEQ_ID_NO_471
SEQ_ID_NO_473
SEQ_ID_NO_475
SEQ_ID_NO_476
SEQ_ID_NO_477
SEQ_ID_NO_478
SEQ_ID_NO_479
SEQ_ID_NO_480
SEQ_ID_NO_481
SEQ_ID_NO_482
SEQ_ID_NO_483
SEQ_ID_NO_484
SEQ_ID_NO_485
SEQ_ID_NO_487
SEQ_ID_NO_488
SEQ_ID_NO_489
SEQ_ID_NO_490
SEQ_ID_NO_491
SEQ_ID_NO_492
SEQ_ID_NO_493
SEQ_ID_NO_495

| | | | | | |
|---|---|---|---|---|---|
| SEQ_ID_NO_99 | MAGSDEVNRN | ECKTVVPLHT | WLISNFKLS | YNILRRADGT | 40 |
| SEQ_ID_NO_101 | MAGSDEVNRN | ECKTAVPIHT | WLISNFKLA | YNMLRRADGT | 40 |
| SEQ_ID_NO_103 | MAGSDEVNRN | ECKGAVPIHT | WLISNFKLA | YNMLRRADGT | 40 |
| SEQ_ID_NO_104 | MAGSDEVNRN | ECKTVVPLHT | WLISNFKVS | YHMLRRPDGT | 40 |
| SEQ_ID_NO_105 | MAGSDEVNRN | ECKGAVPIHT | WLISNFKLA | YNMLRRADGT | 40 |
| SEQ_ID_NO_106 | MAGSDEVNRN | ECKTVVPLHT | WLISNFKVS | YHMLRRPDGT | 40 |
| SEQ_ID_NO_107 | MAGSDEVNRN | ECKGAVPIHT | WLISNFKLA | YNMLRRADGT | 40 |
| SEQ_ID_NO_108 | MARSNEVNLN | ECKMVVPLNT | WLISNFKLA | YNLLRRPDGT | 40 |
| SEQ_ID_NO_110 | MAGSNGVNLN | ESKRVVPLNT | WLISNFKLA | YNLLRRPDGT | 40 |
| SEQ_ID_NO_111 | MAGSNEVNLN | ESKMVVPLNT | WLISNFKLA | YNLLRRPDGT | 40 |
| SEQ_ID_NO_112 | MAGSDEVNHN | ESKRVVPLNT | W LISNFKLA | YNLLRRPDGT | 40 |
| SEQ_ID_NO_113 | MAGGNEVNLN | ECKRI VPLNT | WLISNFKLA | YTLLRRPDGS | 40 |
| SEQ_ID_NO_114 | MAGSNEVNLN | ESKRVVPLNT | WLISNFKLA | YTILRRSDGT | 40 |
| SEQ_ID_NO_115 | MAGSNEI NVN | ESKKVVPLNT | W LISNFKLA | YNMLRRPDGT | 40 |

| | | | | | |
|---|---|---|---|---|---|
| SEQ_ID_NO_99 | FERDLGEYLD | RRVPANARPL | EGVSSFDHII | DQSVGLEVRI | 80 |
| SEQ_ID_NO_101 | FDRDLAEYLD | RRVPPDARAQ | EGVSSFDHVI | DPSVGLEVRI | 80 |
| SEQ_ID_NO_103 | FDRDLAEFLD | RRVPPDARAQ | EGVSSFDHVI | DTSTGLEVRI | 80 |
| SEQ_ID_NO_104 | FERDLAEYMD | RRVPANPKPV | EGVSSFDHVI | DHSVGLEARI | 80 |
| SEQ_ID_NO_105 | FDRDLAEFLD | RRVPPDARAQ | EGVSSFDHVI | DTSTGLEVRI | 80 |
| SEQ_ID_NO_106 | FERDLAEYMD | RRVPANPRPV | EGVSSFDHFI | DLSVGLEARI | 80 |
| SEQ_ID_NO_107 | FDRDLAEFLD | RRVPPDARAQ | EGVSSSDHVI | DTSTGLEVRI | 80 |
| SEQ_ID_NO_108 | FNRHLAEFLD | RKVPANANPV | DGVFSFDVLI | DRGTSLLSRI | 80 |
| SEQ_ID_NO_110 | FNRHLAEFLD | RKVPANANPV | DGVFSFDVII | DRGTSLLSRI | 80 |
| SEQ_ID_NO_111 | FNRHLAEFLD | RKVPPNANPV | DGVFSFDVVI | DRGTSLLSRI | 80 |
| SEQ_ID_NO_112 | FERELAEFLE | RKAPANSFPV | DGVFSFDL-V | DKTTGLLNRV | 79 |
| SEQ_ID_NO_113 | FNRDLAEFLD | RKVPANSFPV | DGVFSFDH-V | DTSTSLLTRI | 79 |
| SEQ_ID_NO_114 | FNRELAEYLE | RKVPANVNPV | DGVFSFDN-V | DRASGLLNRV | 79 |
| SEQ_ID_NO_115 | FNRDLAEFLE | RKVPPNA PV | DGVFSFDV-V | DSSTSLLNRI | 79 |

Figure 2A

```
SEQ_ID_NO_99    YRAAAEGDA- -EEGAAAVTR PILEFLTDAP AAEPFPVIIF  118
SEQ_ID_NO_101   YRAAANNAAG AGAGAAAVTL PILDFLTGAP SPDPFPVILF  120
SEQ_ID_NO_103   YRAAAAAAN- NNGGAAAVTL PILDFLAGAP SPDPFPVILF  119
SEQ_ID_NO_104   YRAVAGNAA- AAEGAAALTL PILEFLSGAP SPDPLPVIIF  119
SEQ_ID_NO_105   YRGAAAANN- GAAGAGAVTL PILDFLAGAP SPDPFPVILF  119
SEQ_ID_NO_106   YRAVAGNAAG AAEGAAALTL PILEFLGGAP SPDPLPVIIF  120
SEQ_ID_NO_107   YRAAANNGG- AGAGA----A AVLDFLGGGP SPDPFPVILF  115
SEQ_ID_NO_108   YRPTTAEEP- -RLNIAELEK P-------V- MAAVVPVIIF  110
SEQ_ID_NO_110   YRRADAQES- -QPNIVDLEK P-------V- NSEVVPVIIF  110
SEQ_ID_NO_111   YRPAEGEQL- -QPNIAELEK P-------V- TSDVVPVILF  110
SEQ_ID_NO_112   YQPAPENEA- -QWGIIELEK P-------LS TTEIVPVILF  110
SEQ_ID_NO_113   YLPAPLDPS- -RHGSVDLTE P-------LS TTDIVPVLVF  110
SEQ_ID_NO_114   YQPAPDNEA- -RWGIIDLEK P-------LS KSKVVPVILF  110
SEQ_ID_NO_115   YRPSPETEAN SQFGIDDLQK P-------LS TTEIVPVILF  112

SEQ_ID_NO_99    FHGGSFVHSS ASSTIYDSLC RRFVKLSKGV VVSVNYRRAP  158
SEQ_ID_NO_101   FHGGSFAHSS SSTAIYDNLC RRFVKLSKGV VLSVNYRRAP  160
SEQ_ID_NO_103   FHGGSFAHSS SGTAIYDNLC RRFVKLSKGV VVSVNYRRAP  159
SEQ_ID_NO_104   FHGGSFAHSA SSTTIYDNLC RQLVKLSKGV VVSVNYRRAP  159
SEQ_ID_NO_105   FHGGSFAHSS SGTAIYDNLC RRFVKLSKGV VVSVNYRRAP  159
SEQ_ID_NO_106   FHGGSFAHSA SSTTIYDNLC RQLVKLSKGV VVSVNYRRAP  160
SEQ_ID_NO_107   FHGGSFAHSS SGTAIYDNLC RRFVKLSKGV VVSVNYRRAP  155
SEQ_ID_NO_108   FHGGSFAHSS ANSAIYDTLC RRLVSLCKAV VVSVNYRRAP  150
SEQ_ID_NO_110   FHGGSFAHSS SNSAIYDTLC RRLVGLCKAV VVSVNYRRAP  150
SEQ_ID_NO_111   FHGGSFAHSS ANSAIYDTLC RRLVGLCRAV VVSVNYRRAP  150
SEQ_ID_NO_112   FHGGSFTHSS ANSAIYDYFC RRLVGNCKAV VVSVNYRRSP  150
SEQ_ID_NO_113   FHGGSFTHSS ANSAIYDTFC RRLVTICGVV VVSVDYRRSP  150
SEQ_ID_NO_114   FHGGSFAHSS ANSAIYDTFC RRIVSVCKAV VVSVNYRRSP  150
SEQ_ID_NO_115   FHGGSFTHSS ANSAIYDTFC RRLVSICKAV VVSVNYRRSP  152
```

Figure 2B

```
SEQ_ID_NO_99    EHRYPCAYDD GWTALKWWMS QPFMRSGG-- DAQARVFLSG 196
SEQ_ID_NO_101   EHRYPCAYDD GWAALKWAMS QPFLRSGE-- GAQPRVFLSG 198
SEQ_ID_NO_103   EHRYPCAYDD GWTALKWAMS QPFLRSGRGG DARPRVFLSG 199
SEQ_ID_NO_104   EHRYPCAYDD GWTALKWAQA QPFLRSGE-- DAQPRVFLAG 197
SEQ_ID_NO_105   EHRYPCAYED GWTALKWAMS QPFLRSGA-- DARPRVFLSG 197
SEQ_ID_NO_106   EHRYPCAYDD GWAALKWAQA QPFLRSGS-- DARLRVFLAG 198
SEQ_ID_NO_107   EHRYPCAYDD GWAALKWATS QPFLRSGG-- DGRPRVFLSG 193
SEQ_ID_NO_108   ENRYPCAYDD GWTALKWWNS RPWLQSQK-- DSKVHIYLAG 188
SEQ_ID_NO_110   ENRYPCAYDD GWTALKWWNS RTWLQSKK-- DSKVHIYLAG 188
SEQ_ID_NO_111   ENRYPCAYDD GWTALKWWNS RTWLESKK-- DAKVHMYLAG 188
SEQ_ID_NO_112   EHRYPCAYDD GWAALKWWKS RSWLQSGK-- DSKVHVYLAG 188
SEQ_ID_NO_113   EHRYPCAYDD GWNALKWWKS RVWLQSGK-- DSNVYVYLAG 188
SEQ_ID_NO_114   EFRYPCAYED GWTALKWWKS KKWLQSGK-- DSKVHVYLAG 188
SEQ_ID_NO_115   ENRYPSAYDD GWAALKWWHS RPWLHSGK-- DSKAYVYLAG 190

SEQ_ID_NO_99    DSSGGNIAHH VAVRAADEGV KVCGNILLNA MFGGTERTES 236
SEQ_ID_NO_101   DSSGGNIAHH VAVRAADAGI RICGNILLNA MFGGTERTDS 238
SEQ_ID_NO_103   DSSGGNIAHH VAVRAADAGI NICGNILLNA MFGGTERTES 239
SEQ_ID_NO_104   DSSGGNIAHH VAVRAAEEGI KIHGNILLNA MFGGKERTES 237
SEQ_ID_NO_105   DSSGGNIAHH VAVRAADAGI SICGNILLNA MFGGTERTES 237
SEQ_ID_NO_106   DSSGGNIAHH VAVRAAEEGI KIHGNILLNA MFGGVERTES 238
SEQ_ID_NO_107   DSSGGNIAHH VAVRAADAGI NICGNILLNA MFGGTERTES 233
SEQ_ID_NO_108   DSSGGNIAHH VALRAIESGI DILGSILLNP MFGGQERTES 228
SEQ_ID_NO_110   DSSGGNIVHH VALRAVESGI DVLGNILLNP MFGGQERTES 228
SEQ_ID_NO_111   DSSGGNIVHH VALRALESGI EVLGNILLNP MFGGQERTES 228
SEQ_ID_NO_112   DSSGGNITHH VAVRAAESGI EVLGNILLHP MFGGQERTES 228
SEQ_ID_NO_113   DSSGGNIAHN VAVRATNEGV KVLGNILLHP MFGGLERTQS 228
SEQ_ID_NO_114   DSSGGNIAHH VAARAAEEDI EVLGNILLHP MFGGEKRTES 228
SEQ_ID_NO_115   DSSGGTLAHH VAHRAAESGV EVLGNILLHP MFGGQERTES 230
```

Figure 2C

| | | | | | |
|---|---|---|---|---|---|
| SEQ_ID_NO_99 | ERRLDGKYFV | TLQDRDWYWK | AYLPEDADRD | HPACNPFGPN | 276 |
| SEQ_ID_NO_101 | ERRLDGKYFV | TLQDRDWYWK | AYLPEDADRD | HPACNPFGPN | 278 |
| SEQ_ID_NO_103 | ERRLDGKYFV | TLQDRDWYWK | AYLPEDADRD | HPACNPFGPN | 279 |
| SEQ_ID_NO_104 | ERRLDGKYFV | TMQDRDWYWK | AYLPEDADRD | HPACNPFGPN | 277 |
| SEQ_ID_NO_105 | ERRLDGKYFV | TLQDRDWYWK | AYLPEDTDRD | HPACNPFGPN | 277 |
| SEQ_ID_NO_106 | ERRLDGKYFV | TLQDRDWYWK | AYLPEDADRD | HPACNPFGPN | 278 |
| SEQ_ID_NO_107 | ERRLDGKYFV | TLQDRDWYWK | AYLPEDADRD | HPACNPFGPN | 273 |
| SEQ_ID_NO_108 | EKRLDGKYFV | TLRDRDWYWR | AYLPEGEDRD | HPACNPFGPN | 268 |
| SEQ_ID_NO_110 | EKRLDGKYFV | TLQDRDWYWR | AFLPEREDRD | HPACNPFGPK | 268 |
| SEQ_ID_NO_111 | EKRLDGKYFV | TVQDRDWYWR | AFLPEEADRD | HPACNPFGPK | 268 |
| SEQ_ID_NO_112 | EKRLDGKYFV | TIQDRDWYWR | AFLPEGEDRD | HPACNPFGPR | 268 |
| SEQ_ID_NO_113 | EKRLDGKYFV | TIHDRDWYWR | AYLPEGEDRD | HPACNPFGPR | 268 |
| SEQ_ID_NO_114 | EKKLDGKYFV | TIQDRDWYWK | AYLPEGEDRD | HPACNIFGPK | 268 |
| SEQ_ID_NO_115 | EKKLDGKYFV | TIQDRDWYWR | AYLPEGEDRD | HPACNPFGPR | 270 |

| | | | | | |
|---|---|---|---|---|---|
| SEQ_ID_NO_99 | GRRLGGLPFA | KSLIIVSGLD | LTCDRQLAYA | DALREDGHHV | 316 |
| SEQ_ID_NO_101 | GRRLRGLPFT | KSLIIVSGLD | LTCDRQLAYA | EGLREDGHHV | 318 |
| SEQ_ID_NO_103 | GRRLRGLPFT | KSLIIVSGLD | LTCDRQLAYA | EGLQEDGHHA | 319 |
| SEQ_ID_NO_104 | GRRLKGLPFA | KSLIIVSGLD | LTCDRQLGYA | EGLREDGHHV | 317 |
| SEQ_ID_NO_105 | GRRLRGLPFT | KSLIIVSGLD | LTCDRQLAYA | EGLQEDGHHV | 317 |
| SEQ_ID_NO_106 | GRRLRGLPFA | KSLIIVSGLD | LTCDRQLGYA | EGLREDGHDV | 318 |
| SEQ_ID_NO_107 | GRRLRGLPFP | KSLIIVSGLD | LTCDRQLAYA | EGLQQDGHHV | 313 |
| SEQ_ID_NO_108 | GRSLEGIKFP | KSLVVVAGLD | LIQDWQLAYV | EGLKKAGQEV | 308 |
| SEQ_ID_NO_110 | GKSLEGIKFP | KSLVVVAGLD | LVHDRQITYA | EGLKKAGQDV | 308 |
| SEQ_ID_NO_111 | GRSLEGMKFP | KSLVVVAGLD | LIQDWQLAYV | EGLKKAGQVV | 308 |
| SEQ_ID_NO_112 | GKSLEGLNFP | KSLVVVAGFD | LVQDWQLAYV | EGLKKAGQDV | 308 |
| SEQ_ID_NO_113 | GQSLEGVNFP | KSLVVVAGLD | LVQDWQLAYV | DGLKRTGHHV | 308 |
| SEQ_ID_NO_114 | AKSLEGINFP | KSLVVVAGLD | LMQDWQLAYV | QGLKNSGHDV | 308 |
| SEQ_ID_NO_115 | GVSLEGLSFP | KSLVVVAGLD | LVQDWQLAYV | EGLKNAGQEV | 310 |

Figure 2D

```
SEQ_ID_NO_188    MKREYQEAGG SSGGG----- --SS---ADM G-SCKDKVMA   29
SEQ_ID_NO_221    MKREYQEAGG SSGGG----- --SS---ADM G-SCKDKVMA   29
SEQ_ID_NO_201    MKREYQDAGG SGG------- --------DM G-SSKDKMMA   24
SEQ_ID_NO_194    MKREYQDAGG SGG------- --------DM G-SSKDKMMA   24
SEQ_ID_NO_215    MKREYQDAGG SGG------- --------DM G-SSKDKMMV   24
SEQ_ID_NO_202    MKREYQDGGG SGGGG----- -------DEM G-SSRDKMMV   27
SEQ_ID_NO_207    MKREYQDAGG SGG------- --------DM G-SSKDKMMV   24
SEQ_ID_NO_283    MKREYQDAGG SGGGG----- -------GGM G-SSEDKMMV   27
SEQ_ID_NO_196    MKRDLLDGCG GGGGGGGGGK GEEG---SSM V-SAKGKMWD   36
SEQ_ID_NO_235    MKRDHQETIG GAGNSIGNKA ESSS---SSM A-TGKGKLWW   36
SEQ_ID_NO_245    MKRDFQQACA GGPV-----K G-DS---SSM P-NGKAKMWE   30
SEQ_ID_NO_286    MKRDHRDSRA TVTARENNSK PEYSSPPSSA L-NGKAKIWE   39
SEQ_ID_NO_282    MKRDHRDSCG GGGGG--SVK GEC----SSM PSNGKANMWE   34
SEQ_ID_NO_239    MKREHQESKG DSS------- ---S---SCS A-MAKGKLWQ   26
SEQ_ID_NO_277    MKRDRDRDRE REKR------ AFSN---GAV S-SGKSKIWE   30

SEQ_ID_NO_188    GAA--G---- EEEDVDELLA ALGYKVRSSD MADVAQKLEQ   63
SEQ_ID_NO_221    GAA--G---- EEEDVDELLA ALGYKVRSSD MADVAQKLEQ   63
SEQ_ID_NO_201    AAA--G--E- QDEEVDELLA ALGYKVRSSD MADVAQKLEQ   59
SEQ_ID_NO_194    AAAGAG--EQ EEEDVDELLA ALGYKVRSSD MADVAQKLEQ   62
SEQ_ID_NO_215    AAAGAG--E- QEEELDEMLA SLGYKVRSSD MADVAQKLEQ   61
SEQ_ID_NO_202    SSSEAG---- EGEEVDELLA ALGYKVRASD MADVAQKLEQ   63
SEQ_ID_NO_207    AAAGAG--E- QEEEMDEMLA AVGYKVRSSD MADVAQKLEQ   61
SEQ_ID_NO_283    SAA-AG---- EGEEVDELLA ALGYKVRASD MADVAQKLEQ   62
SEQ_ID_NO_196    DGQ-----Q- QDAGMDELLA VLGYNVRSSD MVDVAQKLEQ   70
SEQ_ID_NO_235    EDD-----Q- DAGGMDELLA VLGYKIKSSE MADVAQKLEQ   70
SEQ_ID_NO_245    ED--RH--Q- QGGGMDELLA ALGYKVRASD MADVAQKLEQ   65
SEQ_ID_NO_286    DDQ-DG-YS- AGGDMDELLA VLGYKVRSDD MADVAEKLEQ   76
SEQ_ID_NO_282    EQQ-----Q- QQQGMDELLA ALGYKVRASD MADVAQKLEQ   68
SEQ_ID_NO_239    EEE-EQQQQ- DGGGMDELLA VLGYKVRSSD MAEVAQKLEQ   64
SEQ_ID_NO_277    EDE--E-EK- PDAGMDELLA VLGYKVKSSD MADVAQKLEQ   66
```

Figure 3A

```
SEQ_ID_NO_188   LEMAMGMGGV SAP-GAADDG FVSHLATDTV HYNPSDLSSW  102
SEQ_ID_NO_221   LEMAMGMAGV SAP-GAADDG FVSHLATDTV HYNPSDLSSW  102
SEQ_ID_NO_201   LEMAMGMGGV GGAATAVDDG FVSHLATDTV HYNPSNLSSW  99
SEQ_ID_NO_194   LEMAMGMGGV GGAGATADDG FVSHLATDTV HYNPSDLSSW  102
SEQ_ID_NO_215   LEMAMGMGGV GGAGATADDG FISHLATDTV HYNPSDLSSW  101
SEQ_ID_NO_202   LEMAMGMGG- ----PAPDDG FATHLATDTV HYNPTDLSSW  98
SEQ_ID_NO_207   LEMAMGMGGV GGAGATADDG FISHLATDTV HYNPSDLSSW  101
SEQ_ID_NO_283   LEMAMGMGGV GA-GAAPDDS FATHLATDTV HYNPTDLSSW  101
SEQ_ID_NO_196   LEMVMGN--- -----AQEDG -ISHLSSGTV HYNPSDLSGW  101
SEQ_ID_NO_235   LEMVLGS--- -------EDG -ISHLASDTV HYNPSDLSGW  99
SEQ_ID_NO_245   LEMVMGS--- -----AQEEG -ISHLSSYTV HYDPTDLHSW  96
SEQ_ID_NO_286   LEMVMGS--- -----AQEDG -ISQL-SDTV HYNPSDLSGW  106
SEQ_ID_NO_282   LEMVMGC--- -----AQEEG -ISHLASDTV HYDPTDLYSW  99
SEQ_ID_NO_239   LEMVMGL--- -----AQEDG -ISHL-SDTV HYNPSDLSGW  94
SEQ_ID_NO_277   LEMAMGT--- -----TMEDG -LTHLSTDTV HKNPSDMAGW  97

SEQ_ID_NO_188   VESMLSELNA PLPP-IPP-- ------A--P -PAARHASTS  130
SEQ_ID_NO_221   VESMLSELNA PLPP-IPP-- ------A--P -PAARHASTS  130
SEQ_ID_NO_201   VESMLSELNA PPPP-LPT-- ------A--P -PAPRLASTS  127
SEQ_ID_NO_194   VESMLSELNA PPAP-LPP-- ------A--T -PAPRLASTS  130
SEQ_ID_NO_215   LESMLSELNA PPPP-LPP-- ------ATTP -PAPRLASTS  131
SEQ_ID_NO_202   VESMLSELNA PPPP-LPP-- ------A--P -PQ-LNASTS  125
SEQ_ID_NO_207   VESMLSELNA PPPP------ ---------- --APRLASTS  123
SEQ_ID_NO_283   VESMLSELNA PPPP-LPP-- ------A--P --Q-LNASTS  127
SEQ_ID_NO_196   VQSMLTELNP PSSA-FASSS QQTPLDD--P LL---APSES  135
SEQ_ID_NO_235   VQSMLSELNN LPSSDLDS-- ------S--T LLSNNQDSNP  129
SEQ_ID_NO_245   VQSMLSELNP EPTT-L---- ---------- -------DPS  115
SEQ_ID_NO_286   VQSMLSELNT GDDM-P---- ---SLDD--P LL---APAES  133
SEQ_ID_NO_282   VQTMLTELNP EPNN-NNN-- ------S--- ----LL-GPS  122
SEQ_ID_NO_239   VQSMLSELNN PLDT-LQN-- ---------- -----QQDSS  116
SEQ_ID_NO_277   VQSMLSSLST NFDM-CN--- ---------- -------QEN  116
```

Figure 3B

```
SEQ_ID_NO_188   STVTGGG--G -SGFFEL-PA AADSSSSTYA LRPISLPVV-   165
SEQ_ID_NO_221   STVTGGG--G -SGFFEL-PA AADSSSSTYA LRPISLPVV-   165
SEQ_ID_NO_201   STVTGGAAAG -GGYFDL-PP AVDSSSSTYA LKPIPSPVA-   164
SEQ_ID_NO_194   STVTSGAAAG -AGYFDL-PP AVDSSSSTYA LKPIPSPVA-   167
SEQ_ID_NO_215   STVTSGAAAG -AGYFDL-PP AVDSSSSTYA LKPIPSPVAV   169
SEQ_ID_NO_202   STVTGG---- -GGYFDL-PP SVDSSSSTYA LRPILSPPV-   158
SEQ_ID_NO_207   STVTSGAAAG -AGYFDL-PP AVDSSSSTYA LKPIPSPVV-   160
SEQ_ID_NO_283   STVTGS---- -GGYFDL-PP SVDSSSSIYA LRPIPSPAG-   160
SEQ_ID_NO_196   STITTLDFSG SRQQSEH-QS RIYNDNSDYD LSAIPGVAV-   173
SEQ_ID_NO_235   STMTSLDFPN -----NS-QS KAFVDDSEYD LRAIPGVAA-   162
SEQ_ID_NO_245   SFLIDNPVHS -SPLLT-TTS RVFNDDSEYD LRAIPGIAA-   152
SEQ_ID_NO_286   SSITSMSFSN -----SQ-RS RVFSDDSEYD LRAIPGVAA-   166
SEQ_ID_NO_282   SLLID----- -----N-NTA PVFNDDSEYD LRAIPGIAA-   150
SEQ_ID_NO_239   SVISF---G- -----NS-QS GLFNDDSEYD LRAIPGVAA-   145
SEQ_ID_NO_277   DVLVSGCGSS -SSLIDFSQN HRTSTISDDD LRAIPGGAV-   154

SEQ_ID_NO_188   AT--ADPSAA DSA---RDTK RMRT-GGGST SSSSSSSSSL   199
SEQ_ID_NO_221   AT--ADPSAA DSA---RDTK RMRT-GGGST SSSSSSSSSL   199
SEQ_ID_NO_201   AS--ADP-ST DST---REPK RMRT-GGGST SSSSSSSSSL   197
SEQ_ID_NO_194   AP-SADP-ST DSA---REPK RMRT-GGGST SSSSSSSSSM   201
SEQ_ID_NO_215   AS--ADPSST DST---REPK RMRT-GGGST SSSSSSSSSM   203
SEQ_ID_NO_202   AP--ADL-SA DSV---RDPK RMRT-GGSST SSSSSSSSSL   191
SEQ_ID_NO_207   AS--ADPSST DST---REPK RMRT-GGGST SSSSSSSSSM   194
SEQ_ID_NO_283   ATAPADL-SA DSV---RDPK RMRT-GGSST SSSSSSSSSL   195
SEQ_ID_NO_196   YR--RPDQQG DGE---KSSK RMKT-ASSSS SSSTQQVQ--   205
SEQ_ID_NO_235   YP--Q-Q-EF DKS---NDRK RMKLTLVGSN TAPTLAVNSL   195
SEQ_ID_NO_245   YP--PQH-A- ---------T SNAT----TI STTTATSPTT   175
SEQ_ID_NO_286   YP--PAYSPS DSE---STRK RLKT-SIGSD SNGSSS----   196
SEQ_ID_NO_282   YP--PPP-P- ---------Q DNNN----N- ----------   162
SEQ_ID_NO_239   YP--PQPESS DSNNNSSSRK RMKT-STLAN SDSTL-----   177
SEQ_ID_NO_277   EN--SDS-N- ---------K RHRS----TT SSFSTTSSS-   176
```

Figure 3C

```
SEQ_ID_NO_188   GGGASRGSVV EAAPP----- ------ATQ- GAAAANAPAV  227
SEQ_ID_NO_221   GGGASRGSVV EAAPP----- ------AMQ- GAAAANAPAV  227
SEQ_ID_NO_201   DGGRTRSSVV EAAPP----- ------ATQ- ASAAANAPAV  225
SEQ_ID_NO_194   DGGRTRSSVV EAAPP----- ------ATQ- ASAAANGPAV  229
SEQ_ID_NO_215   DGGRTRSSVV EAAPP----- ------ATQ- APAAANGPAV  231
SEQ_ID_NO_202   GGGAARSSVV EAAPP----- ------VA-- --AAAAAPAL  216
SEQ_ID_NO_207   DGGRTRSSVV EAAPP----- ------ATQ- ASAAANGPAV  222
SEQ_ID_NO_283   GGG-ARSSVV EAAPP----- ------VA-- -AAANATPAL  220
SEQ_ID_NO_196   ---------- ---------- --------EN GLASVAESTR  217
SEQ_ID_NO_235   QSSNS-SCTP SSSPQ----- ------AIMA VSGTLSEPTR  223
SEQ_ID_NO_245   TVATTNTQTV EEIEPG--TN KRLKASPIE- SSESASEPTR  212
SEQ_ID_NO_286   ---------- ---------- ---------- --GAVSDPTR  204
SEQ_ID_NO_282   ------NNNL DEIETANNIN KRLKPSPVE- SADSASEPTR  195
SEQ_ID_NO_239   ---------- ---------- ---------- -PTNLSEPNR  186
SEQ_ID_NO_277   ---------- ---------- ---------- -MVTDSSATR  185

SEQ_ID_NO_188   PVVVVDTQEA GIRLVHALLA CAEAVQQENF AAAEALVKQI  267
SEQ_ID_NO_221   PVVVVDTQEA GIRLVHALLA CAEAVQQENF AAAEALVKQI  267
SEQ_ID_NO_201   PVVVVDTQEA GIRLVHALLA CAEAVQQENF TAAEALVKQI  265
SEQ_ID_NO_194   PVVVVDTQEA GIRLVHALLA CAEAVQQENF SAAEALVKQI  269
SEQ_ID_NO_215   PVVVMDTQEA GIRLVHALLA CAEAVQQENF SAADALVKQI  271
SEQ_ID_NO_202   PVVVVDTQEA GIRLVHALLA CAEAVQQENL SAAEALVKQI  256
SEQ_ID_NO_207   PVVVMDTPEA GIRLVHALLA CAEAVQQENF SAADALVKQI  262
SEQ_ID_NO_283   PVVVVDTQEA GIRLVHALLA CAEAVQQENL SAAEALVKQI  260
SEQ_ID_NO_196   PVVVVDSQET GVRLVHTLMA CADAVQQDNM KLADALVKHI  257
SEQ_ID_NO_235   PVVLIDSQET GVRLVHTLLA CAEAIQQENL KLADALVKHI  263
SEQ_ID_NO_245   PVVLVDSQEA GVRLVHTLMA CAEAVQQENL KLADALVKHV  252
SEQ_ID_NO_286   PRVLVDSQET GVRLVHTLMA CAEAVQQENL KLADALVKHV  244
SEQ_ID_NO_282   TVLLVDHQEA GVRLVHTLLA CAEAVQQENL KLADALVKHV  235
SEQ_ID_NO_239   PMVLIDSQET GVRLVHTLLA CAEAIQQDNF KLAEALLKHI  226
SEQ_ID_NO_277   PVVLVDSQET GVRLVHTLMA CAEAVQQENL TLADQLVRHI  225
```

Figure 3D

```
SEQ_ID_NO_188    PTLAASQGGA MRKVAAYFGE ALARRVYRFR PA-DSTLLDA  306
SEQ_ID_NO_221    PTLAASQGGA MRKVAAYFGE ALARRVYRFR PA-DSTLLDA  306
SEQ_ID_NO_201    PMLASSQGGA MRKVAAYFGE ALARRVYRFR PAPDSSLLDA  305
SEQ_ID_NO_194    PMLASSQGGA MRKVAAYFGE ALARRVYRFR PPPDSSLLDA  309
SEQ_ID_NO_215    PMLASSQGGA MRKVAAYFGE ALARRVYRFR PTPDTSLLDA  311
SEQ_ID_NO_202    PLLAASQGGA MRKVAAYFGE ALARRVFRFR PQPDSSLLDA  296
SEQ_ID_NO_207    PMLASSQGGA MRKVAAYFGE ALARRVYRFR PTPDSSLLDA  302
SEQ_ID_NO_283    PLLAASQGGA MRKVAAYFGE ALARRVFRFR PQPDSSLLDA  300
SEQ_ID_NO_196    GLLAASQAGA MRKVATYFAE ALARRIYRIY PQ-D--SLES  294
SEQ_ID_NO_235    GVLAASQAGA MRKVATYFAE ALARRIYKIF PQ-D-HCLDS  301
SEQ_ID_NO_245    GILAASQAGA MRKVATYFAQ ALARRIYGIF PE-E--TLES  289
SEQ_ID_NO_286    GLLAASQTGA MRKVATYFAE ALARRIYRIY PQ-D--CLDS  281
SEQ_ID_NO_282    GILAASQAGA MRKVASYFAQ ALARRIYGIF PE-E--TLDS  272
SEQ_ID_NO_239    GLLAASQASS MRKVATYFAE ALARRIYKIY PQ-E--SLDP  263
SEQ_ID_NO_277    GILAVSQSGA MRKVATYFAE ALARRIYKIY PQ-D--SMES  262

SEQ_ID_NO_188    AFADLLHAHF YESCPYLKFA HFTANQAILE AFAGCHRVHV  346
SEQ_ID_NO_221    AFADLLHAHF YESCPYLKFA HFTANQAILE AFAGCRRVHV  346
SEQ_ID_NO_201    AFADLLHAHF YESCPYLKFA HFTANQAILE AFAGCRRVHV  345
SEQ_ID_NO_194    AFADLLHAHF YESCPYLKFA HFTANQAILE AFAGCRRVHV  349
SEQ_ID_NO_215    AVADFLHAHF YESCPYLKFA HFTANQAILE AFAGCRRVHV  351
SEQ_ID_NO_202    AFADLLHAHF YESCPYLKFA HFTANQAILE AFAGCRRVHV  336
SEQ_ID_NO_207    AVADFLHAHF YESCPYLKFA HFTANQAILE AFAGCRRVHV  342
SEQ_ID_NO_283    AFADLLHAHF YESCPYLKFA HFTANQAILE AFAGCRRVHV  340
SEQ_ID_NO_196    SYSDILQMHF YEACPYLKFA HFTANQAILE AFAGANRVHV  334
SEQ_ID_NO_235    SYSDTLEMHF YETCPYLKFA HFTANQAILE AFANASRVHV  341
SEQ_ID_NO_245    SLSDLLHMHF YESCPYLKFA HFTANQAILE AFATAGRVHV  329
SEQ_ID_NO_286    SYSDILEMHF YETCPYLKFA HFTANQAILE AFATASRVHV  321
SEQ_ID_NO_282    SFSDVLHMHF YESCPYLKFA HFTANQAILE AFATAGRVHV  312
SEQ_ID_NO_239    SYSDTLEMHF YETCPYLKFA HFTANQAILE AFGTANRVHV  303
SEQ_ID_NO_277    SYTDVLQMHF YETCPYLKFA HFTANQAILE AFTGCNKVHV  302
```

Figure 3E

```
SEQ_ID_NO_188    QPEGEADANE EPEVIAVNSV FELHRLLAQP GALEKVLGTV   466
SEQ_ID_NO_221    QPEGEADANE EPEVIAVNSV FELHRLLAQP GALEKVLGTV   466
SEQ_ID_NO_201    QPDGE-DTDD EPEVIAVNSV FELHRLLAQP GALEKVLGTV   464
SEQ_ID_NO_194    QPEGD-DTDD EPEVIAVNSV FELHRLLAQP GALEKVLGTV   468
SEQ_ID_NO_215    QPEGD-DKDE EPEVIAVNSV FELHRLLAQP GALEKVLGTV   470
SEQ_ID_NO_202    QPEGEEDPNE EPEVIAVNSV FEMHRLLAQP GALEKVLGTV   456
SEQ_ID_NO_207    QPEGD-DKDE EPEVIAVNSV FELHRLLAQP GALEKVLGTV   461
SEQ_ID_NO_283    QPEGEEDPNE EPEVIAVNSV FEMHRLLAQP GALEKVLGTV   460
SEQ_ID_NO_196    QIRP-----P EVEAVAVNSV LELHRLLARP GAIEKVLSSI   449
SEQ_ID_NO_235    DLRP-----P EVEAVAVNSV FELHRLLDRP GGIDKVLGSI   456
SEQ_ID_NO_245    EIRP------ -GEAVAVNSV FELHRMLARP GSVDKVMDTV   442
SEQ_ID_NO_286    DIRP-----S EGEVVAVNSV FELHRLLARP GAVDKVLSSI   436
SEQ_ID_NO_282    EIRP------ -GEAVAVNSV FELHRMLARP GSVDKVLDTV   425
SEQ_ID_NO_239    DLRP-----P DVETVAVNSV FELHRLLARP GGMEKVLSSI   418
SEQ_ID_NO_277    DIRP-----S ETEAVAINSV FELHRLLSRP GALEKVLNSI   417

SEQ_ID_NO_188    HAVRPRIVTV VEQEANHNSG SFLDRFTESL HYYSTMFDSL   506
SEQ_ID_NO_221    HAVRPRIVTV VEQEANHNSG SFLDRFTESL HYYSTMFDSL   506
SEQ_ID_NO_201    RAVRPRIVTV VEQEANHNSV SFLDRFTESL HYYSTMFDSL   504
SEQ_ID_NO_194    RAVRPRIVTV VEQEANHNSG TFLDRFTESL HYYSTMFDSL   508
SEQ_ID_NO_215    RAVRPRIVTV VEQEANHNSG TFLDRFTESL HYYSTMFDSL   510
SEQ_ID_NO_202    RAVRPRIVTV VEQEANHNSG SFLDRFTESL HYYSTMFDSL   496
SEQ_ID_NO_207    RAVRPRIVTV VEQEANHNSG TFLDRFTESL HYYSTMFDSL   501
SEQ_ID_NO_283    RAVRPRIVTV VEQEANHNSG TFLDRFTESL HYYSTMFDSL   500
SEQ_ID_NO_196    KAMKPKIVTV VEQEASHNGP VFLDRFTEAL HYYSNLFDSL   489
SEQ_ID_NO_235    KAMRPKIVTI VEQEANHNGP VFLDRFTEAL HYYSSLFDSL   496
SEQ_ID_NO_245    KNLNPKIVTI VEQEANHNGP VFLDRFTEAL HYYSSLFDSL   482
SEQ_ID_NO_286    KAMKPKIVTI VEQEANHNGP VFLDRFTEAL HYYSNLFDSL   476
SEQ_ID_NO_282    KKIKPKIVTI VEQEANHNGP GFLDRFTEAL HYYSSLFDSL   465
SEQ_ID_NO_239    KAMKPKIVTV VEQEASHNGP VFLDRFTEAL HYYSSLFDSL   458
SEQ_ID_NO_277    KQINPKIVTL VEQEANHNAG VFLDRFNEAL HYYSTMFDSL   457
```

Figure 3G

```
SEQ_ID_NO_188  EGGSSG--Q- -AEL----SP PAAGGGGGTD QVMSEVYLGR  538
SEQ_ID_NO_221  EGGSSG--Q- -AEL----SP PAAGGGGGTD QVMSEVYLGR  538
SEQ_ID_NO_201  EGAGSG--Q- -SAD----AA PA--AAGGTD QVMSEVYLGR  534
SEQ_ID_NO_194  EGAGAGSGQ- -STD----AS PA--AAGGTD QVMSEVYLGR  540
SEQ_ID_NO_215  EGAGSG--Q- -STD----AS PA--AAGGTD QVMSEVYLGR  540
SEQ_ID_NO_202  EGGSSG--G- PSEVSSGGAA PA--AAAGTD QVMSEVYLGR  531
SEQ_ID_NO_207  EGAGSG--Q- -STD----AS PA--AAGGTD QVMSEVYLGR  531
SEQ_ID_NO_283  EGGSSG--GG PSEVSSGAAA AP--AAAGTD QVMSEVYLGR  536
SEQ_ID_NO_196  EGCGVS--P- ---------- -----PSSQD LMMSEIYLGR  511
SEQ_ID_NO_235  EGSGVT--P- ---------- ------TSQD LVMSELYLGR  517
SEQ_ID_NO_245  EGSSSS--T- -GL------- ----GSPSQD LLMSEVYLGK  507
SEQ_ID_NO_286  EGSSG----- ---------- ------PSQD LVMSEVYLGR  495
SEQ_ID_NO_282  EGSSSS--T- -GL------- ----GSPNQD LLMSELYLGR  490
SEQ_ID_NO_239  EGSGLN--V- ---------- ------PSQD LVMSELYLGR  479
SEQ_ID_NO_277  ESSGSS--S- -SASPTGILP Q--PPVNNQD LVMSEVYLGR  491

SEQ_ID_NO_188  QICNVVACEG AERTERHETL GQWRNRLGRA GFEPVHLGSN  578
SEQ_ID_NO_221  QICNVVACEG AERTERHETL GQWRNRLGRA GFEPVHLGSN  578
SEQ_ID_NO_201  QICNVVACEG AERTERHETL GQWRNRLGGA GFEPVHLGSN  574
SEQ_ID_NO_194  QICNVVACEG AERTERHETL GQWRSRLGGS GFAPVHLGSN  580
SEQ_ID_NO_215  QICNVVACEG AERTERHETL SQWRGRLVGS GFEPVHLGSN  580
SEQ_ID_NO_202  QICNVVACEG TERTERHETL GQWRNRLGNA GFETVHLGSN  571
SEQ_ID_NO_207  QICNVVACEG AERTERHETL GQWRNRLGGS GFEPVHLGSN  571
SEQ_ID_NO_283  QICNVVACEG AERTERHETL GQWRNRLGNA GFETVHLGSN  576
SEQ_ID_NO_196  QICNVVACEG AERVERHETL SQWRSRMGSA GFDPVHLGSN  551
SEQ_ID_NO_235  QICNVVACEG ADRVERHETL AQWRTRFDSA GFDPVHLGSN  557
SEQ_ID_NO_245  QICNVVAYEG VERVERHETL SQWRGRMGSA GFDPVHLGSN  547
SEQ_ID_NO_286  QICNVMACEG GDRVERHETL SQWRGRMDSA GFDPVHLGSN  535
SEQ_ID_NO_282  QICNVVANEG ADRVERHETL SQWRGRLDSA GFDPVHLGSN  530
SEQ_ID_NO_239  QICNVVACEG AHRVERHESL PHWRTRFESA GFDRVHLGSN  519
SEQ_ID_NO_277  QICNVVACEG SDRVERHETL NQWRVRMNSS GFDPVHLGSN  531
```

Figure 3H

```
SEQ_ID_NO_188    AYKQASTLLA LFAGGDGYRV EEKEGCLTLG WHTRPLIATS    618
SEQ_ID_NO_221    AYKQASTLLA LFAGGDGYRV EEKEGCLTLG WHTRPLIATS    618
SEQ_ID_NO_201    AYKQASTLLA LFAGGDGYRV EEKDGCLTLG WHTRPLIATS    614
SEQ_ID_NO_194    AYKQASTLLA LFAGGDGYRV EEKDGCLTLG WHTRPLIATS    620
SEQ_ID_NO_215    AYKQASTLLA LFNGGDGYRV EEKDGCLTLG WHTRPLIATS    620
SEQ_ID_NO_202    AYKQASTLLA LFAGGDGYKV EEKEGCLTLG WHTRPLIATS    611
SEQ_ID_NO_207    AYKQASTLLA LFNGGDGYKV EEKDGCLTLG WHTRPLIATS    611
SEQ_ID_NO_283    AYKQASTLLA LFAGGDGYKV EEKEGCLTLG WHTRPLIATS    616
SEQ_ID_NO_196    AFKQASMLLA LFAGGDGYRV EENNGCLMLG WHTRPLIATS    591
SEQ_ID_NO_235    AFKQASMLLA LFAGGDGYRV EENNGCLMLG WHTRPLIATS    597
SEQ_ID_NO_245    AFKQASMLLA LFAGGDGYRV EENNGCLMLG WHTRPLIATS    587
SEQ_ID_NO_286    AFKQASMLLA LFAGGDGYRV EENNGSLMLG WHTRPLIATS    575
SEQ_ID_NO_282    AFKQASMLLA LFAGGDGYRV EENNGCLMLG WHTRPLIATS    570
SEQ_ID_NO_239    AFKQASMLLA LFAGGDGYRV EENNGCLMLG WHTRPLIATS    559
SEQ_ID_NO_277    AFKQASMLLA LFAGGDGYRV EENDGCLMLG WHTRPLIATS    571

SEQ_ID_NO_188    AWRVA---A- ---------- -----A    625
SEQ_ID_NO_221    AWRVA---A- ---------- -----A    625
SEQ_ID_NO_201    AWRVA---A- ---------- -----P    621
SEQ_ID_NO_194    AWRVAAAAA- ---------- -----P    630
SEQ_ID_NO_215    AWRLA---A- ---------- -----P    627
SEQ_ID_NO_202    AWRLA---A- ---------- -----P    618
SEQ_ID_NO_207    AWRLA---A- ---------- -----P    618
SEQ_ID_NO_283    AWRLA---G- ---------- -----P    623
SEQ_ID_NO_196    AWQLN---SN FN-PTSTSAS TSAHSQ    613
SEQ_ID_NO_235    AWQLA---AG DSRLRVNSAE FELPSQ    620
SEQ_ID_NO_245    AWKLP---SP ---------- ----ES    596
SEQ_ID_NO_286    AWQLA---SA ---------- ----TE    584
SEQ_ID_NO_282    AWKLP---SP ND-------- -LHCKL    584
SEQ_ID_NO_239    AWQLS---D- ---------- ----SK    567
SEQ_ID_NO_277    AWKLL---PD SG------TG AGEVEL    588
```

Figure 3I

```
SEQ_ID_NO_1     MPTP-A---- --HLS----- ---KDPHYFD FRAARRVPET  25
SEQ_ID_NO_2     MPTP-S---- --HLS----- ---KDPHYFD FRAARRVPET  25
SEQ_ID_NO_3     MPTP-S---- --HLS----- ---NDPRYFD FRAARRVPET  25
SEQ_ID_NO_4     MPTP-A---- --HLS----- ---KDPHYFD FRAARRVPET  25
SEQ_ID_NO_6     MPTP-S---- ---------- -HLANPRYFD FRAARRVPET  24
SEQ_ID_NO_8     MPTP-S---- --HL------ ---KNPLYFD FRAARRVPES  24
SEQ_ID_NO_9     MPTP-S---- --HLK----- ----NPLCFD FRAARRVPET  24
SEQ_ID_NO_10    MQSS-S---- --SSAST--P AA-ASGLVFD LGSAAGVPET  30
SEQ_ID_NO_11    MPSL-S---- --MEQPIHFP QPIHHPKHFD LGSAHEVPDS  33
SEQ_ID_NO_12    MPSR-I---- --SDAFKAHP LH-LNHRHLD LNSVQELPDL  32
SEQ_ID_NO_13    MPAR-LSDAF KSHPL----- -NL-QLKHPD FSSLQELPDS  32
SEQ_ID_NO_14    MPAPRI---- --MDPYKDKS SHYHHRRHLD FQSVEELPDA  34
SEQ_ID_NO_15    MHTN-I---- --SM------ ---INQKHLD LNSMKVLPES  24
SEQ_ID_NO_16    MPSR-I---- --SDSFRA-- ---HSQKHLD LNSIKELPES  28
SEQ_ID_NO_17    MPSL------ --SEAYRAHP VH-VNHKHPD FNSLQELPES  31
SEQ_ID_NO_18    MPTR-I---- --SDSFRPH- ---HSQKHFD LNSIKELPES  29
SEQ_ID_NO_19    MPSR-P---- --SRVVK--E QHPTKKSFLD LESLNELPDS  31
SEQ_ID_NO_20    MPSL------ --SEAYRAHP VH-VNHKHPD FNSLQELPES  31
SEQ_ID_NO_21    MPVR-I---- --SEAFPSHP H---KHYPAD FNSLHELPDS  30
```

Figure 4A

```
SEQ_ID_NO_1     HAWPGLHD-H PVV- DGSGA- G-- GEPDAVP VVDMR----D   56
SEQ_ID_NO_2     HAWPGLHD-H PVV- DGGGA- G-- GGPDAVP VVDMR----D   56
SEQ_ID_NO_3     HAWPGLHD-H PVV- DGGEA- G-- GGPDAVP VVDMR----D   56
SEQ_ID_NO_4     HAWPGLHE-H PVV- DGR-A- G-- AGEDAVL VVDTR----D   55
SEQ_ID_NO_6     HAWPGLHD-H PVV- DGGLA- --- PGPDAVP VVDLAGAADE   57
SEQ_ID_NO_8     HAWPGLHE-H PVV- DGGGA- P-- GTPDAVP VVDLR----E   55
SEQ_ID_NO_9     HAWPGLDD-H PVV- DGG-G- G-- GGEDAVP VVDVR----A   54
SEQ_ID_NO_10    HAWPGVNE-Y PSV- ES---- --- AGRDVVP VVDMG----V   57
SEQ_ID_NO_11    HTWPTIQP-N PP-- ------ N-- GPNESIP VIDLS----S   58
SEQ_ID_NO_12    YAWAGVDE-N PSG- DS---- --- LITESVP VIDLT----D   59
SEQ_ID_NO_13    YAWSQNDDQY PSS- PGS-F- G-- AEQDSVP VIDLS----D   63
SEQ_ID_NO_14    YEWGPLES-H G--- GP-V-- --- GADQGVP IVDLK----G   60
SEQ_ID_NO_15    HAWLSLES-S PLY- SS---- --- LSPDLVP VISLT----D   51
SEQ_ID_NO_16    HAWTSSND-Y PSE- NS---- --- CNFESIP VIDLD----N   55
SEQ_ID_NO_17    YTWTHLDD-H TLI- NSNNTM KES ANSSSVP IIDLN----D   65
SEQ_ID_NO_18    HAWTSSND-H YTQE NS---- --- CNFESIP VIDLD----N   57
SEQ_ID_NO_19    FAWGSFED-P CSI- DNPS-- G-- YGPDSVP VINLQ----D   61
SEQ_ID_NO_20    YNWTHLDD-H TLI- DSNNIM K-- ESTTTVP VIDLN----D   63
SEQ_ID_NO_21    YAWTNQLDEC PSL- DSS--- F-- GSDLCVP VIDLN----D   60
```

Figure 4B

```
SEQ_ID_NO_1    -------P--F AAEAVGLAAQ DWGAFLLVGH GVPLDLLVRV 88
SEQ_ID_NO_2    -------P--C AAEAVALAAQ DWGAFLLQGH GVPLELLARV 88
SEQ_ID_NO_3    -------P--C AAEAVALAAQ DWGAFLLEGH GVPLELLERV 88
SEQ_ID_NO_4    -------P--G AAEAVARAAE QWGAFLLEGH GVSRELLQRV 87
SEQ_ID_NO_6    -------PRAA VVAQVARAAE QWGAFLLTGH GVPAELLARV 91
SEQ_ID_NO_8    -------SGAA AAAGVARAAE LWGAFLLTGH GVPAELLARV 89
SEQ_ID_NO_9    -------G--D AAARVARAAE QWGAFLLVGH GVPAALLSRV 86
SEQ_ID_NO_10   -------ACPD ATRALARAAD EWGVFLLVGH GVPREVAARA 91
SEQ_ID_NO_11   -------P--D VISLIGHACE SWGVFQVISH GVDLNLLHNL 90
SEQ_ID_NO_12   -------P--N ASELVGHACK SWGVFQVTNH GIPGSLLDDI 91
SEQ_ID_NO_13   -------P--N ALKLTGHACR TWGVFQVTNH GIPSKLLDDI 95
SEQ_ID_NO_14   -------P--N ARELIGSACK SWGAFQVINH GVPQRFLEEV 92
SEQ_ID_NO_15   -------P--N AMNLVGHACK TWGVFQVTNH GVPINLLEKM 83
SEQ_ID_NO_16   YI NNNNI--N VLEHIGQACK KWGAFQIINH NISERLLQDI 93
SEQ_ID_NO_17   -------P--N ASKLIGHACK TWGVYQVVNH GIPISLLDEI 97
SEQ_ID_NO_18   NNN-NNNN--N ILDHIGHACK KWGAFQIINH SISERLLQDI 94
SEQ_ID_NO_19   -------P--Q AQQLVGLACR SWGVFQVTNH GIQKSLLDDI 93
SEQ_ID_NO_20   -------P--N ASKLIGLACK TWGVYQVMNH GIPLSLLEDI 95
SEQ_ID_NO_21   -------Q--N VIKLIGHACK TWGVFQVTNH GVPQKLVHDI 92
```

Figure 4C

| Sequence | | | | | Position |
|---|---|---|---|---|---|
| SEQ_ID_NO_1 | EAAIAGMFAL | PASEKMRAVR | RPGD--SCGY | GSPPISSFFS | 126 |
| SEQ_ID_NO_2 | EAAIAGMFAL | PASEKMRAVR | RPGD--SCGY | GSPPISSFFS | 126 |
| SEQ_ID_NO_3 | EAAIAGMFAL | PASEKMRAVR | RPGD--SCGY | GSPPISSFFS | 126 |
| SEQ_ID_NO_4 | EARIAGMLAL | PAQEKMRAVR | RPGD--SCGY | GSPPISSFFA | 125 |
| SEQ_ID_NO_6 | EDRIATMFAL | PADDKMRAVR | GPGD--ACGY | GSPPISSFFS | 129 |
| SEQ_ID_NO_8 | EDRIARMFAL | PAADKMRAVR | GPGD--ACGY | GSPPISSFFS | 127 |
| SEQ_ID_NO_9 | EERVARVFSL | PASEKMRAVR | GPGE--PCGY | GSPPISSFFS | 124 |
| SEQ_ID_NO_10 | EEQVARLFVL | PAPDKARAGR | RPGEPTATGY | GRPPLALRFS | 131 |
| SEQ_ID_NO_11 | ESQARRLFSL | PTQQKLKAGR | SPNS--ISGY | GLAPISSLFS | 128 |
| SEQ_ID_NO_12 | ESAGRSLFSL | PAQQKLKAAR | SPDG--VAGY | GLARISSFFN | 129 |
| SEQ_ID_NO_13 | ESAGRSLFSL | PVQQKLKAAR | SPDG--ISGY | GFARISSFFQ | 133 |
| SEQ_ID_NO_14 | ESAGRRLFSL | PLHQKLKAAR | APDG--VTGY | GPARISSFFP | 130 |
| SEQ_ID_NO_15 | EAAGRKLFAL | PLQQKLKAAR | APDG--VSGY | GVARISSFFP | 121 |
| SEQ_ID_NO_16 | ELAGKSLFSL | PMQQKLKAAR | SPEG--VTGY | GVARISSFFS | 131 |
| SEQ_ID_NO_17 | QWLGQTLFTL | PSHQKLKAIR | SPDG--VSGY | GLARISSFFP | 135 |
| SEQ_ID_NO_18 | DVAGKTLFSL | PMQQKLKAAR | SPDG--VTGY | GAAQISSLFS | 132 |
| SEQ_ID_NO_19 | EAAGKSLFAL | PVNQKLKAAR | SSCG--VTGY | GPAGISSFFP | 131 |
| SEQ_ID_NO_20 | QWLGQTLFSL | PSHQKHKATR | SPDG--VSGY | GIARISSFFP | 133 |
| SEQ_ID_NO_21 | ESTCRSLFSL | PVQQKLKAAR | PADG--ISGY | GIHRISSFFQ | 130 |

Figure 4D

```
SEQ_ID_NO_1    KCMWSEGYTF  SPANLRSDLR  KLWPKAGHDY  RHFCAVMEEF  166
SEQ_ID_NO_2    KCMWSEGYTF  SPANLRSDLR  KLWPKAGHDY  RHFCAVMEEF  166
SEQ_ID_NO_3    KCMWSEGYTF  SPANLRSDLR  KLWPKAGHDY  RHFCAVMEEF  166
SEQ_ID_NO_4    KSMWSEGYTF  SPANLRSDLR  KLWPKQGHDY  RLFCDVMEEF  165
SEQ_ID_NO_6    KCMWSEGYTF  SPANLRADLR  KLWPKAGDDY  TSFCDVMEEF  169
SEQ_ID_NO_8    KCMWSEGYTF  SPASLRADLR  KLWPKAGDDY  ASFCDVMEEF  167
SEQ_ID_NO_9    KLMWSEGYTF  SPSSLRSELR  RLWPKSGDDY  LLFCDVMEEF  164
SEQ_ID_NO_10   KLMWSEGYTF  RAATVREEFR  RVWPDGGDDY  LRFCDVMEEY  171
SEQ_ID_NO_11   KLMWSEGFTI  SGSPL-DHAR  SLWPD---DY  FNFCEVLEEY  164
SEQ_ID_NO_12   KLMWYEGFTI  FGSPL-EHAR  QLWPQ---DY  TKFCDVTEEF  165
SEQ_ID_NO_13   KLMWSEGFTI  VGSPL-DHFR  QLWPQ---DY  NKFCNIIEEY  169
SEQ_ID_NO_14   KLLWSEGFTI  FGSPE-DHAR  QLWPQ---DY  QNFCEIIEEY  166
SEQ_ID_NO_15   KLMWSEGFTI  MGSPY-EHAL  KLWPN---SY  TRFCDVIEEY  157
SEQ_ID_NO_16   KLMWSEGFTI  VGSPL-EHAR  QIWPH---DY  QKFCDVIEEY  167
SEQ_ID_NO_17   KLMWSEGFTI  VGSPL-DHFR  QLWPQ---DY  AKHCDTVLQY  171
SEQ_ID_NO_18   KLMWSEGFTI  VGSPI-EHAR  QLWPK---DY  KKFCEVIEEY  168
SEQ_ID_NO_19   KRMWSEGFTI  LGSPL-DHAR  QLWPN---NY  NKFCDIIEKY  167
SEQ_ID_NO_20   KLMWYEGFTI  VGSPL-DHFR  ELWPQ---DY  TRFCDIVVQY  169
SEQ_ID_NO_21   KLMWSEGFTL  VGSPL-EHFR  QLWPQ---DY  NKFCCMVEEY  166
```

Figure 4E

```
SEQ_ID_NO_1    HREMRALADK LLELFLVALG LTGEQVA- AV E- SEQKIAET 204
SEQ_ID_NO_2    HREMRVLADK LLELFLVALG LTGEQVA- AV E- SEHKIAET 204
SEQ_ID_NO_3    HREMRALADK LLELFLVALG LTVEQVA- AV E- SEQQIAET 204
SEQ_ID_NO_4    HGEMRALSDR LMELFLAALG LTGEQAA- AV E- AEHRIAET 203
SEQ_ID_NO_6    HKHMRALADK LLELFLMALG LTDEQVG- GV E- AERRIAET 207
SEQ_ID_NO_8    HKEMRVLAGK LLELFLRALG LTDEEVA- AV E- EERRIGET 205
SEQ_ID_NO_9    HKEMRRLADE LLRLFLRALG LTGEEVA- GV E- AERRIGER 202
SEQ_ID_NO_10   DREMRALGGR LLDLFFMALG LTDVQFA- TG E- TERRIRET 209
SEQ_ID_NO_11   NKEMKRVAER LMQLMLLSLG LTEETIK- WA G- PMNEL-QD 201
SEQ_ID_NO_12   EKEMNQLAER LMWLMLGSLG ITKEDVN- WA G- SKGD---- 199
SEQ_ID_NO_13   EKVMKRLAGR LMWLMLGSLG ISMEDVK- WA G- PKGDFR-D 206
SEQ_ID_NO_14   DRDMKRLAGR LMWLVLGSLG IAKDDVE- WA G- PTGDFNDT 204
SEQ_ID_NO_15   KEEMNKLAQT LMSLMLGSLG VTMEDVK- WA G- SQG----- 190
SEQ_ID_NO_16   EREMEKLAGR LMWLMLGSLG ITKEEVK- WA VC PKGES-KG 205
SEQ_ID_NO_17   DEAMKKLAGK LMWLMLDSLG ITMEDIE- WA G- SKAQFDEK 209
SEQ_ID_NO_18   EKEMEKLAGR LMWLILGSLG ITKDEVK- WA VG PKGET-KE 206
SEQ_ID_NO_19   QKEMNQLAKK LMQLVVGSLG ISNQDIMN WA D- ---LL-EG 202
SEQ_ID_NO_20   DETMKKLAGT LMCLMLDSLG ITKEDIK- WA G- SKAQF-EK 206
SEQ_ID_NO_21   ETEMKKLAGR LMWLIFGSLG ISKEDVS- WA G- PKGDFE-D 203
```

Figure 4F

| | | | | | |
|---|---|---|---|---|---|
| SEQ_ID_NO_1 | MTATMHLNWY | PKCPDPKRAL | GLIAHTDSGF | FTFVLQSLVP | 244 |
| SEQ_ID_NO_2 | MTATMHLNWY | PKCPDPKRAL | GLIAHTDSGF | FTFVLQSLVP | 244 |
| SEQ_ID_NO_3 | MTATMHLNWY | PKCPDPKRAL | GLIAHTDSGF | FTFVLQSLVP | 244 |
| SEQ_ID_NO_4 | MTATMHLNWY | PKCPDPKRAL | GLIAHTDSGF | FTFVLQSLVP | 243 |
| SEQ_ID_NO_6 | MTATMHLNWY | PRCPDPRRAL | GLIAHTDSGF | FTFVLQSLVP | 247 |
| SEQ_ID_NO_8 | MTTTMHLNWY | PRCPDPRRAL | GLIAHTNSGF | FTFVLQSLVP | 245 |
| SEQ_ID_NO_9 | MTATVHLNWY | PRCPEPRRAL | GLIAHTDSGF | ETFVLQSLVP | 242 |
| SEQ_ID_NO_10 | WTATMHPILY | PRCPEPERAI | GLTAHTDSGF | ITLIMQSPVP | 249 |
| SEQ_ID_NO_11 | LSSVLQLNSY | PACPNPDRAI | GLAAHTDSSL | LTILYQSNTS | 241 |
| SEQ_ID_NO_12 | FKAALQLNSY | PACPEPDRAM | GLAAHTDSSL | FTILYQNTVS | 239 |
| SEQ_ID_NO_13 | ASAALQLNSY | PACPDPDRAM | GLAAHTDSTL | LTILYQNNTS | 246 |
| SEQ_ID_NO_14 | CSAALQLNSY | PKCPNPGRAM | GLAAHTDSTL | LTILYQNNTT | 244 |
| SEQ_ID_NO_15 | SCPALQLNSY | PACPDPDRAM | GLAAHTDSTL | LTILHQNNTS | 230 |
| SEQ_ID_NO_16 | GSAALQLNSY | PACPDPDRAM | GLAAHTDSTI | LTILHQNNTS | 245 |
| SEQ_ID_NO_17 | ACAAMQLNSY | PSCPDPDHAM | GLAPHTDSTF | LTILSQNDIS | 249 |
| SEQ_ID_NO_18 | GCAALQLNSY | PACPDPGRAM | GLAAHTDSTI | LTILHQNNTS | 246 |
| SEQ_ID_NO_19 | ANGAMQLNSY | PIRPDPNRAM | GLAAHTDSTL | LTILHQSNTT | 242 |
| SEQ_ID_NO_20 | ACAALQLNSY | PSCPDPDHAM | GLTPHTDSTF | LTILSQNDIS | 246 |
| SEQ_ID_NO_21 | ASNALQLNSY | PACPDPSRAM | GLAEHTDSTL | LTILHQSNIS | 243 |

Figure 4G

```
SEQ_ID_NO_1    GLQLFRHG-- ---PDRWWTV PA- VPGAMVV NVGDLFQILT 278
SEQ_ID_NO_2    GLQLFRHG-- ---PDRWWTV PA- VPGAMVV NVGDLFHILT 278
SEQ_ID_NO_3    GLQLFRHG-- ---PDRWWTV PA- VPGAMVV NVGGLFQILT 278
SEQ_ID_NO_4    GLQLFRHG-- ---PDRWWTV PAD VQDAFVV NVGDLFQILT 278
SEQ_ID_NO_6    GLQLFRHA-- ---PDRWWAV PA- VPGAFVV NVGDLFHILT 281
SEQ_ID_NO_8    GLQLFRHA-- ---PDRWWAV PA- VPGAFVV NVGDLFQILT 279
SEQ_ID_NO_9    GLQLFRRG-- ---PDRWWAV PA- VAGAFVV NVGDLFHILT 276
SEQ_ID_NO_10   GLQLLRRG-- ---PDRWWTV PA- PPGALIV MLGDLFQVLT 283
SEQ_ID_NO_11   GLQVLRPNKE SSPT-QWWTV PP- IPGALVV NVGDLCHILS 279
SEQ_ID_NO_12   GLQVQREG-- ---A-GWITV PP- LPGALVI NVGDLLHILS 272
SEQ_ID_NO_13   GLQVLREG-- ---T-GWWTV PP- LPGALVV NVGDLIHILS 279
SEQ_ID_NO_14   GLQVHRDG-- ---L-GWWMV PP- VPGALVV NIGDLLHILS 277
SEQ_ID_NO_15   GLQAHRDG-- ---A-GWWTV PP- IPGALVI NVGDLLHILS 263
SEQ_ID_NO_16   GLQVFKEG-- ---S-GWWTV PP- FPGALVV NVGDLLHILS 278
SEQ_ID_NO_17   GLQVQREG-- ---S-GWWTV PP- LHGGLVV NVGDLFHILS 282
SEQ_ID_NO_18   GLQVYQEG-- ---N-GWWTV PP- IPGALVV NVGDLLHILS 279
SEQ_ID_NO_19   GLQVFRER-- ---S-GWWTV PP- ISGGLVI NIGDLLHILS 275
SEQ_ID_NO_20   GLQVNREG-- ---S-GWITV PP- LQGGLVV NVGDLFHILS 279
SEQ_ID_NO_21   GLQVLREG-- ---A-GWLTV PP- VAGALVI NIGDLIHILS 276
```

Figure 4H

| | | | | | |
|---|---|---|---|---|---|
| SEQ_ID_NO_1 | NGRFHSVYHR | AVVNRESDRI | SLGYFLGPPA | HVKVAPLREA | 318 |
| SEQ_ID_NO_2 | NGRFHSVYHR | AVVNRDSDRI | SLGYFLGPPA | HVKVAPLREA | 318 |
| SEQ_ID_NO_3 | NGRFHSVYHR | AVVNRDSDRI | SLGYFLGPPA | HVKVAPLREA | 318 |
| SEQ_ID_NO_4 | NGRFHSVYHR | AVVNRDSDRI | SLGYFHGPPA | DTKVAPLREA | 318 |
| SEQ_ID_NO_6 | NGRFHSVYHR | AVVNRDLDRI | SLGYFLGPPP | HAKVAPLREA | 321 |
| SEQ_ID_NO_8 | NGRFHSVYHR | AVVNRDLDRI | SLGYFLGPPP | HAKVAPLREA | 319 |
| SEQ_ID_NO_9 | NGRFHSVYHR | AVVNRDRDRV | SLGYFLGPPP | DAEVAPLPEA | 316 |
| SEQ_ID_NO_10 | NGRFRSPIHR | AVVSRERERI | SVPYFLCPPE | DMTVAPLASA | 323 |
| SEQ_ID_NO_11 | NGRFHSVVHR | AVVNRTEHRY | SAAYLCGPPA | HVKVSPIVKP | 319 |
| SEQ_ID_NO_12 | NGXFPSVVHR | ALVNRTKHRL | SVAYLYGPPA | GVPISPVPKL | 312 |
| SEQ_ID_NO_13 | NGLYPSVLHR | AVVNRSRHRL | SIAYLYGPPA | SVQISPLSKL | 319 |
| SEQ_ID_NO_14 | NGLYPSVLHR | AVVNRTHHRL | SVAYLFGPPQ | SVRISPLERL | 317 |
| SEQ_ID_NO_15 | NGLYPSVLHR | AMVNRTKHRL | SVAYLYGPPS | NVQISPLSKL | 303 |
| SEQ_ID_NO_16 | NGLYPSVLHR | AVVNRTRHRL | SVAYLYGPPS | RVKVSPLAKL | 318 |
| SEQ_ID_NO_17 | NGLYTSVLHR | VLVNRTRQRF | SVAYLYGPPS | NVEICPHEKL | 322 |
| SEQ_ID_NO_18 | NGSYPSVLHR | AVVNRTRHRL | SVAYLYGPPT | GVRVSPLSKL | 319 |
| SEQ_ID_NO_19 | NGRYPSVYHR | AMVNRVQHRL | SVAYLYGPAS | GVRVQPLPKL | 315 |
| SEQ_ID_NO_20 | NGLYPSVLHR | VLVNRTRQRF | SVAYLYGPPS | NVEICPHAKL | 319 |
| SEQ_ID_NO_21 | NGEYQNVFHR | AIVNRSQQRL | SVAYLYGPPL | NVQISPHSKL | 316 |

Figure 4I

```
SEQ_ID_NO_1    LA--GTPAAY RAVTWPEYMG VRKKAFTTGA SALKMVAIST 356
SEQ_ID_NO_2    LA--GTPAAY RAVTWPEYMG VRKKAFTTGA SALKMVAIST 356
SEQ_ID_NO_3    LA--GTPAAY RAVTWPEYMG VRKKAFTTGA SALKMVAIPT 356
SEQ_ID_NO_4    VGRTGGKPAY RAVTWPEYMA VRKKAFTTGA SALKMVAIIT 358
SEQ_ID_NO_6    VPP-GRTPAY RAVTWPEYMG VRKKAFTTGA SALKMVALAA 360
SEQ_ID_NO_8    VPP-GRTPAY RAVTWPEYMG VRKKAFTTGA SALKMVAAAA 358
SEQ_ID_NO_9    VPA-GRSPAY RAVTWPEYMA VRKKAFATGG SALKMVSTDA 355
SEQ_ID_NO_10   LLP-GRKAVF RAVTWPEYME VKHKVFGTDA PALEMLQLQV 362
SEQ_ID_NO_11   VG-----PAY RPITWREYLG IKARLFDKAL ASVLISEE-- 352
SEQ_ID_NO_12   VDS-THPPLY RPVTWSEYLC TKAKHFDKAL SLVRLCMPRN 351
SEQ_ID_NO_13   LGP-SQPPLY RPITWNEYLG TKAKHFNKAL SSVRLCAPLN 358
SEQ_ID_NO_14   VDP-DHPALY RPISWTEYLS TKAKHFNKAL SSVRLCGPPV 356
SEQ_ID_NO_15   TDQ-VHPPLY RPVTWSEYLG TKAKHFNKAL SSVRVCAPLN 342
SEQ_ID_NO_16   VDQ-RHPPLY RAVTWSEYLG TKARHFDKAL SSVRLCAPLS 357
SEQ_ID_NO_17   VGP-TQPPLY RSVTWNEYLG TKAKHFNKAL SSVSLCAPIN 361
SEQ_ID_NO_18   LDH-RHPPLY RAVTWSEYLG TKAKYFDKAL SSVRLCVPLS 358
SEQ_ID_NO_19   IDA-THPPLY RPVTWSEYLG IKSEHLTKAL SLIRINHNTN 354
SEQ_ID_NO_20   IGP-TKPPLY RSVTWNEYLG TKAKHFNKAL SSVRLCTPIN 358
SEQ_ID_NO_21   VTP-SHPSLY RPVTWKEYLG LEGKLYNKAL SSIKFHDHQ- 354
```

Figure 4J

```
SEQ_ID_NO_287    MAVLSKP-VA I---------- ---P-K--SG F-S--LIPVI   21
SEQ_ID_NO_288    MVVLSKP--T IADFPPIL-- NCKS-T--TL F-P--VIPTV   30
SEQ_ID_NO_290    MVLVPKP--A LQQFSFIR-- NIKP-T--TF F-S--GIPLI   30
SEQ_ID_NO_291    MVILSKP--A LEQFSCLR-- NKQA-A--TL FPP--LIPLV   31
SEQ_ID_NO_292    MAAASSF--S ---------- -----A--AF Y-S--GIPLI   18
SEQ_ID_NO_293    MVVLSQT--A LDHYSSMK-- TCRP-AN-GL F-T--GIPVI   31
SEQ_ID_NO_294    MVVLSKP--E IQQLSS---- ---------SS S-S--GVPLI   23
SEQ_ID_NO_295    MVFVTKS--A SEHFSYPR-- TSTKVS--KL F-S--GIPLV   31
SEQ_ID_NO_296    MVALSKP--S IEQFFMKPSK PNTN-P--LI F-P--TIPLI   32
SEQ_ID_NO_297    MVVLSKF--S S----VVK-- TCKP-P--AL F-PAGAVPLI   28
SEQ_ID_NO_298    MVVLTKP--G IDHFPIVK-- NCKL-S--SF F-N--GVPLI   30
SEQ_ID_NO_299    MVVLSQT--A LDHFSLIK-- TCKPSS--GL F-N--GIPVI   31
SEQ_ID_NO_300    MVTVSKP--I LEQFLVKP-- NTS--P--LV I-P--DIPLI   29
SEQ_ID_NO_301    MVVLTEP--D NDHLPIINSN SCKS-P--SF F-N--DIPVI   32
SEQ_ID_NO_303    MVVLSQP--A LNQFFLLK-- TCKP-T--PL F-A--GIPVV   30
SEQ_ID_NO_305    MVVLSQL--A LEPFSVIK-- TCKP-I--GL F-S--EIPVI   30
SEQ_ID_NO_306    MVVLTNT--T LERITLPV-- APKP-S--TY F-S--GIPVI   30
SEQ_ID_NO_308    MVVLAST-PA VDHIPLLR-- SPDP-G--DY F-S--GMPVV   31
SEQ_ID_NO_309    MVVLAGT-PA VDHIPLLR-- SPDP-G--DN F-S--GMPVV   31
SEQ_ID_NO_310    MVVLAGP-PA VDHIPLLR-- SPDP-G--DV F-S--GVPVV   31
SEQ_ID_NO_311    MVVLAKP-AA LEQISLLR-- TPEP-W--ET F-S--GVPAV   31
SEQ_ID_NO_313    MVVLAKPPPA LDQISLLR-- CPQP-GDAAS F-E--GVPAV   34
SEQ_ID_NO_314    MVVLSQP-VE HVNFPALK-- S--C-N--GN S-T--HLPVV   29
```

Figure 5A

```
SEQ_ID_NO_287  DMSDPESKHA LVKACEDFGF FKVI NHGVSA ELVSVLEHET  61
SEQ_ID_NO_288  DLSEPDSKHL VVKSCEEFGF FKVI NHGI PL ELI SRLETEV  70
SEQ_ID_NO_290  DLSKPDSKHL LVKACEEFGF FKVVNHGVPL EFI SKLESEA  70
SEQ_ID_NO_291  DLSKPDSRQQ I I KACEEFGF FKVI NHGVPM DFI SRLESEA  71
SEQ_ID_NO_292  DLSAPDAKQL I VKACEELGF FKVVKHGVPM ELI SSLESES  58
SEQ_ID_NO_293  DLKDPEAKTR I VEACQEFGF FKLVNHGVPF EFMTRLEYLA  71
SEQ_ID_NO_294  DLSAPDAKHL I VKACEELGF FKVI NHGVPM EFI STLESES  63
SEQ_ID_NO_295  DLTKPDSKQL I VNACEEYGF FKI I NHGVPM DFI TRLESEA  71
SEQ_ID_NO_296  DLSKPESKQH LVKACQDFGF FKVVNHGVPT KFI KKLESEA  72
SEQ_ID_NO_297  DLSKPDSKHL LVKACEEFGF FKVVNHGVPS DFI STLESEA  68
SEQ_ID_NO_298  DLSKPNSKNL I VKACEEFGF FKVI NHSVPT EFI TKLESEA  70
SEQ_ID_NO_299  DLTDPEAKNL LVQACQEFGF FKLVNHGVPI DFMTRLESLA  71
SEQ_ID_NO_300  DLSKPESKQH LVKACQDFGF FKVVNHGVPL KFI NKLESEA  69
SEQ_ID_NO_301  DLSKPDSKNL I VEACEEFGF FKVVNHDVPI EFI SKLESEA  72
SEQ_ID_NO_303  DLTDPDAKTH I VNACRDFGF FKLVNHGVPL QFMANLENET  70
SEQ_ID_NO_305  DLTDPHAKTL I I KACEEFGF FKLVNHGVPM EVMTKLEALA  70
SEQ_ID_NO_306  NLAQPGSETL LVRACEELGF FKVTNHGI PM ELI ARLEEEA  70
SEQ_ID_NO_308  DLSSPGAPRA I ADACERFGF FKLVNHGVPA DTMDRLESEA  71
SEQ_ID_NO_309  DLSRPGAPRA I ADACERFGF FKLVNHGVAL DAMDRLESEA  71
SEQ_ID_NO_310  DLGSPGAARA VVDACERYGF FKVVNHGVAT DTMDKAESEA  71
SEQ_ID_NO_311  DLSGPDAAGD VVRACEQFGF FSVVNHGVPA GVVDRLEAEA  71
SEQ_ID_NO_313  DLSSPGAALA VVDACERFGF FKVVNHGVPT GVVDRLEAEA  74
SEQ_ID_NO_314  DLSNPDAKTQ I VNACQEFGF FKVI NHGVPM EI VTKLEAQA  69
```

Figure 5B

```
SEQ_ID_NO_287   VDFFSLPKSE  KTQVA---GY  PFGYGNSKIG  RNGDVGWWEY   98
SEQ_ID_NO_288   IEFFSLSLSE  KQKAGP--PD  PFGYGNRSIG  PNGDVGWWEY  108
SEQ_ID_NO_290   VKFFSLPLSE  KEKASP--PN  PFGYGKKSIG  QNGDVGWWEY  108
SEQ_ID_NO_291   TKFFSLPLSE  KEKTGQ--PK  PYGYGNKRIG  PNGDVGWWEY  109
SEQ_ID_NO_292   TKFFSLPLSE  KQRAGP--PS  PFGYGNKQIG  RNGDVGWWEY   96
SEQ_ID_NO_293   MNFFNLPQSE  KDKAGP--PD  PFGYGNKRIG  PNGDVGWIEY  109
SEQ_ID_NO_294   TKFFSLPLSE  KQRAGP--PS  PFGYGNKQIG  RNGDVGWWEY  101
SEQ_ID_NO_295   IKFFSLPLSE  KEKSGP--PN  PLGYGNKHIG  KNGDVGWWEY  109
SEQ_ID_NO_296   LKFFSSPLST  KEKAGP--PD  PFGYGNKRIG  RNGDVGWWEY  110
SEQ_ID_NO_297   LRFFSSPLSE  KLKAGP--PD  PFGYGNKNVG  ACGDIGWWEY  106
SEQ_ID_NO_298   IKFFSSPLSE  KQKAGP--AD  PFGYGNKKIG  PNGDVGWWEY  108
SEQ_ID_NO_299   INFFNLPQSE  KDKAGP--PD  PFGYGNKRIG  PNGDIGWIEY  109
SEQ_ID_NO_300   VNFFNSPLAT  KEKFGP--PD  PFGYGNKCIG  RNGDVGWWEY  107
SEQ_ID_NO_301   IKFFSSPLSE  KLKAGP--AD  PFGYGNKQIG  QSGDIGWWEY  110
SEQ_ID_NO_303   LGFFKKPQSE  KDRAGP--PD  PFGYGSKRIG  PNGDVGWWEY  108
SEQ_ID_NO_305   TNFFNLPQPE  KDKAGP--PN  PFGYGNKKIG  PNGDVGWWEY  108
SEQ_ID_NO_306   VKFFSLAQVE  KERAGT--GN  PFGYGNKTIG  HTGDVGWWEY  108
SEQ_ID_NO_308   VRFFSLPQAD  KDRSGP--AY  PFGYGSKRIG  LNGDMGWLEY  109
SEQ_ID_NO_309   VRFFSLPQAD  KDRSGP--AY  PFGYGSKRIG  LNGDMGWLEY  109
SEQ_ID_NO_310   VRFFSQTQPD  KDRSGP--AY  PFGYGSKRIG  FNGDMGWLEY  109
SEQ_ID_NO_311   VRFFGSSPAV  KDASAPAGAD  PFGYGSKRIG  RNGDMGWLEY  111
SEQ_ID_NO_313   VRFFASPQAD  KDACGP--AN  PLGYGNKRIG  RNGDMGWLEY  112
SEQ_ID_NO_314   LSFFKQPQNH  KNKA-----A  PFGYGNKNIG  RKGDTGWWEY  104
```

Figure 5C

```
SEQ_ID_NO_287   LLMNANH- DS GSGPLFPSLL -KSPGTFRNA LEEYITSVRK   136
SEQ_ID_NO_288   LLLTMNQ- ER NSQKLATIFG -KYPEKLCSA LNDYVLAVKK   146
SEQ_ID_NO_290   LLLTTNQ- ES VSQRLSSVFG -DNPEKFRCA LNDYVSAVKK   146
SEQ_ID_NO_291   LLLTTNQ- DP N-----LLGT -ENPESFRLA LDNYMAAVKK   142
SEQ_ID_NO_292   LLLNTHL- ES NSDGFLSMFG -QDPQKLRSA VNDYISAVRN   134
SEQ_ID_NO_293   LLLNTNP- QV NCNKTLSIFQ -EYPQNFRSA VEDYILEVKR   147
SEQ_ID_NO_294   LLLQSNS- HA F----LSIFG -QDPQKLRSA LNDYIWAVRN   135
SEQ_ID_NO_295   LLLTTNT- ES ISQRFLSVFG -NNAEEFCSA LNDYVSAVKK   147
SEQ_ID_NO_296   LLLNAKP- ES DYQRYLSVFE -ENPEIFQGV VNDYVTAVKK   148
SEQ_ID_NO_297   ILLSTRHP QL NFQKFSSIMG -LSPENLRTA VNEYVTAVKR   145
SEQ_ID_NO_298   ILLSTNS- EF NYHKFASILG -VNPETIRAA VNDYVSAVKK   146
SEQ_ID_NO_299   LLLNTNP- QI TSQTTLSIFK -ENPQIFRSA VEDYLLAVKK   147
SEQ_ID_NO_300   LLLNAKP- ES ---------- -DYPENFQGI VNDYATSVKA   135
SEQ_ID_NO_301   ILLSTNS- EF NYQKFASVLG -VNPENIRAA VNDYVTAVKR   148
SEQ_ID_NO_303   LLLNTNP- DV ISPKSQFIFR -EGPQNFRAV VEEYIRAVKN   146
SEQ_ID_NO_305   LLLNTNP- QI SSQKT-SIFQ -ENPQIFRSA VEDYILAVKR   145
SEQ_ID_NO_306   LLFDVTS- KP MSHTALAFLE EPSASSLCSA LNEYVSAMRK   147
SEQ_ID_NO_308   LLLAVES- AS LSGA-CTV-- -PSCALFRAA LNEYIAAVRK   144
SEQ_ID_NO_309   LLLAVDS- AS LPAA-SAV-- -PSCALFRAA LNEYIAAVRK   144
SEQ_ID_NO_310   LLLALDD- AS LADA-CTV-- -PSCAVFRAA LNEYISGVRK   144
SEQ_ID_NO_311   LLLAIDR- DA LSEKASRA-- -ATSTALRDA INEYVVAMRG   147
SEQ_ID_NO_313   LLLALDG- AS SVSKASPV-- --PSSSLRDA VNQYVAAVRG   147
SEQ_ID_NO_314   LLFGTDT- QL ISQNSLTI-- --LPNDFWAM VNKYLSAVKN   139
```

Figure 5D

| | | | | | |
|---|---|---|---|---|---|
| SEQ_ID_NO_287 | MTFDVLEKIT | DGLGIKPRNT | LSKLVSDQNT | DSILRLNHYP | 176 |
| SEQ_ID_NO_288 | MACELLELMA | DGLRIKPRNV | FSKLLMDEQS | DSVFRLNHYP | 186 |
| SEQ_ID_NO_290 | MACEILEMMA | DGLKIQNRNV | FSKLLMDEQS | DSVFRLNHYP | 186 |
| SEQ_ID_NO_291 | MACEILEMIA | DGLKIQPRNV | LSKLMMDEQS | DSVFRLNHYP | 182 |
| SEQ_ID_NO_292 | MAGEILELMA | EGLKIQQRNV | FSKLVMDEQS | DSVFRVNHYP | 174 |
| SEQ_ID_NO_293 | MTYEVLELMA | DGLGIEPRNV | LSKLVSDEKS | DSCFRLNYYP | 187 |
| SEQ_ID_NO_294 | MACEIVELMA | EGLKIQQRNA | LSKLLMGEES | DSVFRVNHYP | 175 |
| SEQ_ID_NO_295 | MTCEILELMS | EGLKIQPRNV | FSKLLMDEQS | DSCFRLNHYP | 187 |
| SEQ_ID_NO_296 | MACEILELLA | DEMKLQPRNV | FSKLLMDEQS | DSVFRVNHYL | 188 |
| SEQ_ID_NO_297 | MACEILELLA | DGLKIHPRNV | FSKLLMDEQS | DSVFRLNHYP | 185 |
| SEQ_ID_NO_298 | MACEILEMLA | EGLNIHPRNV | FSKLLMDEKS | DSVFRLNHYP | 186 |
| SEQ_ID_NO_299 | MAYEVLELMA | DGLGIKPRNV | LSRMLKDDKS | DSCFRLNYYP | 187 |
| SEQ_ID_NO_300 | MACEILELLA | DELKLQPRNV | FSKLLKDEQS | DSVFRVNHYP | 175 |
| SEQ_ID_NO_301 | MSCEILEKLA | EGLKIHPTNV | FSKLLKDEKS | DSVFRLNHYP | 188 |
| SEQ_ID_NO_303 | MCYEVLELMA | EGLGITQRNV | LSRLLKDEKS | DSCFRLNHYP | 186 |
| SEQ_ID_NO_305 | MAFEVLELMA | DGLEIESRNV | FSRLLRDDKS | DSCFRLNHYP | 185 |
| SEQ_ID_NO_306 | LVCEVLELMA | EGLRVQPRNI | LSKLVMDEES | DSILRLNHYP | 187 |
| SEQ_ID_NO_308 | VAVRVMEAMA | EGLGIAPVDA | LSAMVTAGGS | DQVFRVNHYP | 184 |
| SEQ_ID_NO_309 | VAVRVMEAMA | EGLGIAQADA | LSAMVAAEGS | DQVFRVNHYP | 184 |
| SEQ_ID_NO_310 | LAVRVMEAMS | EGLGIAQADA | LSALVTAEGS | DQVFRVNHYP | 184 |
| SEQ_ID_NO_311 | LARTVLEMVA | DGLGVSPRGA | LADMVTGDAS | DQVFRLNHYP | 187 |
| SEQ_ID_NO_313 | LATSVLEAVA | EGLGVAPRDA | LSGMVTDAAS | DQVFRINHYP | 187 |
| SEQ_ID_NO_314 | LACEILKLMA | EELNLQPKNV | LSRLLSDKKS | DSFERINHYP | 179 |

Figure 5E

```
SEQ_ID_NO_287    PCPL-SNKK--TN-GGKNVI  GFGEHTDPQI  ISVLRSNNTS    212
SEQ_ID_NO_288    PCSE-LQAS--N---GKNMI  GFGEHTDPQI  ISVLRSNNTS    220
SEQ_ID_NO_290    PCPE-IQAL--K---DHNMI  GFGEHTDPQI  ISVLRSNNTS    220
SEQ_ID_NO_291    PCPEVVQSL--NG-TSSNVI  GFGEHTDPQI  ISVLRSNNTS    219
SEQ_ID_NO_292    PCPD-LQAL--K---GTNMI  GFGEHTDPQI  ISVLRSNNTS    208
SEQ_ID_NO_293    PCPE-LQAL--S---GRNLI  GFGEHTDPQI  ISVLRSNNTT    221
SEQ_ID_NO_294    PCPEELQAL--E---GTNMI  GFGEHTDPQI  ISVLRSNNTS    210
SEQ_ID_NO_295    PCPE-LQGL--SSAGARNVI  GFGEHTDPQI  ISVLRSNNTS    224
SEQ_ID_NO_296    PCPE-FQENERN---GRKLV  GFGEHTDPQI  ISVLRSNNTS    224
SEQ_ID_NO_297    PCPE-L----------GKNLI GFGEHTDPQI  ISVLRSNNAS    215
SEQ_ID_NO_298    PCPE-IQQF--S---DNNLI  GFGEHTDPQI  ISVLRSNNTS    220
SEQ_ID_NO_299    PCPE-LQLQ--PL-SGRNLV  GFGEHTDPQI  ISVLRSNNTT    223
SEQ_ID_NO_300    PCPE-FQEKERN---GSKLV  GFGEHTDPQI  ISVLRSNNTS    211
SEQ_ID_NO_301    PCPD-IQEF--N---AKNLI  GFGEHTDPQI  ISVLRSNNTS    222
SEQ_ID_NO_303    PCPE-VQAL--N---GRNLV  GFGEHTDPQI  ISVLRSNSTS    220
SEQ_ID_NO_305    PCSE-LQAL--S---GGNLI  GFGEHTDPQI  ISVLRSNNTS    219
SEQ_ID_NO_306    PCPH-LPEL------DSSLT  GFGEHTDPQI  ISILRSNNTS    220
SEQ_ID_NO_308    PCHA-LQGL------GCSAT  GFGEHTDPQL  ISVLRSNGTS    217
SEQ_ID_NO_309    PCHA-LQGL------GCSAT  GFGEHTDPQL  ISVLRSNGTS    217
SEQ_ID_NO_310    PCRA-LQGL------GCSVT  GFGEHTDPQL  VSVLRSNGTS    217
SEQ_ID_NO_311    PCPL-LQGL--P--PSCSVT  GFGEHTDPQL  VSILHSNGTA    222
SEQ_ID_NO_313    ACPL-LQRL--P--DSCGVT  GFGEHTDPQL  VSVLRSNGTA    222
SEQ_ID_NO_314    AS-------------DRNEL  GFGEHTDPQI  LSVLRSNNAS    206
```

Figure 5F

```
SEQ_ID_NO_287   GLQINLND--  GSWSVPPDH  TSFFFNVGDS  LQVMTNGRFK  250
SEQ_ID_NO_288   GLQISLGN--  GSWSVPPDA  NSFFINVGDS  LQVMTNGRFK  258
SEQ_ID_NO_290   GLQISLND--  GSWSVPPDP  SSFFINVGDS  LQVMTNGRFK  258
SEQ_ID_NO_291   GLQISLRD--  GTWSVPPDQ  YSFFINVGDS  LQVMTNGRFK  257
SEQ_ID_NO_292   GFQISLAD--  GNWSVPPDH  SSFFINVGDS  LQVMTNGRFK  246
SEQ_ID_NO_293   GLQICLRD--  GTWWSVPPDQ TSFFINIGDA  LQVMTNGRFR  259
SEQ_ID_NO_294   GLQISLPD--  ANWSVPPDQ  TSFFINVGDS  LQVMTNGRFK  248
SEQ_ID_NO_295   GLQISLRD--  GSWSVPPDQ  NSFFINVGDS  LQVLTNGRFE  262
SEQ_ID_NO_296   GLEISLRD--  GSWMSVPADS DSFFINVGDS  LQVMTNGRFK  262
SEQ_ID_NO_297   GLQIALND--  GSWMSVPPDQ HSFFINVGDS  LQVMANGRFK  253
SEQ_ID_NO_298   GLQILLKN--  GHWSVPPDP  NSFFINVGDS  LQVMTNGRFK  258
SEQ_ID_NO_299   GLQICLRD--  GTWWSVPPDQ TSFFINVGDA  LQVMTNGRFK  261
SEQ_ID_NO_300   GLEISLRD--  GSWMSVPPDS ESFFINVGDS  LQVMTNGRFK  249
SEQ_ID_NO_301   GLQILLKN--  GNWFSVPPDQ SSFFVNVGDS  LQVMTNGRFK  260
SEQ_ID_NO_303   GLQICLTD--  GTWWSVPPDQ TSFFINVGDT  LQVMTNGRFK  258
SEQ_ID_NO_305   GLQICLKE--  GTWWSVPPDQ TSFFINVGDA  LQVMTNGRFR  257
SEQ_ID_NO_306   GLQIYLRD--  GSWWTVPPDQ DSFFINVGDS  LQVLTNGRFR  258
SEQ_ID_NO_308   GLQIALQN--  GQWWSVPSDR DAFFVNVGDS  LQVLTNGRFK  255
SEQ_ID_NO_309   GLQIALQS--  GHWWSVPSDR DAFFVNVGDS  LQVLTNRRFK  255
SEQ_ID_NO_310   GLQIALRD--  GQWWSVPSDR DSFFVNVGDS  LQVLTNGRFK  255
SEQ_ID_NO_311   GLQVALHD--  GRWWSVPPNR DAFFVNVGDS  LQVLTNGRLK  260
SEQ_ID_NO_313   GLQVALHDDG  GRWWPVPPDR DAFFVIVGDS  LQVLTNGRLK  262
SEQ_ID_NO_314   GLEIALKD--  GTWTQVPADP SSFFITVDDC  LQVMTNGRFR  244
```

Figure 5G

```
SEQ_ID_NO_287   SVRHRVLANC -KKSRVSMIY FAGPSLTQRI APLTCLIDNE   289
SEQ_ID_NO_288   SVRHRVLANS -IKSRISMIY FGGPPLNEKI APLPSLVE-G   296
SEQ_ID_NO_290   SVRHRVLANS -IKARISMIY FGGPPLREKI APLPSLME-G   296
SEQ_ID_NO_291   SVKHRVLANS -VKSRLSMIY FCGPPLSEKI APLPSLMRGD   296
SEQ_ID_NO_292   SVKHRVLTNS -SKSRVSMIY FGGPPLSEKI APLASLMQGE   285
SEQ_ID_NO_293   SVKHRVLADD -MKSRISMIY FGGPPLSEKI APFPSLLAEG   298
SEQ_ID_NO_294   SVKHRVLTNS -LKSRISMIY FGGPPLSEKI APLPSLMKG-   286
SEQ_ID_NO_295   SVRHRVLANG -LKSRLSMIY FGGPPLSEKI APLQSVMNGE   301
SEQ_ID_NO_296   SVKHRVVANS -TKSRVSMIY FGGPPLSEKI APLPSLIQGE   301
SEQ_ID_NO_297   SVRHRVLSNS -AKSRLSMIY FGGPPLSEKI APLPSLMEAE   292
SEQ_ID_NO_298   SVRHRVLANS -VKSRLSMIY FGGPPLSEKI APLASLME-G   296
SEQ_ID_NO_299   SVKHRVLADT -MRSRISMIY FGGPPLSEKI APLPSVLREG   300
SEQ_ID_NO_300   SVKHRVVANG -TKSRVSMIY FGGPPLSEKI APLPSLMQGE   288
SEQ_ID_NO_301   SVKHRVLTNS -VKSRLSMIY FGGPPLSEKI APLPSLMEGE   299
SEQ_ID_NO_303   SVKHRVLADP -TKSRLSMIY FGGPPLCEKI APLPSLMLKG   297
SEQ_ID_NO_305   SVKHRVLADP -LKPRISMIF FGGPPLSEKI APLPSLMAER   296
SEQ_ID_NO_306   SVKHRVLAHG -LKSRVSMIY FGGPPSGERL APLPLLMGEG   297
SEQ_ID_NO_308   SVKHRVVANS -LKSRVSMIY FGGPAMTQRI APLPQLLGAG   294
SEQ_ID_NO_309   SVKHRVVANS -LKSRVSMIY FGGPALTQRI APLPQLLREG   294
SEQ_ID_NO_310   SVKHRVVANS -LKSRVSFIY FGGPPLAQRI APLPQLLGEG   294
SEQ_ID_NO_311   SVRHRVVAGS GLKSRVSMIY FGGPPLAQRI APLPQLLAG-   299
SEQ_ID_NO_313   SVRHRVVANS -LKPRVSMIY FAGPAPAQRI APLPQVLGHG   301
SEQ_ID_NO_314   SVKHRVITES -LKERLSMIY FGGPPLSEKI APSTSLMQG-   282
```

Figure 5H 329
332
332
332
321
339
322
337
337
328
332
321
324
335
333
332
329
326
326
327
341
334
317

```
SEQ_ID_NO_1429    ----RKG-SV VPLANPPDSL -FGTGKTRRS FVKLSREILA    73
SEQ_ID_NO_1430    ----RKG-SV VPLANPPESL -FGTGKTRRS FVKLSREILA    68
SEQ_ID_NO_1431    RWSLDSL-KH LPIVNNKEWY SLSGRKAKLR FLAESKSLLE    75
SEQ_ID_NO_1432    ---RSAF-DA LPIVNKPKFG PIFSILARWR FIHQSKKILE    80
SEQ_ID_NO_1433    ---RAHL-KH LPLLNPSKGL PLFNIESKRE FVFNSKELLA    78
SEQ_ID_NO_1434    ----SK--PN APCLNPQGFF DIASGRAKKQ FLFGLRSMLK    77
SEQ_ID_NO_1435    ----RFP-KN IKHLNPKGPL EFSDTRPKKE FVYGSRQMLA    85
SEQ_ID_NO_1436    ---GPKP-TV LPVVNPPGTF ELTANRVKKE WLVDARQIIR    98
SEQ_ID_NO_1437    ----DFPHTD YPLQNPRKFW DVTAWKSKWD FIFGVRKILE   100
SEQ_ID_NO_1438    ----RFP-KN IKHLNPKGPL EFSDTRPKKE FVHGSRPMLA    85
SEQ_ID_NO_1439    ----KAA-GH IPLVNPPKFY DIGAIWAKID CILHARRLLA    78

SEQ_ID_NO_1429    KARSLFPNEP FRLI-TDWGE VLILPPDFAD EIRNDPRLSF   112
SEQ_ID_NO_1430    KARNLFPDEP FRLI-TDWGE VLILPPEFAD EIRNDPRLSF   107
SEQ_ID_NO_1431    EARKRYPQQP FRIL-SNWGV LLVLPSCFAD EIRNDQRLSF   114
SEQ_ID_NO_1432    EGQKCYSNRP FRIW-TDWGE VLMLTPDYAH EIRNDPHLSF   119
SEQ_ID_NO_1433    KGRKLFPKSP YRMI-TDLGE IVFLPVEQTD EIRNDPRLSF   117
SEQ_ID_NO_1434    TWFDANPHKP ASVF-SDIGP MTVLPPSMAN EIRSDPRLSF   116
SEQ_ID_NO_1435    NWFKANPNKP CRVI-SDFGE AIVLPPRMAN EIKNDDRLSF   124
SEQ_ID_NO_1436    RGFEKFPGKP FNMIAADVGL TTVLPPEYAS EIRNNPSLSF   138
SEQ_ID_NO_1437    KRIAEAPDQP YRIL-TDFGD MTILPPDYAN EIRNSDDLSF   139
SEQ_ID_NO_1438    NWFKANPNKP CRVI-SDFGE AIVLPPRMAN EIKNDDRLSF   124
SEQ_ID_NO_1439    RGV--SSGRP FRLL-TDLGE MIVLPAHFAT EIRSDPRLSF   115
```

Figure 6B

```
SEQ_ID_NO_1429   SKAAMQDNHA GIPGFETVAL VGREDQLIQK VARKQLTKHL   152
SEQ_ID_NO_1430   SKAAMQDNHA GIPGFETVAL VGREDQLIQK VARKQLTKHL   147
SEQ_ID_NO_1431   SKAALQDSHG HIPGLETVKL VARDDQLIQT VARKHLTKHL   154
SEQ_ID_NO_1432   SGAVKIDGHA DIPGFETVKL ISHPDNLIQL VARKQLTRHL   159
SEQ_ID_NO_1433   GSAFGEDFHG HLPGFQGAAV DSYDDAVLQT LVRKQLTKCI   157
SEQ_ID_NO_1434   VEFSAKFFHT SIPGFEAFNE GTRD-SITLT VINKDLTKRL   155
SEQ_ID_NO_1435   TRWTYKAFHG HLPGFEGFGE ASRESHIVQE VIMRDLTKYL   164
SEQ_ID_NO_1436   VAFMAHLFFS ELPGFEPTRE GMFDNDIGIT VVHKYLTVNL   178
SEQ_ID_NO_1437   DRVVEKNFQA HLPGLDVFKE ENLHKTVLRH VIRTRLTQFL   179
SEQ_ID_NO_1438   TRWTYKAFHG HLPGFEGFGE VSRESHIVQE VIMRDLTKYL   164
SEQ_ID_NO_1439   AEVIEQNFHS RFPGFEGFRM GTTDAHLSRD IANNQLTHTL   155

SEQ_ID_NO_1429   SAVIEPLSRE STLAVSLNFG E--TTEWRAI RLKPAILDII   190
SEQ_ID_NO_1430   S--------- ---------- ---------- -----ILDII   153
SEQ_ID_NO_1431   AKVIQPLSEE TEFALDQNFG H--N------ ---PAILDII   183
SEQ_ID_NO_1432   AAVIQPLSSV TEEALIKNLG K--SQEWSEI YLKYAVLDII   197
SEQ_ID_NO_1433   AQIIEPVSAE AAQALADKFG D--SEDWREM EVKSVVLDTV   195
SEQ_ID_NO_1434   AQVTQPLAEE TTLAMQEIFT D--NKEWHLI NVREKILHLV   193
SEQ_ID_NO_1435   NKVTEPLAQE TSMAMEANLP KAANGEWSTI NLRSKILPIV   204
SEQ_ID_NO_1436   ARITEPLSRE ATAALKDIFT D--NSEWHDA NLKAINLALV   216
SEQ_ID_NO_1437   SKVTAPLSNE TALTLQDVFT D--QKEWHTI ILKDEIVKIV   217
SEQ_ID_NO_1438   NKVTEPLAQE TSMAMEAILP KAANGEWSTI NLRSKILPIV   204
SEQ_ID_NO_1439   AKVTEALSEE CTAAMTDHFP A--TKEWAEI CLREHVLQLV   193
```

Figure 6C

Figure 6D
SEQ_ID_NO_1429 ARISSRIYLG DQLCRNEAWL KITKTYTTNF YTASTNLRMF 230
SEQ_ID_NO_1430 ARISSRIYLG DQLCRNEAWL KITKTYTTNF YTASTNLRMF 193
SEQ_ID_NO_1431 ARISSRIYLG DELCRNTAWL ATTKVYTSAF FAAPVKLGLI 223
SEQ_ID_NO_1432 ARLSSRIYFG ELLYQNEEWL SIVKNYATHF FTASSDLRKV 237
SEQ_ID_NO_1433 ARLSARVFLG EELCRNEDWL RATKEYTVNF FVAGTHLRMI 235
SEQ_ID_NO_1434 ARISSRVFLG EELCRDEAWL KITREHAMNG FVAADLLRAW 233
SEQ_ID_NO_1435 ARISSRVFLG EELCRNEEWL KVTQQYTIDG FGAAEDLRLW 244
SEQ_ID_NO_1436 ARLSSRIFLG EELCRNEEWL KITVNYTVDV MKAAERLRRV 256
SEQ_ID_NO_1437 SRISARVFTG EILCRNPEWQ KITADYAMTC FLAADMVRMF 257
SEQ_ID_NO_1438 ARISSRVFLG EELCRNVEWL KVTQQYTIDG FGAAEDLRLW 244
SEQ_ID_NO_1439 ARLSSRVFLG DAGANNSAWL RITTEYTKTA YIAAYLLRLW 233
SEQ_ID_NO_1429 PRSIRPLAHW FLPECRKLRQ ERKDAIGIIT PLIERRRELR 270
SEQ_ID_NO_1430 PRSIRPLAHW FLPECRKLRQ ERKDAVGIIT PLIERRRELR 233
SEQ_ID_NO_1431 PAPLRRLAHW LIPECKILRE QVQEARRIIE PLVRRRQALR 263
SEQ_ID_NO_1432 PWAFRSLVHW FVPSCRALRL ERYNARRVLE PVISQRRQLK 277
SEQ_ID_NO_1433 PRPLRRVLHW FVPKCRELRA SFDEARRIIL PYIEKRRAAR 275
SEQ_ID_NO_1434 PEALRPVVSW FMPHCRTARS QIREAEKIIG PVISKRREAK 273
SEQ_ID_NO_1435 PAALRPIVHW FLPSCQRARA DVRVARSILD PVLKKRRQEK 284
SEQ_ID_NO_1436 PGPLRRIVHW FLPEAQKCRD EVKRAGKVIR PVLEKRRREK 296
SEQ_ID_NO_1437 PKPIRPLVHR ILPLSIKVRS DVKKARAIVE PVLAERKKIK 297
SEQ_ID_NO_1438 PAALRPIVHW FLPSCQRARA DVRVARSILD PVLKKRRQEK 284
SEQ_ID_NO_1439 PPVLRPFVHW FIPHCRKLRA QVAEARHIIV GIIEQRHQGR 273

| Sequence | | | | | |
|---|---|---|---|---|---|
| SEQ_ID_NO_1429 | RAAIAAGQPL | PVFHDAIDWS | EQEAEAAGTG | ASFDPVIFQL | 310 |
| SEQ_ID_NO_1430 | RAAIAAGQPL | PVFHDAIDWS | EQEAEAAGSG | SAFDPVIFQL | 273 |
| SEQ_ID_NO_1431 | AKALAEGCPT | PQFNDALGWA | AEESA--KNG | KDYDPAITQL | 301 |
| SEQ_ID_NO_1432 | EAAKTAGGTP | LHFEDAIEWA | EVEAR--VKG | TKYDPVIFQL | 315 |
| SEQ_ID_NO_1433 | AAALAAGKKI | PEFHDAIDWA | DQEAA--ARG | VTYDPAILQL | 313 |
| SEQ_ID_NO_1434 | DAALRAGREA | PIHNDAIEWF | EQAS----KG | KPYNPALSQL | 309 |
| SEQ_ID_NO_1435 | AAN--GG--K | AEHDDAIEWF | ERTA----KG | KYYDPAVAQL | 316 |
| SEQ_ID_NO_1436 | ATMESEGKEA | LQYNDAIEWF | EQMAK--SQG | TSYDPEVVQL | 334 |
| SEQ_ID_NO_1437 | EEARRRGEPI | PKFDDAIEWC | EEIE----QD | VGFDMATFQL | 333 |
| SEQ_ID_NO_1438 | AAN--GG--K | AQHDDAIEWF | ERTA----KG | EYYDPAVAQL | 316 |
| SEQ_ID_NO_1439 | VAAELASQPV | PQYNDAIEWF | EQDFAV-TRD | GRHDPAVAQL | 312 |

| Sequence | | | | | |
|---|---|---|---|---|---|
| SEQ_ID_NO_1429 | TLSLLAIHTT | YDLLQQTMID | LGRHPEYIEP | LRQEVVQLLR | 350 |
| SEQ_ID_NO_1430 | TLSLLAIHTT | YDLLQQTMID | LGRHPEYIEP | LRQEVVQLLR | 313 |
| SEQ_ID_NO_1431 | ALSMLAIHTT | YDLFQQCILD | LAQNPHFIEP | LRQEAIEVIQ | 341 |
| SEQ_ID_NO_1432 | TLSLLAIHTT | YDLLEMCMID | LAKRPDCIED | LRKEVITVLR | 355 |
| SEQ_ID_NO_1433 | MLAVAAIHTT | ADLVTEIVLQ | LALHPEHFGP | LRGEVLHILR | 353 |
| SEQ_ID_NO_1434 | FLSTVAIHTT | TDLLCQTMID | IARHPEYFEP | LREEVTRVLA | 349 |
| SEQ_ID_NO_1435 | VLSLVAIHTT | SDLTCQVMTN | LMQNPEFIAP | LREEMIQVLS | 356 |
| SEQ_ID_NO_1436 | FLSTVAIHTT | SDLLTVVMAD | LARNPELIEP | LREEISSVLR | 374 |
| SEQ_ID_NO_1437 | AMAVAAIHTT | SDFLTQILLD | LAQHPEYIEP | LRAEIAAVLK | 373 |
| SEQ_ID_NO_1438 | VLSLVAIHTT | SDLTCQVMTN | LMQNPEFIGP | LREEMIRVLS | 356 |
| SEQ_ID_NO_1439 | ILAQAAIETT | TDLLTQVILD | LAQHPELIGT | LREEVAGAIQ | 352 |

Figure 6E

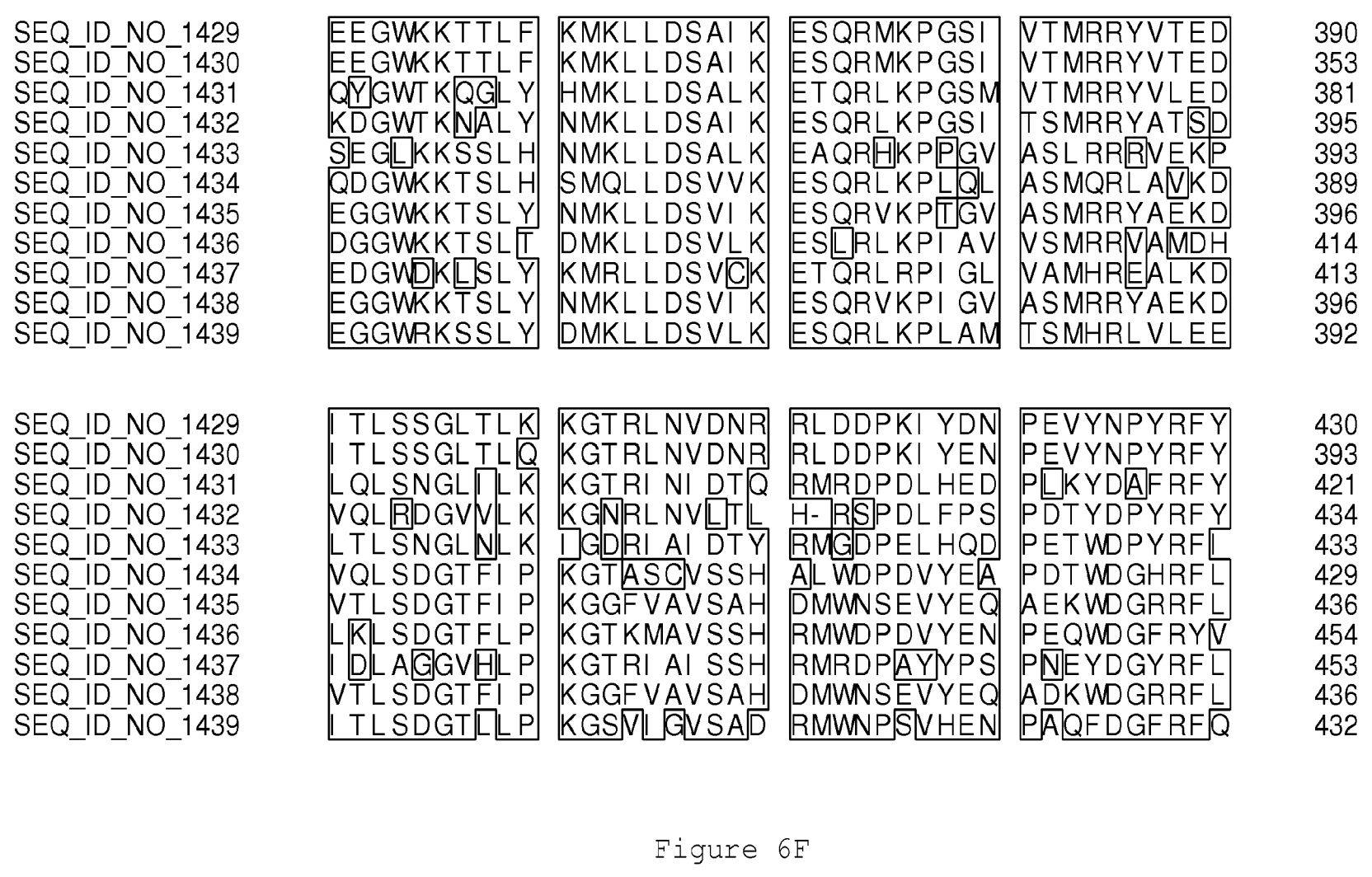

```
SEQ_ID_NO_1429    EEGWKKTTLF KMKLLDSAIK ESQRMKPGSI VTMRRYVTED   390
SEQ_ID_NO_1430    EEGWKKTTLF KMKLLDSAIK ESQRMKPGSI VTMRRYVTED   353
SEQ_ID_NO_1431    QYGWTKQGLY HMKLLDSALK ETQRLKPGSM VTMRRYVLED   381
SEQ_ID_NO_1432    KDGWTKNALY NMKLLDSAIK ESQRLKPGSI TSMRRYATSD   395
SEQ_ID_NO_1433    SEGLKKSSLH NMKLLDSALK EAQRHKPPGV ASLRRRVEKP   393
SEQ_ID_NO_1434    QDGWKKTSLH SMQLLDSVVK ESQRLKPLQL ASMQRLAVKD   389
SEQ_ID_NO_1435    EGGWKKTSLY NMKLLDSVIK ESQRVKPTGV ASMRRYAEKD   396
SEQ_ID_NO_1436    DGGWKKTSLT DMKLLDSVLK ESLRLKPIAV VSMRRVAMDH   414
SEQ_ID_NO_1437    EDGWDKLSLY KMRLLDSVCK ETQRLRPIGL VAMHREALKD   413
SEQ_ID_NO_1438    EGGWKKTSLY NMKLLDSVIK ESQRVKPIGV ASMRRYAEKD   396
SEQ_ID_NO_1439    EGGWRKSSLY DMKLLDSVLK ESQRLKPLAM TSMHRLVLEE   392

SEQ_ID_NO_1429    ITLSSGLTLK KGTRLNVDNR RLDDPKIYDN PEVYNPYRFY   430
SEQ_ID_NO_1430    ITLSSGLTLQ KGTRLNVDNR RLDDPKIYEN PEVYNPYRFY   393
SEQ_ID_NO_1431    LQLSNGLILK KGTRINIDTQ RMRDPDLHED PLKYDAFRFY   421
SEQ_ID_NO_1432    VQLRDGVVLK KGNRLNVLTL H-RSPDLFPS PDTYDPYRFY   434
SEQ_ID_NO_1433    LTLSNGLNLK IGDRIAIDTY RMGDPELHQD PETWDPYRFL   433
SEQ_ID_NO_1434    VQLSDGTFIP KGTASCVSSH ALWDPDVYEA PDTWDGHRFL   429
SEQ_ID_NO_1435    VTLSDGTFIP KGGFVAVSAH DMWNSEVYEQ AEKWDGRRFL   436
SEQ_ID_NO_1436    LKLSDGTFLP KGTKMAVSSH RMWDPDVYEN PEQWDGFRYV   454
SEQ_ID_NO_1437    IDLAGGVHLP KGTRIAISSH RMRDPAYYPS PNEYDGYRFL   453
SEQ_ID_NO_1438    VTLSDGTFIP KGGFVAVSAH DMWNSEVYEQ ADKWDGRRFL   436
SEQ_ID_NO_1439    ITLSDGTLLP KGSVIGVSAD RMWNPSVHEN PAQFDGFRFQ   432
```

Figure 6F

```
SEQ_ID_NO_1429   DMRSEA--GK DHGAQLVSTG SNHMGFGHGQ HSCPGRFFAA   468
SEQ_ID_NO_1430   DMRSEA--GK DHGAQLVSTG SNHMGFGHGQ HSCPGRFFAA   431
SEQ_ID_NO_1431   KMRQQP--GG EHTAQLVSTS PDHLGFGHGE HSCPGRFFAA   459
SEQ_ID_NO_1432   NIRGQP--GK ENWAQLVSTS VEHMGFGHGE HSCPGRFFAA   472
SEQ_ID_NO_1433   RMAEQP--GK ANYAQLVVTS PDHLAFGHGD HACPGRFFAA   471
SEQ_ID_NO_1434   RQRGIP--GK ENFSQLVSTS ENHLGFGHGK HACPGRFFAA   467
SEQ_ID_NO_1435   RMRETPGAGK ENVAQLVSTA PEHLGFGHGQ HACPGRFFAA   476
SEQ_ID_NO_1436   NLRETP--GQ DKHAQFVSTS ERHLGFGHGK HACPGRFFAS   492
SEQ_ID_NO_1437   RMRDELGAGK DGDAHFVTTS PQHLGFGHGK HACPGRFFAS   493
SEQ_ID_NO_1438   RMRETPGAGK ENAAQLVSTA PEHLGFGHGQ HACPGRFFAA   476
SEQ_ID_NO_1439   RMRDQPG-GS TNQAHLVSTS VNHLAFGHGK HACAGRFFVA   471

SEQ_ID_NO_1429   NEIKVALCHI LVKYDWKLCP DT-ETKPDTR GMIAKSSPVT   507
SEQ_ID_NO_1430   NEIKVALCHI LVKYDWKLCP DT-ETKPDTR GMIAKSSPVT   470
SEQ_ID_NO_1431   NEIKVAMAHM LIKYEWKPAG HS-SAGPDVK GLLMKSGAGA   498
SEQ_ID_NO_1432   NEIKVALAHI LVKYDWKLSD EA-GGCTEVK GMVEKAGSKV   511
SEQ_ID_NO_1433   YEIKIIMCHL LLKYEWEALP AT-DVSPMVL GFTNASNPTA   510
SEQ_ID_NO_1434   NEIKIALAHL LLEYEWRLPE GE-ALDVEDF GITPIMNQTL   506
SEQ_ID_NO_1435   NEIKIALVHL LLNYEWRLPE GS-DPKIRTF GFSMGVDPSL   515
SEQ_ID_NO_1436   SELKVALCHI LMKYDFELAP GT-VVQHRYS GASYYADPAI   531
SEQ_ID_NO_1437   NEVKVALCHI LLKYNWRLAP GV-EPKIFQF GLTIGCDPVA   532
SEQ_ID_NO_1438   NEIKIALVHL LLNYEWRLPE GS-DPKIRTF GFSMGVDPSL   515
SEQ_ID_NO_1439   HEAKIALTHL LLKYDWKLAS TSANAKPMEF GLVLQANPKA   511
```

Figure 6G

```
SEQ_ID_NO_1542   MPHKDNLLES PVGKSVTATI AYHSGPALPT SPIAGVTTLQ   40
SEQ_ID_NO_1543   MPHKDTPLES PVGKNVTATI AYHSGPALPT SPIAGVTTLQ   40
SEQ_ID_NO_1544   MPHKDTPLEQ PVGKNVTATI AYHSGPALPT SPIAGVTTLQ   40
SEQ_ID_NO_1545   MSQQDTHHEP PVGKNVTATI AYHSGPALPT SPIAGVTTLE   40

SEQ_ID_NO_1542   DCTQQAVAVT DIRPSVSSFT LDGNGFQVVK HTSAVGSPPY   80
SEQ_ID_NO_1543   DCTQQVVAVT DIRPSVSSFT LDGNGFQVVK HASAVGSPPY   80
SEQ_ID_NO_1544   DCTQQVVAVT DIRPSVSSFT LDGNGFQVVK HTSVVGSPPY   80
SEQ_ID_NO_1545   DCTQQLVAVT DIRPSVSSFT LDGNGFQVVK HISAVSSPPY   80

SEQ_ID_NO_1542   DHSSWTDPVV RKEVYDPEII ELAKSLTGAK KVMILLASSR   120
SEQ_ID_NO_1543   NHSSWTDPVV RKEVYDPEII ELAKSLTGAK KVMILLASSR   120
SEQ_ID_NO_1544   DHSSWTDPVV RKEVYDPEII ELAKSLTGAK KVMILLASSR   120
SEQ_ID_NO_1545   DHSSWTGPVV RKEVYDPEII ELAKSVTGAK KVMILLASSR   120

SEQ_ID_NO_1542   NVPFKEPELA PPYPMPGKSS SGSKERE--- -AIPANELPT   156
SEQ_ID_NO_1543   NVPFKEPELA PPYPMPGKSN SGSKEGG--- -ANPANELPT   156
SEQ_ID_NO_1544   NVPFKEPELA PPYPMPSKSN KGSKEEV--- -AKPTDELPT   156
SEQ_ID_NO_1545   NVPFKEPELA PPYPMPSKSS NGCNGGETGP AVRPQHELPT   160

SEQ_ID_NO_1542   TRAKGFQKGE EEGPVRKPHK DWGPSGAWNT LRNWSQELID   196
SEQ_ID_NO_1543   TRAKGFQKGE EEGPVRKPHK DWGPSGAWNT LRNWSQELID   196
SEQ_ID_NO_1544   TRAKGFQKGE EEGPVRKPHK DWGPSGAWNT LRNWSQELID   196
SEQ_ID_NO_1545   TRAKGFQKGE EEGPVRKPHK DWGPSGAWNT LRNWSQELID   200

SEQ_ID_NO_1542   EAGDIIKAGD EAAKLPGGRA KNYQGRRWAL YTTWRPLKTV   236
SEQ_ID_NO_1543   EAGDIIKAGD EAAKLPGGRA KNYQGRRWAL YTTWRPLKPV   236
SEQ_ID_NO_1544   EADDIIKAGD EAAKLPGGRA KNYQGRRWAL YTPWRPLKPV   236
SEQ_ID_NO_1545   EAGDIIKAGD VAAELPGGRA KNYQGRRWAL YTTWRPLKPV   240
```

Figure 7A

```
SEQ_ID_NO_1542    KRDPMAYVDY WTADEEDGVS FWRNPPGVHG TFESDVLLTK    276
SEQ_ID_NO_1543    KRDPMAYVDY WTADGEDGVS FWRNPPGVHG TFESDVLLTK    276
SEQ_ID_NO_1544    KRDPMAYVDY WTADDEDGVS LWRNPPGVHG TFESDVLLTK    276
SEQ_ID_NO_1545    KRDPMAYVDY WTADEQDGVS FWRNPPGVHG TFESDVLLTK    280

SEQ_ID_NO_1542    ANPKHKWYWI SDQTPDEVLL MKIMDTESEK DGSEIAGGVH    316
SEQ_ID_NO_1543    ANPKHKWYWI SDQTPDEVLL MKIMDTESEK DGSGIAGGVH    316
SEQ_ID_NO_1544    ANPKHKWYWI SDQTPDEVLL MKIMDTESEK DGSDIAGGVH    316
SEQ_ID_NO_1545    ANPKHKWYWI SDQTPDEVLL MKIMDTESEK DGSDVAGGVH    320

SEQ_ID_NO_1542    HCSFHLPGTE KEEVRESIET KFIAFW    342
SEQ_ID_NO_1543    HCSFHLPGTE KEEVRESIET KFIAFW    342
SEQ_ID_NO_1544    HCSFHLPGTE KEEVRESIET KFIAFW    342
SEQ_ID_NO_1545    HCSFHLPGTE DEEVRESIET KFIAFW    346
```

Figure 7B

```
SEQ_ID_NO_1386   MTNHS--SSY YYEFYKDHSH TFRRSMSENT LISSCLALAT   38
SEQ_ID_NO_1387   MANHS--SSY YHEFYKDHSH TVLTLMSEKP VILPSLILGT   38
SEQ_ID_NO_1388   MATLEPTTGY IAELIS---- -----TSNLP SVTFVVTAVT   31

SEQ_ID_NO_1386   CAILLSIQWL KPQPLIMVNG RKFGELSNVR AKRDFTFGAR   78
SEQ_ID_NO_1387   CAVLLCIQWL KPQPLIMVNG RKFGELSNVR AKRDFTFGAR   78
SEQ_ID_NO_1388   LAVFYTLQRR KS-TVPLINP KRWFEFSDYR IKQEFVHNAI   70

SEQ_ID_NO_1386   QLLEKGFKMS PDKPFRIMGD VGELHILPPK YAYEVRNNEK   118
SEQ_ID_NO_1387   QLLEKGLKMS PDKPFRIMGD VGELHILPPK YAYEVRNNEK   118
SEQ_ID_NO_1388   PLVKQGFAAT GNKPFRILAD SGELTVLPPD VANEIKSNDH   110

SEQ_ID_NO_1386   LSFTMAAFKW FYAHLPGFEG FREGTNESHI MKLVARHQLT   158
SEQ_ID_NO_1387   LSFTMAAFKW FYAHLPGFEG FREGTNESHI MKLVARHQLT   158
SEQ_ID_NO_1388   MSFELSTAKQ FFGHLPGFEV FNATGMNTKV SKSLVQRQLT   150

SEQ_ID_NO_1386   HQLTLVTGAV SEECALVLKD VYTDSPEWHD ITAKDANMKF   198
SEQ_ID_NO_1387   HQLTLVTGAV SEECALVLKD VYTDSPEWHD ITAKDANMKL   198
SEQ_ID_NO_1388   THLNKVTKPL SDEASLSLQE ILTDNKEWHE ITLKNEVLQI   190

SEQ_ID_NO_1386   MARITFRVFL GKEMCRNPQW LRITSTYAVI AFRAVEELRL   238
SEQ_ID_NO_1387   MARITSRVFL GKEMCRNPQW LRITSTYAVI AFRAVEELRL   238
SEQ_ID_NO_1388   IARLSSKVFT GDELCHDKRW LDLTVNYTLM AFAAADSLRM   230

SEQ_ID_NO_1386   WPSWLRPVVQ WFMPHCTQSR ALVQEARDLI NPLLERRREE   278
SEQ_ID_NO_1387   WPSWLRPVVQ WFMPHCTQSR ALVQEARDLI NPLLERRREE   278
SEQ_ID_NO_1388   WPPYLRSIVH WFLPKCRASR AEVARARTVI EPILKRRAEQ   270
```

Figure 8A

```
SEQ_ID_NO_1386   KAEAERTGEK V-TYNDAVEW LDDLAREKGV GYDPACAQLS   317
SEQ_ID_NO_1387   KAEAERTGEK V-TYNDAVEW LDDLAREKGV GYDPACAQLS   317
SEQ_ID_NO_1388   KAALAAQGKK APEINDAIEW FTTATTIEGF TLDPVIAQLG   310

SEQ_ID_NO_1386   LSVAALHSTT DFFTQVMFDI AQNPELIEPL REEIISVLGK   357
SEQ_ID_NO_1387   LSVAALHSTT DFFTQVMFDI AQNPELIEPL REEIIAVLGK   357
SEQ_ID_NO_1388   LSLAAIHTTS DLSTQVILDI ASHPEIIEPL RKEMIESLSE   350

SEQ_ID_NO_1386   QGWSKNSLYN LKLMDSVLKE SQRLKPIAIA SMRRFTTHNV   397
SEQ_ID_NO_1387   QGWSKNSLYN LKLIDSVLKE SQRLKPIAIA SMRRFTTHNV   397
SEQ_ID_NO_1388   GGWKKNSLYK LKLLDSVIKE SQRMKPIASI SMSRLTTTNV   390

SEQ_ID_NO_1386   ELSDGVILPK NKLTLVSAHQ HWDPEYYKDP LKFDGYRFFN   437
SEQ_ID_NO_1387   KLSDGVILPK NKLTLVSAHQ HWDPEYYKDP LKFDGYRFFN   437
SEQ_ID_NO_1388   SLSDGTFIPR NTATAVSSHR MWDPSIHTNP DQWDGYRFYN   430

SEQ_ID_NO_1386   MRREPGKESK AQLVSATPDH MGFGYGLHAC PGRFFASEEI   477
SEQ_ID_NO_1387   MRREPGKESK AQLVSATPDH MGFGYGLHAC PGRFFASEEI   477
SEQ_ID_NO_1388   KRQEPGQENL SQLVSTSPDH LAFGHGQHAC PGRFFAANEI   470

SEQ_ID_NO_1386   KIALSHILLK YDFKPVEGSS MEPRKYGLNM NANPTAKLSV   517
SEQ_ID_NO_1387   KIALSHILLK YDFKPVEGSS MEPRKYGLNM NANPTAKLSV   517
SEQ_ID_NO_1388   KVFLCHLLLK YDLKIVEGSM IKPFPYSFSM NANPFAPLMI   510

SEQ_ID_NO_1386   RRRKEEIA-- ---I   526
SEQ_ID_NO_1387   RRRKEEIA-- ---I   526
SEQ_ID_NO_1388   RRREDVIDLD ALDA   524
```

Figure 8B

```
SEQ_ID_NO_1274    MK-------- ---------- ---------- ----------    2
SEQ_ID_NO_1275    ML-------- ---------- ---------- ----------    2
SEQ_ID_NO_1276    MS-------- ---------- ---------- ----------    2
SEQ_ID_NO_1277    MS-------- ---------- ---------- ----------    2
SEQ_ID_NO_1278    MPRLSSLVIF SIASKKILII FTGQKVLHLY WIILKDSRDD    40
SEQ_ID_NO_1279    MD-------- ---------- ---------- ----------    2

SEQ_ID_NO_1274    ---------- ---------- --YTT----- -------C--    6
SEQ_ID_NO_1275    ---------- ---------- ---------- ----------    2
SEQ_ID_NO_1276    ---------- ---------- ---------- ----PALFDK    8
SEQ_ID_NO_1277    ---------- ---------- ---------- ----PPFLNE    8
SEQ_ID_NO_1278    PLPTRRHHPS EGVVGLITDM DNYTW---HS GTLIPS--DS    75
SEQ_ID_NO_1279    ---------- ---------- -NYTLLSLHT GNLKPP--DS    19

SEQ_ID_NO_1274    ---------- --------QM NIFPSLWSMK TSFRW-----    23
SEQ_ID_NO_1275    ------WQIW LPVAVATAVL AVQRLRKKYK PSYDLPVVGS    36
SEQ_ID_NO_1276    SKDMTMSPLF LGASALIVLA YVIKAILSRP QKLDLPIVGK    48
SEQ_ID_NO_1277    SKGTTMSPVL LGASAFLLLA YVVRAILARP QKLDFPVVGK    48
SEQ_ID_NO_1278    PSSIDRSQLY LEILGVLSVV YLLQTLVAYS KSFKAPFVGF    115
SEQ_ID_NO_1279    SSSIDRSQLY LGVIGVLSVI YLLQTLVACT KSFKAPFVGF    59

SEQ_ID_NO_1274    ---------- ---------- ---------- ----------    23
SEQ_ID_NO_1275    P--------- ---TDQSMAE ALVEGHQKYP ESAFVVP-SD    63
SEQ_ID_NO_1276    P--------- ---GADYWQE ALLEGTTKYP NTPFVLP-SD    75
SEQ_ID_NO_1277    P--------- ---GDANFEA ALLEGTAKYP NTPYIIP-SV    75
SEQ_ID_NO_1278    RFWYEPKWLV GLRFSQGALA QVNEGYAKYK NAMFKVARND    155
SEQ_ID_NO_1279    RSSFEPKWLV GLRFSQGALA QVNEGYEKYK NAMFKIARND    99
```

Figure 9A

| | | | | | |
|---|---|---|---|---|---|
| SEQ_ID_NO_1274 | ---------- | ---------- | ---------- | ---------- | 23 |
| SEQ_ID_NO_1275 | PPRVVLPMNL | YQEVLHAPES | ELSFGAEIYD | IFLGKYTH-- | 101 |
| SEQ_ID_NO_1276 | PPLVVLPHCT | HEEVRTLTEE | KVSFQEEVHR | MFLSAHTK-- | 113 |
| SEQ_ID_NO_1277 | PELVVLPMST | HDEMRNLPED | KASFMQDLSH | VFFGKHTG-- | 113 |
| SEQ_ID_NO_1278 | SDILVIPNKY | VEELRSLPDE | KISAIRAHIK | NLLGKYSTTL | 195 |
| SEQ_ID_NO_1279 | SDILVIPNKY | VEELRSLPDE | KISAIRAHIK | NLLGKYSTTL | 139 |

| | | | | | |
|---|---|---|---|---|---|
| SEQ_ID_NO_1274 | ---------- | ---------- | ---------- | ---------- | 23 |
| SEQ_ID_NO_1275 | LGEPRMEVVE | AIRVDMTRNL | SGILLPIQEE | VKFAMKQMF- | 140 |
| SEQ_ID_NO_1276 | VGTDFPVVVK | TVKTDLTRHS | ASTVGALEDE | TNYALDTEF- | 152 |
| SEQ_ID_NO_1277 | IGENTPPLIK | TIKADLTRHM | ASTVEALQDE | ARYALNE-F- | 151 |
| SEQ_ID_NO_1278 | ILLESDLHTR | MLQTKLTPNL | GSFIEVIESE | LLFAMDQEIP | 235 |
| SEQ_ID_NO_1279 | ILLESDLHTR | MLQTKLTPNL | GSFIEVIESE | LHFAMEKEIP | 179 |

| | | | | | |
|---|---|---|---|---|---|
| SEQ_ID_NO_1274 | PRTSKWSSVS | LYDMMLRTVA | LLSGRAFVGL | PLCRDEGWLQ | 63 |
| SEQ_ID_NO_1275 | GVLEDWKSFN | AYHLVLRLVA | LMSGRVFVGL | PLSRDEEWIQ | 180 |
| SEQ_ID_NO_1276 | GTGESWTKVV | LFEKVVRIVA | LVSGRVFVGR | PLSRNEEWLQ | 192 |
| SEQ_ID_NO_1277 | GSCENWTKVD | LTKAIPRMVA | LLSGRAFVGK | PLSRNEEWIN | 191 |
| SEQ_ID_NO_1278 | ANLDDWQSVN | VFHIVLRIVA | RISARVFLGV | PACRNEEWLQ | 275 |
| SEQ_ID_NO_1279 | ADLHDWQNVN | VFHIVLRIVA | RISARVFLGV | PACRNEEWLQ | 219 |

| | | | | | |
|---|---|---|---|---|---|
| SEQ_ID_NO_1274 | ASIGYTVQCV | SIRDQLFTWS | PVLRPIIGPF | LPSVRSVRRH | 103 |
| SEQ_ID_NO_1275 | ASITFATDCG | KCRMAALEWN | PWVRPWVLPF | LPEVRHMRRT | 220 |
| SEQ_ID_NO_1276 | ASIQYTIDCA | KARDAANEWP | VWTRYFVVPF | LPEIKKVKSH | 232 |
| SEQ_ID_NO_1277 | ATVDYTVDTV | KAKDEVLQYP | ALIQNLAVSF | LSQIRTVKQH | 231 |
| SEQ_ID_NO_1278 | TSIHYTENVF | ATVMLLRRFP | KWMHPIVGHL | LPSYWAIHRN | 315 |
| SEQ_ID_NO_1279 | TSIHYTENVF | ATVMLLRRFP | KWMHPIVGHL | LPSYWAIHSN | 259 |

Figure 9B

```
SEQ_ID_NO_1274  LRFAAEIMAP LISQALQDEK QHRA-DTLLA DQ-TEGRGTF  141
SEQ_ID_NO_1275  LQKANEWMRP LVDEVLRNES ALEE-----K PAKPGAPGAF  255
SEQ_ID_NO_1276  TVKAAELLKP LINQCIQRFK EGKGIGGESG DEFDDDQGTF  272
SEQ_ID_NO_1277  KSKVAKLLRP IIEECMRKFK EEKTADKESS DGFDDNQGSF  271
SEQ_ID_NO_1278  LRTAKRIISP MVRQRRAEEA KRN------- -PDYVKPNDL  347
SEQ_ID_NO_1279  LRTAKRIISP MVRQRRAEEA K--------G DPTYEKPNDL  291

SEQ_ID_NO_1274  ISWLLRHLPE ELR-TPEQVG LDQMLVSFAA IHTTTMALTK  180
SEQ_ID_NO_1275  VSWMMKHTAP QKK-TSENMG TNQMLLSFAA IHTTSSTATF  294
SEQ_ID_NO_1276  VSWIMKHTSP ELRENPYSLA INQLTLSFAS IHTTTMAVCH  312
SEQ_ID_NO_1277  ISWLLKWTDE KSREDPFALA DTQLMLSFAA IHTTSMALSH  311
SEQ_ID_NO_1278  LQWMMDGANE NDG-QPDKLA HRQLLLSLAS IHTTTMAAAH  386
SEQ_ID_NO_1279  LQWMMDGANE NDG-QPDKLA HRQLLLSLAS IHTTTMAAAH  330

SEQ_ID_NO_1274  VVWELVKRPE YIEPLRTEMQ DVFGPDAVSP D----ICINK  216
SEQ_ID_NO_1275  ALYDLLSRPE YIGPLREEIE QVIAQDGAEK DEDGQMFLSK  334
SEQ_ID_NO_1276  ILFDLASHPE FIAPLREEIE QVIAEDGFEV DGSGKKCLKK  352
SEQ_ID_NO_1277  ILYDIASHPE FIEPLREEIE QVIAEDGDEI DGSGSTNLKK  351
SEQ_ID_NO_1278  CFYDLCQHPE YFEPLREEIN DVIAQDGG-- -------WKK  417
SEQ_ID_NO_1279  CFYDLCQHPE YFEPLREEIN DVIAQDGG-- -------WKK  361

SEQ_ID_NO_1274  EALSRLHKLD SFIREVQRWC PSTFVTPSRR VMKSMTLSNG  256
SEQ_ID_NO_1275  VSLSKLKKLD SFIKESQRMN PLNFGGTSRR LQKDQTFSNG  374
SEQ_ID_NO_1276  QSMAKLKKLD SLLKESQRVN PPGIIANSRI TTAPLHLSTG  392
SEQ_ID_NO_1277  QSFAKLKKLD SFMKESQRFS PPALVTNFRR TTSTLHLSTG  391
SEQ_ID_NO_1278  TTLNKMRKLD SFLKESQRIN PPSLLAFNRI VSEDLTLSDG  457
SEQ_ID_NO_1279  TTLNKMRKLD SFLKESQRIN PPSLLAFNRI VSEDLTLSDG  401
```

Figure 9C

```
SEQ_ID_NO_1274   IKLQRGTSIA FPAHAIHMSE ETPTFSP-DF SSDFENPSPR   295
SEQ_ID_NO_1275   LKLPAGTPIS FPLWGVYNSS STNTFSD-AY NEGTGNAPPT   413
SEQ_ID_NO_1276   HTIPKGTRIG YDAQVLNTAG PNLSLLPHDP STMPQLDPPS   432
SEQ_ID_NO_1277   HTIPKGTRIC YDTVSVNMSN PDLSSIPHDP SNVTSLDPPT   431
SEQ_ID_NO_1278   TLLPKGTHFS MPSAAILQDN GV-------- -----EPGAD   484
SEQ_ID_NO_1279   TLLPKGTHFS MPSAAILQDN AV-------- -----EPDAD   428

SEQ_ID_NO_1274   IFDGFRYLNL RSIKGQGSQH QAATTGPDYL IFNHGKHACP   335
SEQ_ID_NO_1275   EFDGFRFARL REQPGRETKH QAATTGPDAF NFGHGPHACP   453
SEQ_ID_NO_1276   VFSPFRFASI RETPGNESKY QFVTTSKEAM NFGHGNHACP   472
SEQ_ID_NO_1277   TFSPFRWSSL RDTPGNESKF QFVTTSKQSM NFGHGNHACP   471
SEQ_ID_NO_1278   QFDGFRYYKK RLNPEEANKH QFAMTDNNNL HFGHGKYSCP   524
SEQ_ID_NO_1279   QFDAFRYYKK RLNPEEANKH QFAMTDNNNL HFGHGKYSCP   468

SEQ_ID_NO_1274   GRFFAISEIK MILIELLAKY DFRLE----- DGKPGPELMR   370
SEQ_ID_NO_1275   GRFFAVYVIK CIFIEFLLNY DIRLKGSGGK DAGSRPPNTI   493
SEQ_ID_NO_1276   GRFFAGVEIK VILIELLRGW DFRNVGDTEM KGGGRPENFC   512
SEQ_ID_NO_1277   GRFFAGLELK VAIVELLRNW EFRLVGDEGA KGGERPKNLV   511
SEQ_ID_NO_1278   GRFFASNEIK IIMAHLLTDY EFKYP----- RGATRPRNLT   559
SEQ_ID_NO_1279   GRFFASNEIK IIMAHLLTDY EFKYP----- PGASRPRNLT   503

SEQ_ID_NO_1274   VGTETRLDTK AGLEMRRR-- ---------- ----   388
SEQ_ID_NO_1275   RKMIVMPDFG REVEVRKRTG ---------- ---A   514
SEQ_ID_NO_1276   VDTAINPNPV AEIEFKRR-- ---------- ---V   531
SEQ_ID_NO_1277   YDVTIMPDPV GQLEFRRRK- ---------- ---F   531
SEQ_ID_NO_1278   ADENLYPDPS ARLLMRRRVV APPQASITPQ LVSA   593
SEQ_ID_NO_1279   ADENLYPDPS ARLLMRRRMV AEGQAQITPE IVLV   537
```

Figure 9D

TRANSGENIC PLANTS HAVING ALTERED BIOMASS COMPOSITION

CROSS-REFERENCE TO RELATED APPLICATIONS

This application is a divisional of U.S. application Ser. No. 16/992,793, filed Aug. 13, 2020 (pending, which application is a divisional of U.S. application Ser. No. 16/406,702, filed May 8, 2019 (now U.S. Pat. No. 10,822,616), which application is a divisional of U.S. application Ser. No. 14/363,151, filed Jun. 5, 2014 (now U.S. Pat. No. 10,323,256), which application is a National Stage Entry of PCT/US2012/068756, filed Dec. 10, 2012, which application claims priority to U.S. Application Ser. No. 61/568,747, filed on Dec. 9, 2011, the disclosures each of which is incorporated herein by reference.

TECHNICAL FIELD

This document relates to methods and materials involved in modulating biomass composition in plants. For example, this document provides plants having altered sugar content or conversion efficiency, as well as materials and methods for making plants and plant products having altered sugar content or conversion efficiency.

INCORPORATION-BY-REFERENCE OF SEQUENCE LISTING

The accompanying file, named 116960300WO1SEQLISTING is 2.82 MB. The file can be accessed using Microsoft Word on a computer that uses Windows OS.

BACKGROUND

Plants store energy from sunlight in the form of chemical bonds that compose plants. The energy stored in plant materials can be converted to forms of energy such as heat, electricity and liquid fuels, depending upon the plant material employed and the process applied to extract energy from it. Other processes can produce chemical intermediates from plant biomass that are useful in a variety of industrial processes, for instance lactic acid, succinic acid, etc.

Plant materials have been used for millennia by humans to generate heat by direct combustion in air. For building and process heating purposes, this heat is typically used to generate steam, which is a more transportable heat source used to heat buildings and public areas using heat exchangers of various design. The production of steam may also be used to drive turbines, which transform heat energy into electrical energy. These processes typically involve a simple, direct combustion process of the plant material alone, or a co-firing process with coal or other energy source.

Fuels such as ethanol can be produced from plant materials by a number of different processes. For example, the sucrose in sugarcane can be extracted from the plant material and directly fermented to ethanol using a microorganism, such as brewer's yeast. Brazil has converted a significant portion of its transportation sector over to ethanol derived from sugarcane, proving this can be done on a very large scale over broad geography. As another example, the starch from corn can be processed using α-amylase and glucoamylase to liberate free glucose that is subsequently fermented to ethanol. The US uses a significant portion of its corn crop to produce ethanol from starch. While these advances are significant, the ability to increase the amount of liquid transportation fuel obtained from plant material is limited because only a small fraction of the solar energy captured and transformed into chemical energy in plants is converted into biofuels in these industrial processes.

Plant material can be used for the production of cellulosic biofuels by biochemical processes employing enzymes and/or microorganisms or by thermochemical processes such as Biomass to Liquids (BtL) technology using high temperature and non-enzymatic catalysts. There are also examples of hybrid thermochemical/biochemical processes. Biochemical processes typically employ physical and chemical pretreatments, enzymes, and microorganisms to deconstruct the lignocellulose matrix of biomass in order to liberate the fermentable from cellulose, hemicellulose, and other cell wall carbohydrates, which are subsequently fermented to ethanol by a microorganism. Currently, many different processing methods are being developed for biofuel production that employ different strategies for pretreatment, enzyme cocktails, and microorganisms. Many of these processes are focused on the production of ethanol, but butanol and other useful molecules (e.g., lactic acid, succinic acid, polyalkanoates, etc.) can also be produced in this type of process. The conversion product molecule produced is usually defined by the microorganisms selected for fermentation.

Thermochemical processes employ very high temperatures in a low oxygen (i.e., $O_2$) environment to completely degrade the organic constituents of biomass to syngas, largely composed of molecular hydrogen ($H_2$) and carbon monoxide (CO) gas. These simple molecules are then reformed into more useful and valuable molecules (fuels or chemical intermediates) utilizing a Fischer-Tropsch process or other methods usually employing a chemical catalyst of some sort. These processes are effective at producing biofuels that are similar to current petrochemical-based hydrocarbon fuels (i.e., gasoline, diesel, jet fuel), although other biofuel molecules can also be produced in these types of processes (i.e., ethanol, butanol, kerosene).

A variant form of thermochemical process uses pyrolysis (i.e., thermal degradation in the complete absence of oxygen) to partially degrade the organic constituents present in plant biomass to a chemically heterogeneous liquid bio-oil. This serves to increase the energy density of the biomass to facilitate transport to centralized processing facilities where the bio-oil is further processed to a desired product slate.

The economic viability of biomass conversion processes is significantly impacted by the composition of the plant material and its conversion efficiency to heat, electricity, biofuels or chemical intermediates under specific processing conditions. For biochemical processes producing biofuels or other chemicals, the recalcitrance of the lignocellulose matrix of the biomass is a major factor in conversion efficiency.

SUMMARY

The present invention relates to methods of altering biomass composition in plants. Plants having altered biomass composition are useful for agriculture, forage, horticulture, biomass to energy conversion, paper production, plant product production, and other industries. For example, this document features dedicated energy crops such as *Panicum virgatum* L. (switchgrass), *Miscanthus* sp., e.g. *Miscanthus* x *gigantus* (*Miscanthus*), Sorghum sp., *Saccharum* sp. (sugar cane), or *Arundo donax* having altered biomass composition.

Thus, in one aspect, this document features a sorghum, *Miscanthus, Panicum*, or sugarcane plant cell comprising an exogenous nucleic acid. The exogenous nucleic acid comprises a regulatory region operably linked to a nucleotide sequence encoding a polypeptide, wherein the HMM bit score of the amino acid sequence of the polypeptide is greater than about 65, based on the amino acid sequences depicted in one of FIG. 1, 2, 4, 6, 7, 8, or 9. Furthermore, a plant produced from the plant cell has a difference in biomass composition as compared to the corresponding composition of a control plant that does not comprise the nucleic acid. In another aspect, the exogenous nucleic acid in the sorghum, *Miscanthus, Panicum*, or sugarcane plant comprises a regulatory region operably linked to a nucleotide sequence encoding a polypeptide having 80 percent or greater sequence identity to an amino acid sequence selected from the group consisting of SEQ ID NO: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836, 837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, 1139, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, and 1567. A plant produced from such a plant cell has a difference in biomass composition as compared to the corresponding composition of a control plant that does not comprise the nucleic acid. The difference in biomass composition in the plant can be an increase in the total sugar content, an increase in sugar availability from the cell wall, increase in total glucose released from pretreatment, an increase in total sugar content in juice, increased juice brix, increase in yield of juice, increase in sucrose purity in juice, increase in sugar yield in juice from the plant, a decrease in ash content, and/or an increase in total glucan content. The difference in biomass composition in the plant can be at least a 1.5 fold, 2.0 fold, or 2.5 fold increase in glucose from cell well as compared to that of a control plant that does not comprise the nucleic acid. The difference in biomass composition in the plant can be at least a 3 fold, 4 fold, or 6 fold increase in sugar yield as compared to that of a control plant that does not comprise the nucleic acid. The difference in biomass composition in the plant can be an increase in conversion efficiency as compared to that of a control plant that does not comprise said nucleic acid. This document also features methods of producing such sorghum, switchgrass, sugarcane or *Miscanthus* plants. The plant or plant cell can also contain a second exogenous nucleic acid that comprises a regulatory region operably linked to a sequence of interest.

The polypeptide can comprise a 2OG-Fe(II) oxygenase superfamily domain having 60 percent or greater sequence identity to residues 211-309 of SEQ TD NO: 471 or to residues 209-306 of SEQ ID NO:1. In some embodiments, the polypeptide comprises an alpha/beta hydrolase fold domain having 60 percent or greater sequence identity to residues 116-329 of SEQ ID NO: 99 and a carboxylesterase family domain having 60 percent or greater sequence identity to residues 110-210 of SEQ ID NO: 99. Such polypeptides include GA 20-oxidases. The polypeptide can comprise a cytochrome P450 domain having 60 percent or greater sequence identity to residues 142-500 of SEQ ID NO:1429, to residues 176-504 of SEQ ID NO:1386, or to residues 98-368 of SEQ ID NO: 1274.

In another aspect, this document features a plant cell comprising an exogenous nucleic acid. The exogenous nucleic acid encodes a transcription product that inhibits expression of a polypeptide having 80 percent or greater sequence identity to an amino acid sequence selected from the group consisting of SEQ ID NO: 188, 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 287, 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 1009, 1010, 1011, 1012, 1013, 1014, 1015, 1016, 1017, 1018, 1019, 1020, 1021, 1022, 1023, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, and 1273.

This document also features a plant cell that include an exogenous nucleic acid encoding a transcription product that inhibits expression of a polypeptide, wherein the HMM bit score of the amino acid sequence of the polypeptide is greater than about 65, the HMM based on the amino acid sequences depicted in one of FIGS. 1, 2, 4, 6, 7, 8, and 9.

A plant produced from the plant cell has a difference in biomass composition as compared to the corresponding composition of a control plant that does not comprise the nucleic acid. The transcription product can be an interfering RNA. The difference in biomass composition in the plant can be an increase in the total sugar content, an increase in sugar availability from the cell wall, increase in total glucose released from pretreatment, an increase in total sugar content in juice, increased juice brix, increase in yield of juice, increase in sucrose purity in juice, and/or increase in sugar yield in juice from the plant. The difference in biomass composition in the plant also can be selected from the group consisting of a decrease in ash content and an increase in the total glucan content.

This document features a method of producing biomass. Such a method comprises growing a plurality of the transgenic plants described herein; and harvesting biomass from the plants. The plurality of plants can be sorghum plants and the harvesting step can comprise harvesting stalks from the plants. The method can further comprise pretreating the harvested biomass. The method can further comprise the step of enzymatically processing the harvested biomass.

This document also features a method of processing biomass. Such a method comprises extracting sugars from biomass from a plurality of transgenic plants described herein. The method can further include the step of crystallizing the sugars (e.g., sucrose).

This document also features a method of altering biomass composition in sorghum, *Miscanthus, Panicum*, or sugarcane. Such a method comprises modifying an endogenous biomass composition-modulating nucleic acid in a sorghum, *Miscanthus, Panicum*, or sugarcane plant. The nucleic acid comprises a nucleotide sequence with an open reading frame having 80 percent or greater sequence identity to the nucleotide sequence selected from the group consisting of SEQ ID NO: 5, 7, 34, 43, 68, 73, 78, 80, 93, 100, 102, 109, 118, 122, 125, 130, 147, 149, 153, 165, 168, 174, 178, 192, 200, 210, 212, 214, 218, 223, 227, 229, 234, 237, 246, 253, 263, 271, 281, 289, 302, 304, 307, 312, 318, 327, 331, 343, 345, 359, 366, 369, 372, 381, 385, 390, 401, 411, 416, 426, 431, 439, 442, 448, 450, 455, 461, 472, 474, 486, 494, 497, 507, 516, 543, 557, 560, 565, 581, 591, 596, 598, 603, 611, 616, 642, 662, 687, 694, 704, 722, 753, 755, 766, 771, 774, 786, 798, 811, 819, 840, 848, 903, 977, 979, 1030, 1039, 1043, 1054, 1065, 1075, 1078, 1081, 1088, 1090, 1098, 1103, 1107, 1109, 1112, 1118, 1132, 1134, 1137, 1153, 1178, 1190, 1201, 1203, 1207, 1212, 1246, 1253, and 1265.

This document also features methods of altering biomass composition in *Miscanthus* that comprise inhibiting an endogenous biomass composition-modulating nucleic acid in a *Miscanthus* plant. In such methods, an RNAi sequence may comprise a sequence having 80 percent or greater sequence identity to the nucleotide sequence selected from the group consisting of SEQ ID NO: 1568, 1569, 1570, 1571, 1572, 1573, 1574, 1575, 1576, 1577, 1578, 1579, and 1580, or a fragment thereof.

The plant has a difference in biomass composition as compared to the corresponding composition of a control plant in which the nucleic acid has not been modified. The difference in biomass composition in the plant can be an increase in total sugar content, an increase in sucrose content, a decrease in ash content or an increase in total glucan content. The modification can be effected by introducing a genetic modification in the locus comprising the nucleic acid. The method can further include selecting for plants having altered biomass composition.

This document also features a sorghum, *Miscanthus, Panicum*, or sugarcane plant cell containing a modified endogenous nucleic acid encoding a polypeptide. The HMM bit score of the amino acid sequence of the polypeptide is greater than about 65, with the HMM based on the amino acid sequences depicted in one of FIGS. 1-9. A plant produced from the plant cell has a difference in biomass composition as compared to the corresponding composition of a control plant where the nucleic acid has not been modified. The difference in biomass composition in the plant can be an increase in total sugar content, an increase in sucrose content, a decrease in ash content or an increase in total glucan content. This document also features a method of producing such sorghum, *Miscanthus, Panicum*, or sugarcane plants.

This document also features a sorghum, *Miscanthus, Panicum*, or sugarcane plant cell containing a modified biomass composition-modulating endogenous nucleic acid. The endogenous nucleic acid comprises a nucleotide sequence with an open reading frame having 80 percent or greater sequence identity to the nucleotide sequence selected from the group consisting of SEQ ID NO: 5, 7, 34, 43, 68, 73, 78, 80, 93, 100, 102, 109, 118, 122, 125, 130, 147, 149, 153, 165, 168, 174, 178, 192, 200, 210, 212, 214, 218, 223, 227, 229, 234, 237, 246, 253, 263, 271, 281, 289, 302, 304, 307, 312, 318, 327, 331, 343, 345, 359, 366, 369, 372, 381, 385, 390, 401, 411, 416, 426, 431, 439, 442, 448, 450, 455, 461, 472, 474, 486, 494, 497, 507, 516, 543, 557, 560, 565, 581, 591, 596, 598, 603, 611, 616, 642, 662, 687, 694, 704, 722, 753, 755, 766, 771, 774, 786, 798, 811, 819, 840, 848, 903, 977, 979, 1030, 1039, 1043, 1054, 1065, 1075, 1078, 1081, 1088, 1090, 1098, 1103, 1107, 1109, 1112, 1118, 1132, 1134, 1137, 1153, 1178, 1190, 1201, 1203, 1207, 1212, 1246, 1253, and 1265.

This document also features a *Miscanthus* plant cell containing a modified biomass composition-modulating endogenous nucleic acid. In such methods, an RNAi sequence may comprise a sequence having 80 percent or greater sequence identity to the nucleotide sequence selected from the group consisting of SEQ ID NO: 1568, 1569, 1570, 1571, 1572, 1573, 1574, 1575, 1576, 1577, 1578, 1579, and 1580, or a fragment thereof.

A plant produced from such a sorghum, *Miscanthus, Panicum*, or sugarcane plant cell has a difference in biomass composition as compared to the corresponding composition of a control plant where the nucleic acid has not been modified. The difference in biomass composition in the plant can be an increase in total sugar content, an increase in sucrose content, a decrease in ash content or an increase in total glucan content.

In another aspect, this document features a method of modulating biomass composition of a plant. Such a method comprises introducing into a sorghum, *Miscanthus, Panicum*, or sugarcane plant an exogenous nucleic acid. The exogenous nucleic acid encodes or affects a polypeptide in the gibberellin (GA) biosynthesis or signaling pathway so as to increase levels of, or sensitivity to, active gibberellins. The plant has a difference in biomass composition as compared to the corresponding composition of a control plant that does not comprise the exogenous nucleic acid. The difference in biomass composition in the plant can be an increase in total sugar content, an increase in sucrose content, a decrease in ash content or an increase in total glucan content.

In another aspect, this document features a method of modulating biomass composition of a plant. Such a method comprises introducing into a plant first and second exogenous nucleic acids. The first exogenous nucleic acid encodes or affects a polypeptide in the GA biosynthesis or signaling pathway so as to increase levels of, or sensitivity to, active gibberellins and the second exogenous nucleic acid encodes a sequence of interest. The plant has a difference in biomass composition as compared to the corresponding composition of a control plant that does not comprise the exogenous nucleic acids. The difference in biomass composition in the plant can be an increase in total sugar content, an increase in sucrose content, a decrease in ash content or an increase in total glucan content.

This document also features a sorghum, *Miscanthus, Panicum*, or sugarcane plant cell or plant comprising an exogenous nucleic acid. The exogenous nucleic acid encodes or affects a polypeptide in the GA biosynthesis or signaling pathway so as to increase levels of, or sensitivity to, active gibberellins. The plant has a difference in biomass composition as compared to the corresponding level of a control plant that does not comprise the exogenous nucleic acid. The difference in biomass composition in the plant can be an increase in total sugar content, an increase in sucrose content, a decrease in ash content or an increase in total glucan content.

This document also features a sorghum plant containing an exogenous biomass composition-modulating nucleic acid. The plant has an increase in total sugar content in juice, increase in juice brix, and/or increase in yield of sugar from juice from the plant that is statistically significantly greater than that of a corresponding control plant that lacks the biomass composition-modulating nucleic acid. The plant can have a sucrose content that is statistically significantly greater than the sucrose content of a corresponding control plant that lacks the biomass composition-modulating nucleic acid.

This document also features a sorghum, *Panicum, Miscanthus*, or sugarcane plant containing an exogenous biomass composition-modulating nucleic acid. The plant has a biomass composition that is statistically significantly different from the biomass composition of a corresponding control plant that lacks the biomass composition-modulating nucleic acid. Biomass from the plant can have an increase in the total sugar content, an increase in sugar availability from the cell wall, increase in total glucose released from pretreatment, an increase in total sugar content in juice, increase in juice brix, increase in yield of juice, increase in sucrose purity in juice, and/or increase in sugar yield in juice from the plant relative to a corresponding control plant that lacks the biomass composition-modulating nucleic acid.

In another aspect, this document features a method of producing biomass, comprising applying a gibberellin (e.g., GA3) to a population of plants (e.g., sorghum, *Panicum, Miscanthus*, sugarcane, or *Arundo donax*), and harvesting cellulosic biomass from the plants.

This document also features a method of processing biomass. The method includes pretreating biomass harvested from a plurality of plants (e.g., sorghum, switchgrass, *Miscanthus*, sugarcane, or *Arundo donax* plants) to which a gibberellin has been applied; and extracting sugars from the pretreated biomass. The pretreating step can include a physical or chemical pretreatment of biomass harvested from plants to which a gibberellin has been applied a plurality of times. The method further can include the step of saccharifying the pretreated biomass before extracting cell wall-associated sugars. The total amount of sugar extracted from the biomass can be statistically significantly increased compared to that of biomass from corresponding control plants to which a gibberellin has not been applied.

In another aspect, this document features a method of processing biomass, comprising pretreating biomass harvested from a plurality of plants to which a gibberellin has been applied, fermenting the biomass and producing a fuel from the fermented biomass. The pretreating step can be a physical or chemical treatment of the harvested biomass. The method can further comprise the step of saccharifying the pretreated biomass before fermenting. The saccharifying step can comprise saccharifying biomass harvested from plants to which a gibberellin has been applied a plurality of times. The pretreating step releases a significant increase in cell wall associated sugars compared to pretreating biomass from corresponding control plants to which a gibberellin has not been applied. The biomass can have an increased yield of fuel compared to biomass from corresponding control plants to which a gibberellin has not been applied. The plants can be transgenic switchgrass, sorghum, sugarcane, or *Miscanthus* plants as described herein. The plants can be sugarcane plants. The gibberellin can be GA3.

In another aspect, this document features a method of processing biomass, comprising pyrolysing biomass harvested from a plurality of plants to which a gibberellin has been applied and producing a fuel from the pyrolysed biomass.

This document also features a method of processing biomass, comprising gasifying biomass harvested from a plurality of plants to which a gibberellin has been applied, and producing a fuel from the gasified biomass. The biomass can have a decreased ash content compared to biomass from corresponding control plants to which a gibberellin has not been applied.

This document also features a method of processing biomass, comprising pyrolysing biomass harvested from a plurality of transgenic plants described herein, and producing a fuel from the pyrolysed biomass.

This document also features a method of processing biomass, comprising gasifying biomass harvested from a plurality of transgenic plants described herein, and producing a fuel from the gasified biomass. The biomass can have a decreased ash content compared to biomass from corresponding control plants that lack the exogenous nucleic acid. The biomass can be harvested from plants to which a gibberellin has been applied.

This document also features a method of producing a forage product that includes growing a plurality of the plants described herein; harvesting biomass from the plants; chopping or cutting the harvested biomass; and ensiling the chopped or cut biomass to produce the forage product.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

FIGS. 1A-1K contain an alignment of the amino acid sequence of GI_115456701 (SEQ ID NO: 471) with homologous and/or orthologous amino acid sequences. In all the alignment figures shown herein, a dash in an aligned sequence represents a gap, i.e., a lack of an amino acid at that position. Identical amino acids or conserved amino acid substitutions among aligned sequences are identified by boxes.

FIG. 1 and the other alignment figures provided herein were generated using the program MUSCLE version 3.52.

FIGS. 2A-2E contain an alignment of the amino acid sequence of GI_75324272 (SEQ ID NO: 99) with homologous and/or orthologous amino acid sequences.

FIGS. 4A-4L contain an alignment of the amino acid sequence of GI_85540948 (SEQ ID NO: 1) with homologous and/or orthologous amino acid sequences.

FIGS. 5A-5J contain an alignment of the amino acid sequence of G2OX1_ARATH (SEQ ID NO: 287) with homologous and/or orthologous amino acid sequences.

FIGS. 6A-6H contain an alignment of the amino acid sequence of Cytochrome P450 CYP68B1 GiGA20-oxidase (SEQ ID NO: 1429) with homologous and/or orthologous amino acid sequences.

FIGS. 7A-7B contain an alignment of the amino acid sequence of GA4 desaturase (SEQ ID NO: 1542) with homologous and/or orthologous amino acid sequences.

FIGS. 8A-8B contain an alignment of the amino acid sequence of Cytochrome P450 GA14-synthase (SEQ ID NO: 1386) with homologous and/or orthologous amino acid sequences.

FIGS. 9A-9D contain an alignment of the amino acid sequence of Cytochrome P450 CYP69A1 C13-oxidase (SEQ ID NO: 1274) with homologous and/or orthologous amino acid sequences.

DETAILED DESCRIPTION

Figure 1A:
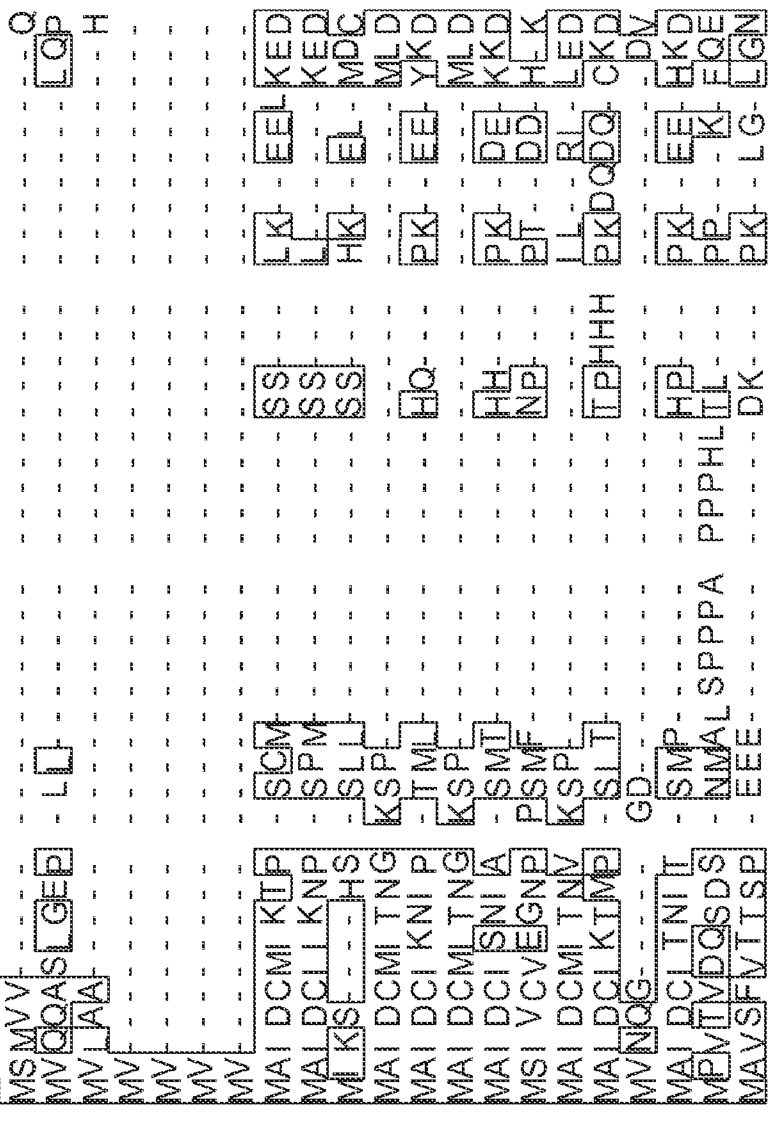

This document features methods and materials related to modulating biomass composition (e.g., one or more of total sugar content, sucrose content, ash content and total glucan content, an increase in sugar availability from the cell wall, increase in total glucose released from pretreatment, an increase in total sugar content in juice, increase in juice brix, increase in yield of juice, increase in sucrose purity in juice, increase in sugar yield in juice from the plant, or increase in conversion efficiency) in plants. For example, this document features methods and materials for increasing or decreasing total sugar content, ash content and/or total glucan content in plants. In some embodiments, a plant can have one or more of increased total sugar content, increased sucrose content, an increase in sugar availability from the cell wall, increase in total glucose released from pretreatment, an increase in total sugar content in juice, increase in juice brix, increase in yield of juice, increase in sucrose purity in juice, increase in sugar yield in juice from the plant, increased conversion efficiency, decreased ash content, and increased total glucan content. In some embodiments, the plants also may have modulated levels of, for example, lignin, modified root architecture, modified herbicide resistance, or modified carotenoid biosynthesis. The methods can include, for example, (i) transforming a plant cell with a nucleic acid encoding a biomass composition-modulating polypeptide, wherein expression of the polypeptide results in modulated biomass composition or (ii) transforming a plant cell with a nucleic acid encoding a transcription product that inhibits expression of a biomass composition-modulating polypeptide, wherein decreased expression of the polypeptide results in modulated biomass composition. Plant cells produced using such methods can be grown to produce plants having an increased or decreased sugar content and/or conversion efficiency. Such plants may produce more grazable forage. Increased brix levels and/or sugar content can result in increased palatability as a forage crop. Biomass harvested from such plants can be cut or chopped and ensiled, with or without additives, to produce a forage product. In addition, such plants, and the seeds of such plants, may be used to produce, for example, switchgrass, *Miscanthus*, Sorghum sp., and sugar cane plants having increased value as a biofuel feedstock.

I. DEFINITIONS

"Accessible Carbohydrate" refers to mono- and oligosaccharides released into the aqueous phase after processing of a biomass feedstock. The amount of accessible carbohydrate in a feedstock is related to the pretreatment and enzymatic saccharification conditions chosen for the saccharification process and to the composition and structure of the initial biomass feedstock.

"Amino acid" refers to one of the twenty biologically occurring amino acids and to synthetic amino acids, including D/L optical isomers.

"Ash" refers to inorganic material that contributes to the dry weight of the feedstock. Ash content in biomass feedstocks can be determined using published, standard methods such as ASTM Standard E1755.

"Biochemical processing" refers to a primarily biological process where plant materials are converted to liquid products using enzymes and/or fermentation organisms. Biochemical processing may require thermochemical pretreatments.

"Biofuels" include, but are not limited to, biodiesel, methanol, ethanol, butanol, linear alkanes ($C_5$-$C_{20}$), branched-chain alkanes ($C_5$-$C_{26}$), mixed alkanes, linear alcohols ($C_1$-$C_{20}$), branched-chain alcohols ($C_1$-$C_{26}$), linear carboxylic acids ($C_2$-$C_{20}$), and branched-chain carboxylic acids ($C_2$-$C_{26}$). In addition, ethers, esters and amides of the aforementioned acids and alcohols, as well as other conjugates of these chemicals may be of interest. Many of these chemicals can be subsequently converted by chemical reactions to other high value, high volume chemicals.

"Biomass" refers to organic matter. Biomass includes plant matter derived from herbaceous and woody energy crops, agricultural food and feed crops, agricultural crop wastes and residues, wood wastes and residues, aquatic plants, and other plant-derived materials. Biomass may also include algae, yard wastes, and include some municipal wastes. Biomass is a heterogeneous and chemically complex renewable resource. Components of biomass include glucan, xylan, fermentable sugars, arabinan, sucrose, lignin, protein, ash, extractives, ferulate, and acetate.

In some embodiments, biomass primarily encompasses above ground plant parts. In some embodiments, biomass primarily encompasses stem plant parts. In some embodiments, biomass primarily encompasses those above ground plant parts other than inflorescence and seed parts of a plant. Biomass can be quantified as dry matter yield, which is the mass of biomass produced (usually reported in Tons/acre) if the contribution of water is subtracted from the fresh mater weight. Dry matter yield (DMY) yield is calculated using the fresh matter weight (FMW) and a measurement of weight percent moisture (M) in the following equation: $DMY=(100-M)/100)*FMW$. Biomass can be quantified as fresh matter yield, which is the mass of biomass produced (usually reported in Tons/acre) on an as-received basis, which includes the weight of moisture. Biomass can sometimes be quantified as juice yield, e.g., the volume of juice separated from bagasse or sorghum or sugarcane stalks, which can be reported per unit area.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Conversion efficiency" refers to the percentage of biomass feedstock converted to product relative to one or more inputs. The product can be energy, automotive fuel, jet fuel, free sugars, fermentable sugars, syngas, ethanol, heat, electricity, or energy, and the input can a parameter such as the amount of biomass, total carbohydrate, amount and type of saccharification enzyme(s), or accessible carbohydrate. The concept of conversion efficiency describes the yield of energy (in terms of biofuel, heat, and/or electricity) derived from a biomass starting material subjected to a particular process as compared to a theoretical yield of energy stored in the biomass starting material. The efficiency by which biomass can be converted into energy via these processes is dependent upon a number of compositional characteristics of the biomass. The relevant compositional characteristics differ based on the conversion process design.

Generally, the conversion efficiency of biochemical processes is most influenced by the concentration of carbohydrate in the biomass and the ease with which that carbohydrate can be hydrolyzed to fermentable sugars. In biochemical processing the lignin in the feedstock is typically converted to energy by burning to generate heat and electricity. Similarly, the efficiency and yield of thermochemical processes for the production of biofuels are most influenced by the overall amounts of carbon to hydrogen to oxygen (C:H:O weight percents) and ash content of the biomass. The efficiency of thermochemical combustion processes is most influenced by the higher heating value (HHV) and ash content of the biomass. The HHV of biomass is a function of carbon, hydrogen and oxygen content of the biomass. The relevant conversion efficiency parameters are dependent on the type of conversion process employed (biochemical, thermochemical to biofuel, or thermochemical to heat and electricity).

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Glucan," "Xylan" and "Arabinan" refer to the anhydro forms of glucose, xylose and arabinose that are found in cellulose and hemicellulose carbohydrate polymers. Thus, for example, "glucan" refers to a polysaccharide of D-glucose monomers linked by glycosidic bonds. The following are glucans: cellulose (β-1,4-glucan), dextran (α-1,6-glucan) and starch (α-1,4- and α-1,6-glucan). See, Technical Report NREL/TP-510-42618, Determination of Structural Carbohydrates and Lignin in Biomass.

"Hemicellulose" is a general term used to refer to cell wall polysaccharides that are not celluloses or pectins. Hemicelluloses contain repeating monomeric units of a five-carbon sugar (usually D-xylose or L-arabinose) and/or a six-carbon sugar (D-galactose, D-glucose, and D-mannose). See, U.S. Pat. No. 7,112,429. Hemicelluloses typically are shorter in length than cellulose and are highly branched. Xylan is often the structural backbone of hemicelluloses from hardwoods and grasses, and hydrolysis of these biomass types releases products high in the five-carbon sugar, xylose. Hemicelluloses from softwoods are most commonly gluco-galacto-mannans, which have a mannan backbone and yield mannose as the main product of hydrolysis. Hemicelluloses often contain side groups such as acetyl groups, uronic acids and ferulates.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Higher heating value" (HHV) refers to the amount of heat released by a specified quantity of a fuel at an initial temperature of 25° C., following combustion, and return of the combustion products to a temperature of 25° C. The HHV is also known as the gross calorific value or gross energy.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Lignin" refers to a polyphenolic polymeric substance of plant cells, with a complex, cross-linked, highly aromatic structure. Lignin is synthesized in plants principally from three monolignol monomers, which can be methoxylated to various degrees: sinapyl alcohol ($C_{11}H_{14}O_4$) that is incorporated into lignin as (S) syringyl units; coniferyl alcohol ($C_{10}H_{12}O_3$) that is incorporated into lignin as (G) guaiacyl units; and p-coumaryl alcohol ($C_9H_{10}O_2$) that is incorporated into lignin as (H) p-hydroxyphenyl units. These monomers can be synthesized into lignin by extensive condensation polymerization. The lignin present in different plant varieties can have different syringyl:guaiacyl:p-hydroxyphenyl weight percents (S:G:H weight percents). For example, certain grass varieties can have lignin composed almost entirely of guaiacyl (G). Lignin is a major structural constituent of plant cells in woody species.

"Modulation" of the level of biomass refers to the change in the level of the biomass that is observed as a result of expression of, or transcription from, an exogenous nucleic acid in a plant cell and/or plant. The change in level is measured relative to the corresponding level in control plants.

"NOX emissions" refers to mono-nitrogen oxides (NOx), such as NO and NO2, released into the atmosphere. While oxygen and nitrogen gases do not typically react at ambient temperatures, oxygen and nitrogen gases can react at higher temperatures to create various oxides of nitrogen, including mono-nitrogen oxides. Mono-nitrogen oxides can also be produced by combusting materials including elemental nitrogen. Mono-nitrogen oxides (NOx) released into the atmosphere can react with volatile organic compounds to produce smog. Accordingly, NOX emissions may be regulated by various governmental agencies. Oxides of sulfur (SOx), specifically sulfur dioxide, are often generated in the same processes. SOx emissions are known to contribute to acid rain.

"Nucleic acid" and "polynucleotide" are used interchangeably herein, and refer to both RNA and DNA, including cDNA, genomic DNA, synthetic DNA, and DNA or RNA containing nucleic acid analogs. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Recalcitrant carbohydrate material" refers to mono- and oligo-saccharides that are not released into the aqueous phase after processing of a biomass feedstock. It is related to the pretreatment and enzymatic saccharification conditions chosen for the saccharification process.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell,* 1:977-984 (1989).

"Saccharification" refers to the hydrolysis of carbohydrate material to the mono- and disaccharides that constitute the polymer. For example, saccharification of xylan results in the production of xylose, the monosaccharide constituent of xylan. Saccharification occurs during the biochemical processing of biomass in biorefineries, ultimately leading to the production of biofuels such as ethanol.

"Saccharification efficiency" of a feedstock sample refers to the total amount of mono and disaccharides solubilized by a pretreatment/enzymatic saccharification process, divided by the theoretical maximum amount of mono and disaccharides in the biomass sample that could have been released based on compositional analysis, converted to a percentage by multiplying by 100.

"Sustainability indicators" refer to components of biomass processing byproducts, such as the expected ash composition and soil nutrients, which may be recycled.

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. METHODS

This document features methods and materials related to modulating biomass composition. These methods and materials are based on the surprising discovery that biomass from plants overexpressing polypeptides in the GA pathway that increase levels of active gibberellins such as GA 20-oxidases can exhibit an altered compositional profile, such that biomass from such plants provides improved efficiency and/or has increased yield when used for biofuel or energy production. For example, transgenic plants overexpressing an exogenous nucleic acid encoding a GA 20-oxidase can exhibit an increased yield of glucose after pretreatment and enzymatic saccharification, and/or equivalent yields of glucose at lower amounts of saccharification enzymes relative to the enzyme amounts required for corresponding plants that do not overexpress the nucleic acid. Such plants can also exhibit modulation in the ash content and/or total glucan content.

Thus, this document features methods of producing biomass that involve growing a plurality of plants that overexpress a transgene encoding a polypeptide in the GA pathway that increase levels of active gibberellins such as GA 20-oxidase, GA 3-oxidase, GA 2-oxidase or a GA receptor, and harvesting biomass from such plants. Alternatively, such methods can comprise growing a plurality of plants that express an exogenous nucleic acid that downregulates genes such as DELLA. Suitable exogenous nucleic acids are described in more detail below, as well as techniques for increasing expression of endogenous genes. Suitable plants include sorghum plants, *Miscanthus* plants and switchgrass plants, as described in more detail below.

In some embodiments, methods for processing biomass from plants described herein include subjecting the biomass to a pretreatment and/or subjecting the biomass to enzymatic processing. Such methods are particularly suitable when biomass is to be fermented for biofuel production or to be used for energy production.

Typically, enzymatic processing conditions are defined by the type of enzymes used and the amount of each enzyme(s) used during the saccharification process in a biorefinery. For example, an enzymatic processing condition can entail the use of a single enzyme preparation such as Spezyme® CP (Genencor, USA) or Celluclast 1.5L (Novozymes, Franklinton, North Carolina). Spezyme® CP and Celluclast 1.5L are commercially available enzyme mixtures containing cellulases that are prepared by submerged culture fermentation of the filamentous fungus, *Trichoderma reesei*. These cellulase preparations are deficient in β-glucosidase activity, so they are often supplemented with a β-glucosidase preparation such as Novozyme 188, obtained by submerged culture fermentation of *Aspergillus niger*. Novozyme 188 is available from Sigma (St. Louis, MO, USA) as catalog number C6105.

Enzyme cocktails containing a plurality of enzymes are sometimes used in biomass processing, such cocktails differing from each other in the type and amount of each enzyme. In some embodiments, an enzymatic processing condition includes the use of two types or three types of enzyme, e.g., Spezyme® CP in combination with a xylanase, or an endo-β-(1,4)-glucanase (EC 3.2.1.4), an exo-β-(1,4)-glucanase (EC 3.2.1.91) and a β-D-glucosidase (EC 3.2.1.21). See, e.g., U.S. Pat. Nos. 5,874,274; 6,333,181; 7,059,993 and U.S. Patent Publication 2007/0092935. Other enzymes include β-1,4-cellobiohydrolases (CBH I & CBH II); xylanases (XYN I & XYN II); β-glucosidase; α-L-arabinofuranosidase; acetyl xylan esterase; β-mannanase; and α-glucuronidase.

Biomass processing sometimes includes a physical or chemical pretreatment before enzymatic processing. A typical pretreatment is a dilute-acid thermochemical pretreatment, which partially or completely hydrolyzes the hemicellulose and can also hydrolyze some of the lignin. See, e.g., U.S. Pat. No. 6,090,595. Other types of pretreatment include sulfite pretreatment and ozone pretreatment. Thus, in some embodiments, a method described herein involves pretreating biomass prior to enzymatic processing.

Biomass processing can also include a fermentation step, which typically results in the production of fuels such as ethanol. In some cases, the enzymatic saccharification and fermentation steps are carried out simultaneously. If enzymatic saccharification and fermentation are carried out sequentially, the product of the saccharification step can be separated into an aqueous mixture containing mono- and disaccharides, and residual materials, primarily lignin. The aqueous mixture is then subjected to fermentation. Suitable organisms for use in fermentation include *Saccharomyces* spp., *Zymomonas mobilis* and *Clostridium* spp.

In other embodiments, biomass from plants described herein can be processed by thermochemical techniques to produce fuels, energy or heat. Accordingly, a method of processing biomass can involve subjecting biomass from plants described herein to heat and/or pressure under reduced oxygen conditions, which results in the formation of syngas (primarily carbon monoxide and hydrogen). The gasification step typically uses temperatures from about 800° C. to 1400° C. The syngas is then conditioned to remove particulates, light hydrocarbons such as methane, and tar. The syngas can then be used to produce fuels such as gasoline, diesel or methanol. Alternatively, a method of processing biomass can involve subjecting biomass from plants described herein to pyrolysis, i.e., heat and/or pressure in the absence of oxygen. The pyrolysis step typically uses temperatures from about 400° C. to 800° C., and results in the formation of biomass tars. The resulting tars can be then used to produce products such as olefins, oils and specialty chemicals. Saccharification can be determined and saccharification efficiency can be calculated for individual monosaccharides, e.g., glucose conversion efficiency, for combinations of monosaccharides, e.g., glucose+xylose conversion efficiency, or for all monosaccharides. The choice of mono and disaccharide(s) for which saccharification efficiency is calculated in a method is based on factors such as the type of biomass to be processed, and the capability of the conversion process to use all or just some of the sugars made available for biofuel or energy production.

In some embodiments, sugars are extracted from plants described herein for use as a food. Alternatively, sugars can be extracted from plants described herein and further processed for other industrial uses. In these cases, a method can involve the steps of extracting sugars (mono- and disaccharides) from harvested biomass and, optionally, crystallizing the extracted sugars. For example, the stalks of sorghum plants described herein can be harvested by hand or mechanical harvesters, and the juice, containing mono- and disaccharides, extracted by crushing and pressing the stalks with a horizontal or vertical mill. Mono- and disaccharide solids can be produced by crystallization from the juice, which typically involves techniques such as filtering, clarifying, decolorizing, and repeated concentration.

Methods of producing biomass and methods of processing biomass disclosed herein can also involve the use of a gibberellin to facilitate modulation of biomass composition. Gibberellins are tetracyclic diterpene acids that function as plant hormones in dormancy and other aspects of germination. Gibberellins are named GA1 . . . GAn in the order of their discovery. One of the most potent is gibberellic acid, also called GA3. Other active GAs include GA4 and GA7. Thus, a method of producing biomass can comprise applying a gibberellin to a population of plants, either transgenic plants described herein or non-transgenic sorghum, switchgrass, sugarcane or *Miscanthus* plants. The gibberellin typically is applied to foliage in the mid- to late stages of a growing season by spraying, either with a mechanical sprayer or by airplane. A single treatment of a gibberellin can be applied, but more typically, multiple applications are made during a growing season, e.g., 2, 3, 4, 5 or 6 applications. Biomass is then harvested from such plants, which has a composition that differs from that of corresponding control plants to which a gibberellin has not been applied, e.g., such biomass has an increase in total sugar content, a decrease in ash content and/or an increase in total glucan content. Biomass from gibberellin-treated plants can be processed for fuel or energy production, e.g., can be subjected to a pretreatment, and/or enzymatic processing, and/or fermentation, to produce a biofuel. In some embodiments, biomass from gibberellin-treated plants such as sorghum or sugarcane is subjected to an extraction process to obtain sugars. In some embodiments, the resulting juice is purified to obtain sucrose, e.g., crystallized sucrose.

In some aspects the invention relates to methods for breeding plants with composition characteristics that make them more valuable as dedicated food, fuel or energy feedstocks. The $F_1$ or later generation progeny are selected for those plants having desirable attributes related to biomass composition and/or conversion efficiency. Conversion efficiency may be in terms of saccharification efficiency, the conversion of biomass feedstock to free sugars, fermentable sugars, syngas, or a biofuel. The relevant conversion efficiency parameter(s) are dependent on the type of conversion process employed (biochemical, thermochemical to biofuel, or thermochemical to biopower, heat and electricity). Thus, for example, a method of breeding a plant variety comprises crossing two or more parent plants and selecting progeny of the cross that have higher saccharification efficiency relative to the saccharification efficiency of at least one of the parents, or selecting progeny of the cross that have a higher sucrose content relative to the sucrose content of at least one of the parents.

Techniques suitable for use in a plant breeding program are known in the art and include, without limitation, backcrossing, polycrossing, mass selection, pedigree breeding, bulk selection, crossing to another population and recurrent selection.

These techniques can be used alone or in combination with one or more other techniques in a breeding program.

The number of plants used in the initial cross is chosen based on the biology of the species to be used in the method and on breeding programs suitable for that species. The monocotyledonous and dicotyledonous plants mentioned herein can be used in the breeding methods described herein. Plants such as switchgrass, sorghum or sudangrass, and *Miscanthus* are particularly suitable. Breeding techniques applicable to various biomass species are known in the art. See, e.g., Allard, Principles of Plant Breeding, John Wiley & Sons, Inc. (1960); Simmonds, Principles of Crop Improvement, Longman Group Limited (1979); and, Jensen, Plant Breeding Methodology, John Wiley & Sons, Inc. (1988). For example, breeding techniques applicable to open-pollinated species such as switchgrass are known. See, e.g., Vogel and Jung, Critical Rev. Plant Sci. 20:15-49 (2001).

Progeny of the cross of parental plants are screened for those that have a different biomass composition relative to corresponding control plants. Progeny that can be screened include descendants of $F_1$, $F_2$, $F_3$, $F_4$, $F_5$, $F_6$ and subsequent generation plants, $BC_1$, $BC_2$, $BC_3$, and subsequent generation plants, or $F_1BC_1$, $F_1BC_2$, $F_1BC_3$, and subsequent generation plants. Those progeny that have a difference in biomass composition are selected for further breeding.

Selection can be applied beginning with the $F_1$ generation progeny, or can be applied beginning with progeny of a subsequent generation. For example, an open-pollinated population can utilize a program of selection with progeny testing. Examples of selection with progeny testing breeding programs for switchgrass include Restricted Recurrent Phenotypic Selection (RRPS) and Between and Within Half-Sib Family Selection (B&WFS). Alternatively, a program of mass selection can be used. In mass selection, desirable individual plants are chosen, seed harvested, and the seed composited without testing to produce the next generation. Since selection is based on the maternal parent only, and there is no control over pollination, mass selection amounts to a form of random mating with selection. Mass selection typically increases the proportion of desired genotypes in the population.

As another alternative, plants of an open-pollinated species can be used as parents in an initial cross to generate a synthetic variety. A synthetic variety is produced by crossing several parental plants. The number of parental plant varieties, populations, wild accessions, ecotypes, and the like, that are used to generate a synthetic can vary from as little as 10 to as many as 500. Typically, about 100 to 300 varieties, populations, etc., are used parents to generate a synthetic variety. Seed from the parental seed production plot of a synthetic variety can subsequently undergo one or two generations of multiplication, depending on the amount of seed produced in the parental plot before being subjected to selection as discussed herein.

Selection and/or screening can be carried out over one or more generations, and/or in more than one geographic location. In addition, selection and/or screening can be applied during a particular developmental stage in which the phenotype is expected to be exhibited by the plant. Selection and/or screening is carried out to choose those plants having a statistically significant difference in biomass composition relative to a control plant or to the average of a control population and/or those plants having a statistically significant difference in conversion efficiency relative to a control plant or to the average of a control population.

Plant lines and varieties obtained by the methods described herein typically have a difference in biomass composition that is statistically significantly different relative to a control at $p \leq 0.05$ with an appropriate parametric or non-parametric statistic, e.g., Chi-square test, Student's t-test, Mann-Whitney test, or F-test. In some embodiments, the difference is statistically significant at $p<0.01$, $p<0.005$, or $p<0.001$.

In some cases, selection for other useful traits is also carried out, e.g., selection for fungal resistance or drought tolerance. Selection for such other traits can be carried out before, during or after identification of individual plants that possess a difference in biomass composition.

III. POLYPEPTIDES

Polypeptides described herein include biomass composition-modulating polypeptides. In some embodiments, biomass composition-modulating polypeptides are effective to modulate biomass composition when expressed in a plant or plant cell. In some embodiments, reduced expression of biomass composition-modulating polypeptides is effective to modulate biomass composition in a plant or plant cell. Such polypeptides typically contain at least one domain indicative of a biomass composition-modulating polypeptide, as described in more detail herein. Biomass composition-modulating polypeptides also typically have an HMM bit score that is greater than 65 as described in more detail herein. In some embodiments, biomass composition-modulating polypeptides have greater than 80% identity to SEQ ID NOs: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 188, 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 287, 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630,631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836,837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, 1139, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, or 1567 as described in more detail herein.

A. Domains Indicative of Biomass Composition-Modulating Polypeptides

A biomass composition-modulating polypeptide can contain a 2OG-Fe(II) oxygenase superfamily domain, which is predicted to be characteristic of a biomass composition-modulating polypeptide. SEQ ID NO: 471 sets forth the amino acid sequence of a *Oryza sativa* clone, identified herein as GI_115456701, that is predicted to encode a polypeptide containing a 2OG-Fe(II) oxygenase superfamily domain. For example, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to residues 211 to 309 of SEQ ID NO: 471. In some embodiments, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to the 2OG-Fe(II) oxygenase superfamily domain of one or more of the polypeptides set forth in SEQ ID NOs: 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836,837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, and 976. The 2OG-Fe(II) oxygenase superfamily domains of such sequences are set forth in the Sequence Listing. The 2OG-Fe(II) oxygenase superfamily contains members of the 2-oxoglutarate (2OG) and Fe(II)-dependent oxygenase superfamily. See Aravind and Koonin, *Genome Biol.* 2(3): RESEARCH0007 (2001). Gibberellin (GA) 20-oxidases are a class of 2OG-dependent dioxygenases that catalyze the conversion of GA12 and GA53 to GA9 and GA20, respectively, via a three-step oxidation at C-20 of the GA skeleton, and uses iron, ascorbate, and 2-oxoglutarate as co-factors. See Oikawa, et al., *Plant Mol. Biol.* 55: 687-700 (2004).

A biomass composition-modulating polypeptide can contain an alpha/beta hydrolase fold (Abhydrolase_3) domain and a carboxylesterase (CO esterase) domain, which are predicted to be characteristic of a biomass composition-modulating polypeptide. A polypeptide containing such Abhydrolase_3 and CO esterase domains can be useful, for example, for modulating sugar content or conversion efficiency. SEQ ID NO: 99 sets forth the amino acid sequence of an *Oryza sativa* clone, identified herein as GI_75324272 that is predicted to encode a polypeptide containing Abhydrolase_3 and CO esterase domains. For example, a biomass composition-modulating polypeptide can comprise an Abhydrolase_3 domain having 60 percent or greater (e.g., 65, 70, 75, 80, 85, 90, 95, 97, 98, 99, or 100 percent) sequence identity to residues 116 to 329 of SEQ ID NO: 99 and a CO esterase domain having 60 percent or greater (e.g., 65, 70, 75, 80, 85, 90, 95, 97, 98, 99, or 100 percent) sequence identity to residues 110 to 210 of SEQ TD NO: 99. In some embodiments, a biomass composition-modulating polypeptide can comprise an Abhydrolase_3 domain and a CO esterase domain having 60 percent or greater (e.g., 65, 70, 75, 80, 85, 90, 95, 97, 98, 99, or 100 percent) sequence identity to the Abhydrolase_3 and CO esterase domains of one or more of the polypeptides set forth in SEQ ID NOs: 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, and 1139. The Abhydrolase_3 and CO esterase domains of such sequences are set forth in the Sequence Listing. The alpha/beta hydrolase fold is common to a number of hydrolytic enzymes of differing phylogenetic origin and catalytic function (e.g., proteases, lipases, peroxidases, esterases, epoxide hydrolases and dehalogenases). The core of each enzyme is an alpha/beta-sheet, rather than a barrel, containing 8 strands connected by helices. See, Ollis et al., *Protein Eng.* 5 (3): 197-211 (1992); and Nardini, et al., *Curr. Opin. Struct. Biol.* 9 (6): 732-7 (1999). The CO esterases are in the family of proteins containing an Alpha/beta hydrolase fold.

A biomass composition-modulating polypeptide can be a GID1 GA receptor and can contain one or more N-terminal helical GID1 regions, DELLA protein-interacting sites, and GA-binding amino acids as described in Voegele et al., *J. Exp. Botany* 62(14):5131-5147 (2011). For example, a biomass composition-modulating polypeptide can be a GID1 GA receptor and can contain include an alpha-helix a corresponding to approximately residues 9 to 13 of SEQ ID NO:1072, an alpha-helix b corresponding to approximately residues 18 to 34 of SEQ ID NO: 1072, an alpha-helix c corresponding to approximately residues 42 to 49 of SEQ TD NO: 1072, DELLA protein-interacting sites corresponding to approximately residues 6 to 7, 9, 18 to 19, 21 to 23, 25 to 30, 32, 44 to 45, 48 to 49, 51, 125 to 126, 129, and/or 322 to 326 of SEQ ID NO: 1072, GA-binding amino acids corresponding to approximately residues 24, 27, 28, 31, 35, 113 to 116, 126, 127, 191, 238, 239, 243, 244, 247, 320, 322, and/or 323 of SEQ ID NO: 1072, and HGG GA-binding amino acid motif corresponding to approximately residues 114 to 116 of SEQ TD NO: 1072, and/or a GXSXG motif corresponding to approximately residues 189 to 193 of SEQ ID NO: 1072.

A biomass composition-modulating polypeptide can contain a GRAS family transcription factor domain (GRAS) and a transcriptional regulator DELLA protein N terminal domain (DELLA), which are predicted to be characteristic of a biomass composition-modulating polypeptide. Decreased expression of a polypeptide containing such domains can be useful, for example, for modulating sugar content and/or conversion efficiency. SEQ ID NO: 188 sets forth the amino acid sequence of an *Oryza sativa* clone, identified herein as GI_75139772 that is predicted to encode a polypeptide containing a GRAS domain and a DELLA domain. For example, a biomass composition-modulating polypeptide can comprise a GRAS domain having 60 percent or greater (e.g., 65, 70, 75, 80, 85, 90, 95, 97, 98, 99, or 100 percent) sequence identity to residues 168 to 528 of SEQ TD NO: 188 and a DELLA domain having 60 percent or greater (e.g., 65, 70, 75, 80, 85, 90, 95, 97, 98, 99, or 100 percent) sequence identity to residues 27 to 97 of SEQ ID NO: 188. In some embodiments, a biomass composition-modulating polypeptide can comprise a GRAS domain and a DELLA domain having 60 percent or greater (e.g., 65, 70, 75, 80, 85, 90, 95, 97, 98, 99, or 100 percent) sequence identity to the GRAS and DELLA domains of one or more of the polypeptides set forth in SEQ ID NOs: 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 1009, 1010, 1011, 1012, 1013, 1014, 1015, 1016, 1017, 1018, 1019, 1020, 1021, 1022, and 1023. Transcription factors in the GRAS family share a variable amino-terminus and a highly conserved carboxyl-terminus that contains five recognizable motifs. The transcription factors may be involved in development and other processes. See, e.g., Pysh et al., *Plant J.,* 18:111-119 (1999); and Bolle, et al., *Genes Dev.,* 14:1269-1278 (2000). DELLA proteins are transcriptional regulators that are down regulated when gibberellins bind to a nuclear receptor GIBBERELLIN INSENSITIVE DWARF1 (GID1). GID1 forms a complex with DELLA proteins and targets the DELLA proteins for degradation through the 26S proteasome. The N terminal of DELLA proteins contains conserved DELLA and VHYNP motifs that are important for GID1 binding and proteolysis of the DELLA proteins. See, Murase, et al., *Nature,* 456:459-463 (2008).

A biomass composition-modulating polypeptide can contain a 2OG-Fe(II) oxygenase superfamily domain, which is predicted to be characteristic of a biomass composition-modulating polypeptide. A polypeptide containing such a domain can be useful, for example, for modulating sugar content or conversion efficiency. SEQ ID NO: 1 sets forth the amino acid sequence of a *Triticum aestivum* clone, identified herein as GI_85540948, that is predicted to encode a polypeptide containing a 2OG-Fe(II) oxygenase superfamily domain. For example, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to residues 209 to 306 of SEQ ID NO: 1. In some embodiments, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to the 2OG-Fe(II) oxygenase superfamily domain of one or more of the polypeptides set forth in SEQ ID NOs: 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, and 1008. The 2OG-Fe(II) oxygenase superfamily domain of such sequences are set forth in the Sequence Listing. The 2OG-Fe(II) oxygenase superfamily is described above. GA 3-oxidases are a class of 2OG-dependent dioxygenases, classified under EC 1.14.11.15, that convert GA9 and GA20 to GA4 and GA1, respectively. See, Oikawa, et al., 2004, supra.

A biomass composition-modulating polypeptide can contain a 2OG-Fc(II) oxygenase superfamily domain, which is predicted to be characteristic of a biomass composition-modulating polypeptide. Decreased expression of a polypeptide containing such a domain can be useful, for example, for modulating sugar content or conversion efficiency. SEQ ID NO: 287 sets forth the amino acid sequence of a *Arabidopsis thaliana* clone, identified herein as G2OX1_ARATH, that is predicted to encode a polypeptide containing a 2OG-Fe(II) oxygenase superfamily domain. For example, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to residues 167 to 273 of SEQ ID NO: 287. In some embodiments, a biomass composition-modulating polypeptide can comprise a 2OG-Fe(II) oxygenase superfamily domain having 60 percent or greater (e.g., 65, 70, 75, 80, 85, 90, 95, 97, 98, 99, or 100 percent) sequence identity to the 2OG-Fe(II) oxygenase superfamily domain of one or more of the polypeptides set forth in SEQ ID NOs: 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, and 1273. The 2OG-Fe(II) oxygenase superfamily domain of such sequences are set forth in the Sequence Listing. The 2OG-Fe(II) oxygenase superfamily is described above. GA 2-oxidases are a class of 2OG-dependent dioxygenases, classified under EC 1.14.11.13, that inactivate GAs by 2 beta-hydroxylation. See, Hedden and Phillips, *Trends Plant Sci.,* 5:523-530 (2000).

A biomass composition-modulating polypeptide can contain a cytochrome P450 domain, which is predicted to be characteristic of a biomass composition-modulating polypeptide. Decreased expression of a polypeptide containing such a domain can be useful, for example, for modulating sugar content or conversion efficiency. SEQ ID NO: 1429 sets forth the amino acid sequence of a *Gibberella intermedia* clone, identified herein as cytochrome P450 or CYP68B1 or GiGA20-oxidase, that is predicted to encode a polypeptide containing a Cytochrome P450 domain. For example, a biomass composition-modulating polypeptide can comprise a cytochrome P450 domain having 60 percent or greater (e.g., 65, 70, 75, 80, 85, 90, 95, 97, 98, 99, or 100 percent) sequence identity to residues 142 to 500 of SEQ ID NO: 1429. In some embodiments, a biomass composition-modulating polypeptide can comprise a cytochrome P450 domain having 60 percent or greater (e.g., 65, 70, 75, 80, 85, 90, 95, 97, 98, 99, or 100 percent) sequence identity to the cytochrome P450 domain of one or more of the polypeptides set forth in SEQ ID NOs: 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, and 1541. The cytochrome P450 domains of such sequences are set forth in the Sequence Listing. The Cytochrome P450 family is described by, for example, Pinot and Beisson, *FEBS J.,* 78(2):195-205 (2011).

A biomass composition-modulating polypeptide can contain a Cytochrome P450 domain, which is predicted to be characteristic of a biomass composition-modulating polypeptide. Decreased expression of a polypeptide containing such a domain can be useful, for example, for modulating sugar content or conversion efficiency. SEQ ID NO: 1386 sets forth the amino acid sequence of a *Gibberella intermedia* clone, identified herein as cytochrome P450 or GA14-synthase, that is predicted to encode a polypeptide containing a cytochrome P450 domain. For example, a biomass composition-modulating polypeptide can comprise a cytochrome P450 domain having 60 percent or greater (e.g., 65, 70, 75, 80, 85, 90, 95, 97, 98, 99, or 100 percent) sequence identity to residues 176 to 504 of SEQ ID NO: 1386. In some embodiments, a biomass composition-modulating polypeptide can comprise a Cytochrome P450 domain having 60 percent or greater (e.g., 65, 70, 75, 80, 85, 90, 95, 97, 98, 99, or 100 percent) sequence identity to the Cytochrome P450 domain of one or more of the polypeptides set forth in SEQ ID NOs: 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, and 1428. The cytochrome P450 domains of such sequences are set forth in the Sequence Listing. The Cytochrome P450 family is described, for example, by Pinot and Beisson, *FEBS J.,* 78(2):195-205 (2011).

A biomass composition-modulating polypeptide can contain a cytochrome P450 domain, which is predicted to be characteristic of a biomass composition-modulating polypeptide. Decreased expression of a polypeptide containing such a domain can be useful, for example, for modulating sugar content or conversion efficiency. SEQ ID NO: 1274 sets forth the amino acid sequence of a *Gibberella intermedia* clone, identified herein as cytochrome P450 or CYP69A1 or C13-oxidase, that is predicted to encode a polypeptide containing a cytochrome P450 domain. For example, a biomass composition-modulating polypeptide can comprise a cytochrome P450 domain having 60 percent or greater (e.g., 65, 70, 75, 80, 85, 90, 95, 97, 98, 99, or 100 percent) sequence identity to residues 98 to 368 of SEQ ID NO: 1274. In some embodiments, a biomass composition-modulating polypeptide can comprise a cytochrome P450 domain having 60 percent or greater (e.g., 65, 70, 75, 80, 85, 90, 95, 97, 98, 99, or 100 percent) sequence identity to the Cytochrome P450 domain of one or more of the polypeptides set forth in SEQ ID NOs: 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, and 1385. The cytochrome P450 domains of such sequences are set forth in the Sequence Listing. The Cytochrome P450 family is described, for example, by Pinot and Beisson, *FEBS J.,* 78(2):195-205 (2011).

In some embodiments, a biomass composition-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the biomass composition-modulating activity of a truncated polypeptide. In some embodiments, a truncated polypeptide is a dominant negative polypeptide. Expression in a plant of such a truncated polypeptide confers a difference in biomass composition of a plant as compared to the corresponding level of a control plant that does not comprise the truncation.

B. Functional Homologs Identified by Reciprocal BLAST

In some embodiments, one or more functional homologs of a reference biomass composition-modulating polypeptide defined by one or more of the Pfam descriptions indicated above are suitable for use as biomass composition-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a biomass composition-modulating polypeptide, or by combining domains from the coding sequences for different naturally-occurring biomass composition-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of biomass composition-modulating polypeptides. Sequence analysis can involve BLAST, Reciprocal BLAST, or PSI-BLAST analysis of nonredundant databases using a biomass composition-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a biomass composition-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in biomass composition-modulating polypeptides, e.g., conserved functional domains.

Conserved regions can be identified by locating a region within the primary amino acid sequence of a biomass composition-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Softwarc/Pfam/and pfam.janelia.org/. A description of the information included at the Pfam database is described in Sonnhammer et al., *Nucl. Acids Res.,* 26:320-322 (1998); Sonnhammer et al., *Proteins,* 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 1K:
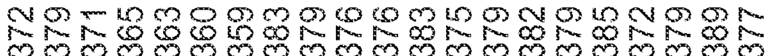
Figure 1K:
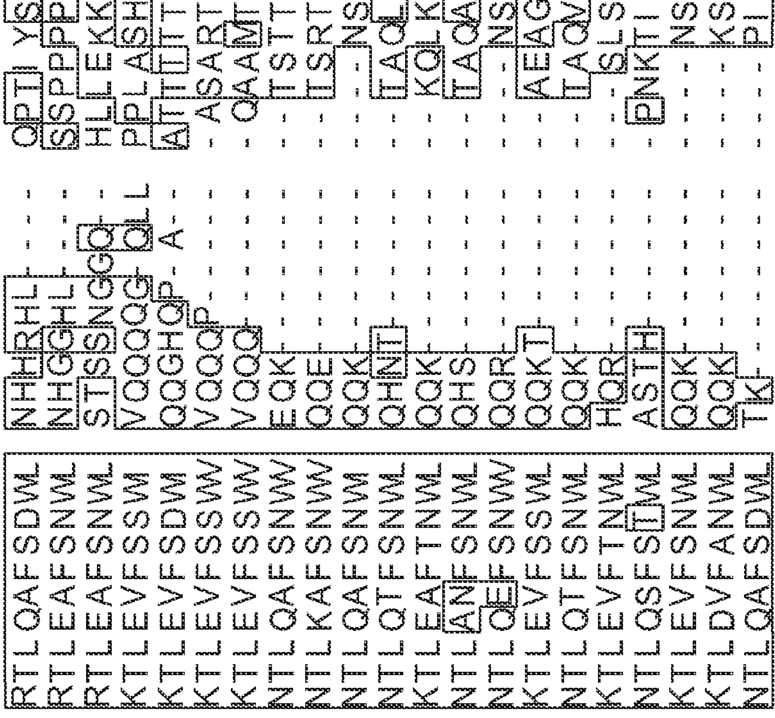

Examples of amino acid sequences of functional homologs of the polypeptide set forth in SEQ ID NO: 471 are provided in FIG. 1 and in the Sequence Listing. Such functional homologs include, for example, CeresAnnot_8631464_Sb (SEQ ID NO: 473), CeresClone_329121_Zm (SEQ ID NO: 475), GI_75276875_Ta (SEQ ID NO: 476), GI_13625523_Lp (SEQ TD NO: 477), GI_49065946_Hv (SEQ ID NO: 478), GI_157683559_*Dasypyrum_villosum* (SEQ ID NO: 479), GI_4164141_*Lactuca_sativa* (SEQ ID NO: 480), GI_187455574_*Helianthus_annuus* (SEQ ID NO: 481), GI_190192210_*Chrysanthemum* (SEQ ID NO: 482), GI_7328337_*Solanum_dulcamara* (SEQ ID NO: 483), GI_8919865_Citrus (SEQ ID NO: 484), GI_326581983_*Capsicum_annuum* (SEQ ID NO: 485), CeresClone_1842451_Gh (SEQ ID NO: 487), GI_99032729_*Vitis_vinifera* (SEQ ID NO: 488), GI_3327245_*Nicotiana_tabacum* (SEQ ID NO: 489), GI_34013374_*Populus_alba* (SEQ ID NO: 490), GI_303303656_*Ipomoea_nil* (SEQ ID NO: 491), GI 18496057_*Fagus_sylvatica* (SEQ ID NO: 492), GI_255541396_*Ricinus_communis* (SEQ ID NO: 493), CeresAnnot_878887_*Arabidopsis thaliana* (SEQ ID NO: 495), GI 210142296 (SEQ ID NO: 496), CeresAnnot_8669917 (SEQ ID NO: 498), GI_15242189 (SEQ ID NO: 499), GI_255927093 (SEQ TD NO: 500), GI_67462129 (SEQ TD NO: 501), GI_10800974 (SEQ ID NO: 502), GI_6855711 (SEQ ID NO: 503), GI_223943497 (SEQ ID NO: 504), GI_210142300 (SEQ ID NO: 505), GI 255927115 (SEQ ID NO: 506), CeresAnnot_1497117 (SEQ ID NO: 508), G1_255927101 (SEQ ID NO: 509), GI_335056045 (SEQ ID NO: 510), GI 125546514 (SEQ ID NO: 511), GI_208609486 (SEQ ID NO: 512), GI_20149239 (SEQ ID NO: 513), GI_109452794 (SEQ TD NO: 514), GI_255927111 (SEQ TD NO: 515), CeresAnnot_881675 (SEQ ID NO: 517), GI 9791186 (SEQ ID NO: 518), G1_255927119 (SEQ ID NO: 519), GI_255927105 (SEQ ID NO: 520), GI_30102973 (SEQ ID NO: 521), GI_1854637 (SEQ ID NO: 522), GI_210142292 (SEQ ID NO: 523), GI 82568041 (SEQ ID NO: 524), GI_297795983 (SEQ ID NO: 525), GI_255927103 (SEQ ID NO: 526), GI_62320340 (SEQ ID NO: 527), GI_125546516 (SEQ ID NO: 528), GI_77632796 (SEQ ID NO: 529), GI_125528619 (SEQ ID NO: 530), GI_335056055 (SEQ ID NO: 531), GI_255927121 (SEQ ID NO: 532), GI 210142286 (SEQ ID NO: 533), GI_147782450 (SEQ ID NO: 534), GI 226492950 (SEQ ID NO: 535), GI_218196824 (SEQ ID NO: 536), GI_15219842 (SEQ ID NO: 537), GI_2108432 (SEQ ID NO: 538), GI_4164143 (SEQ ID NO: 539), GI_297724127 (SEQ ID NO: 540), GI_21322508 (SEQ ID NO: 541), GI_162458757 (SEQ ID NO: 542), CeresClone_100845866 (SEQ ID NO: 544), GI 242055211 (SEQ ID NO: 545), GI_210142298 (SEQ TD NO: 546), GI_326529611 (SEQ TD NO: 547), GI_1109695 (SEQ ID NO: 548), G1_169403818 (SEQ ID NO: 549), GI 2108428 (SEQ ID NO: 550), GI_1848146 (SEQ ID NO: 551), GI_210142288 (SEQ ID NO: 552), GI_13625525 (SEQ ID NO: 553), GI_188474853 (SEQ ID NO: 554), GI_75276876 (SEQ ID NO: 555), GI_335056059 (SEQ ID NO: 556), CeresClone_624633 (SEQ ID NO: 558), GI_210142302 (SEQ ID NO: 559), CeresClone_818172 (SEQ ID NO: 561), GI_297810833 (SEQ ID NO: 562), GI_115441469 (SEQ ID NO: 563), GI_27124556 (SEQ ID NO: 564), CeresClone_639483 (SEQ ID NO: 566), GI_255927091 (SEQ ID NO: 567), GI_48475183 (SEQ ID NO: 568), GI_13625519 (SEQ ID NO: 569), GI_210142290 (SEQ ID NO: 570), GI 30519873 (SEQ ID NO: 571), GI_225453833 (SEQ ID NO: 572), GI_297201566 (SEQ ID NO: 573), GI_159902527 (SEQ ID NO: 574), GI 302797527 (SEQ ID NO: 575), GI_168044400 (SEQ ID NO: 576), GI_233142142 (SEQ ID NO: 577), GI_330985521 (SEQ TD NO: 578), GI_225431689 (SEQ TD NO: 579), GI_168015263 (SEQ ID NO: 580), CeresAnnot_1474270 (SEQ ID NO: 582), GI_296089115 (SEQ ID NO: 583), GI_89574456 (SEQ ID NO: 584), GI_295691295 (SEQ ID NO: 585), GI_219362733 (SEQ ID NO: 586), G1_147865914 (SEQ ID NO: 587), GI_53139594 (SEQ ID NO: 588), GI_187455576 (SEQ ID NO: 589), GI_320462770 (SEQ ID NO: 590), CeresAnnot_1503804 (SEQ ID NO: 592), GI_198286468 (SEQ TD NO: 593), GI_4321498 (SEQ ID NO: 594), GI_118470389 (SEQ ID NO: 595), CeresClone_539430 (SEQ ID NO: 597), CeresClone_518341 (SEQ ID NO: 599), GI_89574455 (SEQ ID NO: 600), GI_330958505 (SEQ ID NO: 601), GI_254419812 (SEQ ID NO: 602), CeresAnnot_1452184 (SEQ ID NO: 604), GI_86605411 (SEQ ID NO: 605), GI_329847655 (SEQ ID NO: 606), GI_237682458 (SEQ ID NO: 607), GI_49065948 (SEQ ID NO: 608), GI_255558510 (SEQ ID NO: 609), GI_326332772 (SEQ ID NO: 610), CeresClone_473318 (SEQ ID NO: 612), GI_116785413 (SEQ ID NO: 613), GI 297242535 (SEQ ID NO: 614), GI_195976661 (SEQ ID NO: 615), CeresAnnot_8644543 (SEQ ID NO: 617), GI_125486693 (SEQ ID NO: 618), GI_53139630 (SEQ ID NO: 619), GI_109729787 (SEQ ID NO: 620), GI_53139646 (SEQ ID NO: 621), GI_53139614 (SEQ ID NO: 622), GI_12320815 (SEQ ID NO: 623), GI_256420048 (SEQ ID NO: 624), GI_255583171 (SEQ ID NO: 625), GI 159902523 (SEQ ID NO: 626), GI_213876865 (SEQ TD NO: 627), GI_195976665 (SEQ TD NO: 628), GI_1666094 (SEQ ID NO: 629), GI_9650811 (SEQ ID NO: 630), GI 2108434 (SEQ ID NO: 631), GI_167644154 (SEQ ID NO: 632), GI 302882991 (SEQ ID NO: 633), GI_160623443 (SEQ ID NO: 634), GI_311899282 (SEQ ID NO: 635), GI_125572881 (SEQ ID NO: 636), GI_53139590 (SEQ ID NO: 637), GI_55978167 (SEQ ID NO: 638), GI_331699132 (SEQ ID NO: 639), GI_325106136 (SEQ ID NO: 640), GI_53139664 (SEQ ID NO: 641), CeresClone_1827193 (SEQ ID NO: 643), GI_160623445 (SEQ ID NO: 644), GI 134075373 (SEQ ID NO: 645), GI_222875436 (SEQ ID NO: 646), GI 2224890 (SEQ ID NO: 647), GI_226305722 (SEQ ID NO: 648), GI_50428327 (SEQ ID NO: 649), GI_302797040 (SEQ ID NO: 650), GI_104295012 (SEQ ID NO: 651), GI_159043926 (SEQ ID NO: 652), GI_254253748 (SEQ ID NO: 653), GI_60498576 (SEQ ID NO: 654), GI_297852192 (SEQ ID NO: 655), GI_302141747 (SEQ ID NO: 656), GI 111224710 (SEQ ID NO: 657), GI_53139592 (SEQ TD NO: 658), GI_320324375 (SEQ TD NO: 659), GI_68509984 (SEQ ID NO: 660), G1_339470611 (SEQ ID NO: 661), CeresAnnot_1468944 (SEQ ID NO: 663), GI_330890071 (SEQ ID NO: 664), GI_225459697 (SEQ ID NO: 665), GI 239817805 (SEQ ID NO: 666), GI_195976667 (SEQ ID NO: 667), GI_51011360 (SEQ ID NO: 668), GI_255572455 (SEQ ID NO: 669), GI_189409355 (SEQ ID NO: 670), GI 302800904 (SEQ ID NO: 671), GI_168012845 (SEQ TD NO: 672), GI_217037949 (SEQ TD NO: 673), GI_312195518 (SEQ ID NO: 674), GI 4321496 (SEQ ID NO: 675), G1_5359492 (SEQ ID NO: 676), GI_53139608 (SEQ ID NO: 677), GI_320588046 (SEQ ID NO: 678), GI_53139640 (SEQ ID NO: 679), GI_333440997 (SEQ ID NO: 680), GI_325189696 (SEQ ID NO: 681), GI 4321494 (SEQ ID NO: 682), GI_53139588 (SEQ ID NO: 683), GI_325184325 (SEQ ID NO: 684), GI 255556241 (SEQ ID NO: 685), GI_302790077 (SEQ ID NO: 686), CeresAnnot_1444168 (SEQ ID NO: 688), GI_159902531 (SEQ ID NO: 689), GI 3402332 (SEQ ID NO: 690), GI_294011471 (SEQ ID NO: 691), GI_320462774 (SEQ ID NO: 692), GI 255556243 (SEQ ID NO: 693), CeresAnnot_1456250 (SEQ ID NO: 695), GI_320462772 (SEQ ID NO: 696), GI_187729689 (SEQ ID NO: 697), GI 114570248 (SEQ ID NO: 698), GI_74273643 (SEQ ID NO: 699), GI_317029127 (SEQ ID NO: 700), GI 1381673 (SEQ ID NO: 701), GI_317158331 (SEQ ID NO: 702), GI_168041562 (SEQ ID NO: 703), CeresClone_1647898 (SEQ TD NO: 705), GI_168004189 (SEQ TD NO: 706), GI_195976671 (SEQ ID NO: 707), GI 168033355 (SEQ ID NO: 708), GI_255637063 (SEQ ID NO: 709), GI 218764876 (SEQ ID NO: 710), GI_47499085 (SEQ ID NO: 711), GI_229489577 (SEQ ID NO: 712), GI 53139616 (SEQ ID NO: 713), GI_16124455 (SEQ ID NO: 714), GI_92115002 (SEQ ID NO: 715), GI_262200288 (SEQ ID NO: 716), GI_53139668 (SEQ ID NO: 717), GI_20149241 (SEQ ID NO: 718), GI_311109251 (SEQ ID NO: 719), GI_222875432 (SEQ ID NO: 720), GI_190192208 (SEQ ID NO: 721), CeresClone_1370404 (SEQ ID NO: 723), GI_298486918 (SEQ ID NO: 724), GI_53139624 (SEQ ID NO: 725), GI_40233167 (SEQ ID NO: 726), GI_301123383 (SEQ ID NO: 727), GI 48057695 (SEQ ID NO: 728), GI_168050680 (SEQ ID NO: 729), GI_29831348 (SEQ ID NO: 730), GI_115470777 (SEQ ID NO: 731), GI 255642379 (SEQ ID NO: 732), GI_302797547 (SEQ ID NO: 733), GI_53139648 (SEQ ID NO: 734), GI_326385638 (SEQ TD NO: 735), GI_147916856 (SEQ TD NO: 736), GI 486625 (SEQ TD NO: 737), G1_197090668 (SEQ ID NO: 738), G1_154705630 (SEQ ID NO: 739), GI_168032021 (SEQ ID NO: 740), GI_58700543 (SEQ ID NO: 741), GI_317454944 (SEQ ID NO: 742), GI_198286476 (SEQ ID NO: 743), G1_332531325 (SEQ ID NO: 744), GI_302821145 (SEQ ID NO: 745), GI 255927085 (SEQ ID NO: 746), GI_8778664 (SEQ ID NO: 747), GI 229490954 (SEQ ID NO: 748), GI_255927099 (SEQ TD NO: 749), GI_34013370 (SEQ TD NO: 750), GI_225455655 (SEQ TD NO: 751), G1_168046914 (SEQ ID NO: 752), CeresClone_156575 (SEQ ID NO: 754), CeresClone_1962928 (SEQ ID NO: 756), GI_37359180 (SEQ ID NO: 757), US20040010815-0080 (SEQ ID NO: 758), GI_308810887 (SEQ ID NO: 759), GI_296084082 (SEQ ID NO: 760), GI 102139962 (SEQ ID NO: 761), GI_46127407 (SEQ ID NO: 762), GI_255927107 (SEQ ID NO: 763), GI 13625521 (SEQ ID NO: 764), GI_224083474 (SEQ ID NO: 765), CeresAnnot_1509446 (SEQ ID NO: 767), GI_28316358 (SEQ ID NO: 768), GI_302821073 (SEQ ID NO: 769), GI_217037951 (SEQ ID NO: 770), CeresClone_526491 (SEQ ID NO: 772), GI_224082360 (SEQ ID NO: 773), CeresAnnot_835213 (SEQ ID NO: 775), GI_53139612 (SEQ ID NO: 776), GI_224120176 (SEQ ID NO: 777), GI 210142294 (SEQ ID NO: 778), GI_9971219 (SEQ ID NO: 779), GI_326475334 (SEQ ID NO: 780), GI 255539617 (SEQ ID NO: 781), GI_255927109 (SEQ ID NO: 782), GI_186695270 (SEQ ID NO: 783), GI_10800976 (SEQ TD NO: 784), GI_255927097 (SEQ TD NO: 785), CeresClone_100062984 (SEQ ID NO: 787), GI 115361480 (SEQ ID NO: 788), GI_2262201 (SEQ ID NO: 789), GI_3327247 (SEQ ID NO: 790), GI_335056001 (SEQ ID NO: 791), GI_111225835 (SEQ ID NO: 792), GI_317106632 (SEQ ID NO: 793), GI_255927087 (SEQ ID NO: 794), GI_9791188 (SEQ ID NO: 795), GI_9791187 (SEQ ID NO: 796), GI_146270975 (SEQ ID NO: 797), CeresAnnot_8732690 (SEQ ID NO: 799), GI_51011362 (SEQ ID NO: 800), GI_303283824 (SEQ ID NO: 801), GI 320589215 (SEQ ID NO: 802), GI_255927089 (SEQ ID NO: 803), GI 330992883 (SEQ ID NO: 804), GI_222875434 (SEQ ID NO: 805), GI_53139620 (SEQ ID NO: 806), GI_297799454 (SEQ ID NO: 807), GI_304570785 (SEQ ID NO: 808), GI_89574458 (SEQ ID NO: 809), GI_238507652 (SEQ ID NO: 810), CeresAnnot_1471005 (SEQ ID NO: 812), WO2011060920-24495 (SEQ ID NO: 813), GI_50428325 (SEQ ID NO: 814), GI_60390163 (SEQ TD NO: 815), GI_158392463 (SEQ TD NO: 816), GI_1144390 (SEQ ID NO: 817), GI_225431709 (SEQ ID NO: 818), CeresAnnot_8461546 (SEQ ID NO: 820), GI_255573359 (SEQ ID NO: 821), GI_302759260 (SEQ ID NO: 822), GI_16118889 (SEQ ID NO: 823), GI 217072494 (SEQ ID NO: 824), GI_340519930 (SEQ ID NO: 825), GI_301123381 (SEQ ID NO: 826), GI 53139652 (SEQ ID NO:827), GI 302790059 (SEQ ID NO:828), GI 257484083 (SEQ ID NO:829), GI_12231168 (SEQ ID NO:830), GI_82568007 (SEQ TD NO:831), GI_53139654 (SEQ ID NO: 832), GI_255927117 (SEQ ID NO: 833), GI_119501723 (SEQ ID NO: 834), GI_189206996 (SEQ ID NO: 835), GI_60498578 (SEQ ID NO: 836), GI_15422154 (SEQ ID NO: 837), GI_198286472 (SEQ ID NO: 838), GI_255927113 (SEQ ID NO: 839), CeresClone_1101515 (SEQ ID NO: 841), GI 208609488 (SEQ ID NO: 842), GI_197103783 (SEQ ID NO: 843), GI_53139600 (SEQ ID NO: 844), GI_1581592 (SEQ ID NO: 845), GI_302381882 (SEQ ID NO: 846), GI_198286480 (SEQ ID NO: 847), CeresAnnot_1522333 (SEQ ID NO: 849), GI:225465379 (SEQ ID NO: 850), GI:357114308 (SEQ ID NO: 851), GI:242076892 (SEQ ID NO: 852), GI:255548069 (SEQ ID NO: 853), GI:356521217 (SEQ ID NO: 854), GI:147865705 (SEQ ID NO: 855), GI:350540006 (SEQ ID NO: 856), GI:326491817 (SEQ ID NO: 857), GI:225426514 (SEQ ID NO: 858), GI:225453648 (SEQ ID NO: 859), GI:226498686 (SEQ ID NO: 860), GI:326494732 (SEQ ID NO: 861), GI:116311010 (SEQ ID NO: 862), GI:115460102 (SEQ ID NO: 863), GI:242040385 (SEQ TD NO: 864), GI:116783156 (SEQ ID NO: 865), GI:297808467 (SEQ ID NO: 866), GI:116791020 (SEQ ID NO: 867), GI:302769898 (SEQ ID NO: 868), GI: 116793430 (SEQ ID NO: 869), GI:18402081 (SEQ ID NO:

870), GI:116792100 (SEQ ID NO: 871), GI:168014854 (SEQ ID NO: 872), GI:194703858 (SEQ ID NO: 873), GI:357475523 (SEQ ID NO: 874), GI: 116784279 (SEQ ID NO: 875), GI: 116793277 (SEQ ID NO: 876), GI:294463977 (SEQ ID NO: 877), GI:357468779 (SEQ ID NO: 878), GI:268638403 (SEQ ID NO: 879), GI:159902533 (SEQ ID NO: 880), GI:224286184 (SEQ ID NO: 881), GI:357475519 (SEQ ID NO: 882), GI:125562561 (SEQ ID NO: 883), GI:116780785 (SEQ ID NO: 884), GI:116786939 (SEQ ID NO: 885), GI:357461273 (SEQ ID NO: 886), GI:222613187 (SEQ ID NO: 887), GI:357475529 (SEQ ID NO: 888), GI:168003319 (SEQ ID NO: 889), GI:297809271 (SEQ ID NO: 890), GI:224284972 (SEQ ID NO: 891), GI:297809269 (SEQ ID NO: 892), GI:116794322 (SEQ TD NO: 893), GI:116792196 (SEQ ID NO: 894), GI:357475525 (SEQ ID NO: 895), GI:357440313 (SEQ ID NO: 896), GI:313471276 (SEQ ID NO: 897), GI:357492715 (SEQ ID NO: 898), GI:255557477 (SEQ ID NO: 899), GI:358347250 (SEQ ID NO: 900), GI:357111461 (SEQ ID NO: 901), GI:255575141 (SEQ ID NO: 902), CeresAnnot:8454419 (SEQ ID NO: 904), GI:297820344 (SEQ ID NO: 905), GI: 110618325 (SEQ ID NO: 906), GI: 166798287 (SEQ TD NO: 907), GI:60476845 (SEQ TD NO: 908), GI:51493449 (SEQ ID NO: 909), GI:326366179 (SEQ ID NO: 910), GI:42566572 (SEQ ID NO: 911), GI:378749126 (SEQ ID NO: 912), GI:219944305 (SEQ ID NO: 913), GI:366047645 (SEQ ID NO: 914), GI:237682460 (SEQ ID NO: 915), GI:333362482 (SEQ ID NO: 916), GI: 169793771 (SEQ ID NO: 917), GI:729503 (SEQ ID NO: 918), GI:80973282 (SEQ ID NO: 919), GI:21392365 (SEQ ID NO: 920), GI:222478425 (SEQ ID NO: 921), GI: 164454785 (SEQ ID NO: 922), GI:46850468 (SEQ ID NO: 923), GI:225194715 (SEQ ID NO: 924), GI:355645974 (SEQ ID NO: 925), GI: 113205138 (SEQ ID NO: 926), GI:2570827 (SEQ ID NO: 927), GI:300834841 (SEQ ID NO: 928), GI: 157169280 (SEQ ID NO: 929), GI:348686932 (SEQ ID NO: 930), GI:223997880 (SEQ ID NO: 931), GI:194371667 (SEQ ID NO: 932), GI:297306658 (SEQ ID NO: 933), GI:158515829 (SEQ ID NO: 934), GI:241898888 (SEQ ID NO: 935), GI:62824273 (SEQ ID NO: 936), GI:520802 (SEQ ID NO: 937), GI:307727667 (SEQ TD NO: 938), GI:359359094 (SEQ ID NO: 939), GI:145248559 (SEQ TD NO: 940), GI:227536376 (SEQ ID NO: 941), GI:339495204 (SEQ ID NO: 942), GI:334344062 (SEQ ID NO: 943), GI: 145352595 (SEQ ID NO: 944), GI:354570727 (SEQ ID NO: 945), GI:66043929 (SEQ ID NO: 946), GI:302884057 (SEQ ID NO: 947), GI:379063357 (SEQ ID NO: 948), GI:153011110 (SEQ ID NO: 949), GI:19115385 (SEQ ID NO: 950), GI:30060226 (SEQ ID NO: 951), GI:169615517 (SEQ ID NO: 952), GI:149280311 (SEQ ID NO: 953), GI:322705051 (SEQ ID NO: 954), GI:88856654 (SEQ ID NO: 955), GI:117617896 (SEQ ID NO: 956), GI:381201565 (SEQ ID NO: 957), GI:170089053 (SEQ ID NO: 958), GI:379655258 (SEQ ID NO: 959), GI:321253745 (SEQ ID NO: 960), GI:343425662 (SEQ ID NO: 961), GI:226294156 (SEQ ID NO: 962), GI:169768582 (SEQ ID NO: 963), GI:380602393 (SEQ ID NO: 964), GI:315044917 (SEQ ID NO: 965), GI:332529892 (SEQ ID NO: 966), GI:116695054 (SEQ ID NO: 967), GI:346974225 (SEQ ID NO: 968), GI:361126689 (SEQ TD NO: 969), GI:226292680 (SEQ TD NO: 970), GI:119478814 (SEQ ID NO: 971), GI:347829892 (SEQ ID NO: 972), GI:150951140 (SEQ ID NO: 973), GI:149245084 (SEQ ID NO: 974), GI:156064337 (SEQ ID NO: 975), and GI:242780807 (SEQ ID NO: 976). In some cases, a functional homolog of SEQ ID NO: 471 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 471. In some cases, a functional homolog of SEQ ID NO: 471 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 471 described above or set forth in the Sequence Listing.

Figure 2E:
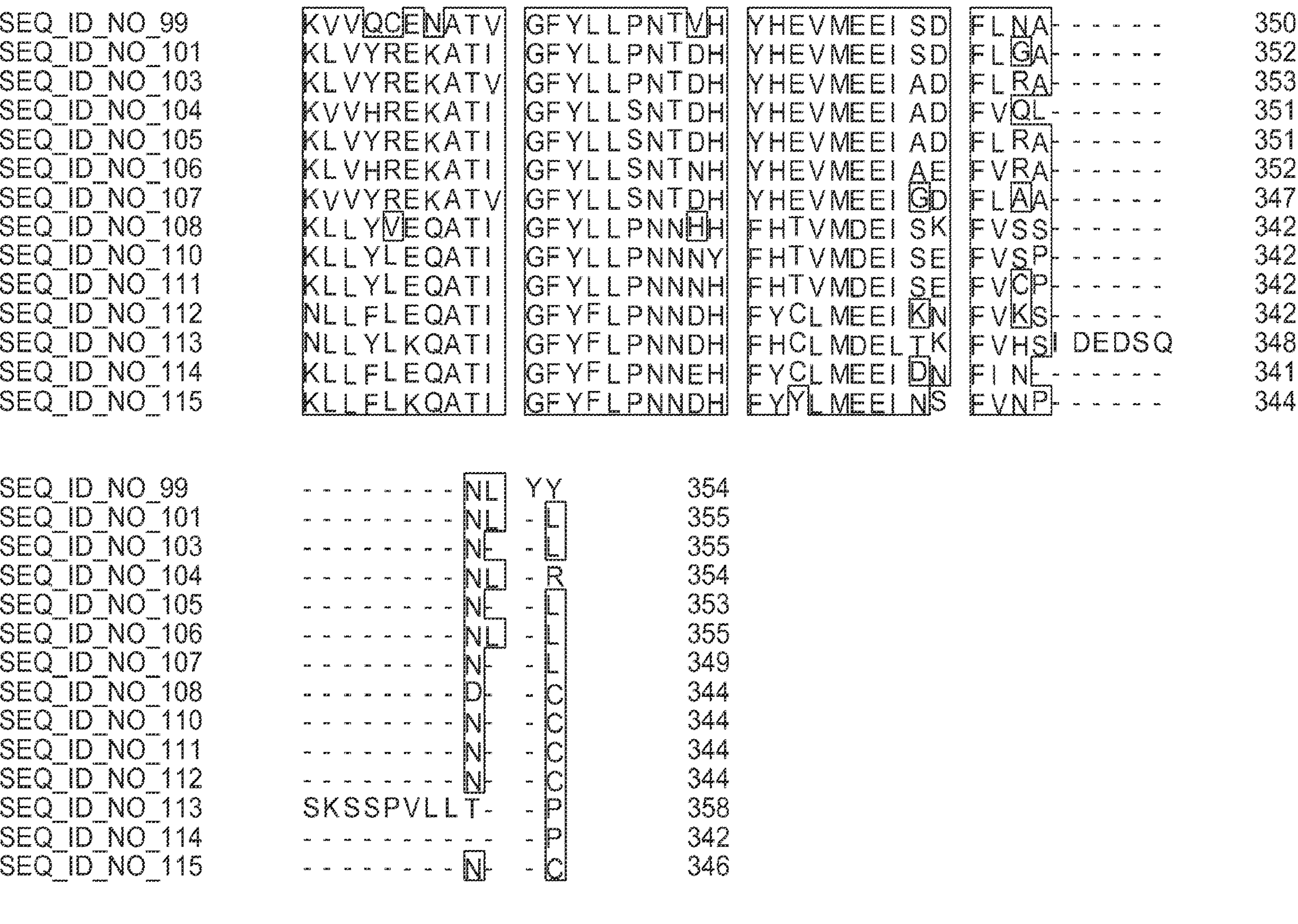

Examples of amino acid sequences of functional homologs of the polypeptide set forth in SEQ ID NO: 99 are provided in FIG. 2 and in the Sequence Listing. Such functional homologs include, for example, CeresClone_1857760 (SEQ ID NO: 101), CeresAnnot_8732528 (SEQ ID NO: 103), GI_156616217 (SEQ ID NO: 104), GI_169159254 (SEQ ID NO: 105), GI 169159270 (SEQ ID NO: 106), GI_169159256 (SEQ ID NO: 107), GI 225346677 (SEQ ID NO: 108), CeresAnnot_1488901 (SEQ ID NO: 110), GI_255542494 (SEQ ID NO: 111), GI_225436847 (SEQ TD NO: 112), GI_315075933 (SEQ TD NO: 113), G1_238654635 (SEQ ID NO: 114), GI_82697973 (SEQ ID NO: 115), G1_218196784 (SEQ ID NO: 116), GI_169159258 (SEQ ID NO: 117), CeresClone_1941624 (SEQ ID NO: 119), GI_225346675 (SEQ ID NO: 120), GI_148612415 (SEQ ID NO: 121), CeresAnnot_1522790 (SEQ ID NO: 123), GI_110747150 (SEQ ID NO: 124), CeresAnnot_1469390 (SEQ ID NO: 126), GI 225346679 (SEQ ID NO: 127), GI_224068739 (SEQ ID NO: 128), GI_225346671 (SEQ ID NO: 129), CeresAnnot_1471748 (SEQ ID NO: 131), GI_147774750 (SEQ ID NO: 132), GI_15240483 (SEQ ID NO: 133), GI_225346673 (SEQ ID NO: 134), GI_298205013 (SEQ ID NO: 135), GI_255567576 (SEQ ID NO: 136), GI_307752615 (SEQ ID NO: 137), GI_297817636 (SEQ ID NO: 138), GI_15229371 (SEQ ID NO: 139), GI_15229905 (SEQ ID NO: 140), GI 307752613 (SEQ ID NO: 141), GI_169159264 (SEQ ID NO: 142), GI_307752617 (SEQ ID NO: 143), GI 297812999 (SEQ ID NO: 144), GI_238654633 (SEQ TD NO: 145), GI_308220216 (SEQ TD NO: 146), CeresAnnot_1444948 (SEQ ID NO: 148), CeresClone_1172108 (SEQ ID NO: 150), GI_169159250 (SEQ ID NO: 151), GI 169159262 (SEQ ID NO: 152), CeresClone_1924067 (SEQ ID NO: 154), GI_169159252 (SEQ ID NO: 155), GI_116794075 (SEQ ID NO: 156), GI 169159248 (SEQ ID NO: 157), GI_169159246 (SEQ ID NO: 158), GI 256772632 (SEQ ID NO: 159), GI_302794147 (SEQ TD NO: 160), GI_296086662 (SEQ TD NO: 161), GI_302782397 (SEQ ID NO: 162), GI 302787771 (SEQ ID NO: 163), GI_156446298 (SEQ ID NO: 164), CeresClone_1843446 (SEQ ID NO: 166), GI_168008743 (SEQ ID NO: 167), CeresAnnot_1449351 (SEQ ID NO: 169), GI_125533918 (SEQ ID NO: 170), GI 297728173 (SEQ ID NO: 171), GI_159902513 (SEQ ID NO: 172), GI 225463177 (SEQ ID NO: 173), CeresClone_566899 (SEQ ID NO: 175), GI_294460127 (SEQ ID NO: 176), GI_147856212 (SEQ ID NO: 177), CeresClone_1647753 (SEQ ID NO: 179), GI_115473685 (SEQ ID NO: 180), GI_82697933 (SEQ ID NO: 181), GI_302788858 (SEQ ID NO: 182), GI_168013809 (SEQ ID NO: 183), GI 302788854 (SEQ ID NO: 184), GI_242068025 (SEQ ID NO: 185), GI_302769524 (SEQ ID NO: 186), GI_148270935 (SEQ ID NO: 187), GI:356535621 (SEQ ID NO: 1024), (SEQ ID NO: 1025), GI:225346669 (SEQ ID NO: 1026), GI:326517960 (SEQ ID NO: 1027), (SEQ TD NO: 1028), GI:168011953 (SEQ TD NO: 1029), GI:21618039_CeresClone:42187_CeresClone:9482 (SEQ ID NO: 1031), (SEQ ID NO: 1032), GI:297829024 (SEQ ID NO: 1033), GI:356576751 (SEQ ID NO: 1034), (SEQ ID NO: 1035), GI:125559352 (SEQ ID NO: 1036), GI:357116238 (SEQ ID NO: 1037), GI:326513536 (SEQ ID NO: 1038), GI:225314775 (SEQ ID NO: 1040), GI:359493559 (SEQ ID NO: 1041), GI:225451094 (SEQ ID NO: 1042), CeresAnnot:8657013_GI:242051064 (SEQ ID NO: 1044), (SEQ ID NO: 1045), GI:381218259 (SEQ ID NO: 1046), GI:357441531 (SEQ ID NO: 1047), (SEQ ID NO: 1048), GI:115467742 (SEQ ID NO: 1049), GI:357510077 (SEQ ID NO: 1050), GI:302823479 (SEQ ID NO: 1051), GI:357442625 (SEQ ID NO: 1052), GI:357498883 (SEQ ID NO: 1053), CeresClone:1911189 (SEQ ID NO: 1055), (SEQ ID NO: 1056), GI:356559967 (SEQ ID NO: 1057), (SEQ ID NO: 1058), GI:255574873 (SEQ ID NO: 1059), GI:225460002 (SEQ ID NO: 1060), (SEQ ID NO: 1061), GI:224056763 (SEQ ID NO: 1062), (SEQ TD NO: 1063), GI:297611539 (SEQ ID NO: 1064), CeresClone:1815446 (SEQ ID NO: 1066), GI:82697971 (SEQ ID NO: 1067), GI:255564916 (SEQ ID NO: 1068), (SEQ ID NO: 1069), GI:225459998 (SEQ ID NO: 1070), GI:169159268 (SEQ ID NO: 1071), GI:215261125 (SEQ ID NO: 1072), GI:356500238 (SEQ ID NO: 1073), (SEQ ID NO: 1074), CeresClone:1448852 (SEQ ID NO: 1076), GI:326532822 (SEQ ID NO: 1077), CeresClone:1991076 (SEQ TD NO: 1079), GI:326497909 (SEQ TD NO: 1080), GI:242068027_CeresAnnot:8684742 (SEQ ID NO: 1082), GI:225463175 (SEQ ID NO: 1083), (SEQ ID NO: 1084), GI:357498903 (SEQ ID NO: 1085), GI:125555059 (SEQ ID NO: 1086), GI:357133715_Bradi2g25600 (SEQ ID NO: 1087), CeresClone:892953 (SEQ ID NO: 1089), GI:226498284_CeresClone:330490 (SEQ ID NO: 1091), GI:169159266 (SEQ ID NO: 1092), GI:255564994 (SEQ ID NO: 1093), (SEQ ID NO: 1094), GI:15237783 (SEQ ID NO: 1095), GI:116781798 (SEQ ID NO: 1096), GI:380040722 (SEQ ID NO: 1097), CeresAnnot:1442123 (SEQ ID NO: 1099), GI:356504896 (SEQ ID NO: 1100), GI:356559969 (SEQ ID NO: 1101), (SEQ ID NO: 1102), CeresAnnot:8657010 (SEQ ID NO: 1104), GI:357152486 (SEQ ID NO: 1105), GI:357498895 (SEQ ID NO: 1106), CeresClone:1996207 (SEQ ID NO: 1108), GI:226504948_CeresClone:335133 (SEQ ID NO: 1110), GI:357116047 (SEQ ID NO: 1111), CeresClone:625081 (SEQ ID NO: 1113), (SEQ ID NO: 1114), GI:147820116 (SEQ ID NO: 1115), GI:380040720 (SEQ ID NO: 1116), GI:329756574 (SEQ ID NO: 1117), GI:225316828 (SEQ ID NO: 1119), GI:218185506 (SEQ ID NO: 1120), GI:302769530 (SEQ ID NO: 1121), GI:357152492 (SEQ ID NO: 1122), (SEQ ID NO: 1123), (SEQ ID NO: 1124), GI:168029383 (SEQ ID NO: 1125), GI:125559371 (SEQ ID NO: 1126), GI:357498899 (SEQ ID NO: 1127), GI:357116242 (SEQ ID NO: 1128), GI:380040724 (SEQ ID NO: 1129), (SEQ ID NO: 1130), GI:297812501 (SEQ ID NO: 1131), GI:210144144 (SEQ ID NO: 1133), CeresClone: 568611 (SEQ ID NO: 1135), GI:326527329 (SEQ ID NO: 1136), CeresAnnot:1483390 (SEQ ID NO: 1138), and GI:255553969 (SEQ ID NO: 1139). In some cases, a functional homolog of SEQ ID NO: 99 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 99. In some cases, a functional homolog of SEQ TD NO: 99 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 99 described above or set forth in the Sequence Listing.

Figure 3F:
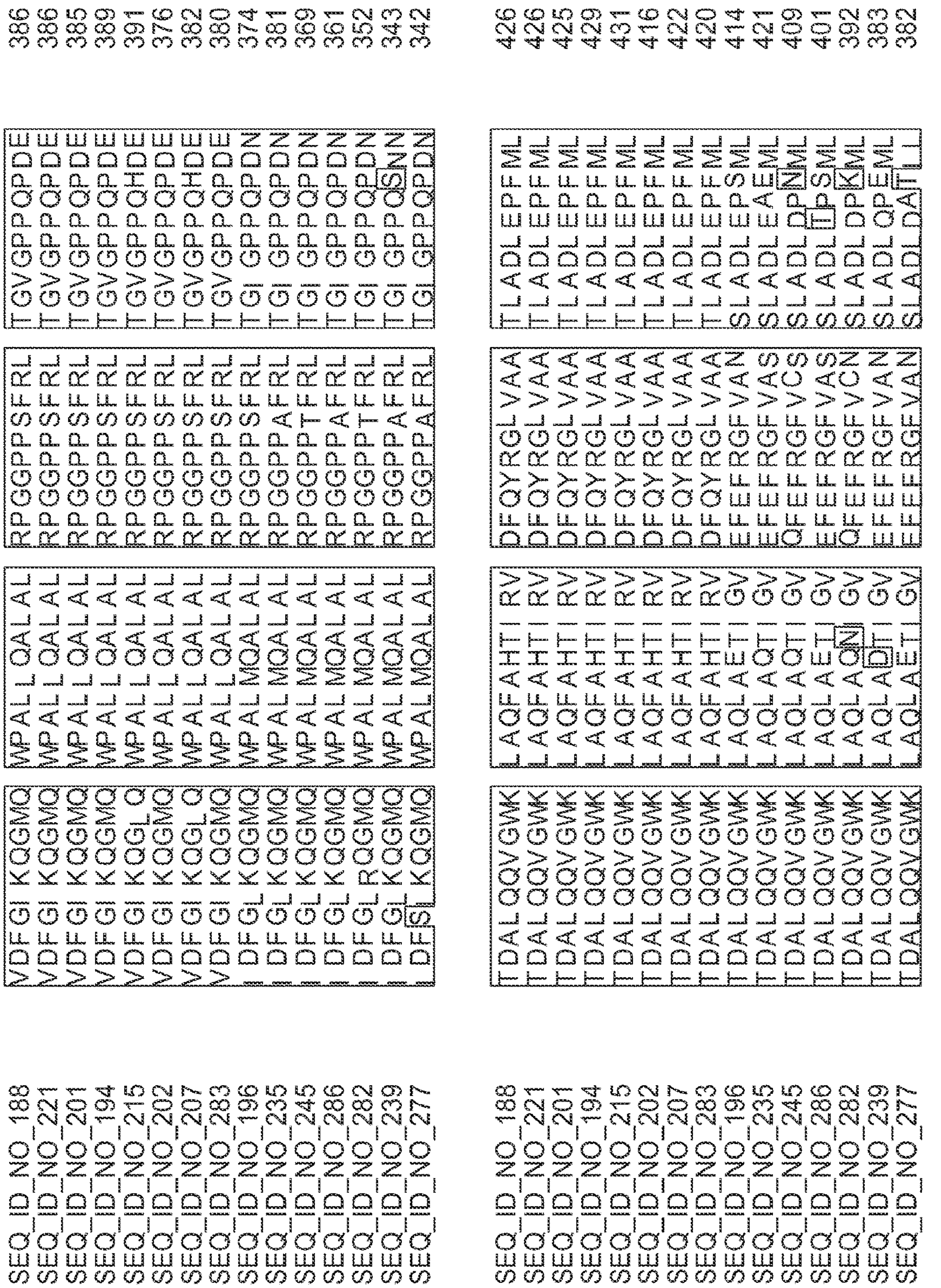
FIGS. 3A-3T contain an alignment of the amino acid sequence of GI_75139772 (SEQ ID NO: 188) with homologous and/or orthologous amino acid sequences.
Figure 4K:
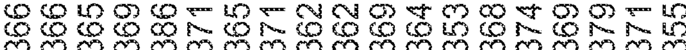
Figure 4K:
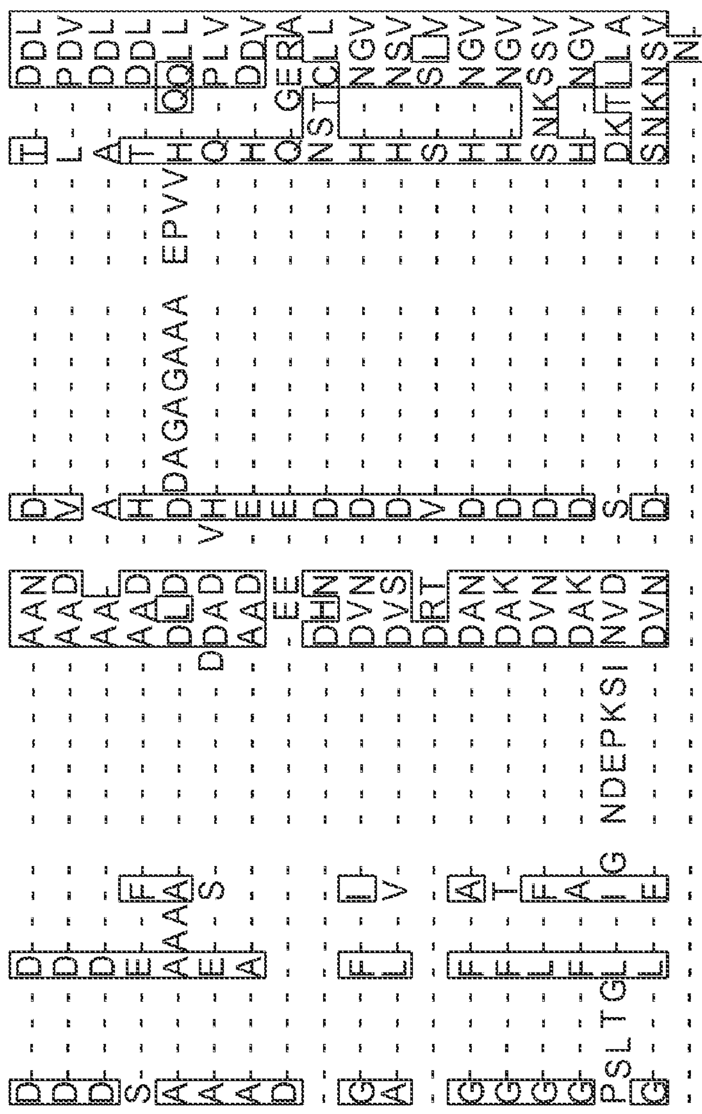
Figure 4K:
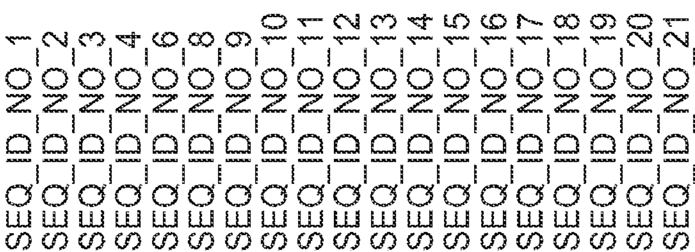
Figure 4L:
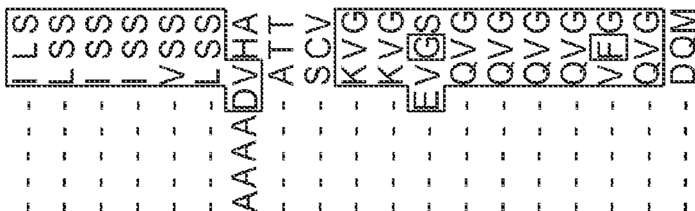
Figure 5I:
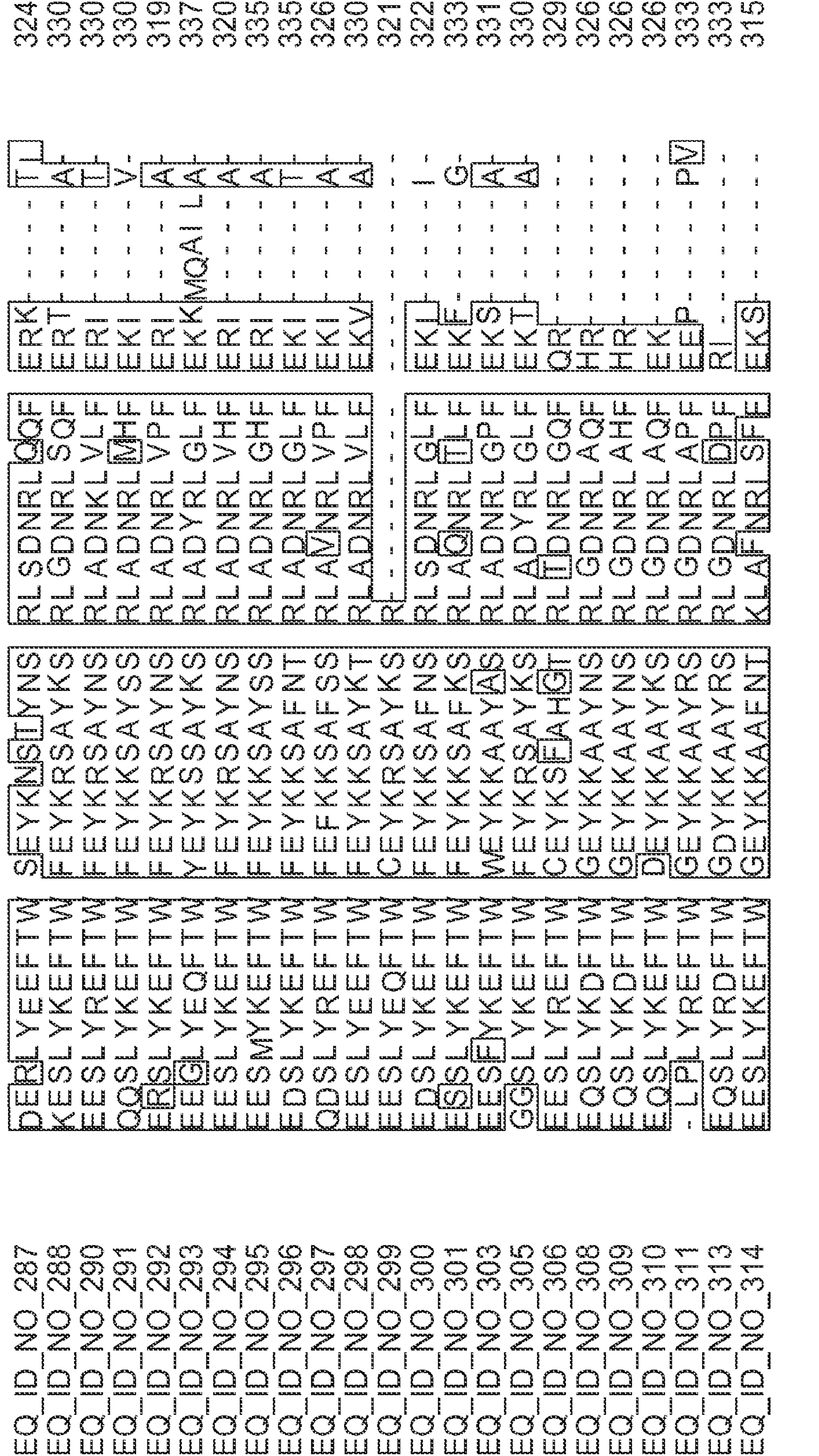
Figure 5J:
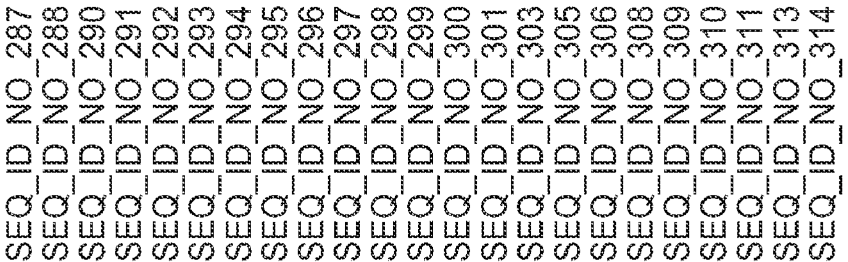
Figure 5J:
Figure 5J:
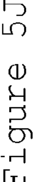

Examples of amino acid sequences of functional homologs of the polypeptide set forth in SEQ TD NO: 188 are provided in FIG. 3 and in the Sequence Listing. Such functional homologs include, for example, GI_2569938 (SEQ ID NO: 189), GI_66816765 (SEQ ID NO: 190), GI 282759334 (SEQ ID NO: 191), CeresClone_1884375 (SEQ ID NO: 193), GI_75207626 (SEQ ID NO: 194), GI_115184057 (SEQ ID NO: 195), GI 225451399 (SEQ ID NO: 196), GI_20257430 (SEQ ID NO: 197), GI_20257459 (SEQ ID NO: 198), GI_20257428 (SEQ ID NO: 199), CeresClone_1776298 (SEQ ID NO: 201), GI_75161835 (SEQ ID NO: 202), GI_204022232 (SEQ ID NO: 203), GI_20257432 (SEQ ID NO: 204), GI_225424291 (SEQ ID NO: 205), GI_20257447 (SEQ ID NO: 206), GI_70797560 (SEQ ID NO: 207), GI_15219630 (SEQ ID NO: 208), GI_225457448 (SEQ ID NO: 209), CeresAnnot_1502385 (SEQ ID NO: 211), CeresClone_1809677 (SEQ ID NO: 213), CeresAnnot_8633163 (SEQ ID NO: 215), GI 302786358 (SEQ ID NO: 216), GI_204022230 (SEQ ID NO: 217), CeresAnnot_1463794 (SEQ ID NO: 219), GI_296804670 (SEQ TD NO: 220), GI_59800349 (SEQ TD NO: 221), GI_75121087 (SEQ ID NO: 222), CeresAnnot_870628 (SEQ ID NO: 224), GI 219964535 (SEQ ID NO: 225), GI_113171199 (SEQ ID NO: 226), CeresClone_1945971 (SEQ ID NO: 228), CeresAnnot_1440830 (SEQ ID NO: 230), GI_238821220 (SEQ ID NO: 231), GI_257219873 (SEQ ID NO: 232), GI 113206404 (SEQ ID NO: 233), CeresAnnot_1445496 (SEQ ID NO: 235), GI_147812753 (SEQ ID NO: 236), CeresAnnot_857982 (SEQ ID NO: 238), GI_255586838 (SEQ ID NO: 239), GI_15237971 (SEQ ID NO: 240), GI 20257436 (SEQ ID NO: 241), GI_225424293 (SEQ ID NO: 242), GI_297844400 (SEQ ID NO: 243), GI_75104298 (SEQ ID NO: 244), GI_148189864 (SEQ ID NO: 245), CeresClone_1884754 (SEQ ID NO: 247), GI_264688602 (SEQ ID NO: 248), GI_219886839 (SEQ ID NO: 249), GI_222154139 (SEQ ID NO: 250), GI 20257420 (SEQ ID NO: 251), GI_119214959 (SEQ ID NO: 252), GI_119214959 (SEQ ID NO: 254), GI 75104297 (SEQ ID NO: 255), GI_66816755 (SEQ TD NO: 256), GI_238821222 (SEQ TD NO: 257), GI_26451075 (SEQ ID NO: 258), G1_152968454 (SEQ ID NO: 259), GI_75121086 (SEQ ID NO: 260), GI_242058173 (SEQ ID NO: 261), GI 225451401 (SEQ ID NO: 262), CeresAnnot_832619 (SEQ ID NO: 264), GI_171702837 (SEQ ID NO: 265), GI_75148243 (SEQ ID NO: 266), GI 20257457 (SEQ ID NO: 267), GI_20257422 (SEQ ID NO: 268), GI_312281569 (SEQ ID NO: 269), GI_125545440 (SEQ ID NO: 270), CeresAnnot_1449379 (SEQ TD NO: 272), GI_290988843 (SEQ TD NO: 273), GI_224032153 (SEQ ID NO: 274), GI 225451515 (SEQ ID NO: 275), GI_339779229 (SEQ ID NO: 276), GI_75146039 (SEQ ID NO: 277), GI_115184074 (SEQ ID NO: 278), GI_321442634 (SEQ ID NO: 279), GI 63054405 (SEQ ID NO: 280), CeresClone_479467 (SEQ ID NO: 282), GI_75207630 (SEQ ID NO: 283), GI_297817754 (SEQ ID NO: 284), GI 2339978 (SEQ ID NO: 285), GI_66816747 (SEQ ID NO: 286), GI:119713908 (SEQ ID NO: 1009), GI:15866400 (SEQ ID NO: 1010), GI:20257442 (SEQ ID NO: 1011), GI:380504012 (SEQ ID NO: 1012), GI:380503998 (SEQ ID NO: 1013), GI:380504056 (SEQ ID NO: 1014), GI:15866316 (SEQ ID NO: 1015), GI:20257440 (SEQ ID NO: 1016), GI:20257463 (SEQ ID NO: 1017), GI:20257451 (SEQ ID NO: 1018), GI:380503968 (SEQ ID NO: 1019), GI:15866328 (SEQ ID NO: 1020), GI:15866334 (SEQ ID NO: 1021), GI:15866348 (SEQ ID NO: 1022), and GI:157154012 (SEQ ID NO: 1023). In some cases, a functional homolog of SEQ TD NO: 188 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 188. In some cases, a functional homolog of SEQ ID NO: 188 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 188 described above or set forth in the Sequence Listing.

Examples of amino acid sequences of functional homologs of the polypeptide set forth in SEQ ID NO: 1 are provided in FIG. 4 and in the Sequence Listing. Such functional homologs include, for example, GI_49065952 (SEQ ID NO: 2), GI_157683561 (SEQ ID NO: 3), GI 291586147 (SEQ ID NO: 4), CeresAnnot_8658260 (SEQ ID NO: 6), CeresClone_1784588 (SEQ ID NO: 8), GI_15005015 (SEQ TD NO: 9), GI_194700302 (SEQ TD NO: 10), GI_188035730 (SEQ ID NO: 11), GI_147852208 (SEQ ID NO: 12), GI_61651585 (SEQ ID NO: 13), GI_109729785 (SEQ ID NO: 14), GI_190192212 (SEQ ID NO: 15), GI_6691485 (SEQ ID NO: 16), G1_145206857 (SEQ ID NO: 17), G1_225421147 (SEQ ID NO: 18), GI_27261175 (SEQ ID NO: 19), GI_2316018 (SEQ ID NO: 20), GI_77632798 (SEQ ID NO: 21), GI_302811181 (SEQ ID NO: 22), GI_20149245 (SEQ ID NO: 23), GI_15004943 (SEQ TD NO: 24), GI_297849984 (SEQ TD NO: 25), GI_145206861 (SEQ ID NO: 26), GI_225421145 (SEQ ID NO: 27), GI_2289032 (SEQ ID NO: 28), GI_27123661 (SEQ ID NO: 29), GI 49065950 (SEQ ID NO: 30), GI_226508364 (SEQ ID NO: 31), GI_312197436 (SEQ ID NO: 32), GI_218196191 (SEQ ID NO: 33), CeresClone_1045013 (SEQ ID NO: 35), GI 134303282 (SEQ ID NO: 36), GI_14780049 (SEQ ID NO: 37), GI_340796369 (SEQ ID NO: 38), GI_4164147 (SEQ ID NO: 39), GI_9971221 (SEQ ID NO: 40), GI_3982753 (SEQ ID NO: 41), GI_85540947 (SEQ ID NO: 42), CeresAnnot_8725416 (SEQ ID NO: 44), GI_50428333 (SEQ ID NO: 45), GI 50428331 (SEQ ID NO: 46), GI_340796371 (SEQ ID NO: 47), GI_219887767 (SEQ ID NO: 48), GI_15418962 (SEQ ID NO: 49), GI_320462776 (SEQ ID NO: 50), GI 225430186 (SEQ ID NO: 51), GI_2314805 (SEQ ID NO: 52), GI_224070877 (SEQ ID NO: 53), GI 50428329 (SEQ ID NO: 54), GI_297743334 (SEQ ID NO: 55), GI_8247213 (SEQ ID NO: 56), GI_255040357 (SEQ TD NO: 57), GI_297839907 (SEQ TD NO: 58), GI_8894936 (SEQ TD NO: 59), GI_114329242 (SEQ ID NO: 60), G1_304636271 (SEQ ID NO: 61), GI_4164145 (SEQ ID NO: 62), GI_255549086 (SEQ ID NO: 63), GI_224141841 (SEQ ID NO: 64), GI_194459446 (SEQ ID NO: 65), sp_Q39103_G30X1_ARATH (SEQ ID NO: 66), GI_85540946 (SEQ ID NO: 67), CeresClone_442759 (SEQ ID NO: 69), GI_115462397 (SEQ ID NO: 70), GI_190192214 (SEQ ID NO: 71), GI_304636273 (SEQ ID NO: 72), CeresClone_476411 (SEQ ID NO: 74), GI_2291080 (SEQ ID NO: 75), GI_304636275 (SEQ ID NO: 76), GI_255549006 (SEQ ID NO: 77), CeresClone_1653303 (SEQ ID NO: 79), CeresAnnot_1508682 (SEQ ID NO: 81), GI_294471308 (SEQ ID NO: 82), GI_3834350 (SEQ ID NO: 83), GI_2316102 (SEQ ID NO: 84), GI_11034551 (SEQ ID NO: 85), GI_15418964 (SEQ ID NO: 86), GI_71532877 (SEQ ID NO: 87), GI_40714039 (SEQ ID NO: 88), GI 3834352 (SEQ ID NO: 89), GI_255546615 (SEQ ID NO: 90), GI_38154346 (SEQ ID NO: 91), GI_145206859 (SEQ TD NO: 92), CeresAnnot_1438976 (SEQ ID NO: 94), GI_115434856 (SEQ ID NO: 95), sp_Q9ZT84_G30X2_ARATH (SEQ ID NO: 96), GI_40714037 (SEQ ID NO: 97), GI 20149243 (SEQ ID NO: 98), CeresClone:1787734 (SEQ ID NO: 978), CeresClone: 704370 (SEQ ID NO: 980), GI:357136088 (SEQ ID NO: 981), GI:326502098 (SEQ ID NO: 982), GI:357152716 (SEQ ID NO: 983), GI:242089739 (SEQ ID NO: 984), GI:225442751 (SEQ ID NO: 985), GI:357455059 (SEQ TD NO: 986), GI:365176184 (SEQ TD NO: 987), GI:356522371 (SEQ ID NO: 988), GI:356550578 (SEQ ID NO: 989), GI:357436835 (SEQ ID NO: 990), GI:356563832 (SEQ ID NO: 991), GI:297839909 (SEQ ID NO: 992), GI:356518262 (SEQ ID NO: 993), GI:301332976 (SEQ ID NO: 994), GI:301332946 (SEQ ID NO: 995), GI:301332982 (SEQ ID NO: 996), GI:301332866 (SEQ ID NO: 997), GI:301332872 (SEQ ID NO: 998), GI:356552539 (SEQ ID NO: 999), GI:301332918 (SEQ ID NO: 1000), GI:301332984 (SEQ ID NO: 1001), GI:301332974 (SEQ ID NO: 1002), GI:301332896 (SEQ ID NO: 1003), GI:301332906 (SEQ ID NO: 1004), GI:301333008 (SEQ ID NO: 1005), GI:116831381 (SEQ ID NO: 1006), GI:93007346 (SEQ ID NO: 1007), and GI:255552993 (SEQ ID NO: 1008). In some cases, a functional homolog of SEQ ID NO: 1 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1. In some cases, a functional homolog of SEQ ID NO: 1 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1 described above or set forth in the Sequence Listing.

Examples of amino acid sequences of functional homologs of the polypeptide set forth in SEQ ID NO: 287 are provided in FIG. 5 and in the Sequence Listing. Such functional homologs include, for example, GI_147838135 (SEQ ID NO: 288), CeresAnnot_1466321 (SEQ ID NO: 290), GI_340796359 (SEQ ID NO: 291), GI_27123665 (SEQ ID NO: 292), GI 254935149 (SEQ ID NO: 293), GI_1666096 (SEQ ID NO: 294), GI_255040359 (SEQ ID NO: 295), GI_9971227 (SEQ ID NO: 296), GI_305677553 (SEQ ID NO: 297), GI 46849529 (SEQ ID NO: 298), GI_255557309 (SEQ ID NO: 299), GI 213032421 (SEQ ID NO: 300), GI_126843239 (SEQ TD NO: 301), CeresClone_572987 (SEQ TD NO: 303), CeresAnnot_1501920 (SEQ ID NO: 305), GI_192910888 (SEQ ID NO: 306), CeresClone_704889 (SEQ ID NO: 308), GI_326511994 (SEQ ID NO: 309), GI_125527760 (SEQ ID NO: 310), G1_84180617 (SEQ ID NO: 311), CeresAnnot_8733572 (SEQ ID NO: 313), GI 50428335 (SEQ ID NO: 314), GI_46576018 (SEQ ID NO: 315), GI_15221037 (SEQ ID NO: 316), GI_168044732 (SEQ TD NO: 317), CeresAnnot_8734027 (SEQ ID NO: 319), GI_67077820 (SEQ ID NO: 320), G1_67077812 (SEQ ID NO: 321), G1_212721130 (SEQ ID NO: 322), GI_49065954 (SEQ ID NO: 323), GI_320462780 (SEQ ID NO: 324), GI_297847044 (SEQ ID NO: 325), GI_190192216 (SEQ ID NO: 326), CeresAnnot_1497828 (SEQ ID NO: 328), GI_51011366 (SEQ ID NO: 329), GI_9971229 (SEQ ID NO: 330), CeresClone_615793 (SEQ ID NO: 332), GI_119477815 (SEQ ID NO: 333), GI_126843206 (SEQ ID NO: 334), GI_226505220 (SEQ ID NO: 335), GI_49035968 (SEQ ID NO: 336), GI_242057261 (SEQ ID NO: 337), GI 15226777 (SEQ ID NO: 338), GI_147838315 (SEQ ID NO: 339), GI_108755538 (SEQ ID NO: 340), GI_224064641 (SEQ ID NO: 341), GI 152003423 (SEQ ID NO: 342), CeresAnnot_1448918 (SEQ ID NO: 344), CeresClone_909614 (SEQ ID NO: 346), GI_297845928 (SEQ ID NO: 347), GI 225470621 (SEQ ID NO: 348), GI_115462223 (SEQ ID NO: 349), GI 327179117 (SEQ ID NO: 350), GI_15220645 (SEQ TD NO: 351), GI_327179119 (SEQ TD NO: 352), GI 6446413 (SEQ TD NO: 353), GI_297823239 (SEQ ID NO: 354), GI_27261179 (SEQ ID NO: 355), GI_49035760 (SEQ ID NO: 356), GI 297843038 (SEQ ID NO: 357), GI_168063557 (SEQ ID NO: 358), CeresClone_829454 (SEQ ID NO: 360), sp_Q9C6I4_G2OX7_ARATH (SEQ ID NO: 361), GI_125552976 (SEQ ID NO: 362), GI_79318890 (SEQ ID NO: 363), GI_60202574 (SEQ ID NO: 364), GI_67077818 (SEQ ID NO: 365), CeresClone_900331 (SEQ ID NO: 367), GI_222630276 (SEQ ID NO: 368), CeresAnnot_8657905 (SEQ ID NO: 370), GI_126843224 (SEQ ID NO: 371), CeresClone_313261 (SEQ ID NO: 373), GI_32127337 (SEQ ID NO: 374), GI_51011364 (SEQ ID NO: 375), GI_330752217 (SEQ ID NO: 376), sp_049561_G2OX8_ARATH (SEQ ID NO: 377), GI_251821339 (SEQ ID NO: 378), GI_37544101 (SEQ ID NO: 379), GI_225432055 (SEQ ID NO: 380), CeresClone_1076347 (SEQ ID NO: 382), GI 46849531 (SEQ ID NO: 383), GI_225468310 (SEQ TD NO: 384), CeresAnnot_1441748 (SEQ TD NO: 386), GI_223953574 (SEQ ID NO: 387), GI_49035759 (SEQ ID NO: 388), GI_327179113 (SEQ ID NO: 389), CeresClone_1239118 (SEQ ID NO: 391), GI_125550923 (SEQ ID NO: 392), GI 326520938 (SEQ ID NO: 393), GI_297804032 (SEQ ID NO: 394), GI_27261177 (SEQ ID NO: 395), GI_312196334 (SEQ ID NO: 396), GI_23491590 (SEQ ID NO: 397), GI_168024874 (SEQ ID NO: 398), GI_261863286 (SEQ TD NO: 399), GI_134303284 (SEQ TD NO: 400), CeresClone_1856391 (SEQ ID NO: 402), GI_242054465 (SEQ ID NO: 403), GI_157382968 (SEQ ID NO: 404), GI_15217753 (SEQ ID NO: 405), GI_109729789 (SEQ ID NO: 406), GI_126843214 (SEQ ID NO: 407), GI 327179125 (SEQ ID NO: 408), GI_340796367 (SEQ ID NO: 409), GI_312195240 (SEQ ID NO: 410), CeresAnnot_1511928 (SEQ ID NO: 412), GI_226501026 (SEQ ID NO: 413), GI_224108798 (SEQ ID NO: 414), GI_119475961 (SEQ ID NO: 415), CeresClone_539037 (SEQ ID NO: 417), GI 50293061 (SEQ ID NO: 418), GI_50428337 (SEQ ID NO: 419), GI 225437645 (SEQ ID NO: 420), GI_115440025 (SEQ ID NO: 421), GI_326522773 (SEQ ID NO: 422), GI 218187724 (SEQ ID NO: 423), GI_340796363 (SEQ ID NO: 424), GI_67077816 (SEQ ID NO: 425), CeresClone_156482 (SEQ ID NO: 427), GI 340796365 (SEQ ID NO: 428), GI_242086999 (SEQ ID NO: 429), GI 226501846 (SEQ ID NO: 430), CeresAnnot_1444853 (SEQ ID NO: 432), GI_29825611 (SEQ ID NO: 433), GI_125572075 (SEQ ID NO: 434), GI 297842621 (SEQ ID NO: 435), GI_320462782 (SEQ ID NO: 436), GI 340796361 (SEQ ID NO: 437), GI_225443855 (SEQ ID NO: 438), CeresClone_1860822 (SEQ ID NO: 440), GI_126843218 (SEQ ID NO: 441), CeresClone_1831422 (SEQ ID NO: 443), GI_255548359 (SEQ ID NO: 444), GI 115465423 (SEQ ID NO: 445), GI_255644878 (SEQ ID NO: 446), GI_6478200 (SEQ ID NO: 447), CeresClone_1831239 (SEQ ID NO: 449), CeresClone_1918532 (SEQ ID NO: 451), GI_49065956 (SEQ ID NO: 452), GI_326532306 (SEQ ID NO: 453), GI_327179123 (SEQ ID NO: 454), CeresAnnot_1471538 (SEQ ID NO: 456), GI_284468804 (SEQ ID NO: 457), GI_67077814 (SEQ ID NO: 458), GI_224101511 (SEQ ID NO: 459), GI_87240601 (SEQ ID NO: 460), CeresClone_467671 (SEQ ID NO: 462), GI_134303286 (SEQ ID NO: 463), GI 109729791 (SEQ ID NO: 464), GI_338733586 (SEQ TD NO: 465), GI_125553301 (SEQ TD NO: 466), GI_116672836 (SEQ ID NO: 467), GI 327359295 (SEQ ID NO: 468), GI_297744020 (SEQ ID NO: 469), GI 93115317 (SEQ ID NO: 470), GI:124829 (SEQ ID NO: 1140), GI:7595984 (SEQ ID NO: 1141), GI:356571007 (SEQ ID NO: 1142), GI:357134283 (SEQ ID NO: 1143), GI:356660541 (SEQ ID NO: 1144), GI:218188130 (SEQ ID NO: 1145), GI:356558109 (SEQ ID NO: 1146), GI:365872403 (SEQ TD NO: 1147), GI:379749536 (SEQ ID NO: 1148), GI:6016387 (SEQ ID NO: 1149), GI:66735505 (SEQ ID NO: 1150), GI:356532490 (SEQ ID NO: 1151), GI:356533324 (SEQ ID NO: 1152), CeresClone:1724110 (SEQ ID NO: 1154), GI:171680612 (SEQ ID NO: 1155), GI:358380091 (SEQ ID NO: 1156), GI:357447293 (SEQ ID NO: 1157), GI:125532930 (SEQ ID NO: 1158), GI:357127374 (SEQ ID NO: 1159), GI:126724682 (SEQ ID NO: 1160), GI:53139660 (SEQ ID NO: 1161), GI:225555204 (SEQ ID NO: 1162), GI:14916565 (SEQ ID NO: 1163), GI:380851109 (SEQ ID NO: 1164), GI:222632219 (SEQ ID NO: 1165), GI:357128141 (SEQ ID NO: 1166), GI:356564662 (SEQ ID NO: 1167), GI:3779220 (SEQ ID NO: 1168), GI:113202132 (SEQ ID NO: 1169), GI:50261845 (SEQ ID NO: 1170), GI:356549549 (SEQ ID NO: 1171), GI:169631509 (SEQ ID NO: 1172), GI:114562664 (SEQ ID NO: 1173), GI:116783364 (SEQ ID NO: 1174), GI:116788048 (SEQ ID NO: 1175), GI:125575676 (SEQ ID NO: 1176), GI:225680969 (SEQ ID NO: 1177), CeresAnnot:8668753 (SEQ TD NO: 1179), GI:359473878 (SEQ ID NO: 1180), GI:357488573 (SEQ ID NO: 1181), GI:58269616 (SEQ ID NO: 1182), GI:365848372 (SEQ ID NO: 1183), GI:217385866 (SEQ ID NO: 1184), GI:342868843 (SEQ ID NO: 1185), GI:350637890 (SEQ ID NO: 1186), GI:259487966 (SEQ ID NO: 1187), GI:77360864 (SEQ ID NO: 1188), GI:350285025 (SEQ ID NO: 1189), CeresAnnot:550021 (SEQ ID NO: 1191), GI: 126726302 (SEQ ID NO: 1192), GI:377560209 (SEQ ID NO: 1193), GI:356549099 (SEQ ID NO: 1194), GI:125569479 (SEQ ID NO: 1195), GI: 145607820 (SEQ ID NO: 1196), GI:344231610 (SEQ ID NO: 1197), GI:224130932 (SEQ ID NO: 1198), GI:322693186 (SEQ ID NO: 1199), GI:37698286 (SEQ ID NO: 1200), CeresAnnot:1517584 (SEQ ID NO: 1202), CeresAnnot:8670458 (SEQ ID NO: 1204), GI:357448799 (SEQ ID NO: 1205), GI:154296822 (SEQ ID NO: 1206), CeresAnnot:1458668 (SEQ TD NO: 1208), GI:357117693 (SEQ TD NO: 1209), GI:1527191 (SEQ ID NO: 1210), GI:115442079 (SEQ ID NO: 1211), CeresAnnot:8725147 (SEQ ID NO: 1213), GI:357136506 (SEQ ID NO: 1214), GI:302759861 (SEQ ID NO: 1215), GI:168058603 (SEQ ID NO: 1216), GI:356510794 (SEQ ID NO: 1217), GI:159149180 (SEQ ID NO: 1218), GI:331700025 (SEQ ID NO: 1219), GI:117586718 (SEQ ID NO: 1220), GI:41323935 (SEQ TD NO: 1221), GI:297830340 (SEQ TD NO: 1222), GI:53792534 (SEQ ID NO: 1223), GI:54260396 (SEQ ID NO: 1224), GI:357128775 (SEQ ID NO: 1225), GI:327179115 (SEQ ID NO: 1226), GI:327306431 (SEQ ID NO: 1227), GI:356499745 (SEQ ID NO: 1228), GI:358368242 (SEQ ID NO: 1229), GI:254583526 (SEQ ID NO: 1230), GI:115435212 (SEQ ID NO: 1231), GI:255557479 (SEQ ID NO: 1232), GI:357476439 (SEQ ID NO: 1233), GI:356555146 (SEQ ID NO: 1234), GI:83033890 (SEQ ID NO: 1235), GI:358348748 (SEQ ID NO: 1236), GI:261251140 (SEQ ID NO: 1237), GI:297829900 (SEQ ID NO: 1238), GI:39950534 (SEQ ID NO: 1239), GI:356503948 (SEQ ID NO: 1240), GI:343794766 (SEQ ID NO: 1241), GI:347758670 (SEQ ID NO: 1242), GI:357488575 (SEQ ID NO: 1243), GI:7108579 (SEQ ID NO: 1244), GI:327348464 (SEQ ID NO: 1245), CeresAnnot:1464270 (SEQ ID NO: 1247), GI:169777699 (SEQ ID NO: 1248), GI:297803592 (SEQ ID NO: 1249), GI:357127376 (SEQ TD NO: 1250), GI:357128527 (SEQ ID NO: 1251), GI:357485645 (SEQ ID NO: 1252), Ceres-Clone:387918 (SEQ ID NO: 1254), GI:363807830 (SEQ ID NO: 1255), GI:317031438 (SEQ ID NO: 1256), GI:326534020 (SEQ ID NO: 1257), GI: 146292853 (SEQ ID NO: 1258), GI:343925590 (SEQ ID NO: 1259), GI:123906 (SEQ ID NO: 1260), GI:357129744 (SEQ ID NO: 1261), GI:356556910 (SEQ ID NO: 1262), GI:5579094 (SEQ ID NO: 1263), GI:86197901 (SEQ ID NO: 1264), CeresAnnot:8660515 (SEQ ID NO: 1266), GI:169781970 (SEQ ID NO: 1267), GI:357128523 (SEQ ID NO: 1268), GI:261363611 (SEQ ID NO: 1269), GI:356528126 (SEQ ID NO: 1270), GI:380448148 (SEQ ID NO: 1271), GI:125525840 (SEQ ID NO: 1272), and GI:327179111 (SEQ ID NO: 1273). In some cases, a functional homolog of SEQ ID NO: 287 has an amino acid sequence with at least 45% sequence identity, e.g., 50%, 52%, 56%, 59%, 6%, 65%, 70%, 75%, 80%, 85%, 90%, 95%, 97%, 98%, or 99% sequence identity, to the amino acid sequence set forth in SEQ ID NO: 287. In some cases, a functional homolog of SEQ ID NO: 287 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 287 described above or set forth in the Sequence Listing.

Figure 6A:
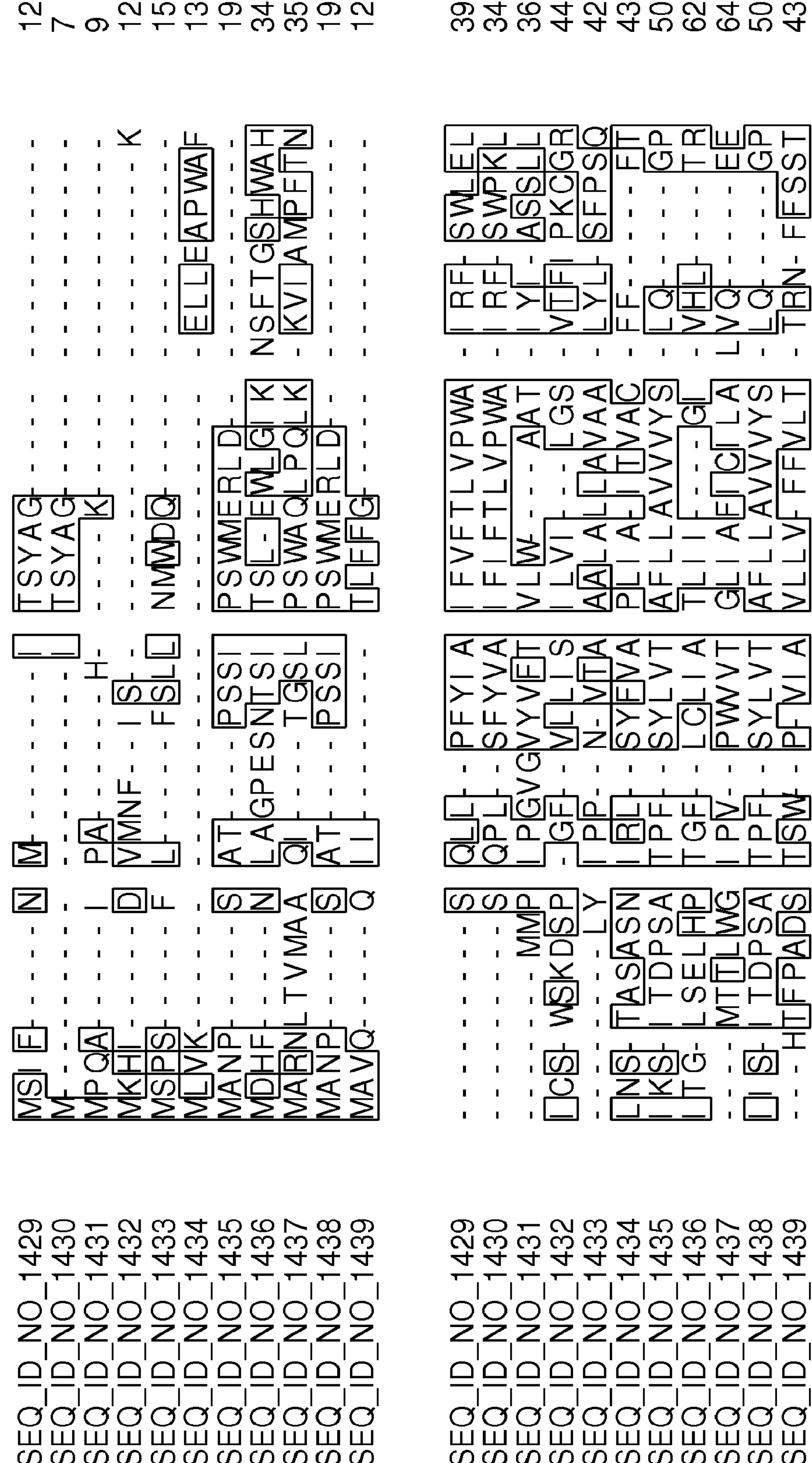
Figure 6D:
Figure 6H:
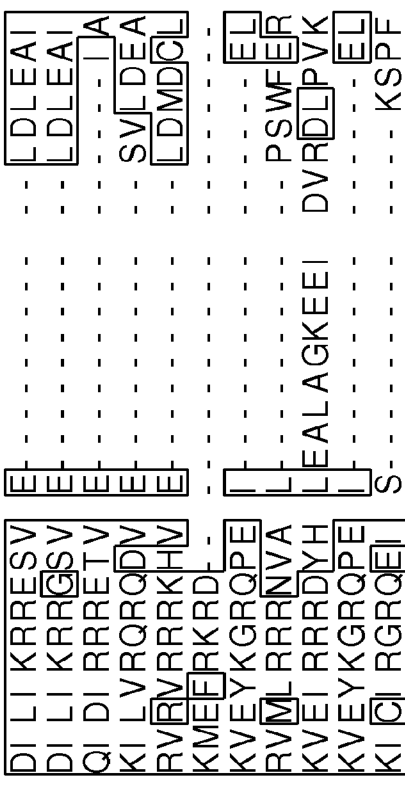

Examples of amino acid sequences of functional homologs of the polypeptide set forth in SEQ TD NO: 1429 are provided in FIG. 6 and in the Sequence Listing. Such functional homologs include, for example, GI:342877779 (SEQ ID NO: 1430), GI:197724593 (SEQ ID NO: 1431), GI:115334279 (SEQ ID NO: 1432), GI:310799037 (SEQ ID NO: 1433), GI:302893705 (SEQ ID NO: 1434), GI:85110002 (SEQ ID NO: 1435), GI:169783174 (SEQ ID NO: 1436), GI:242815592 (SEQ ID NO: 1437), GI:336468679 (SEQ ID NO: 1438), GI:255956889 (SEQ ID NO: 1439), GI:346970804 (SEQ ID NO: 1440), GI:315047883 (SEQ ID NO: 1441), GI:239609926 (SEQ ID NO: 1442), GI:310799765 (SEQ ID NO: 1443), GI:322697028 (SEQ ID NO: 1444), GI:351639827 (SEQ ID NO: 1445), GI:310801951 (SEQ ID NO: 1446), GI:317035847 (SEQ ID NO: 1447), GI:317033079 (SEQ ID NO: 1448), GI:39975659 (SEQ ID NO: 1449), GI:312212422 (SEQ ID NO: 1450), GI:145606901 (SEQ ID NO: 1451), GI:336263834 (SEQ ID NO: 1452), GI:350636399 (SEQ ID NO: 1453), GI:119485937 (SEQ ID NO: 1454), GI:46118584 (SEQ ID NO: 1455), GI:116203015 (SEQ ID NO: 1456), GI:351648588 (SEQ ID NO: 1457), GI:327350850 (SEQ ID NO: 1458), GI:134082570 (SEQ ID NO: 1459), GI:238507153 (SEQ ID NO: 1460), GI:350631552 (SEQ ID NO: 1461), GI:261198797 (SEQ ID NO: 1462), GI:351640230 (SEQ ID NO: 1463), GI:342887718 (SEQ ID NO: 1464), GI:115391085 (SEQ ID NO: 1465), GI:255950818 (SEQ ID NO: 1466), GI:67903086 (SEQ ID NO: 1467), GI:346973227 (SEQ ID NO: 1468), GI:310791795 (SEQ ID NO: 1469), GI:46111581 (SEQ ID NO: 1470), GI:302912247 (SEQ ID NO: 1471), GI:302890983 (SEQ ID NO: 1472), GI:325095532 (SEQ ID NO: 1473), GI:310801736 (SEQ ID NO: 1474), GI:169786189 (SEQ ID NO: 1475), GI:322704477 (SEQ ID NO: 1476), GI:296809607 (SEQ ID NO: 1477), GI:358384333 (SEQ ID NO: 1478), GI:380486688 (SEQ ID NO: 1479), GI:380485723 (SEQ ID NO: 1480), GI:380493657 (SEQ ID NO: 1481), GI:310801960 (SEQ ID NO: 1482), GI:380493536 (SEQ ID NO: 1483), GI:380485117 (SEQ ID NO: 1484), GI:367046496 (SEQ ID NO: 1485), GI:358378098 (SEQ ID NO: 1486), GI:328671361 (SEQ ID NO: 1487), GI:328671376 (SEQ ID NO: 1488), GI:328671358 (SEQ ID NO: 1489), GI:328671355 (SEQ ID NO: 1490), GI:342883913 (SEQ ID NO: 1491), GI:328671364 (SEQ ID NO: 1492), GI:27368044 (SEQ ID NO: 1493), GI:242800740 (SEQ ID NO: 1494), GI:15054396 (SEQ ID NO: 1495), GI:351648133 (SEQ ID NO: 1496), GI:28975428 (SEQ ID NO: 1497), GI:380471186 (SEQ ID NO: 1498), GI:270160636 (SEQ ID NO: 1499), GI:326482954 (SEQ ID NO: 1500), GI:115385677 (SEQ ID NO: 1501), GI:351649667 (SEQ ID NO: 1502), GI:358369247 (SEQ ID NO: 1503), GI:39969835 (SEQ ID NO: 1504), GI:327309580 (SEQ ID NO: 1505), GI:169612674 (SEQ ID NO: 1506), GI:269856265 (SEQ ID NO: 1507), GI:269978413 (SEQ ID NO: 1508), GI:270160664 (SEQ ID NO: 1509), GI:346325649 (SEQ ID NO: 1510), GI:134079537 (SEQ ID NO: 1511), GI:46102962 (SEQ ID NO: 1512), GI:270160658 (SEQ ID NO: 1513), GI:270160632 (SEQ ID NO: 1514), GI:270160623 (SEQ ID NO: 1515), GI:145606494 (SEQ ID NO: 1516), GI:358367412 (SEQ ID NO: 1517), GI:270160641 (SEQ ID NO: 1518), GI:270160627 (SEQ ID NO: 1519), GI:358372883 (SEQ ID NO: 1520), GI:339469697 (SEQ ID NO: 1521), GI:270160647 (SEQ ID NO: 1522), GI:380479505 (SEQ ID NO: 1523), GI:169769747 (SEQ ID NO: 1524), GI:212536382 (SEQ ID NO: 1525), GI:310800499 (SEQ ID NO: 1526), GI:310801547 (SEQ ID NO: 1527), GI:115398866 (SEQ ID NO: 1528), GI:146324413 (SEQ ID NO: 1529), GI:159124267 (SEQ ID NO: 1530), GI:317032179 (SEQ ID NO: 1531), GI:121699333 (SEQ ID NO: 1532), GI:134078874 (SEQ ID NO: 1533), GI:242795502 (SEQ ID NO: 1534), GI:71002914 (SEQ ID NO: 1535), GI:380473273 (SEQ ID NO: 1536), GI:255948452 (SEQ ID NO: 1537), GI:302500503 (SEQ ID NO: 1538), GI:121714683 (SEQ ID NO: 1539), GI:23574644 (SEQ ID NO: 1540), and GI:339469460 (SEQ ID NO: 1541). In some cases, a functional homolog of SEQ ID NO: 1429 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1429. In some cases, a functional homolog of SEQ ID NO: 1429 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1429 described above or set forth in the Sequence Listing.

Examples of amino acid sequences of functional homologs of the polypeptide set forth in SEQ ID NO: 1542 are provided in FIG. 7 and in the Sequence Listing. Such functional homologs include, for example, GI:42661490 (SEQ ID NO: 1543), GI:211970313 (SEQ ID NO: 1544), GI:342877776 (SEQ ID NO: 1545), GI:350295800 (SEQ ID NO: 1546), GI:46139765 (SEQ ID NO: 1547), GI:242809430 (SEQ ID NO: 1548), GI:169619475 (SEQ ID NO: 1549), GI:339467588 (SEQ ID NO: 1550), GI:380495415 (SEQ ID NO: 1551), GI:255955071 (SEQ ID NO: 1552), GI:322704192 (SEQ ID NO: 1553), GI:367036275 (SEQ ID NO: 1554), GI:378732306 (SEQ ID NO: 1555), GI:238497964 (SEQ ID NO: 1556), GI:296803841 (SEQ ID NO: 1557), GI:378731760 (SEQ ID NO: 1558), GI:322696305 (SEQ ID NO: 1559), GI:310795092 (SEQ ID NO: 1560), GI:317141690 (SEQ ID NO: 1561), GI:156043835 (SEQ ID NO: 1562), GI:346978982 (SEQ ID NO: 1563), GI:380482210 (SEQ ID NO: 1564), GI:212545757 (SEQ ID NO: 1565), GI:115399682 (SEQ ID NO: 1566), and GI:302417990 (SEQ ID NO: 1567). In some cases, a functional homolog of SEQ ID NO: 1542 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1542. In some cases, a functional homolog of SEQ ID NO: 1542 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1542 described above or set forth in the Sequence Listing.

Examples of amino acid sequences of functional homologs of the polypeptide set forth in SEQ ID NO: 1386 are provided in FIG. 8 and in the Sequence Listing. Such functional homologs include, for example, GI:122938156 (SEQ TD NO: 1387), GI:240282093 (SEQ ID NO: 1388), GI:3549879 (SEQ ID NO: 1389), GI:380486272 (SEQ ID NO: 1390), (SEQ ID NO: 1391), GI:317030883 (SEQ ID NO: 1392), GI:239614263 (SEQ ID NO: 1393), GI:270160669 (SEQ ID NO: 1394), GI: 119469260 (SEQ ID NO: 1395), GI:242795506 (SEQ ID NO: 1396), GI:226291700 (SEQ ID NO: 1397), GI:4959945 (SEQ ID NO: 1398), GI:74275563 (SEQ TD NO: 1399), (SEQ TD NO: 1400), GI: 159124063 (SEQ TD NO: 1401), GI:367035976 (SEQ ID NO: 1402), GI:159130277 (SEQ ID NO: 1403), GI:67904522 (SEQ ID NO: 1404), (SEQ ID NO: 1405), GI:225679929 (SEQ ID NO: 1406), GI:67902304 (SEQ ID NO: 1407), GI:342877778 (SEQ ID NO: 1408), GI:295667161 (SEQ ID NO: 1409), GI:270160618 (SEQ ID NO: 1410), GI:134076920 (SEQ ID NO: 1411), (SEQ ID NO: 1412), GI:302423784 (SEQ ID NO: 1413), GI:270160651 (SEQ ID NO: 1414), GI:197724589 (SEQ ID NO: 1415), GI:269978406 (SEQ ID NO: 1416), GI:115385431 (SEQ ID NO: 1417), GI:302657172 (SEQ ID NO: 1418), GI:380480560 (SEQ ID NO: 1419), GI:146324548 (SEQ ID NO: 1420), GI:339469066 (SEQ ID NO: 1421), GI:154273751 (SEQ ID NO: 1422), GI: 145616804 (SEQ ID NO: 1423), (SEQ ID NO: 1424), GI:328671370 (SEQ ID NO: 1425), GI:350629557 (SEQ ID NO: 1426), GI:261204397 (SEQ ID NO: 1427), and GI:255939330 (SEQ ID NO: 1428). In some cases, a functional homolog of SEQ TD NO: 1386 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1386. In some cases, a functional homolog of SEQ ID NO: 1386 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1386 described above or set forth in the Sequence Listing.

Examples of amino acid sequences of functional homologs of the polypeptide set forth in SEQ ID NO: 1274 are provided in FIG. 9 and in the Sequence Listing. Such functional homologs include, for example, GI:310790427 (SEQ ID NO: 1275), GI:347831214 (SEQ ID NO: 1276), GI:156047892 (SEQ ID NO: 1277), GI:67522282 (SEQ ID NO: 1278), GI:119494789 (SEQ ID NO: 1279), GI:212539424 (SEQ ID NO: 1280), GI:327343381 (SEQ ID NO: 1281), GI:302404826 (SEQ ID NO: 1282), GI:326484980 (SEQ ID NO: 1283), GI:358384361 (SEQ ID NO: 1284), GI:242804557 (SEQ ID NO: 1285), GI:346979790 (SEQ ID NO: 1286), GI:258578343 (SEQ ID NO: 1287), GI:326483893 (SEQ ID NO: 1288), GI:212542733 (SEQ ID NO: 1289), GI:367032834 (SEQ ID NO: 1290), GI:326470143 (SEQ ID NO: 1291), GI:164428375 (SEQ ID NO: 1292), GI:342886866 (SEQ ID NO: 1293), GI:270124461 (SEQ ID NO: 1294), GI:299744611 (SEQ ID NO: 1295), GI:320036821 (SEQ ID NO: 1296), GI:327343267 (SEQ ID NO: 1297), GI:302890139 (SEQ ID NO: 1298), GI:315039401 (SEQ ID NO: 1299), GI:74691493 (SEQ ID NO: 1300), GI:350631590 (SEQ ID NO: 1301), GI:46109972 (SEQ ID NO: 1302), GI:302502806 (SEQ ID NO: 1303), GI:327292707 (SEQ ID NO: 1304), GI:353240577 (SEQ ID NO: 1305), GI:326484981 (SEQ ID NO: 1306), GI:296416849 (SEQ ID NO: 1307), GI:119186083 (SEQ ID NO: 1308), GI:296818735 (SEQ ID NO: 1309), GI:342877777 (SEQ ID NO: 1310), GI:70992027 (SEQ ID NO: 1311), GI:315040165 (SEQ ID NO: 1312), GI:296420744 (SEQ ID NO: 1313), GI:336371322 (SEQ ID NO: 1314), GI:115390288 (SEQ ID NO: 1315), GI:299740695 (SEQ ID NO: 1316), GI:296818393 (SEQ ID NO: 1317), GI:74676162 (SEQ ID NO: 1318), GI:326475322 (SEQ ID NO: 1319), GI:312212946 (SEQ ID NO: 1320), GI:62318475 (SEQ ID NO: 1321), GI:296422933 (SEQ ID NO: 1322), GI:361126544 (SEQ ID NO: 1323), GI:238487930 (SEQ ID NO: 1324), GI:341599458 (SEQ ID NO: 1325), GI:336369617 (SEQ ID NO: 1326), GI:339475687 (SEQ ID NO: 1327), GI:327343373 (SEQ ID NO: 1328), GI:327343325 (SEQ ID NO: 1329), GI:336365283 (SEQ ID NO: 1330), GI:303318042 (SEQ ID NO: 1331), GI:336382397 (SEQ ID NO: 1332), GI:378728369 (SEQ ID NO: 1333), GI:255955605 (SEQ ID NO: 1334), GI:380489258 (SEQ ID NO: 1335), GI:358389174 (SEQ ID NO: 1336), GI:14278967 (SEQ ID NO: 1337), GI:322705205 (SEQ ID NO: 1338), GI:354952198 (SEQ ID NO: 1339), GI:154289961 (SEQ ID NO: 1340), GI:154290109 (SEQ ID NO: 1341), GI:211970315 (SEQ ID NO: 1342), GI:380481111 (SEQ ID NO: 1343), GI:302897901 (SEQ ID NO: 1344), GI:169635726 (SEQ ID NO: 1345), GI:367046821 (SEQ TD NO: 1346), GI:354961647 (SEQ ID NO: 1347), GI:171679136 (SEQ ID NO: 1348), (SEQ ID NO: 1349), GI:145254738 (SEQ ID NO: 1350), GI:327292709 (SEQ ID NO: 1351), GI:170109428 (SEQ ID NO: 1352), GI:340521233 (SEQ ID NO: 1353), GI:302502804 (SEQ ID NO: 1354), GI:350630566 (SEQ ID NO: 1355), GI:320586089 (SEQ ID NO: 1356), GI:326475321 (SEQ ID NO: 1357), GI:380490852 (SEQ ID NO: 1358), GI:330928050 (SEQ ID NO: 1359), GI:302690250 (SEQ ID NO: 1360), GI:350631043 (SEQ ID NO: 1361), GI:255931839 (SEQ ID NO: 1362), GI:336466767 (SEQ ID NO: 1363), GI:328796058 (SEQ ID NO: 1364), GI:296420105 (SEQ ID NO: 1365), GI:302667711 (SEQ ID NO: 1366), GI:351642318 (SEQ ID NO: 1367), GI: 119470770 (SEQ ID NO: 1368), GI:340514420 (SEQ ID NO: 1369), GI:56609350 (SEQ ID NO: 1370), GI:367046496 (SEQ ID NO: 1371), GI:121718870 (SEQ ID NO: 1372), GI:240274084 (SEQ ID NO: 1373), GI:154290200 (SEQ ID NO: 1374), GI:302693088 (SEQ ID NO: 1375), GI:296804446 (SEQ ID NO: 1376), GI:302682570 (SEQ ID NO: 1377), GI:156045924 (SEQ ID NO: 1378), GI:336377080 (SEQ ID NO: 1379), GI:336365177 (SEQ ID NO: 1380), GI:156045918 (SEQ ID NO: 1381), GI:116178810 (SEQ ID NO: 1382), GI:169609220 (SEQ ID NO: 1383), GI:347829721 (SEQ ID NO: 1384), and GI:159124430 (SEQ ID NO: 1385). In some cases, a functional homolog of SEQ ID NO: 1274 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1274. In some cases, a functional homolog of SEQ ID NO: 1274 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1274 described above or set forth in the Sequence Listing.

The identification of conserved regions in a biomass composition-modulating polypeptide facilitates production of variants of biomass composition-modulating polypeptides. Variants of biomass composition-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1, FIG. 2, FIG. 3, FIG. 4, FIG. 5, FIG. 6, FIG. 7, FIG. 8, or FIG. 9, and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at a position marked by dashes, such a polypeptide has a length that is the sum of the amino acid residues in all conserved regions and all dashes.

C. Functional Homologs Identified by HMMER

In some embodiments, useful biomass composition-modulating polypeptides include those that fit a Hidden Markov Model based on the polypeptides set forth in any one of FIGS. 1-9. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMer 3.0 with default program parameters, using the sequences of the group of functional homologs as input. In some instances, the input files can be in FASTA format. HMMer is provided by the Howard Hughes Medical Institute (http://hmmer.janelia.org).

The multiple sequence alignment is generated by ProbCons (Do et al., *Genome Res.,* 15(2):330-40 (2005)) version 1.12 using default parameters: ProbCons is a public domain software program. ProbCons and HMMer can be found on the world wide web at fr.com/probcons/.

The HMM for a group of functional homologs can be used to determine the likelihood that a candidate biomass composition-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMer hmmsearch program. The following parameter is used when running hmmsearch: the E-value cutoff for reporting is set to 1 ("-E 1"). A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The biomass composition-modulating polypeptides discussed below fit the indicated HMM with an HMM bit score greater than to 65 (e.g., greater than 70, 80, 90, 100, 120, 140, 200, 300, 500, 1000, 1500, or 2000). In some embodiments, the HMM bit score of a biomass composition-modulating polypeptide discussed below is about 50%, 60%, 70%, 80%, 90%, or 95% of the HMM bit score of a functional homolog provided in the Sequence Listing of this application. In some embodiments, a biomass composition-modulating polypeptide discussed below fits the indicated HMM with an HMM bit score greater than 210, and has a domain indicative of a biomass composition-modulating polypeptide. In some embodiments, a biomass composition-modulating polypeptide discussed below fits the indicated HMM with an HMM bit score greater than 210, and has 65% or greater sequence identity (e.g., 75%, 80%, 85%, 90%, 95%, or 100% sequence identity) to an amino acid sequence shown in any one of FIGS. 1-9.

Examples of polypeptides are shown in the sequence listing that have HMM bit scores greater than 65 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 620, 640, 660, 680, 700, 710, 720, or 730) when fitted to an HMM generated from the amino acid sequences set forth in FIG. 1 are identified in the Sequence Listing of this application. Such polypeptides include, for example, SEQ ID NOs: 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623,624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836,837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, and 976.

Examples of polypeptides are shown in the sequence listing that have HMM bit scores greater than 199 (e.g., greater than 200, 210, 220, 230, 240, 250, 260, 270, 280, 290, 300, 320, 340, 260, 380, 400, 420, 440, 460, 480, 500, 520, 540, 560, 580, 600, 620, 640, 660, 680, or 690) when fitted to an HMM generated from the amino acid sequences set forth in FIG. 2 are identified in the Sequence Listing of this application. Such polypeptides include, for example, SEQ ID NOs: 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, and 1139.

Examples of polypeptides are shown in the sequence listing that have HMM bit scores greater than 303 (e.g., greater than 310, 320, 340, 260, 380, 400, 420, 440, 460, 480, 500, 520, 540, 560, 580, 600, 620, 640, 660, 680, 700, 725, 750, 775, 800, 825, 850, 875, 900, 925, 950, 975, 1000, 1025, 1050, 1075, 1100, 1125, 1150, or 1175) when fitted to an HMM generated from the amino acid sequences set forth in FIG. 3 are identified in the Sequence Listing of this application. Such polypeptides include, for example, SEQ ID NOs: 188, 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 1009, 1010, 1011, 1012, 1013, 1014, 1015, 1016, 1017, 1018, 1019, 1020, 1021, 1022, and 1023.

Examples of polypeptides are shown in the sequence listing that have HMM bit scores greater than 79 (e.g., greater than 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, or 620) when fitted to an HMM generated from the amino acid sequences set forth in FIG. 4 are identified in the Sequence Listing of this application. Such polypeptides include, for example, SEQ TD NOs: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, and 1008.

Examples of polypeptides are shown in the sequence listing that have HMM bit scores greater than 65 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 610, or 615) when fitted to an HMM generated from the amino acid sequences set forth in FIG. 5 are identified in the Sequence Listing of this application. Such polypeptides include, for example, SEQ ID NOs: 287, 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, and 1273.

Examples of polypeptides are shown in the sequence listing that have HMM bit scores greater than 352 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 610, or 615) when fitted to an HMM generated from the amino acid sequences set forth in FIG. 6 are identified in the Sequence Listing of this application. Such polypeptides include, for example, SEQ ID NOs: 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, and 1541.

Examples of polypeptides are shown in the sequence listing that have HMM bit scores greater than 57 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 610, or 615) when fitted to an HMM generated from the amino acid sequences set forth in FIG. 7 are identified in the Sequence Listing of this application. Such polypeptides include, for example, SEQ ID NOs: 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, and 1567.

Examples of polypeptides are shown in the sequence listing that have HMM bit scores greater than 399 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 610, or 615) when fitted to an HMM generated from the amino acid sequences set forth in FIG. 8 are identified in the Sequence Listing of this application. Such polypeptides include, for example, SEQ ID NOs: 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, and 1428.

Examples of polypeptides are shown in the sequence listing that have HMM bit scores greater than 259 (e.g., greater than 70, 75, 80, 85, 90, 95, 100, 120, 140, 160, 180, 200, 220, 240, 250, 260, 270, 280, 290, 300, 320, 340, 260, 380, 400, 420, 440, 460, 480, 500, 520, 540, 560, 580, 600, 610, or 615) when fitted to an HMM generated from the amino acid sequences set forth in FIG. 9 are identified in the Sequence Listing of this application. Such polypeptides include, for example, SEQ TD NOs: 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, and 1385.

D. Percent Identity

In some embodiments, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 188, 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 287, 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836,837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, 1139, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, or 1567.

Polypeptides having such a percent sequence identity often have a domain indicative of a biomass composition-modulating polypeptide and/or have an HMM bit score that is greater than 65, as discussed above. Amino acid sequences of biomass composition-modulating polypeptides having at least 80% sequence identity to one of the amino acid sequences set forth in SEQ ID NOs: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 188, 189, 190, 191, 193, 194, 195, 196, 197, 198, 199, 201, 202, 203, 204, 205, 206, 207, 208, 209, 211, 213, 215, 216, 217, 219, 220, 221, 222, 224, 225, 226, 228, 230, 231, 232, 233, 235, 236, 238, 239, 240, 241, 242, 243, 244, 245, 247, 248, 249, 250, 251, 252, 254, 255, 256, 257, 258, 259, 260, 261, 262, 264, 265, 266, 267, 268, 269, 270, 272, 273, 274, 275, 276, 277, 278, 279, 280, 282, 283, 284, 285, 286, 287, 288, 290, 291, 292, 293, 294, 295, 296, 297, 298, 299, 300, 301, 303, 305, 306, 308, 309, 310, 311, 313, 314, 315, 316, 317, 319, 320, 321, 322, 323, 324, 325, 326, 328, 329, 330, 332, 333, 334, 335, 336, 337, 338, 339, 340, 341, 342, 344, 346, 347, 348, 349, 350, 351, 352, 353, 354, 355, 356, 357, 358, 360, 361, 362, 363, 364, 365, 367, 368, 370, 371, 373, 374, 375, 376, 377, 378, 379, 380, 382, 383, 384, 386, 387, 388, 389, 391, 392, 393, 394, 395, 396, 397, 398, 399, 400, 402, 403, 404, 405, 406, 407, 408, 409, 410, 412, 413, 414, 415, 417, 418, 419, 420, 421, 422, 423, 424, 425, 427, 428, 429, 430, 432, 433, 434, 435, 436, 437, 438, 440, 441, 443, 444, 445, 446, 447, 449, 451, 452, 453, 454, 456, 457, 458, 459, 460, 462, 463, 464, 465, 466, 467, 468, 469, 470, 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836,837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, 1139, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, or 1567 are provided in FIGS. 1-9 and in the Sequence Listing.

"Percent sequence identity" refers to the degree of sequence identity between any given reference sequence, e.g., SEQ ID NO: 1, and a candidate biomass composition-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic Acids Res.,* 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 471. Amino acid sequences of polypeptides having greater than 45% sequence identity to the polypeptide set forth in SEQ ID NO: 471 are provided in FIG. 1 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ TD NO: 99. Amino acid sequences of polypeptides having greater than 45% sequence identity to the polypeptide set forth in SEQ ID NO: 99 are provided in FIG. 2 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 188. Amino acid sequences of polypeptides having greater than 45% sequence identity to the polypeptide set forth in SEQ ID NO: 188 are provided in FIG. 3 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1. Amino acid sequences of polypeptides having greater than 45% sequence identity to the polypeptide set forth in SEQ ID NO: 1 are provided in FIG. 4 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 287. Amino acid sequences of polypeptides having greater than 45% sequence identity to the polypeptide set forth in SEQ ID NO: 287 are provided in FIG. 5 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1429. Amino acid sequences of polypeptides having greater than 45% sequence identity to the polypeptide set forth in SEQ ID NO: 1429 are provided in FIG. 6 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1542. Amino acid sequences of polypeptides having greater than 45% sequence identity to the polypeptide set forth in SEQ ID NO: 1542 are provided in FIG. 7 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1386. Amino acid sequences of polypeptides having greater than 45% sequence identity to the polypeptide set forth in SEQ ID NO: 1386 are provided in FIG. 8 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1274. Amino acid sequences of polypeptides having greater than 45% sequence identity to the polypeptide set forth in SEQ ID NO: 1274 are provided in FIG. 9 and in the Sequence Listing.

E. Other Sequences

It should be appreciated that a biomass composition-modulating polypeptide can include additional amino acids that are not involved in biomass modulation, and thus such a polypeptide can be longer than would otherwise be the case. For example, a biomass composition-modulating polypeptide can include a purification tag, a chloroplast transit peptide, a mitochondrial transit peptide, an amyloplast peptide, or a leader sequence added to the amino or carboxy terminus. In some embodiments, a biomass composition-modulating polypeptide includes an amino acid sequence that functions as a reporter, e.g., a green fluorescent protein or yellow fluorescent protein.

IV. NUCLEIC ACIDS

Nucleic acids described herein include nucleic acids that are effective to modulate biomass composition when transcribed in a plant or plant cell. Such nucleic acids include, without limitation, those that encode a biomass composition-modulating polypeptide and those that can be used to inhibit expression of a biomass composition-modulating polypeptide via a nucleic acid based method.

A. Nucleic Acids Encoding Biomass Composition-Modulating Polypeptides

Nucleic acids encoding biomass composition-modulating polypeptides are described herein. Examples of such nucleic acids include SEQ ID NOs: 5, 7, 34, 43, 68, 73, 78, 80, 93, 100, 102, 109, 118, 122, 125, 130, 147, 149, 153, 165, 168, 174, 178, 192, 200, 210, 212, 214, 218, 223, 227, 229, 234, 237, 246, 253, 263, 271, 281, 289, 302, 304, 307, 312, 318, 327, 331, 343, 345, 359, 366, 369, 372, 381, 385, 390, 401, 411, 416, 426, 431, 439, 442, 448, 450, 455, 461, 472, 474, 486, 494, 497, 507, 516, 543, 557, 560, 565, 581, 591, 596, 598, 603, 611, 616, 642, 662, 687, 694, 704, 722, 753, 755, 766, 771, 774, 786, 798, 811, 819, 840, 848, 903, 977, 979, 1030, 1039, 1043, 1054, 1065, 1075, 1078, 1081, 1088, 1090, 1098, 1103, 1107, 1109, 1112, 1118, 1132, 1134, 1137, 1153, 1178, 1190, 1201, 1203, 1207, 1212, 1246, 1253, and 1265 as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 5, 7, 34, 43, 68, 73, 78, 80, 93, 100, 102, 109, 118, 122, 125, 130, 147, 149, 153, 165, 168, 174, 178, 192, 200, 210, 212, 214, 218, 223, 227, 229, 234, 237, 246, 253, 263, 271, 281, 289, 302, 304, 307, 312, 318, 327, 331, 343, 345, 359, 366, 369, 372, 381, 385, 390, 401, 411, 416, 426, 431, 439, 442, 448, 450, 455, 461, 472, 474, 486, 494, 497, 507, 516, 543, 557, 560, 565, 581, 591, 596, 598, 603, 611, 616, 642, 662, 687, 694, 704, 722, 753, 755, 766, 771, 774, 786, 798, 811, 819, 840, 848, 903, 977, 979, 1030, 1039, 1043, 1054, 1065, 1075, 1078, 1081, 1088, 1090, 1098, 1103, 1107, 1109, 1112, 1118, 1132, 1134, 1137, 1153, 1178, 1190, 1201, 1203, 1207, 1212, 1246, 1253, and 1265.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Biomass Composition-Modulating Polypeptide A nucleic acid encoding one of the biomass composition-modulating polypeptides described herein (e.g., a polypeptide set forth in FIG. 1 or a functional homolog thereof, a polypeptide set forth in FIG. 2 or a functional homolog thereof, or a polypeptide set forth in FIG. 4 or a functional homolog thereof, a polypeptide set forth in FIG. 6 or a functional homolog thereof, a polypeptide set forth in FIG. 8 or a functional homolog thereof, or a polypeptide set forth in FIG. 9 or a functional homolog thereof) can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular biomass composition-modulating polypeptide; i.e., for many amino acids, there is more than one nucleotide triplet that serves as the codon for the amino acid. Thus, codons in the coding sequence for a given biomass composition-modulating polypeptide can be modified such that optimal expression in a particular plant species is obtained, using appropriate codon bias tables for that species.

In some cases, expression of a biomass composition-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Biomass Composition-Modulating Polypeptide

Polynucleotides and recombinant constructs described herein can be used to inhibit expression of a biomass composition-modulating polypeptide (e.g. a polypeptide set forth in FIG. 3 or a functional homolog thereof, or a polypeptide set forth FIG. 5 or a functional homolog thereof) in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); and *Nature Reviews RNA interference collection*, October 2005 on the World Wide Web at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding biomass composition-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA,* 92(13):6175-6179 (1995); de Feyter and Gaudron, Methods in Molecular Biology, Vol. 74, Chapter 43, “Expressing Ribozymes in Plants”, Edited by Turner, P. C., Humana Press Inc., Totowa, NJ. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a biomass composition-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the biomass composition-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a biomass composition-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the biomass composition-modulating polypeptide. In other embodiments, one strand of the stem portion of a double stranded RNA comprises a sequence that is similar or identical to the sequence of an intron, or a fragment thereof, in the pre-mRNA encoding a biomass composition-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a biomass composition-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a biomass composition-modulating polypeptide, or a fragment of such sequences. In some embodiments, the sense or antisense sequence is identical or complementary to a sequence of the regulatory region that drives transcription of the gene encoding a biomass composition-modulating polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a biomass composition-modulating polypeptide described herein. The sense sequence complementary to the antisense sequence can be a sequence present within the mRNA of the biomass composition-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have a suitable arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.,* 141:

1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences or the left and right border-like sequences of the P-DNA flank, or are on either side of, the nucleic acid. See, e.g., U.S. Patent Publication No. 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, Antisense *Nucleic Acid Drug Dev.,* 7:187-195 (1997); Hyrup et al., *Bioorgan. Med. Chem.,* 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate biomass composition. A recombinant nucleic acid construct can comprise a nucleic acid encoding a biomass composition-modulating polypeptide as described herein, operably linked to a regulatory region suitable for expressing the biomass composition-modulating polypeptide in the plant or cell. Thus, in one embodiment a nucleic acid can comprise a coding sequence that encodes a biomass composition-modulating polypeptides as set forth in SEQ ID NOs: 1, 2, 3, 4, 6, 8, 9, 10, 11, 12, 13, 14, 15, 16, 17, 18, 19, 20, 21, 22, 23, 24, 25, 26, 27, 28, 29, 30, 31, 32, 33, 35, 36, 37, 38, 39, 40, 41, 42, 44, 45, 46, 47, 48, 49, 50, 51, 52, 53, 54, 55, 56, 57, 58, 59, 60, 61, 62, 63, 64, 65, 66, 67, 69, 70, 71, 72, 74, 75, 76, 77, 79, 81, 82, 83, 84, 85, 86, 87, 88, 89, 90, 91, 92, 94, 95, 96, 97, 98, 99, 101, 103, 104, 105, 106, 107, 108, 110, 111, 112, 113, 114, 115, 116, 117, 119, 120, 121, 123, 124, 126, 127, 128, 129, 131, 132, 133, 134, 135, 136, 137, 138, 139, 140, 141, 142, 143, 144, 145, 146, 148, 150, 151, 152, 154, 155, 156, 157, 158, 159, 160, 161, 162, 163, 164, 166, 167, 169, 170, 171, 172, 173, 175, 176, 177, 179, 180, 181, 182, 183, 184, 185, 186, 187, 471, 473, 475, 476, 477, 478, 479, 480, 481, 482, 483, 484, 485, 487, 488, 489, 490, 491, 492, 493, 495, 496, 498, 499, 500, 501, 502, 503, 504, 505, 506, 508, 509, 510, 511, 512, 513, 514, 515, 517, 518, 519, 520, 521, 522, 523, 524, 525, 526, 527, 528, 529, 530, 531, 532, 533, 534, 535, 536, 537, 538, 539, 540, 541, 542, 544, 545, 546, 547, 548, 549, 550, 551, 552, 553, 554, 555, 556, 558, 559, 561, 562, 563, 564, 566, 567, 568, 569, 570, 571, 572, 573, 574, 575, 576, 577, 578, 579, 580, 582, 583, 584, 585, 586, 587, 588, 589, 590, 592, 593, 594, 595, 597, 599, 600, 601, 602, 604, 605, 606, 607, 608, 609, 610, 612, 613, 614, 615, 617, 618, 619, 620, 621, 622, 623, 624, 625, 626, 627, 628, 629, 630, 631, 632, 633, 634, 635, 636, 637, 638, 639, 640, 641, 643, 644, 645, 646, 647, 648, 649, 650, 651, 652, 653, 654, 655, 656, 657, 658, 659, 660, 661, 663, 664, 665, 666, 667, 668, 669, 670, 671, 672, 673, 674, 675, 676, 677, 678, 679, 680, 681, 682, 683, 684, 685, 686, 688, 689, 690, 691, 692, 693, 695, 696, 697, 698, 699, 700, 701, 702, 703, 705, 706, 707, 708, 709, 710, 711, 712, 713, 714, 715, 716, 717, 718, 719, 720, 721, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 756, 757, 758, 759, 760, 761, 762, 763, 764, 765, 767, 768, 769, 770, 772, 773, 775, 776, 777, 778, 779, 780, 781, 782, 783, 784, 785, 787, 788, 789, 790, 791, 792, 793, 794, 795, 796, 797, 799, 800, 801, 802, 803, 804, 805, 806, 807, 808, 809, 810, 812, 813, 814, 815, 816, 817, 818, 820, 821, 822, 823, 824, 825, 826, 827, 828, 829, 830, 831, 832, 833, 834, 835, 836, 837, 838, 839, 841, 842, 843, 844, 845, 846, 847, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 978, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1031, 1032, 1033, 1034, 1035, 1036, 1037, 1038, 1040, 1041, 1042, 1044, 1045, 1046, 1047, 1048, 1049, 1050, 1051, 1052, 1053, 1055, 1056, 1057, 1058, 1059, 1060, 1061, 1062, 1063, 1064, 1066, 1067, 1068, 1069, 1070, 1071, 1072, 1073, 1074, 1076, 1077, 1079, 1080, 1082, 1083, 1084, 1085, 1086, 1087, 1089, 1091, 1092, 1093, 1094, 1095, 1096, 1097, 1099, 1100, 1101, 1102, 1104, 1105, 1106, 1108, 1110, 1111, 1113, 1114, 1115, 1116, 1117, 1119, 1120, 1121, 1122, 1123, 1124, 1125, 1126, 1127, 1128, 1129, 1130, 1131, 1133, 1135, 1136, 1138, 1139, 1140, 1141, 1142, 1143, 1144, 1145, 1146, 1147, 1148, 1149, 1150, 1151, 1152, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1179, 1180, 1181, 1182, 1183, 1184, 1185, 1186, 1187, 1188, 1189, 1191, 1192, 1193, 1194, 1195, 1196, 1197, 1198, 1199, 1200, 1202, 1204, 1205, 1206, 1208, 1209, 1210, 1211, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1247, 1248, 1249, 1250, 1251, 1252, 1254, 1255, 1256, 1257, 1258, 1259, 1260, 1261, 1262, 1263, 1264, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, and 1567.

Examples of nucleic acids encoding biomass composition-modulating polypeptides are set forth in SEQ ID NOs: 5, 7, 34, 43, 68, 73, 78, 80, 93, 100, 102, 109, 118, 122, 125, 130, 147, 149, 153, 165, 168, 174, 178, 192, 200, 210, 212, 214, 218, 223, 227, 229, 234, 237, 246, 253, 263, 271, 281, 289, 302, 304, 307, 312, 318, 327, 331, 343, 345, 359, 366, 369, 372, 381, 385, 390, 401, 411, 416, 426, 431, 439, 442, 448, 450, 455, 461, 472, 474, 486, 494, 497, 507, 516, 543, 557, 560, 565, 581, 591, 596, 598, 603, 611, 616, 642, 662, 687, 694, 704, 722, 753, 755, 766, 771, 774, 786, 798, 811, 819, 840, 848, 903, 977, 979, 1030, 1039, 1043, 1054, 1065, 1075, 1078, 1081, 1088, 1090, 1098, 1103, 1107, 1109, 1112, 1118, 1132, 1134, 1137, 1153, 1178, 1190, 1201, 1203, 1207, 1212, 1246, 1253, and 1265, or in the Sequence Listing. The biomass composition-modulating polypeptide encoded by a recombinant nucleic acid can be a native biomass composition-modulating polypeptide, or can be heterologous to the cell. In some cases, the recombinant construct contains a nucleic acid that inhibits expression of a biomass composition-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen® (Madison, WI), Clontech® (Palo Alto, CA), Stratagene® (La Jolla, CA), and Invitrogen/Life Technologies® (Carlsbad, CA).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell,* 1:855-866 (1989); Bustos et al., *Plant Cell,* 1:839-854 (1989); Green et al., *EMBO J.,* 7:4035-4044 (1988); Meier et al., *Plant Cell,* 3:309-316 (1991); and Zhang et al., *Plant Physiology,* 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; PCT/US07/62762; PCT/US2009/032485; and PCT/US2009/038792.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phascolin promoter (Bustos et al., *Plant Cell,* 1(9):839-853 (1989)), the soybean trypsin inhibitor promoter (Riggs et al., *Plant Cell,* 1(6):609-621 (1989)), the ACP promoter (Bacrson et al., *Plant Mol. Biol.,* 22(2):255-267 (1993)), the stearoyl-ACP desaturase promoter (Slocombe et al., *Plant Physiol.,* 104(4):167-176 (1994)), the soybean α' subunit of β-conglycinin promoter (Chen et al., *Proc. Natl. Acad. Sci. USA,* 83:8560-8564 (1986)), the oleosin promoter (Hong et al., *Plant Mol. Biol.,* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.,* 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao, *Plant Mol. Biol.,* 32:571-57 (1996); *Conceicao, Plant,* 5:493-505 (1994)); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan, *Genetics,* 142:1009-1020 (1996)); maize Cat3 (see, GenBank No. L05934; Abler, *Plant Mol. Biol.,* 22:10131-1038 (1993)). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* 20:647-654 (2001)), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al.,

*Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab1R promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis thaliana* SUC2 sucrose-H+ symporter promoter (Truernit et al., *Planta,* 196:564-570 (1995)), and thylakoid membrane protein promoters from spinach (psaD, so psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell,* 3(10):1051-1061 (1991)), the *Commelina* yellow mottle virus (CoYMV) promoter (Medberry et al., *Plant Cell,* 4(2):185-192 (1992)), and the rice tungro bacilliform virus (RTBV) promoter (Dai et al., *Proc. Natl. Acad. Sci. USA,* 101(2):687-692 (2004)).

ix. Inducible Promoters

Inducible promoters confer transcription in response to external stimuli such as chemical agents or environmental stimuli. For example, inducible promoters can confer transcription in response to hormones such as gibberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) *Nature Biotech* 17: 287-291).

x. Basal Promoters

A basal promoter is the minimal sequence necessary for assembly of a transcription complex required for transcription initiation. Basal promoters frequently include a “TATA box” element that may be located between about 15 and about 35 nucleotides upstream from the site of transcription initiation. Basal promoters also may include a “CCAAT box” element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and promoters used with Cry1A(b) and Cry1A(c) (Braga et al. 2003, *Journal of New Seeds* 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. In some embodiments, a promoter may preferentially drive expression in reproductive tissues (e.g., P02916 promoter, SEQ ID NO:31 in 61/364,903). Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a biomass composition-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

V. SEQUENCES OF INTEREST

Plants and cells described herein can also have a second exogenous nucleic acid that comprises a sequence of interest, which is preselected for its beneficial effect upon a trait of commercial value. An exogenous nucleic acid comprising a sequence of interest is operably linked to a regulatory region for transformation into plants, and plants are selected whose expression of the sequence of interest achieves a desired amount and/or specificity of expression. A suitable regulatory region is chosen as described herein. In most cases, expression of a sequence of interest is regulated independently of biomass composition-modulating sequences in plants. It will be appreciated, however, that in some embodiments expression of a sequence of interest is regulated by transcription factors that regulate biomass composition-modulating sequences as described herein.

A sequence of interest can encode a polypeptide or can regulate the expression of a polypeptide. A sequence of interest that encodes a polypeptide can encode a plant polypeptide, a non-plant polypeptide such as a mammalian polypeptide, a modified polypeptide, a synthetic polypeptide, or a portion of a polypeptide. In some embodiments, a sequence of interest is transcribed into an antisense or interfering RNA molecule.

More than one sequence of interest can be present in a plant, e.g., two, three, four, five, six, seven, eight, nine, or ten sequences of interest can be present in a plant. Each sequence of interest can be present on the same nucleic acid construct or can be present on separate nucleic acid constructs. The regulatory region operably linked to each sequence of interest can be the same or can be different.

Sequences of interest that can be used in the methods described herein include, but are not limited to, sequences encoding genes or fragments thereof that modulate cold tolerance, frost tolerance, heat tolerance, drought tolerance, water used efficiency, nitrogen use efficiency, pest resistance, biomass, chemical composition, plant architecture, and/or biofuel conversion properties. In particular, exemplary sequences are described in the following applications which are incorporated herein by reference in their entirety: US20080131581, US20080072340, US20070277269, US20070214517, US 20070192907, US 20070174936, US 20070101460, US 20070094750, US20070083953, US 20070061914, US20070039067, US20070006346, US20070006345, US20060294622, US20060195943, US20060168696, US20060150285, US20060143729, US20060134786, US20060112454, US20060057724, US20060010518, US20050229270, US20050223434, US20030217388, WO 2011/011412, WO 2010/033564, and WO2009/102965.

VI. TRANSGENIC PLANTS AND PLANT CELLS

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous biomass composition-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a biomass composition-modulating polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of biomass. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a biomass composition relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Aistroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), Salix spp. (willow), *Eucalyptus* spp. (*eucalyptus*), Triticosecale (*Triticum*—wheat X rye) and bamboo.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava)

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include Rosa spp. (rose), *Dianthus caryophyllus* (carnation), *Petunia* spp. (*petunia*) and Poinsettia *pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), Acer spp. (maple), *Hordeum vulgare* (barley), *Poa pratensis* (bluegrass), *Lolium* spp. (ryegrass) and *Phleum pratense* (timothy).

In some embodiments, a suitable species can be a wild, weedy, or cultivated *Pennisetum* species such as, but not limited to, *Pennisetum alopecuroides, Pennisetum arnhemicum, Pennisetum caffrum, Pennisetum clandestinum, Pennisetum divisum, Pennisetum glaucum, Pennisetum latifolium, Pennisetum macrostachyum, Pennisetum macrourum, Pennisetum orientale, Pennisetum pedicellatum, Pennisetum polystachion, Pennisetum polystachion* ssp. *Setosum, Pennisetum purpureum, Pennisetum setaceum, Pennisetum subangustum, Pennisetum typhoides, Pennisetum villosum*, or hybrids thereof (e.g., *Pennisetum purpureum* x *Pennisetum typhoidum*).

In some embodiments, a suitable species can be a wild, weedy, or cultivated *Miscanthus* species and/or variety such as, but not limited to, *Miscanthus* x *giganteus, Miscanthus sinensis, Miscanthus* x *ogiformis, Miscanthus* floridulus, *Miscanthus transmorrisonensis, Miscanthus oligostachyus, Miscanthus nepalensis, Miscanthus sacchariflorus, Miscanthus* x *giganteus* 'Amuri', *Miscanthus* x *giganteus* 'Nagara', *Miscanthus* x *giganteus* 'Illinois', *Miscanthus sinensis* var. 'Goliath', *Miscanthus sinensis* var. 'Roland', *Miscanthus sinensis* var. 'Africa', *Miscanthus sinensis* var. 'Fern Osten', *Miscanthus sinensis* var. *gracillimus, Miscanthus sinensis* var. *variegates, Miscanthus sinensis* var. *purpurascens, Miscanthus sinensis* var. 'Malepartus', *Miscanthus sacchariflorus* var. '*Robusta', Miscanthus sinensis* var. 'Silberfedher' (aka. Silver Feather), *Miscanthus transmorrisonensis, Miscanthus condensatus, Miscanthus yakushimanum, Miscanthus* var. 'Alexander', *Miscanthus* var. 'Adagio', *Miscanthus* var. 'Autumn Light', *Miscanthus* var. 'Cabaret', *Miscanthus* var. 'Condensatus', *Miscanthus* var. 'Cosmopolitan', *Miscanthus* var. 'Dixieland', *Miscanthus* var. 'Gilded Tower' (U.S. Pat. No. PP14,743), *Miscanthus* var. 'Gold Bar' (U.S. Pat. No. PP15,193), *Miscanthus* var. '*Gracillimus', Miscanthus* var. 'Graziella', *Miscanthus* var. 'Grosse Fontaine', *Miscanthus* var. 'Hinjo aka Little Nicky'™, *Miscanthus* var. 'Juli', *Miscanthus* var. 'Kaskade', *Miscanthus* var. 'Kirk Alexander', *Miscanthus* var. 'Kleine Fontaine', *Miscanthus* var. 'Kleine Silberspinne' (aka. 'Little Silver Spider'), *Miscanthus* var. 'Little Kitten', *Miscanthus* var. 'Little Zebra' (U.S. Pat. No. PP13,008), *Miscanthus* var. 'Lottum', *Miscanthus* var. 'Malepartus', *Miscanthus* var. 'Morning Light', *Miscanthus* var. 'Mysterious Maiden' (U.S. Pat. No. PP16,176), *Miscanthus* var. 'Nippon', *Miscanthus* var. 'November Sunset', *Miscanthus* var. 'Parachute', *Miscanthus* var. 'Positano', *Miscanthus* var. 'Puenktchen'(aka 'Little Dot'), *Miscanthus* var. 'Rigoletto', *Miscanthus* var. 'Sarabande', *Miscanthus* var. 'Silberpfeil' (aka. Silver Arrow), *Miscanthus* var. 'Silverstripe', *Miscanthus* var. 'Super Stripe' (U.S. Pat. No. PP18,161), *Miscanthus* var. 'Strictus', or *Miscanthus* var. 'Zebrinus'.

In some embodiments, a suitable species can be a wild, weedy, or cultivated sorghum species and/or variety such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum* x *almum, Sorghum* x sudangrass or *Sorghum* x *drummondii.*

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (*Miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp. X *Miscanthus* sp., *Sorghum* sp. X *Miscanthus* sp., e.g., *Panicum virgatum* x *Panicum amarum, Panicum virgatum* x *Panicum amarulum*, and *Pennisetum purpureum* x *Pennisetum typhoidum*).

D. Transgenic Plant Phenotypes

In some embodiments, a plant in which expression of a biomass composition-modulating polypeptide is modulated has increased or decreased levels of sugar, ash, or glucan content. A plant in which expression of a biomass composition-modulating polypeptide is modulated also can have increased or decreased conversion efficiency. A component of biomass composition can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of the biomass component in a corresponding control plant that does not express the transgene. In some embodiments, a plant in which expression of a biomass composition-modulating polypeptide is modulated can have decreased levels of a biomass component. The level can be decreased by at least 2 percent, e.g., 2, 3, 4, 5, 10, 15, 20, 25, 30, 35, or more than 35 percent, as compared to the level in a corresponding control plant that does not express the transgene.

Increases in a component of biomass composition (e.g., total sugar content) in such plants can provide improved nutritional availability in geographic locales where intake of plant foods is often insufficient, or for energy production (e.g., conversion efficiency). In some embodiments, decreases in a component of biomass composition in such plants can be useful in energy production.

In some embodiments, a plant in which expression of a biomass composition-modulating polypeptide is modulated can have increased or decreased levels of a biomass component (e.g., sugar content) in one or more plant tissues, e.g., vegetative tissues, reproductive tissues, or root tissues. For example, the level of a biomass component can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level in a corresponding control plant that does not express the transgene. In some embodiments, a plant in which expression of a biomass composition-modulating polypeptide is modulated can have decreased levels of a biomass component in one or more plant tissues. The level can be decreased by at least 2 percent, e.g., 2, 3, 4, 5, 10, 15, 20, 25, 30, 35, or more than 35 percent, as compared to the level in a corresponding control plant that does not express the transgene.

Typically, a difference in the amount of a biomass component in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the amount of a biomass component is statistically significant at $p<0.01$, $p<0.005$, or $p<0.001$. A statistically significant difference in, for example, the amount of a biomass component in a transgenic plant compared to the amount of a control plant indicates that the recombinant nucleic acid present in the transgenic plant results in altered biomass composition.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

Biomass can include harvestable plant tissues such as leaves, stems, and reproductive structures, or all plant tissues such as leaves, stems, roots, and reproductive structures. In some embodiments, biomass encompasses only above ground plant parts. In some embodiments, biomass encompasses only stem plant parts. In some embodiments, biomass encompasses only above ground plant parts except inflorescence and seed parts of a plant. Biomass can be measured as described in the examples section. Biomass can be quantified as dry matter yield, which is the mass of biomass produced (usually reported in T/acre) if the contribution of water is subtracted from the fresh mater weight. Dry matter yield (DMY) yield is calculated using the fresh matter weight (FMW) and a measurement of weight percent moisture (M) in the following equation. $DMY=((100-M)/100)*FMW$. Biomass can be quantified as fresh matter yield, which is the mass of biomass produced (usually reported in T/acre) on an as-received basis, which includes the weight of moisture.

VI. MODIFYING ENDOGENOUS NUCLEIC ACIDS ENCODING BIOMASS COMPOSITION-MODULATING POLYPEPTIDES

This document also features plant cells and plants in which an endogenous biomass composition-modulating nucleic acid described herein has been modified (e.g., a regulatory region, intron, or coding region of the biomass composition-modulating nucleic acid has been modified). The biomass composition of such plants is altered relative to the corresponding composition of a control plant in which the endogenous nucleic acid is not modified. Such plants are referred to herein as modified plants and may be used to produce, for example, increased amounts of a biomass component (e.g., total sugar content).

Endogenous nucleic acid can be modified by homologous recombination techniques. For example, sequence specific endonucleases (e.g., zinc finger nucleases (ZFNs)) and meganucleases can be used to stimulate homologous recombination at endogenous plant genes. See, e.g., Townsend et al., *Nature* 459:442-445 (2009); Tovkach et al., *Plant J.,* 57:747-757 (2009); and Lloyd et al., *Proc. Natl. Acad. Sci. USA,* 102:2232-2237 (2005). In particular, ZFNs engineered to create DNA double strand breaks at specific loci can be used to make targeted sequence changes in endogenous plant genes. For example, an endogenous plant gene can be replaced with a variant containing one or more mutations (e.g., produced using site-directed mutagenesis or directed evolution). In some embodiments, site directed mutagenesis is achieved via non-homologous end joining such that after breaking DNA, endogenous DNA repair mechanisms ligate the break, often introducing slight deletions or additions that can be screened at the cell or plant level for desired phenotypes. Moore and Haber, *Mol Cell Biol.,* 16(5):2164-73 (1996).

In some embodiments, endogenous nucleic acids can be modified by methylation or demethylation such that the expression of the modified endogenous nucleic acid is altered. For example, a double stranded RNA can be used to activate gene expression by targeting noncoding regulatory regions in gene promoters. See Shibuya et al., *Proc Natl Acad Sci USA,* 106(5): 1660-1665 (2009); and Li et al., *Proc Natl Acad Sci USA,* 103(46):17337-42 (2006). In some embodiments, ZFNs engineered to create DNA double strand breaks at specific loci can be used to insert a DNA fragment having at least one region that overlaps with the endogenous DNA to facilitate homologous recombination, such that the non-overlapping portion of the DNA fragment is integrated at the break site. For example, a fragment can be inserted into an endogenous promoter and/or regulatory region at a specific site where a ZFN created a double stranded break to alter the expression of an endogenous gene. For example, a fragment that is inserted into an endogenous gene coding region at a specific site where a ZFN created a double stranded break can result in expression of a chimeric gene. For example, a fragment that functions as a regulatory region or promoter that is inserted into an endogenous DNA region immediately upstream of a gene coding sequence at a specific site where a ZFN creates a double strand break can result in altered expression of the endogenous gene.

In some embodiments, endogenous nucleic acids can be modified using activation tagging. For example, a vector containing multiple copies of an enhancer element from the constitutively active promoter of the cauliflower mosaic virus (CaMV) 35S gene can be used to activate an endogenous gene. See, Weigel et al., *Plant Physiology,* 122:1003-1013 (2000).

In some embodiments, endogenous nucleic acids can be modified by introducing an engineered transcription activation/repression factor (e.g., zinc finger protein transcription factor, or ZFP TF. Sce, for example, the world wide web at sangamo.com/tech/tech_plat_over.html#whatarezfp). For example, a synthetic transcription facto sequence of a zinc finger DNA binding domain and a VP16 activation domain can be designed to bind to a specific endogenous DNA site and alter expression of an endogenous gene. An engineered transcription activation/repression factor (such as ZFP TF) can activate, repress, or switch the target endogenous biomass, sucrose, and/or conversion-gene expression by binding specifically to the promoter region or coding region of the endogenous gene. Engineered nucleases that cleave specific DNA sequences in vivo can also be valuable reagents for targeted mutagenesis. One such class of sequence-specific nucleases can be created by fusing transcription activator-like effectors (TALEs) to the catalytic domain of the FokI endonuclease. Both native and custom TALE-nuclease fusions direct DNA double-strand breaks to specific, targeted sites. Christian, et al., *Genetics* 186: 757-761 (2010).

In some embodiments, endogenous nucleic acids can be modified by mutagenesis. Genetic mutations can be introduced within regenerable plant tissue using one or more mutagenic agents. Suitable mutagenic agents include, for example, ethyl methane sulfonate (EMS), N-nitroso-N-ethylurea (ENU), methyl N-nitrosoguanidine (MNNG), ethidium bromide, diepoxybutane, ionizing radiation, x-rays, UV rays and other mutagens known in the art. Suitable types of mutations include, for example, insertions or deletions of nucleotides, and transitions or transversions in the endogenous nucleic acid sequence. In one embodiment, TILLING (Targeted Induced Local Lesions In Genomes) can be used to produce plants having a modified endogenous nucleic acid. TILLING combines high-density mutagenesis with high-throughput screening methods. See, for example, McCallum et al., *Nat Biotechnol* 18: 455-457 (2000); reviewed by Stemple, *Nat Rev Genet* 5(2):145-50 (2004).

In some embodiments, an endogenous nucleic acid can be modified via a gene silencing technique. See, for example, the section herein regarding "Inhibition of Expression of a Biomass composition-modulating Polypeptide."

A population of plants can be screened and/or selected for those members of the population that have a modified nucleic acid. A population of plants also can be screened and/or selected for those members of the population that have a trait or phenotype conferred by expression of the modified nucleic acid. As an alternative, a population of plants can be screened for those plants having a desired trait, such as a modulated level of biomass. For example, a population of progeny can be screened for those plants having a desired level of expression of a biomass composition-modulating polypeptide or nucleic acid. Physical and biochemical methods can be used to identify modified nucleic acids and/or expression levels as described with transgenic plants. Selection and/or screening can be carried out over one or more generations, and/or in more than one geographic location. In some cases, plants can be grown and selected under conditions which induce a desired phenotype or are otherwise necessary to produce a desired phenotype in a modified plant. In addition, selection and/or screening can be applied during a particular developmental stage in which the phenotype is expected to be exhibited by the plant. Selection and/or screening can be carried out to choose those modified plants having a statistically significant difference in biomass composition relative to a control plant in which the nucleic acid has not been modified. Selected or screened modified plants have an altered phenotype as compared to a corresponding control plant, as described in the "Transgenic Plant Phenotypes" section herein.

Although a plant or plant cell in which an endogenous biomass composition-modulating nucleic acid has been modified is not transgenic for that particular nucleic acid, it will be appreciated that such a plant or cell may contain transgenes. For example, a modified plant can contain a transgene for other traits, such as herbicide tolerance or insect resistance. As another example, a modified plant can contain one or more transgenes that, in conjunction with modifications of one or more endogenous nucleic acids, exhibits an increase in a component of biomass.

As with transgenic plant cells, modified plant cells can constitute part or all of a whole plant. Such plants can be grown in the same manner as described for transgenic plants and can be bred or propagated in the same manner as described for transgenic plants.

VIII. PLANT BREEDING

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs).

SSR polymorphisms can be identified, for example, by making sequence specific probes and amplifying template DNA from individuals in the population of interest by PCR. For example, PCR techniques can be used to enzymatically amplify a genetic marker associated with a nucleotide sequence conferring a specific trait (e.g., nucleotide sequences described herein). PCR can be used to amplify specific sequences from DNA as well as RNA, including sequences from total genomic DNA or total cellular RNA. When using RNA as a source of template, reverse transcriptase can be used to synthesize complementary DNA (cDNA) strands. Various PCR methods are described, for example, in *PCR Primer: A Laboratory Manual*, Dieffenbach and Dveksler, eds., Cold Spring Harbor Laboratory Press, 1995.

Generally, sequence information from polynucleotides flanking the region of interest or beyond is employed to design oligonucleotide primers that are identical or similar in sequence to opposite strands of the template to be amplified. Primers are typically 14 to 40 nucleotides in length, but can range from 10 nucleotides to hundreds of nucleotides in length. Template and amplified DNA is repeatedly denatured at a high temperature to separate the double strand, then cooled to allow annealing of primers and the extension of nucleotide sequences through the microsatellite, resulting in sufficient DNA for detection of PCR products. If the probes flank an SSR in the population, PCR products of different sizes will be produced. See, e.g., U.S. Pat. No. 5,766,847.

PCR products can be qualitative or quantitatively analyzed using several techniques. For example, PCR products can be stained with a fluorescent molecule (e.g., PicoGreen® or OliGreen®) and detected in solution using spectrophotometry or capillary electrophoresis. In some cases, PCR products can be separated in a gel matrix (e.g., agarose or polyacrylamide) by electrophoresis, and size-fractionated bands comprising PCR products can be visualized using nucleic acid stains. Suitable stains can fluoresce under UV light (e.g., Ethidium bromide, GR Safe, SYBR® Green, or SYBR® Gold). The results can be visualized via transillumination or epi-illumination, and an image of the fluorescent pattern can be acquired using a camera or scanner, for example. The image can be processed and analyzed using specialized software (e.g., ImageJ) to measure and compare the intensity of a band of interest against a standard loaded on the same gel.

Alternatively, SSR polymorphisms can be identified by using PCR product(s) as a probe against Southern blots from different individuals in the population. See, Refseth et al., (1997) *Electrophoresis* 18: 1519. Briefly, PCR products are separated by length through gel electrophoresis and transferred to a membrane. SSR-specific DNA probes, such as oligonucleotides labeled with radioactive, fluorescent, or chromogenic molecules, are applied to the membrane and hybridize to bound PCR products with a complementary nucleotide sequence. The pattern of hybridization can be visualized by autoradiography or by development of color on the membrane, for example.

In some cases, PCR products can be quantified using a real-time thermocycler detection system. For example, Quantitative real-time PCR can use a fluorescent dye that forms a DNA-dye-complex (e.g., SYBR® Green), or a fluorophore-containing DNA probe, such as single-stranded oligonucleotides covalently bound to a fluorescent reporter or fluorophore (e.g. 6-carboxyfluorescein or tetrachlorofluorescin) and quencher (e.g., tetramethylrhodamine or dihydrocyclopyrroloindole tripeptide minor groove binder). The fluorescent signal allows detection of the amplified product in real time, thereby indicating the presence of a sequence of interest, and allowing quantification of the copy number of a sequence of interest in cellular DNA or expression level of a sequence of interest from cellular mRNA.

The identification of RFLPs is discussed, for example, in Alonso-Blanco et al. (*Methods in Molecular Biology*, vol. 82, "*Arabidopsis* Protocols", pp. 137-146, J. M. Martinez-Zapater and J. Salinas, eds., c. 1998 by Humana Press, Totowa, NJ); Burr ("Mapping Genes with Recombinant Inbreds", pp. 249-254, in Freeling, M. and V. Walbot (Ed.), *The Maize Handbook*, c. 1994 by Springer-Verlag New York, Inc.: New York, NY, USA; Berlin Germany; Burr et al. *Genetics* (1998) 118: 519; and Gardiner, J. et al., (1993) *Genetics* 134: 917). For example, to produce a RFLP library enriched with single- or low-copy expressed sequences, total DNA can be digested with a methylation-sensitive enzyme (e.g., Pst1). The digested DNA can be separated by size on a preparative gel. Polynucleotide fragments (500 to 2000 bp) can be excised, eluted and cloned into a plasmid vector (e.g., pUC18). Southern blots of plasmid digests can be probed with total sheared DNA to select clones that hybridize to single- and low-copy sequences. Additional restriction endonucleases can be tested to increase the number of polymorphisms detected.

The identification of AFLPs is discussed, for example, in EP 0 534 858 and U.S. Pat. No. 5,878,215. In general, total cellular DNA is digested with one or more restriction enzymes. Restriction halfsite-specific adapters are ligated to all restriction fragments and the fragments are selectively amplified with two PCR primers that have corresponding adaptor and restriction site specific sequences. The PCR products can be visualized after size-fractionation, as described above.

In some embodiments, the methods are directed to breeding a plant line. Such methods use genetic polymorphisms identified as described above in a marker assisted breeding program to facilitate the development of lines that have a desired alteration in biomass composition. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

IX. ARTICLES OF MANUFACTURE

Transgenic plants provided herein have various uses in the agricultural and energy production industries. For example, transgenic plants described herein can be used to make animal feed (e.g., forage products) and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the composition of the plant material, including, but not limited to, content of glucan, cellulose, hemicellulose, and lignin. By providing higher biomass yields at an equivalent or even decreased cost of production, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

X. EXAMPLES

Example 1

GA 20-Oxidase Overexpressing Rice Plants

A rice plant of the Kitaake variety was transformed with a vector intended to overexpress a transgene expected to produce a known phenotype. The phenotype of one transformation event unexpectedly showed a dramatic increase in height.

Sequencing of the rice genomic DNA flanking the vector insertion site revealed that the insertion occurred about 8 kb 5' of the OsGA20ox1 gene. Overexpression of the OsGA20ox1 sequence was observed by RT-PCR. The morphology of the transformed plant was very similar to one previously reported for activation-tagged and transgenic OsGA20ox1 overexpressing rice plants (see Oikawa, et al., 2004, supra). These results indicated that the increase in height and the morphology observed for this plant were due to trans-activation of the rice OsGA20ox1 gene rather than expression of the transgene per se.

Rice plants of the Kitaake variety were transformed separately with a vector to overexpress the transgene encoding a GA20-oxidase enzyme CeresAnnot: 8631464 (SEQ ID NO: 473) from *Sorghum bicolor*, GID1 GA receptor gene CeresClone:1857760 (SEQ ID NO: 101) from *Panicum virgatum*, or RNAi construct (SEQ ID NO: 1568) designed to target the rice locus for SLR1, Os03g49990 (CeresAnnot: 200242600), a gene encoding a DELLA protein. The phenotype of GA20-oxidase and GID1 transformation events showed dramatic increases in height. For the GA20-oxidase enzyme, overexpression of the sequence was observed by RT-PCR. This analysis of expression levels was not conducted for GID1 GA receptor or SLR1 RNAi. The morphology of the plants transformed with the GA20-oxidase and GID1 GA receptor sequences was very similar to the transgenic line described above for OsGA20ox1.

Nucleic acids for GID1 GA receptor, GA20-oxidase enzyme, and SLR1 RNAi were isolated from *Panicum virgatum, Sorghum bicolor*, and *Oryza sativa*, respectively, and cloned into a Ti plasmid vector, CV2, under the control of a PD3580 promoter, which is disclosed in WO2009/146015. Each construct contained a NPTII gene which confers paramyosin resistance to transformed plants. The presence of each vector containing a nucleic acid described above in the respective transgenic rice lines transformed with the vector was confirmed by paramyosin resistance, PCR amplification from green leaf tissue extract, and/or sequencing of PCR products.

*Sorghum* plants of the Wheatland and BTx430 varieties were transformed with a vector to overexpress the transgene encoding a GA20-oxidase enzyme CeresAnnot: 8631464

(SEQ ID NO: 473) from *Sorghum bicolor*. The vector was the same as that described above for the rice transformation.

Example 2

Cellulosic Biomass Conversion Characteristics of Rice Plants Overexpressing a Rice GA 20-Oxidase The transformed plant of Example 1 that was found to overexpress the OsGA20ox1 was crossed to a wild type rice plant. The progeny of the cross segregated 1:1 for the transgene and morphological phenotype. Biomass of transgenic (RiceS-1 No. 2 and RiceS-1 No. 4) and non-transgenic segregants (RiceS-1 No. 10) was harvested at maturity (after three months of growth) and subjected to a conversion assay as follows.

The yield of conversion can be directly calculated as follows: [PLN value+SAC value]/amount of biomass weight, where "PLN" refers to pretreatment liquor neutralized, and "SAC" refers to the sugar value from the saccharification analysis. The following procedures were used to obtain the PLN and SAC values.

Sample preparation and milling: Samples were prepared for analysis by drying the tissue samples for at least 3 days in an incubator set at 45° C. Dried tissues were milled using a Wiley Mill fitted with 2 mm mesh filter.

Microwave pretreatment: Milled tissues were weighed to obtain approximately 0.025 g. The moisture content of the weighed tissues was determined using the Denver Moisture Content analyzer. Tissues were transferred into separate Biotage microwave vials that were previously tared. Appropriate volume of sulfuric acid was then added into the samples to give a final concentration of 1.3% (w/w) in aqueous solution. Samples were pretreated in the Biotage microwave using the following settings: 160° C., 5 minutes, very high absorbance, 2.0-5.0 vial, 600 rpm stir speed (SWAVE default). The vials with the microwaved samples were centrifuged at 4000 rpm for 5 min with a deceleration rate set at ≤5. A minimum of 4 ml of PL (pretreated liquor) from each vial was transferred into pre-labeled 15 ml Corning conical tubes. The pH of the PL fraction was measured. The PL was directly neutralized with calcium carbonate ($CaCO_3$) for PLN and subsequent HPLC analysis or kept frozen until ready to analyze. The solid residue in each vial was washed several times by adding 5 ml water followed by centrifugation step at 4000 rpm for 5 min. The pH of the wash was monitored until it reached between 5 and 6 using appropriate pH indicator strips. The solid fraction was stored for saccharification analysis.

Pretreatment Liquor Analysis: To determine PLN, calcium carbonate ($CaCO_3$) was added to an appropriate aliquot of each PL fraction until its pH reached between 5 and 6. The neutralized mixture was centrifuged at 4000 rpm for 2 min; after which 2 ml of the neutralized liquor was transferred to storage tubes.

To determine the amount of sugar released after acid pretreatment, the neutralized fraction (PLN) was analyzed by HPLC. Table 1 presents the amount of glucose (GLC) and xylose (XYL) released as PLN mg GLC/g dry biomass and PLN mg XYL/g dry biomass for the transgenic (RiceS-1 No. 2 and No. 4) and wild-type (RiceS-1 No. 10) plants.

Saccharification Analysis: Water was added to the solid fraction obtained from the microwave pretreatment. A solution of citrate buffer (50 mM final), tetracycline (0.04 mg/mL final), cycloheximide (0.03 mg/mL final), Spezyme® and Novozyme 188 was added to make 20 mg or 2 mg enzyme/g dry biomass. The reaction mixture was then incubated at 50° C. in a rotating incubator. After 24 hours of incubation, an aliquot from the reaction was transferred to a microcentrifuge tube. The reaction was stopped by boiling the mixture for 5 min. The mixture was centrifuged for 2 min at 14,000 rpm. The supernatant was removed for sugar analysis (glucose monomers) by HPLC. Table 1 presents the amount of glucose (GLC) and xylose (XYL) released after enzymatic hydrolysis as SAC mg GLC/g dry biomass and SAC mg XYL/g dry biomass for the transgenic (RiceS-1 No. 2 and No. 4) and wild-type (RiceS-1 No. 10) plants. Table 1 also presents the total glucose and total xylose released (total from the PLN and SAC assays) for the transgenic and wild-type plants.

TABLE 1

| Sample (mg enzyme) | SAC mg GLC/g dry biomass | SD | SAC mg XYL/g dry biomass | SD |
|---|---|---|---|---|
| RiceS-1 No. 2 (20) | 221.5 | 3.9 | 6.5 | 0.4 |
| RiceS-1 No. 2 (2) | 134.1 | 3.3 | 0.2 | 0.3 |
| RiceS-1 No. 4 (20) | 202.4 | 1.8 | 4.6 | 0.2 |
| RiceS-1 No. 4 (2) | 124.3 | 3.5 | 0.4 | 0.1 |
| RiceS-1 No. 10 (20) | 280.1 | 4.9 | 7.6 | 0.4 |
| RiceS-1 No. 10 (2) | 143.0 | 0.0 | 0.3 | 0.3 |
| **Sample** | **PLN mg GLC/g dry biomass** | **SD** | **PLN mg XYL/g dry biomass** | **SD** |
| RiceS-1 No. 2 (20) | 154.1 | 11.6 | 124.4 | 0.6 |
| RiceS-1 No. 2 (2) | 168.1 | 3.8 | 120.9 | 1.6 |
| RiceS-1 No. 4 (20) | 209.4 | 4.2 | 114.0 | 2.3 |
| RiceS-1 No. 4 (2) | 211.7 | 2.6 | 117.2 | 3.8 |
| RiceS-1 No. 10 (20) | 28.5 | 0.1 | 155.3 | 1.6 |
| RiceS-1 No. 10 (2) | 25.1 | 0.2 | 146.0 | 1.4 |
| **Sample** | **Total Glucose release** | **SD** | **Total Xylose release** | **SD** |
| RiceS-1 No. 2 (20) | 375.6 | 15.5 | 130.9 | 1.0 |
| RiceS-1 No. 2 (2) | 302.2 | 7.1 | 121.1 | 1.9 |
| RiceS-1 No. 4 (20) | 411.8 | 6.0 | 118.6 | 2.5 |
| RiceS-1 No. 4 (2) | 336.0 | 6.1 | 117.6 | 3.9 |
| RiceS-1 No. 10 (20) | 308.6 | 5.0 | 162.9 | 2.0 |
| RiceS-1 No. 10 (2) | 168.1 | 0.2 | 146.3 | 1.7 |

Example 3

Cellulosic Biomass Conversion Characteristics of Rice Plants Overexpressing a GA 20-Oxidase Sequence From *Sorghum bicolor* The transformed rice plants of Example 1 overexpressing the GA 20-oxidase sequence from *Sorghum bicolor* (SEQ TD NO:473) were analyzed for cellulosic biomass conversion characteristics. All plants were of the primary transformant generation, TO. Control plants included plants derived from the same transformation procedure as the transgenic lines but that tested negative for PCR products associated with the transgenes.

The yield of conversion can be directly calculated as follows: [PLN value+SAC value]/amount of biomass weight, where "PLN" refers to pretreatment liquor neutralized, and "SAC" refers to the sugar value from the saccharification analysis. The following procedures were used to obtain the PLN values.

Sample preparation and milling, microwave pretreatment, and pretreatment liquor analysis for GLC only were carried out as described in Example 2.

Saccharification Analysis: Water was added to the solid fraction obtained from the microwave pretreatment. A solution of citrate buffer (50 mM final), tetracycline (0.04 mg/ml final), cycloheximide (0.03 mg/ml final), Novozyme CTec2 was added to make 20 mg, 2 mg, or 1 mg enzyme/g dry biomass. The reaction mixture was then incubated at 50° C. in a rotating incubator. After 24 hours of incubation, an aliquot from the reaction was transferred to a microcentrifuge tube. The reaction was stopped by boiling the mixture for 5 min. The mixture was centrifuged for 2 min at 14,000 rpm. The supernatant was removed for sugar analysis (glucose monomers) by HPLC.

Determining Sucrose and Glucose in dry biomass: Accelerated Solvent Extractor (Dionex ASE 200) cells (22 ml stainless steel cells, Cat no. 049561) were filled with milled biomass (2 mm). Samples were loaded in ASE 200 and both sucrose and glucose compounds in the biomass were extracted using water as a solvent. During the extraction, the cells were filled with water and heated to 100° C. and 1500 psi pressure. The extracts were collected in vials. Volume of the extracts was measured accurately and a homogenized subset of the sample was used to run HPLC to determine the sugar profile.

Two sets of samples were used to characterize the sugars extractable in pretreatment. For one sample set, sucrose and glucose were extracted and measured as explained above to determine the SUG value in Table 2, which is the sum of free glucose and glucose theoretically generated by sucrose hydrolysis. The other sample set was subjected to PLN analysis to determine total glucose (GLC in the PLN group) in Table 2.

HPLC: The neutralized sample from PLN and extracts from ASE were run on HPLC (Agilent 1100 series) to determine the sugar profile. A HPLC carbohydrate analysis column (Aminex® HPX-87P column) was used for the sugar analysis. The column was heated at 80° C. and the flow rate was set at 0.6 ml/min and 1 ml/min for analyzing PLN and ASE extracts, respectively. Corona® CAD® detector (Thermo Scientific) was used to analyze the sugar samples. The data was analyzed using Agilent Chemstation software.

Table 2 presents the amount of glucose (GLC) released after both pretreatment (PLN GLC) and saccharification enzymatic hydrolysis (SAC GLC) as determined for three separate enzyme dose levels (20 mg, 10 mg, and 1 mg) for transgenic and non-transgenic control plants. The GLC from PLN, SUG, and associated standard deviations (SD) were determined based on two replicate samples from a single plant for each enzyme dose level for a total of six samples. CW/Starch (mg/gDry biomass) was then calculated by subtracting the SUG from the GLC to determine the remaining amount of glucose from cell wall release and starch combined. Subsequent evaluations demonstrated that the starch only accounts for a small proportion of the PLN (CW/Starch) (see Example 4). The glucose released from saccharification and associated standard deviations (SD) were measured from two sample replicates for each enzyme dose level. The total GLC was calculated as the sum of PLN GLC and SAC GLC.

TABLE 2

| | PLN GLC | | | | SAC GLC | | | | |
|---|---|---|---|---|---|---|---|---|---|
| | GLC (mg/g Dry biomass) | SUG (mg/g Dry biomass) | CW/Starch (mg/g Dry biomass) | SD | Enzyme dose | GLC (mg/g Dry biomass) | SD | Total GLC | SD |
| Control (NT) | 63.4 | 35.4 | 28.1 | 4.1 | 20 mg | 211.6 | 1.2 | 275.0 | 5.3 |
| | 63.4 | 35.4 | 28.1 | 4.1 | 2 mg | 158.7 | 10.3 | 222.1 | 14.4 |
| | 63.4 | 35.4 | 28.1 | 4.1 | 1 mg | 136.8 | 14.8 | 200.3 | 18.9 |
| Transgenic | 182.2 | 91.6 | 90.6 | 7.8 | 20 mg | 179.7 | 6.5 | 361.9 | 14.3 |
| | 182.2 | 91.6 | 90.6 | 7.8 | 2 mg | 143.2 | 2.3 | 325.4 | 10.1 |
| | 182.2 | 91.6 | 90.6 | 7.8 | 1 mg | 115.3 | 8.4 | 297.5 | 16.2 |

The results demonstrate that the total glucose released increased in transgenic rice plants overexpressing the GA 20-oxidase sequence from *Sorghum bicolor* in comparison to non-transgenic control plants. This increase is based on the significant increases in sugar and glucose release from pretreatment alone (PLN SUG and GLC) and in a greater mobilization of cell wall material in pretreatment to increase PLN (CW/starch). The increase in PLN (CW/starch) increases conversion efficiency with more cell wall material released.

Example 4

Biomass Conversion Characteristics of Rice Plants Overexpressing a GID1 GA Receptor Sequence from *Panicum virgatum* and Rice Plants Overexpressing an RNAi Construct for the Rice SLR1 Gene Three events of the transformed rice plants of Example 1 overexpressing the GID1 GA receptor encoding sequence (SEQ ID NO: 101) were designated Os1043-12, Os1043-13, and Os1043-18. Three events of the transformed plants of Example 1 overexpressing the SLR1 RNAi sequence (SEQ ID NO: 1568) were designated Os1044-06, Os1044-19, and Os1044-27. All plants were of the primary transformant generation, TO. Control plants included untransformed wild-type plants and plants derived from the same transformation procedure as the transgenic lines but that tested negative for PCR products associated with the transgenes.

Sample preparation, milling, microwave pretreatment, and pretreatment liquor analysis were carried out as described in Example 2 for GLC only. Determining sucrose and glucose in dry biomass, and HPLC were carried out as described in Example 3.

Determining Starch in dry biomass: Finely milled (0.5 mm) biomass was used to analyze the starch content in biomass. Megazyme Total Starch assay kit (K-TSTA) was used for determining starch content of the biomass. The absorbance for each sample was read and the D-glucose control (supplied with the kit) at 510 nm against the reagent blank using a spectrophotometer (Agilent 8453 UV-Vis).

Table 3 presents the amount of glucose (GLC) released after pretreatment (PLN GLC) and its portion released from cell wall for transgenic and control plants. The data for each event were based on the average of two tissue sample replicates for single plants. Total free glucose was determined using separate sets of samples of dry material that was placed in aqueous solution and run through HPLC analyses, then total free glucose was calculated by adding half of the sucrose to the glucose measured (HPLC data not shown). Glucose from cell wall was calculated by subtracting the total free sugar value and the total starch value from the PNL glucose value.

TABLE 3

| Samples | PLN GLC (mg/g Dry biomass) | PLN (SD) | Total free GLC (mg/g Dry biomass) | Total Starch (mg/g Dry biomass) | GLC from Cell Wall (mg/g Dry biomass) | Plant height (cm) | Heading time (days) |
|---|---|---|---|---|---|---|---|
| WT | 84.8 | 4.1 | 47.5 | 18.6 | 18.7 | 97 | 41 |
| PCR- | 79.4 | 8.0 | 46.0 | 16.4 | 17.0 | 81 | 39 |
| Os1043-12 | 61.8 | 7.0 | 20.9 | 12.5 | 28.4 | 126 | 40 |
| Os1043-13 | 68.7 | 4.7 | 30.0 | 07.6 | 31.1 | 116 | 41 |
| Os1043-18 | 99.8 | 3.5 | 39.8 | 21.7 | 38.3 | 118 | 41 |
| Os1044-06 | 117.5 | 0.0 | 40.8 | 22.9 | 53.8 | 100 | 44 |
| Os1044-19 | 63.3 | 0.7 | 31.9 | 13.0 | 18.4 | 89 | 38 |
| Os1044-27 | 110.1 | 6.7 | 38.2 | 30.4 | 41.5 | 93 | 41 |

The results demonstrate that the total glucose released by pretreatment from cell wall increased in transgenic rice plants overexpressing the GID1 GA receptor sequence from *Panicum virgatum* or the RNAi construct targeting SLR1 in comparison to control plants. This increase is based on the significant increase in sugar release from a greater mobilization of cell wall material in pretreatment to increase glucose from the cell wall. The increase in availability of sugars from cell wall improves conversion characteristics.

Example 5

Sugar Characteristics of *Sorghum* Plants Overexpressing GA 20-Oxidase Sequence from *Sorghum bicolor*

Four events of the transformed sorghum plants of Example 1 overexpressing the GA20-oxidase enzyme from *Sorghum bicolor* (SEQ ID NO:473) were designated SbGA20-054, SbGA20-071, SbGA20-048, and SbGA20-52. All plants were of the primary transformant generation, TO, in the sorghum variety Wheatland. Control plants were of the Wheatland variety and grown from seed. SbGA20-054 was treated as a negative control based on short height phenotype that matched the control.

Five stalk juice samples were harvested at approximately soft to hard dough stages. After harvesting, the Brix value of each juice sample was measured. HPLC was carried out as described in Example 3, except that juice samples were used instead of dry material derived samples and the amount of fructose (FRU) was also measured.

Table 4 presents the Brix and HPLC-determined sugar profiles from juice samples of transgenic and control plants. The data for each event were based on one juice sample for single plants.

TABLE 4

| Stature | Sample | PGR | Brix % | SUC (mg/ml) | GLC (mg/ml) |
|---|---|---|---|---|---|
| Control (Short) | Wheatland | − | 6.5 | 13.1 | 0.7 |
| Short | SbGA20-054 | + | 13.3 | 71.8 | 2.1 |
| Tall | SbGA20-071 | + | 11.2 | 69.5 | 2.2 |
| Tall | SbGA20-048 | + | 14.2 | 82.1 | 2.2 |
| Tall | SbGA20-052 | + | 7.6 | 30.7 | 1.5 |

TABLE 4-continued

| Stature | FRU (mg/ml) | Total (mg/ml) | Sucrose Purity (%) | Juice volume (ml juice/ Stalk) | Sugar Yield (mg sugar/ Stalk) |
|---|---|---|---|---|---|
| Control (Short) | 0.2 | 14.0 | 93.7% | 27.5 | 385.8 |
| Short | 1.5 | 75.3 | 95.3% | 7.5 | 564.9 |
| Tall | 1.5 | 73.2 | 95.0% | 25.0 | 1830.8 |
| Tall | 1.7 | 86.0 | 95.4% | 40.0 | 3442.0 |
| Tall | 1.1 | 33.3 | 92.2% | 75.0 | 2495.3 |

The SbGA20-071, SbGA20-048, SbGA20-052 transgenic lines all showed an increase in plant height in comparison to control plants.

Total sugar values for SbGA20-054 and SbGA20-052 deviated from the expected trend at 75.3 and 33.3 mg/ml, respectively, although an increase in sugar concentration was seen in all cases. Combining stature and juice yield with sugar profile, the significant advantage of increased sugar yield associated with the transgenic events becomes apparent in comparison to the controls.

Example 6

*Sorghum* seeds are planted in the field and allowed to germinate. At 2 week intervals following planting, the field is sprayed with GA3 at the rate of 50 g per hectare. Biomass of sorghum plants from the field is harvested about four months after planting. The biomass is subjected to a cellulosic sugar extraction process (see Example 2) for use in ethanol fermentation. The process results in increased sugars and/or requires lower amounts of the saccharification enzyme cocktail for sugar release per unit biomass, as compared to similar processing of biomass of sorghum plants of the same variety grown in under the same field conditions except for gibberellin treatment.

Example 7

*Miscanthus* plantlets are transplanted to a field. At 2 week intervals during the second growing season, the field is sprayed with GA3 at a rate of 50 gm per hectare. Biomass from the field is harvested and subjected to a pretreatment and enzymatic saccharification process (see Example 2).

The process yields increased sugars and/or requires lower amounts of the saccharification enzyme cocktail for sugar release per unit biomass, as compared to similar processing of biomass of *Miscanthus* plants of the same variety grown in under the same field conditions except for gibberellin treatment.

Example 8

Switchgrass seeds are planted in the field and allowed to germinate. At 2 week intervals during the third growing season, the field is sprayed with GA3 at the rate of 50 gm per hectare. Biomass from the field is harvested and subjected to a pretreatment and enzymatic saccharification process. The process yields increased sugars and/or requires lower amounts of the saccharification enzyme cocktail for sugar release per unit biomass, as compared to similar processing of biomass of switchgrass plants of the same variety grown in under the same field conditions except for gibberellin treatment.

Example 9

Sugarcane stalk cuttings are transplanted to a field. At 2 week intervals during the growing season, the field is sprayed with GA3 at a rate of 50 gm per hectare. Biomass from the field is harvested and subjected to a pretreatment and enzymatic saccharification process (see Example 2). The process yields increased sugars and/or requires lower amounts of the saccharification enzyme cocktail for sugar release per unit biomass, as compared to similar processing of biomass of sugarcane plants of the same variety grown in under the same field conditions except for gibberellin treatment.

Example 10

Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA,* 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Missouri, USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of 10-5 and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 471, 99, 188, 1, 287, 1429, 1542, 1386, and 1274 are shown in FIGS. 1-9, respectively. Additional exemplary homologs are correlated to certain Figures in the Sequence Listing.

Example 11

Determination of Functional Homologs by Hidden Markov Models

Hidden Markov Models (HMMs) were generated by the program HMMER 3.0. To generate each HMM, the default HMMER 3.0 program parameters were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ TD NO: 471.

The procedure above was repeated and an HMM was generated for each group of sequences shown in FIGS. 1-9, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy sequence listing. A copy of the sequence listing is available in electronic form from the USPTO web site (https://seqdata.uspto.gov/docdetail?docId=US12584142B2). An electronic copy of the sequence listing will also be available from the USPTO upon request and payment of the fee set forth in 37 CFR 1.19(b)(3).

What is claimed is:

1. A rice plant cell from a rice plant comprising an exogenous nucleic acid, said exogenous nucleic acid comprising a regulatory region operably linked to a nucleotide sequence encoding a polypeptide comprising the amino acid sequence of SEQ ID NO: 101, wherein the rice plant was selected for having an increased total glucose release from cell wall after pretreatment as compared to the corresponding composition of a control rice plant that does not comprise said exogenous nucleic acid, and wherein the rice plant cell comprises the exogenous nucleic acid.

2. A rice plant comprising an exogenous nucleic acid, said exogenous nucleic acid comprising a regulatory region operably linked to a nucleotide sequence encoding a polypeptide comprising the amino acid sequence of SEQ ID NO: 101, and wherein the rice plant is selected for having an increased total glucose release from cell wall after pretreatment as compared to the corresponding composition of a control rice plant that does not comprise said exogenous nucleic acid.

3. A progeny of the rice plant of claim 2, wherein the progeny comprises the exogenous nucleic acid.

4. The rice plant of claim 2, wherein the rice plant exhibits an at least 2.0 fold increase in total glucose release from cell wall after pretreatment as compared to that of a control plant that does not comprise said exogenous nucleic acid.

5. The rice plant of claim 2, wherein the rice plant exhibits an at least 2.5 fold increase in total glucose release from cell wall after pretreatment as compared to that of a control plant that does not comprise said exogenous nucleic acid.

6. A method of producing a rice plant, said method comprising growing a rice plant comprising an exogenous nucleic acid, said exogenous nucleic acid comprising a regulatory region operably linked to a nucleotide sequence encoding a polypeptide comprising the amino acid sequence of SEQ ID NO: 101, and selecting the rice plant for having an increased total glucose release from cell wall after pretreatment as compared to a control plant that does not comprise said nucleic acid.

7. The method of claim 6, wherein the rice plant is selected for exhibiting an at least 2 fold increase in total glucose release from cell wall after pretreatment.

8. The method of claim 6, wherein the rice plant is selected for exhibiting an at least 2.5 fold increase in total glucose release from cell wall after pretreatment.

* * * * *